US012679899B2

(12) United States Patent
Moore et al.

(10) Patent No.: US 12,679,899 B2
(45) **Date of Patent: *Jul. 14, 2026**

(54) MATRIX METALLOPROTEINASE SUBSTRATES AND OTHER CLEAVABLE MOIETIES AND METHODS OF USE THEREOF

(71) Applicant: CytomX Therapeutics, Inc., South San Francisco, CA (US)

(72) Inventors: Stephen James Moore, Danville, CA (US); Margaret Thy Luu Nguyen, San Francisco, CA (US); Daniel R. Hostetter, Rocklin, CA (US); Olga Vasiljeva, Highlands Ranch, CO (US); Jeanne Grace Flandez, Benicia, CA (US)

(73) Assignee: CYTOMX THERAPEUTICS, INC., South San Francisco, CA (US)

( * ) Notice: Subject to any disclaimer, the term of this patent is extended or adjusted under 35 U.S.C. 154(b) by 86 days.

This patent is subject to a terminal disclaimer.

(21) Appl. No.: 18/474,134

(22) Filed: Sep. 25, 2023

(65) Prior Publication Data

US 2024/0084022 A1 Mar. 14, 2024

Related U.S. Application Data

(60) Continuation of application No. 16/179,670, filed on Nov. 2, 2018, now Pat. No. 11,814,410, which is a division of application No. 14/497,089, filed on Sep. 25, 2014, now abandoned.

(60) Provisional application No. 61/971,332, filed on Mar. 27, 2014, provisional application No. 61/882,377, filed on Sep. 25, 2013.

(51) Int. Cl.
*C07K 16/28* (2006.01)
*C07K 7/06* (2006.01)
*C07K 16/44* (2006.01)

(52) U.S. Cl.
CPC ............ *C07K 16/2866* (2013.01); *C07K 7/06* (2013.01); *C07K 16/2863* (2013.01); *C07K 16/44* (2013.01); *C07K 2317/73* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Bostwell et al. |
| 4,485,045 | A | 11/1984 | Regen |
| 4,544,545 | A | 10/1985 | Ryan et al. |
| 5,013,556 | A | 5/1991 | Woodle et al. |
| 5,030,719 | A | 7/1991 | Umemoto et al. |
| 6,551,795 | B1 | 4/2003 | Rubenfield et al. |
| 6,558,728 | B1 | 5/2003 | Poulsen et al. |
| 7,276,497 | B2 | 10/2007 | Chari et al. |
| 7,439,319 | B2 | 10/2008 | Smith et al. |
| 7,442,159 | B1 | 10/2008 | Riechmann et al. |
| 7,465,790 | B2 | 12/2008 | Waldmann et al. |
| 7,666,817 | B2 | 2/2010 | Daugherty et al. |
| 7,935,785 | B2 | 5/2011 | Smith et al. |
| 8,513,390 | B2 | 8/2013 | Stagliano et al. |
| 8,518,404 | B2 | 8/2013 | Daugherty et al. |
| 8,524,220 | B1 | 9/2013 | Bermudes |
| 8,529,898 | B2 | 9/2013 | Daugherty et al. |
| 8,541,203 | B2 | 9/2013 | Daugherty et al. |
| 8,563,269 | B2 | 10/2013 | Stagliano et al. |
| 8,809,504 | B2 | 8/2014 | Lauermann |
| 9,120,853 | B2 | 9/2015 | Lowman et al. |
| 9,127,053 | B2 | 9/2015 | West et al. |
| 9,169,321 | B2 | 10/2015 | Daugherty et al. |
| 9,453,078 | B2 | 9/2016 | Stagliano et al. |
| 9,562,073 | B2 | 2/2017 | Moore et al. |
| 10,059,762 | B2 | 8/2018 | Stagliano et al. |
| 10,077,300 | B2 | 9/2018 | Daugherty et al. |
| 10,118,961 | B2 | 11/2018 | Stagliano et al. |
| 10,138,272 | B2 | 11/2018 | Moore et al. |
| 10,179,817 | B2 | 1/2019 | Sagert et al. |
| 10,233,244 | B2 | 3/2019 | Sagert et al. |
| 10,336,824 | B2 | 7/2019 | West et al. |
| 10,513,558 | B2 | 12/2019 | Tipton et al. |
| 10,669,337 | B2 | 6/2020 | Irving et al. |
| 10,669,339 | B2 | 6/2020 | West et al. |

(Continued)

FOREIGN PATENT DOCUMENTS

| | | |
|---|---|---|
| CN | 102482347 | 5/2012 |
| EP | 1 523 503 | 4/2009 |

(Continued)

OTHER PUBLICATIONS

UniProt (A5E4A4_LODEL available Jun. 2007).*
Libre Texts Biology (https://bio.libretexts.org/Bookshelves/Introductory_and_General_Biology/General_Biology_1e_(OpenStax)/1%3A_The_Chemistry_of_Life/3%3A_Biological_Macromolecules accessed Dec. 10, 24).*
S. Ohkubo, et al. "Identification of substrate sequences for membrane type-1 matrix metalloproteinase using bacteriophage peptide display library"; Biochemical and Biophysical Research Communications, Dec. 20, 1999, vol. 266, No. 2, pp. 308-313. (Abstract).
Russian Office Action for corresponding Russian Application No. 2020106752 mailed Mar. 21, 2024 (21 pages) with English translation.

(Continued)

*Primary Examiner* — Tara L Martinez
(74) *Attorney, Agent, or Firm* — ROTHWELL, FIGG, ERNST & MANBECK, P.C.

(57) ABSTRACT

The invention relates generally to polypeptides that include a cleavable moiety that is a substrate for at least one matrix metalloprotease (MMP), to activatable antibodies and other larger molecules that include the cleavable moiety that is a substrate for at least one MMP protease, and to methods of making and using these polypeptides that include a cleavable moiety that is a substrate for at least one MMP protease in a variety of therapeutic, diagnostic and prophylactic indications.

21 Claims, 4 Drawing Sheets

Specification includes a Sequence Listing.

(56) References Cited

U.S. PATENT DOCUMENTS

| | | | |
|---|---|---|---|
| 10,745,481 | B2 | 8/2020 | West et al. |
| 10,875,913 | B2 | 12/2020 | Stagliano et al. |
| 11,028,126 | B2 | 6/2021 | Moore et al. |
| 11,267,896 | B2 | 3/2022 | Sagert et al. |
| 2003/0219402 | A1 | 11/2003 | Rutter et al. |
| 2004/0109855 | A1 | 6/2004 | Waldmann et al. |
| 2004/0123343 | A1 | 6/2004 | La Rosa |
| 2005/0208602 | A1 | 9/2005 | Rosen et al. |
| 2007/0218074 | A1 | 9/2007 | Man |
| 2008/0166375 | A1 | 7/2008 | Leppla et al. |
| 2009/0304719 | A1 | 12/2009 | Daugherty et al. |
| 2010/0041588 | A1 | 2/2010 | Keay et al. |
| 2010/0189651 | A1 | 7/2010 | Stagliano et al. |
| 2010/0221212 | A1 | 9/2010 | Stagliano et al. |
| 2011/0214205 | A1 | 9/2011 | Dietrich |
| 2011/0280908 | A1 | 11/2011 | Leppla et al. |
| 2011/0287517 | A1 | 11/2011 | Steward |
| 2012/0149061 | A1 | 6/2012 | Stagliano et al. |
| 2012/0207756 | A1 | 8/2012 | Stagliano et al. |
| 2012/0237512 | A1 | 9/2012 | Daugherty et al. |
| 2012/0237977 | A1 | 9/2012 | Daugherty et al. |
| 2012/0244154 | A1 | 9/2012 | Daugherty et al. |
| 2012/0321626 | A1 | 12/2012 | Zhou et al. |
| 2013/0150558 | A1 | 6/2013 | Williams et al. |
| 2013/0266568 | A1 | 10/2013 | Brinkmann et al. |
| 2013/0309230 | A1 | 11/2013 | Stagliano et al. |
| 2014/0010810 | A1 | 1/2014 | West et al. |
| 2014/0024810 | A1 | 1/2014 | Stagliano et al. |
| 2014/0045195 | A1 | 2/2014 | Daugherty et al. |
| 2014/0255313 | A1 | 9/2014 | Vasiljeva et al. |
| 2014/0363430 | A1 | 12/2014 | West et al. |
| 2015/0005477 | A1 | 1/2015 | Lowman et al. |
| 2015/0087810 | A1 | 3/2015 | Moore et al. |
| 2016/0122425 | A1 | 5/2016 | Daugherty et al. |
| 2016/0194399 | A1 | 7/2016 | Irving et al. |
| 2016/0228546 | A1 | 8/2016 | Stagliano et al. |
| 2016/0289324 | A1 | 10/2016 | Moore et al. |
| 2016/0311903 | A1 | 10/2016 | West et al. |
| 2016/0355587 | A1 | 12/2016 | West et al. |
| 2016/0355592 | A1 | 12/2016 | Sagert et al. |
| 2016/0355599 | A1 | 12/2016 | Sagert et al. |
| 2017/0044259 | A1 | 2/2017 | Tipton et al. |
| 2017/0081397 | A1 | 3/2017 | Stagliano et al. |
| 2017/0204139 | A1 | 7/2017 | Moore et al. |
| 2018/0303952 | A1 | 10/2018 | Sagert et al. |
| 2019/0016814 | A1 | 1/2019 | Humphrey et al. |
| 2019/0119370 | A1 | 4/2019 | Stagliano et al. |
| 2019/0135864 | A1 | 5/2019 | Moore et al. |
| 2019/0202927 | A1 | 7/2019 | Sagert et al. |
| 2019/0211089 | A1 | 7/2019 | Daugherty et al. |
| 2019/0241652 | A9 | 8/2019 | Moore et al. |
| 2019/0309072 | A1 | 10/2019 | Sagert et al. |
| 2019/0359714 | A1 | 11/2019 | Tipton et al. |
| 2019/0382493 | A1 | 12/2019 | West et al. |
| 2021/0284721 | A1 | 9/2021 | Stagliano et al. |
| 2024/0228603 | A1 | 7/2024 | Stagliano et al. |

FOREIGN PATENT DOCUMENTS

| | | | |
|---|---|---|---|
| EP | 1 324 771 | | 6/2011 |
| TW | 200635946 | A | 10/2006 |
| WO | WO 1994/011026 | | 5/1994 |
| WO | WO 1999/015563 | | 4/1999 |
| WO | WO 2001/057182 | | 8/2001 |
| WO | WO 2001/091798 | | 12/2001 |
| WO | WO 2002/012475 | | 2/2002 |
| WO | WO 2002/030460 | | 4/2002 |
| WO | WO 2002/038796 | | 5/2002 |
| WO | 2003/004681 | A2 | 1/2003 |
| WO | WO 2003/038083 | | 5/2003 |
| WO | 2003/068934 | A2 | 8/2003 |
| WO | WO 2004/009638 | | 1/2004 |
| WO | WO 2006/110599 | | 10/2006 |
| WO | 2007/047995 | A2 | 4/2007 |
| WO | WO 2007/105027 | | 9/2007 |
| WO | WO 2008/052187 | | 5/2008 |
| WO | 2008/083312 | A2 | 7/2008 |
| WO | 2008/149143 | A2 | 12/2008 |
| WO | 2008/149147 | A2 | 12/2008 |
| WO | 2008/149148 | A2 | 12/2008 |
| WO | 2008/149149 | A2 | 12/2008 |
| WO | 2008/149150 | A2 | 12/2008 |
| WO | WO 2009/025846 | | 2/2009 |
| WO | WO 2010/046628 | | 4/2010 |
| WO | WO 2010/081173 | | 7/2010 |
| WO | 2010/091122 | A1 | 8/2010 |
| WO | WO 2010/088691 | | 8/2010 |
| WO | WO 2010/096838 | | 8/2010 |
| WO | WO 2010/129609 | | 11/2010 |
| WO | WO 2011/028698 | | 3/2011 |
| WO | 2011/161260 | A1 | 12/2011 |
| WO | 2012/158818 | A2 | 11/2012 |
| WO | WO 2012/156919 | | 11/2012 |
| WO | 2013/003649 | A2 | 1/2013 |
| WO | WO 2013/163631 | | 10/2013 |
| WO | WO 2013/192546 | | 12/2013 |
| WO | WO 2013/192550 | | 12/2013 |
| WO | WO 2014/026136 | | 2/2014 |
| WO | WO 2014/052462 | | 4/2014 |
| WO | WO 2014/107599 | | 7/2014 |
| WO | WO 2014/176284 | | 10/2014 |
| WO | WO 2014/193973 | | 12/2014 |
| WO | WO 2016/014974 | | 1/2016 |
| WO | 2016/179335 | A1 | 10/2016 |
| WO | WO 2016/179257 | | 10/2016 |
| WO | WO 2020/118109 | | 6/2020 |

OTHER PUBLICATIONS

Russian Office Action issued on Dec. 21, 2022 in RU Application No. 2020106752, 20 pages.

Japanese Office Action issued on Sep. 20, 2022 in JP Application No. 2021-016630, 7 pages.

ADC review, Retrieved on Mar. 17, 2016 from: http://adcreview.com/adc-university/adcs-101/cytotoxic-agents/maytansine/ (4 pages).

Bendig, Mary M., "Humanization of Rodent Monoclonal Antibodies by CDR Grafting", Methods: A Companion to Methods in Enzymology (1995); 8:83-93.

BLAST search of SEQ ID No. 362; Retrieved on Mar. 17, 2016 from http://blast.ncbi.nlm.nih.gov/Blast.cgi (8 pages).

BLAST search of SEQ ID No. 363; Retrieved on Mar. 17, 2016 from http://blast.ncbi.nlm.nih.gov/Blast.cgi (7 pages).

BLAST search of SEQ ID No. 364; Retrieved on Mar. 17, 2016 from http://blast.ncbi.nlm.nih.gov/Blast.cgi (8 pages).

Casadaban et al., "Analysis of gene control signals by DNA fusion and cloning in *Escherichia coli*", JMB (1980) 138(2):179-207.

Chen et al, "Selective Antibody Activation Through Protease-Activated Pro-Antibodies that Mask Binding Sites 2ith Inhibitory Domains", Scientific Reports, (2017) 7(1): 11587 (1-12).

Colman, Peter M. "Effects of amino acid sequence changes on antibody-antigen interactions", Res. Immunol. (1994) 145(1): 33-36.

Database EMBL, Accession No. AF099373 (Jan. 2, 2014) "*Callorhinchus milii* (elephant shark) protein ITFG3", Venkatesh et al. [online]; Retrieved from Internet on Jan. 9, 2017 (2 pages): https://www.ebi.ac.uk/ena/browser/api/embl/AF099373.

Database EMBL, Accession No. OVF07168 (Jun. 1, 20175) "Clavispora lusitaniae hypothetical protein" Durrens et al. [online]; XP055665684, Retrieved from Internet on Feb. 23, 2021 (1 page): https://www.ebi.ac.uk/ena/browser/ api/embl/OVF07168.1?lineLimit=1000.

Database UNIPROTKB, Accession No. T0RF53 (Oct. 1, 20133), "Uncharacterized protein from Saprolegnia diclina", Russ et al [online]; UniProt Consortium, www.uniprot.org; Retrieved from Internet on Feb. 12, 2021: https://www.uniprot.org/uniprot/T0RF53.txt (1 page).

Database UNIPROTKB, Accession No. A0A0D8BN56 (Jun. 17, 2020) "Uncharacterized protein from Frankia torreyi", Oshone et al. [online]; UniProt Consortium, www.uniprot.org; Retrieved from Internet on Feb. 23, 2021 (1 page): https://www.uniprot.org/uniprot/A0A0D8BN56.txt.

(56) References Cited

OTHER PUBLICATIONS

"Derivative (chemistry)", Wikipedia, Accessed Sep. 11, 2017 (1 page); Retrieved from: https://en.wikipedia.org/w/index.php?title=Derivative_ (chemistry)&oldid-779855519.
Donaldson et al., "Design and development of masked therapeutic antibodies to limit off-target effects: application to anti-EGFR antibodies", Cancer Bio. & Therapy (2009) 8(22):2147-2152.
GenBank Accession No. ADA97619, "Sequence 28102 from U.S. Pat. No. 6,551,795" (Rubenfield et al.), Retrieved from internet on Mar. 17, 2016 (3 pages): http://seqdata.uspto.gov/?pageRequest=viewSequence&DocID =06551795B1&seqID=28102.
Genbank Accession No. AKP45152.1, Retrieved from internet on Jul. 25, 2018: https://www.ncbi.nlm.nih.gov/protein/Akp45152.
Genbank Accession No. AEL07912.1 [online], Retrieved from internet on Dec. 18, 2017: https://www.ncbi.nlm.nih.gov/protein/AEL07912,.
Genbank Accession No. YP_005352726.1 [online], Retrieved from internet on Dec. 18, 2017: https://www.ncbi.nlm.nihgov/protein/ YP 005352726.1.
GenBank: EMG45877.1, Yu et al., Mar. 6, 2013, pp. 1-2, (www.ncbi.nlm.gov/protein/).
GenBank: EJK72392.1, Lommer et al., Jul. 25, 2012, pp. 1-3 (www.ncbi.nlm.gov/protein/).
Geneseq Accession No. AAB46481, B. brevis tyrocidine synthetase activating domain 9 (Apr. 9, 2001).
GENPEPT Accession No. P0C9K2.1, RecName: Full-Protein MGF 110-14L; Flags: Precursor (Sep. 28, 2018); https://www.ncbi.nlm.nih.gov/protein/229544532?sat=12&satkev =1040226.
Gerspach et al., "Target-selective activation of a TNF prodrug by urokinase-type plasminogen activator (uPA) mediated proteolytic processing at the cell surface", Cancer Immunol. (2006) 55(12):1590-1600.
Gerspach et al., "Restoration of membrane TNF-like activity by cell surface targeting and matrix metalloproteinase-mediated processing of a TNF prodrug", Cell Death and Differentiation (2006) 13(2):273-284.
Harris et al., "Rapid and general profiling of protease specificity by using combinatorial fluorogenic substrate libraries", PNAS (2000) 97(14): 7754-7759.
Henikoff et al., "Amino acid substitution matrices from protein blocks", Proc Natl Acad Sci USA (1992) 89(22):10915-10919.
Irving, "Probodies Empower a New Generation of Antibody Immunotherapies," presented at Keystone Symposia on Molecular and Cellular Biology, Feb. 2015.
Jabaiah et al., "Directed evolution of protease beacons that enable sensitive detection of endogenous MT1-MMP activity in tumor cell lines", Chem. Biol. (2011) 18(3):392-401.
Jeong et al., "Recombinant antibodies: Engineering and production in yeast and bacterial hosts", Biotechnol. J. (2011) 6(1):16-27.
Juliano et al., "Differences in substrate specificities between cysteine protease CPB isoforms of Leishmania mexicana are mediated by a few amino acid changes", Eur. J. Biochem. (2004) 271(18):3704-3714.
Kawato et al., "Hypothetical protein [Pseudomonas phage PPpW-3]" Accession No. VP_008873205, Dec. 9, 2013.
Ke et al., "Optimal Subsite Occupancy and Design of a Selective Inhibitor of Urokinase", J. Biol. Chem., (1997) 272(33):20456-20462.
Ke et al., "Distinguishing the specificities of closely related proteases role of p3 in substrate and inhibitor discrimination between tissue-type plasminogen activator and urokinase ", J. Bio. Chem. (1997) 272(26):16603-16609.
Khantasup et al., "Design and Generation of Humanized Single-chain Fv Derived from Mouse Hybridoma for Potential Targeting Application", Monoclon. Antib. Immunodiagn. Immunother. (2015) 34(6):404-417.
Kridel et al., "Substrate hydrolysis by matrix metalloproteinase-9", J. Biol. Chem. (2001) 276(23):20572-20578 (Epub Mar. 14, 2001).
Kridel et al., "A Unique Substrate Binding Mode Discriminates Membrane Type-1 Matrix Metalloproteinase from Other Matrix Metalloproteinases", J. Biol. Chem. (2002) 277(26): 23788-23793.
Kukreja at al., "The High Throughput Multiplexed Peptide-Centric Profiling Illustrates Both the Substrate Cleavage Redundancy and Specificity in the MMP Family", Chem. Biol., (2015) 22(8):1122-1133.
LeBeau et al., "Imaging a functional tumorigenic biomarker in the transformed epithelium", Proc. Natl. Assoc. Sci USA (2013) 110(1):93-98.
List et al., "Deregulated matriptase causes ras-independent multi-stage carcinogenesis and promotes ras-mediated malignant transformation", Genes & Develop. (2005) 19:1934-1950.
Liu et al., "Intermolecular complementation achieves high-specificity tumor targeting by anthrax toxin", Nature Biotech. (2005) 23(6):725-730.
Liu et al., "Targeting of Tumor Cells by Cell Surface Urokinase Plasminogen Activator dependent Anthrax Toxin", J. Biol. Chem. (2001) 276(21):17976-17984.
Lopez-Otin et al., "Protease Degradomics: A New Challenge for Proteomics", Nature Rev. Mol. Cell Biol. (2002) 3:509-519.
Maytansinoid DM4, Retrieved from internet on Mar. 17, 2016 (9 pages): https://pubchem.ncbi.nlm.nih.gov/compound/ 46926355#section=Top.
Murphy et al., "Enhancing recombinant antibody performance by optimally engineering its format", J. Immunol. Methods (2018) 463:127-133.
Nangia-Makker et al., "Galectin-3 cleavage: a novel surrogate marker for matrix metalloproteinase activity in growing breast cancers", Cancer Res. (2007) 67(24): 11760-11768.
James J. Neitzel, "Enzyme Catalysis: The Serine Proteases", Nature Ed. (2010) 3(9):21.
Paul, W., Fundamental Immunology, ($3^{rd}$ Edition, Lippincott Williams & Wilkins, (1993) p. 292-295).
Portolano et al., Lack of promiscuity in autoantigen-specific H and L chain combinations as revealed by human H and L chain "roulette", J. Immunol. (1993) 150(3):880-887.
Prudova et al., "Multiplex N-terminome analysis of MMP-2 and MMP-9 substrate degradomes by iTRAQ-TAILS quantitative proteomics", Mol. Cell Prot. (2010) 9(5):894-911 (Epub Mar. 20, 2010).
Ratnikov et al., "Basis for substrate recognition and distinction by matrix metalloproteinases." Proc. Natl. Acad. Sci. USA (2014) 111(4):E4148-55.
Rothenberg et al., "An integrated semiconductor device enabling non-optical genome sequencing", Nature (2011) 475(7356):348-52.
Rudikoff et al., "Single Amino Acid Substitution altering antigen-binding specificity", Proc. Natl. Acad. Sci. USA (1982) 79(6):1979-1983.
Takeuchi T et al., "Cellular Location of Membrane-type Serine Protease 1 and Identification of Protease-activated Receptor-2 and Single-chain Urokinase-type Plasminogen Activator as Substrates", J. Biol. Chem. (2000) 275(34): 26333-26342.
Tateno et al. (Jul. 24, 1998) "Isolation and Characterization of Rhamnose-binding Lectins from Eggs of Steelhead Trout (*Oncorhynchus mykiss*) Homologous to Low Density Lipoprotein Receptor Superfamily", J. Biol. Chem. (1998) 273(30): 19190-19197.
Turk et al., "Determination of protease cleavage site motifs using mixture-based oriented peptide libraries", Nat. Biotechnol. (2001) 19(7):661-667.
Uniprot Accession No. B8J087 (uncharacterized protein), Mar. 3, 2009.
Uniprot Accession No. Q9ZZR8 (Cytochrome b), May 1, 1999.
UniProtKB B1FZS3 (B1FZS3_9Burk), Retrieved from internet on Jul. 25, 2018: https://www.uniprot.org/uniprot/B1FZS3.
Uniprot Accession No. M3HF54 (Yu J et al., Genome sequence of Candida maltosa Xu316, a potential industrial strain for xylitol and ethanol production. (downloaded from https://rest.uniprot.org/unisave/ M3HF54?format=txt&versions=2), 1 page.
Vasiljeva et al., "The Multifaceted Roles of Tumor-Associated Proteases and Harnessing Their Activity for Prodrug Activation", Biol. Chem. (2019) https://doi.org/10.1515/hsz-2018-0451; Accepted Mar. 18, 2019).

(56) References Cited

OTHER PUBLICATIONS

Venkatesh et al., "Elephant shark genome provides unique insights into gnathostome evolution", Nature (2014) 505(7482):174-179.
Villacres et al., "Cloning, Chromosomal Mapping, and Expression of Human Fetal Brain Type I Adenylyl Cyclase", Genomics (1993) 16(2):473-478.
Waterhouse et al., "Jalview Version 2—a multiple sequence alignment editor and analysis workbench", Bioinform. (2009) 9:1189-1191.
Yarmolinskaya et al., "Matrix Metalloproteinases and Inhibitors: Classification, Mechanism of Action", J. Obstetrics and Women's Diseases (2012) 61(1):113-125.
Zhao et al., "A novel strategy to tag matrix metalloproteinases-positive cells for in vivo imaging of invasive and metastatic activity of tumor cells", J. Control Release (2010) 144(1):109-114.
Office Action issued on Sep. 14, 2023 for Chinese Patent Application No. 202111432527.8 (8 pages).
Office Action issued on Aug. 31, 2023 for Chinese Patent Application No. 202210057240.X (14 pages).
Office Action issued on Aug. 30, 2023 for Chinese Patent Application No. 202210057238.2 (16 pages).
Office Action issued on Sep. 7, 2023 for Chinese Patent Application No. 202210057237.8 (16 pages).
Patent Examination Report 1 issued on Dec. 13, 2023 for New Zealand Patent Application No. 733811 (5 pages).
Uniprot C4J4K8 (Integrated into UniProt on Jul. 7, 2009); Retrieved on Jun. 28, 2024.

* cited by examiner

MATRIX METALLOPROTEINASE SUBSTRATES AND OTHER CLEAVABLE MOIETIES AND METHODS OF USE THEREOF

RELATED APPLICATIONS

This application is a continuation of U.S. patent application Ser. No. 16/179,670, filed Nov. 2, 2018, now U.S. Pat. No. 11,814,410, issued Nov. 14, 2023, which is a Divisional of U.S. application Ser. No. 14/497,089, filed Sep. 25, 2014, which claims the benefit of U.S. Provisional Application No. 61/882,377, filed Sep. 25, 2013 and U.S. Provisional Application No. 61/971,332, filed Mar. 27, 2014, the contents of each of which are incorporated herein by reference in their entireties.

DESCRIPTION OF THE TEXT FILE SUBMITTED ELECTRONICALLY

The instant application contains a Sequence Listing which has been submitted electronically in XML file format and is hereby incorporated by reference in its entirety. Said XML copy, created on Sep. 22, 2023, is named CYTX_021_US_CON2_ST.26.SeqList and is 584,050 bytes in size.

FIELD OF THE INVENTION

The invention relates generally to polypeptides that include a cleavable moiety that is a substrate for at least one matrix metalloprotease (MMP), to activatable antibodies and other larger molecules that include the cleavable moiety that is a substrate for at least one MMP protease, and to methods of making and using these polypeptides that include a cleavable moiety that is a substrate for at least one MMP protease in a variety of therapeutic, diagnostic and prophylactic indications.

BACKGROUND OF THE INVENTION

Proteases are enzymes that degrade proteins by cleaving the peptide bonds between amino acid residues. Proteases occur naturally in all organisms and are involved in a variety of physiological reactions from simple degradation to highly regulated pathways. Some proteases are known to break specific peptide bonds based on the presence of a particular amino acid sequence within a protein.

Accordingly, there exists a need to identify new substrates for proteases and to use these substrates in a variety of therapeutic, diagnostic and prophylactic indications.

SUMMARY OF THE INVENTION

The disclosure provides amino acid sequences that include a cleavable moiety (CM) that is a substrate for at least one matrix metalloprotease (MMP). These CMs are useful in a variety of therapeutic, diagnostic and prophylactic indications.

In some embodiments, the CM is a substrate for at least one matrix metalloprotease (MMP). Examples of MMPs include MMP1; MMP2; MMP3; MMP7; MMP8; MMP9; MMP10; MMP11; MMP12; MMP13; MMP14; MMP15; MMP16; MMP17; MMP19; MMP20; MMP23; MMP24; MMP26; and MMP27. In some embodiments, the CM is a substrate for MMP9, MMP14, MMP1, MMP3, MMP13, MMP17, MMP11, and MMP19. In some embodiments, the CM is a substrate for MMP9. In some embodiments, the CM is a substrate for MMP14. In some embodiments, the CM is a substrate for two or more MMPs. In some embodiments, the CM is a substrate for at least MMP9 and MMP14. In some embodiments, the CM comprises two or more substrates for the same MMP. In some embodiments, the CM comprises at least two or more MMP9 substrates. In some embodiments, the CM comprises at least two or more MMP14 substrates.

In some embodiments, the CM is a substrate for an MMP and includes the sequence ISSGLLSS (SEQ ID NO: 14); QNQALRMA (SEQ ID NO: 15); AQNLLGMV (SEQ ID NO: 16); STFPFGMF (SEQ ID NO: 17); PVGYTSSL (SEQ ID NO: 18); DWLYWPGI (SEQ ID NO: 19); MIAPVAYR (SEQ ID NO: 20); RPSPMWAY (SEQ ID NO: 21); WATPRPMR (SEQ ID NO: 22); FRLLDWQW (SEQ ID NO: 23); LKAAPRWA (SEQ ID NO: 24); GPSHLVLT (SEQ ID NO: 25); LPGGLSPW (SEQ ID NO: 26); MGLFSEAG (SEQ ID NO: 27); SPLPLRVP (SEQ ID NO: 28); RMHLRSLG (SEQ ID NO: 29); LAAPLGLL (SEQ ID NO: 30); AVGLLAPP (SEQ ID NO: 31); LLAPSHRA (SEQ ID NO: 32); PAGLWLDP (SEQ ID NO: 33); and/or ISSGLSS (SEQ ID NO: 159).

In some embodiments, the CM comprises the amino acid sequence ISSGLLSS (SEQ ID NO: 14). In some embodiments, the CM comprises the amino acid sequence QNQALRMA (SEQ ID NO: 15). In some embodiments, the CM comprises the amino acid sequence AQNLLGMV (SEQ ID NO: 16). In some embodiments, the CM comprises the amino acid sequence STFPFGMF (SEQ ID NO: 17). In some embodiments, the CM comprises the amino acid sequence PVGYTSSL (SEQ ID NO: 18). In some embodiments, the CM comprises the amino acid sequence DWLYWPGI (SEQ ID NO: 19). In some embodiments, the CM comprises the amino acid sequence MIAPVAYR (SEQ ID NO: 20). In some embodiments, the CM comprises the amino acid sequence RPSPMWAY (SEQ ID NO: 21). In some embodiments, the CM comprises the amino acid sequence WATPRPMR (SEQ ID NO: 22). In some embodiments, the CM comprises the amino acid sequence FRLLDWQW (SEQ ID NO: 23). In some embodiments, the CM comprises the amino acid sequence LKAAPRWA (SEQ ID NO: 24). In some embodiments, the CM comprises the amino acid sequence GPSHLVLT (SEQ ID NO: 25). In some embodiments, the CM comprises the amino acid sequence LPGGLSPW (SEQ ID NO: 26). In some embodiments, the CM comprises the amino acid sequence MGLFSEAG (SEQ ID NO: 27). In some embodiments, the CM comprises the amino acid sequence SPLPLRVP (SEQ ID NO: 28). In some embodiments, the CM comprises the amino acid sequence RMHLRSLG (SEQ ID NO: 29). In some embodiments, the CM comprises the amino acid sequence LAAPLGLL (SEQ ID NO: 30). In some embodiments, the CM comprises the amino acid sequence AVGLLAPP (SEQ ID NO: 31). In some embodiments, the CM comprises the amino acid sequence LLAPSHRA (SEQ ID NO: 32). In some embodiments, the CM comprises the amino acid sequence PAGLWLDP (SEQ ID NO: 33). In some embodiments, the CM comprises the amino acid sequence ISSGLSS (SEQ ID NO: 159).

In some embodiments, the CM is linked or otherwise attached to an antibody. For example, the CM is used to link one or more agents to the antibody or antigen binding fragment thereof (AB) that binds a given target, such that the CM is cleaved when exposed to the MMP and the agent is released from the AB. Exemplary targets include, but are not limited to the targets shown in Table 1. Exemplary ABs include, but are not limited to, the targets shown in Table 2. In some embodiments, the antibody in the uncleaved state has the structural arrangement from N-terminus to C-terminus as follows: Agent-CM-AB or AB-CM-Agent. In some embodiments, the antibody comprises a linking peptide between the AB and the CM. In some embodiments, the antibody comprises a linking peptide between the CM and the conjugated agent.

In some embodiments, the antibody comprises a first linking peptide (LP1) and a second linking peptide (LP2), and the antibody in the uncleaved state has the structural arrangement from N-terminus to C-terminus as follows: Agent-LP1-CM-LP2-AB or AB-LP2-CM-LP1-Agent. In some embodiments, each of LP1 and LP2 is a peptide of about 1 to 20 amino acids in length. In some embodiments, the two linking peptides need not be identical to each other.

In some embodiments, at least one of LP1 or LP2 comprises an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one.

In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8).

In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 155), GSSGGSGGSG (SEQ ID NO: 156), or GSSGGSGGSGS (SEQ ID NO: 157).

In some embodiments, LP2 comprises the amino acid sequence GSS, GGS, GGGS (SEQ ID NO: 158), GSSGT (SEQ ID NO: 12) or GSSG (SEQ ID NO: 13).

In some embodiments, the AB has an equilibrium dissociation constant of about 100 nM or less for binding to the target.

In some embodiments, the antibody includes an antibody or antigen-binding fragment thereof that specifically binds a target. In some embodiments, the antibody or immunologically active fragment thereof that binds the target is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an antibody or immunologically active fragment thereof that binds the target is a mouse, other rodent, chimeric, humanized or fully human monoclonal antibody.

In some embodiments, the MMP protease is co-localized with the target in a tissue, and the MMP protease cleaves the CM in the antibody when the antibody is exposed to the protease.

In some embodiments, the CM is a polypeptide of up to 15 amino acids in length.

In some embodiments, the CM is a substrate for at least one matrix metalloprotease (MMP). Examples of MMPs include MMP1; MMP2; MMP3; MMP7; MMP8; MMP9; MMP10; MMP11; MMP12; MMP13; MMP14; MMP15; MMP16; MMP17; MMP19; MMP20; MMP23; MMP24; MMP26; and MMP27. In some embodiments, the CM is a substrate for MMP9, MMP14, MMP1, MMP3, MMP13, MMP17, MMP11, and MMP19. In some embodiments, the CM is a substrate for MMP9. In some embodiments, the CM is a substrate for MMP14. In some embodiments, the CM is a substrate for two or more MMPs. In some embodiments, the CM is a substrate for at least MMP9 and MMP14. In some embodiments, the CM comprises two or more substrates for the same MMP. In some embodiments, the CM comprises at least two or more MMP9 substrates. In some embodiments, the CM comprises at least two or more MMP14 substrates.

In some embodiments, the CM is a substrate for an MMP and includes the sequence ISSGLLSS (SEQ ID NO: 14); QNQALRMA (SEQ ID NO: 15); AQNLLGMV (SEQ ID NO: 16); STFPFGMF (SEQ ID NO: 17); PVGYTSSL (SEQ ID NO: 18); DWLYWPGI (SEQ ID NO: 19); MIAPVAYR (SEQ ID NO: 20); RPSPMWAY (SEQ ID NO: 21); WATPRPMR (SEQ ID NO: 22); FRLLDWQW (SEQ ID NO: 23); LKAAPRWA (SEQ ID NO: 24); GPSHLVLT (SEQ ID NO: 25); LPGGLSPW (SEQ ID NO: 26); MGLFSEAG (SEQ ID NO: 27); SPLPLRVP (SEQ ID NO: 28); RMHLRSLG (SEQ ID NO: 29); LAAPLGLL (SEQ ID NO: 30); AVGLLAPP (SEQ ID NO: 31); LLAPSHRA (SEQ ID NO: 32); PAGLWLDP (SEQ ID NO: 33); and/or ISSGLSS (SEQ ID NO: 159).

In some embodiments, the CM comprises the amino acid sequence ISSGLLSS (SEQ ID NO: 14). In some embodiments, the CM comprises the amino acid sequence QNQALRMA (SEQ ID NO: 15). In some embodiments, the CM comprises the amino acid sequence AQNLLGMV (SEQ ID NO: 16). In some embodiments, the CM comprises the amino acid sequence STFPFGMF (SEQ ID NO: 17). In some embodiments, the CM comprises the amino acid sequence PVGYTSSL (SEQ ID NO: 18). In some embodiments, the CM comprises the amino acid sequence DWLYWPGI (SEQ ID NO: 19). In some embodiments, the CM comprises the amino acid sequence MIAPVAYR (SEQ ID NO: 20). In some embodiments, the CM comprises the amino acid sequence RPSPMWAY (SEQ ID NO: 21). In some embodiments, the CM comprises the amino acid sequence WATPRPMR (SEQ ID NO: 22). In some embodiments, the CM comprises the amino acid sequence FRLLDWQW (SEQ ID NO: 23). In some embodiments, the CM comprises the amino acid sequence LKAAPRWA (SEQ ID NO: 24). In some embodiments, the CM comprises the amino acid sequence GPSHLVLT (SEQ ID NO: 25). In some embodiments, the CM comprises the amino acid sequence LPGGLSPW (SEQ ID NO: 26). In some embodiments, the CM comprises the amino acid sequence MGLFSEAG (SEQ ID NO: 27). In some embodiments, the CM comprises the amino acid sequence SPLPLRVP (SEQ ID NO: 28). In some embodiments, the CM comprises the amino acid sequence RMHLRSLG (SEQ ID NO: 29). In some embodiments, the CM comprises the amino acid sequence LAAPLGLL (SEQ ID NO: 30). In some embodiments, the CM comprises the amino acid sequence AVGLLAPP (SEQ ID NO: 31). In some embodiments, the CM comprises the amino acid sequence LLAPSHRA (SEQ ID NO: 32). In some embodiments, the CM comprises the amino acid sequence PAGLWLDP (SEQ ID NO: 33). In some embodiments, the CM comprises the amino acid sequence ISSGLSS (SEQ ID NO: 159).

In some embodiments, the CM is a substrate for at least one matrix metalloprotease (MMP) and includes a motif sequence that is recognized by MMP9. In some embodiments, the CM is a substrate for at least one MMP and includes a motif sequence that is recognized by MMP14.

In some embodiments, the CM is a substrate for at least one MMP, and the CM polypeptide and/or the CM portion of any polypeptide that comprises the CM comprises a polypeptide having a length less than 50 amino acids, less than 40 amino acids, less than 30 amino acids, less than 25 amino acids, less than 20 amino acids, less than 19 amino acids, less than 18 amino acids, less than 17 amino acids, less than 16 amino acids, less than 15 amino acids long, less than 14 amino acids, less than 13 amino acids, less than 12 amino acids, less than 11 amino acids, or less than 10 amino acids long.

In some embodiments, the CM is a substrate for at least one MMP and comprises a polypeptide sequence that is not substantially identical to any human polypeptide sequence that is naturally cleaved by the same MMP protease. In some embodiments, the CM is a substrate for at least one MMP and comprises a polypeptide sequence that is no more than 90% or more identical to any human polypeptide sequence that is naturally cleaved by the same MMP protease.

In some embodiments, the motif sequence is a substrate for at least MMP and includes a core CM consensus sequence shown in Tables 8A-8M below. In some embodiments, the motif sequence includes a subgenus, i.e., a subset, of the core CM consensus sequence shown in Tables 8A-8M below.

In some embodiments, the motif sequence is a substrate for at least MMP9 and includes a core CM consensus sequence shown in Tables 8A-8D. In some embodiments, the motif sequence is a substrate for at least MMP9 and includes a subgenus, i.e., a subset, of the core CM consensus sequence shown in Tables 8A-8D below.

In some embodiments, the motif sequence is a substrate for at least MMP14 and includes a core CM consensus sequence shown in Tables 8E-8M. In some embodiments, the motif sequence is a substrate for at least MMP14 and includes a subgenus, i.e., a subset, of the core CM consensus sequence shown in Tables 8E-8M below.

TABLE 8A

MMP9 Cleavable Core CM Consensus Sequence 1

| Core CM Consensus 1 | Subgenus of Core CM Consensus 1 |
|---|---|
| $X_{22}X_{23}X_{24}X_{25}X_{26}X_{27}X_{28}X_{29}$ (SEQ ID NO: 317), wherein $X_{22}$ is A, C, D, G, H, L, P, R, or S; $X_{23}$ is L, M, P, S, or T; $X_{24}$ is A, D, F, G, L, M, N, P, R, S, T, or V; $X_{25}$ is A, D, E, G, H, I, M, P, S, or V; $X_{26}$ is A, C, D, G, L, M, N, R, V, W, or Y; $X_{27}$ is C, F, G, H, P, Q, R, T, V, or W; $X_{28}$ is A, D, G, L, M, S, T, V, or Y; and $X_{29}$ is C, H, L, R, S, V, W, or Y. | Subgenus 1.1: $X_{22}X_{23}X_{24}X_{25}X_{26}X_{27}X_{28}X_{29}$ (SEQ ID NO: 318), wherein $X_{22}$ is G, P, R, or S; $X_{23}$ is P or S; $X_{24}$ is L, M, P, or S; $X_{25}$ is A, G, P, or S; $X_{26}$ is L, M, or R; $X_{27}$ is G or W; $X_{28}$ is A, G, S, or Y; and $X_{29}$ is L, R, V, or Y.<br>Subgenus 1.2: $X_{22}X_{23}X_{24}X_{25}X_{26}X_{27}X_{28}X_{29}$ (SEQ ID NO: 319), wherein $X_{22}$ is G, P or R; $X_{23}$ is P; $X_{24}$ is L, M, or S; $X_{25}$ is G, P, or S; $X_{26}$ is L, M, or R; $X_{27}$ is W; $X_{28}$ is A, G, or S; and $X_{29}$ is R, V, or Y.<br>Subgenus 1.3: $X_{22}X_{23}X_{24}X_{25}X_{26}X_{27}X_{28}X_{29}$ (SEQ ID NO: 320), wherein $X_{22}$ is P or R; $X_{23}$ is P; $X_{24}$ is M or S; $X_{25}$ is G or P; $X_{26}$ is L, M, or R; $X_{27}$ is W; $X_{28}$ is A, G, or S; and $X_{29}$ is R, V, or Y.<br>Subgenus 1.4: $X_{22}X_{23}X_{24}X_{25}X_{26}X_{27}X_{28}X_{29}$ (SEQ ID NO: 321), wherein $X_{22}$ is P or R; $X_{23}$ is P; $X_{24}$ is S; $X_{25}$ is G or P; $X_{26}$ is M, or R; $X_{27}$ is W; $X_{28}$ is A or S; and $X_{29}$ is Y.<br>Subgenus 1.5: $X_{22}X_{23}X_{24}X_{25}X_{26}X_{27}X_{28}X_{29}$ (SEQ ID NO: 322), wherein $X_{22}$ is P or R; $X_{23}$ is P; $X_{24}$ is S; $X_{25}$ is G or P; $X_{26}$ is M, or R; $X_{27}$ is W; $X_{28}$ is A or S; and $X_{29}$ is Y.<br>Subgenus 1.6: $X_{22}X_{23}X_{24}X_{25}X_{26}X_{27}X_{28}X_{29}$ (SEQ ID NO: 323), wherein $X_{22}$ is C, G, H, L, or R; $X_{23}$ is P, S or T; $X_{24}$ is N, R, S or T; $X_{25}$ is P or S; $X_{26}$ is C, M, R, V, or W; $X_{27}$ is C, P, R, or W; $X_{28}$ is A, D, or G; and $X_{29}$ is C or Y. |

TABLE 8B

MMP9 Cleavable Core CM Consensus Sequence 2

| Core CM Consensus 2 | Subgenus of Core CM Consensus 2 |
|---|---|
| $X_{32}X_{33}X_{34}X_{35}X_{36}X_{37}X_{38}X_{39}$ (SEQ ID NO: 324), wherein $X_{32}$ is F, G, V, or W; $X_{33}$ is A, D, L, M, P, R, T, or V; $X_{34}$ is C, G, H, L, Q, S, T, W, $X_{35}$ is D, G, L, P; $X_{36}$ is E, G, I, L, N, P, R, or V; $X_{37}$ is G, L, P, R, S, or V; $X_{38}$ is A, I, L, M, T, or V; and $X_{39}$ is A, G, L, P, Q, R, S, or V. | Subgenus 2.1: $X_{32}X_{33}X_{34}X_{35}X_{36}X_{37}X_{38}X_{39}$ (SEQ ID NO: 325), wherein $X_{32}$ is W; $X_{33}$ is D, P, or T; $X_{34}$ is H, Q, or W; $X_{35}$ is D or P; $X_{36}$ is I or R; $X_{37}$ is S; $X_{38}$ is L, M, or V; and $X_{39}$ is G, L, or S.<br>Subgenus 2.2: $X_{32}X_{33}X_{34}X_{35}X_{36}X_{37}X_{38}X_{39}$ (SEQ ID NO: 326), wherein $X_{32}$ is W; $X_{33}$ is D; $X_{34}$ is H, Q, or W; $X_{35}$ is D or P; $X_{36}$ is I or R; $X_{37}$ is G, S, or V; $X_{38}$ is L, M, or V; and $X_{39}$ is G, L, or S.<br>Subgenus 2.3: $X_{32}X_{33}X_{34}X_{35}X_{36}X_{37}X_{38}X_{39}$ (SEQ ID NO: 327), wherein $X_{32}$ is W; $X_{33}$ is D; $X_{34}$ is H, Q, or W; $X_{35}$ is P; $X_{36}$ is I or R; $X_{37}$ is S; $X_{38}$ is L, M, or V; and $X_{39}$ is L. |

TABLE 8C

MMP9 Cleavable Core CM Consensus Sequence 3

| Core CM Consensus 3 | Subgenus of Core CM Consensus 3 |
|---|---|
| $X_{42}X_{43}X_{44}X_{45}X_{46}X_{47}X_{48}X_{49}$ (SEQ ID NO: 329), wherein $X_{42}$ is G, I, L, M, P, R, S, | Subgenus 3.1: $X_{42}X_{43}X_{44}X_{45}X_{46}X_{47}X_{48}X_{49}$ (SEQ ID NO: 330), wherein $X_{42}$ is I, L, M, or S; $X_{43}$ is D, P, S, or T; $X_{44}$ is F, L, S, or V; $X_{45}$ is L. P, or S; $X_{46}$ is A, F, R, S, or T; $X_{47}$ is G, H, T or Y; $X_{48}$ is G, I, M, V, or W; and $X_{49}$ is F, L, or S. |

TABLE 8C-continued

| MMP9 Cleavable Core CM Consensus Sequence 3 | |
|---|---|
| Core CM Consensus 3 | Subgenus of Core CM Consensus 3 |
| T, or V;<br>$X_{43}$ is A, D, H, I, L, P, S, or T;<br>$X_{44}$ is F, L, S, or V;<br>$X_{45}$ is H, L, M, P, Q, R, S, or T;<br>$X_{46}$ is A, D, F, G, L, M, R, S, T, or V;<br>$X_{47}$ is A, C, G, H, Q, T or Y;<br>$X_{48}$ is C, G, I, M, R, S, T, V, or W; and<br>$X_{49}$ is F, L, S, or Y. | Subgenus 3.2: $X_{42}X_{43}X_{44}X_{45}X_{46}X_{47}X_{48}X_{49}$ (SEQ ID NO: 331), wherein $X_{42}$ is L, M, or S; $X_{43}$ is S or T; $X_{44}$ is F or L; $X_{45}$ is P; $X_{46}$ is A, F, or T; $X_{47}$ is G, H, T or Y; $X_{48}$ is I, M, or W; and $X_{49}$ is F.<br>Subgenus 3.3: $X_{42}X_{43}X_{44}X_{45}X_{46}X_{47}X_{48}X_{49}$ (SEQ ID NO: 332), wherein $X_{42}$ is L, M, or S; $X_{43}$ is S or T; $X_{44}$ is F; $X_{45}$ is P; $X_{46}$ is A, F, or T; $X_{47}$ is G, H, or Y; $X_{48}$ is I, M, or W; and $X_{49}$ is F.<br>Subgenus 3.4: $X_{42}X_{43}X_{44}X_{45}X_{46}X_{47}X_{48}X_{49}$ (SEQ ID NO: 333), wherein $X_{42}$ is L or M; $X_{43}$ is S or T; $X_{44}$ is F; $X_{45}$ is P; $X_{46}$ is A or T; $X_{47}$ is H or Y; $X_{48}$ is I or W; and $X_{49}$ is F.<br>Subgenus 3.5: $X_{42}X_{43}X_{44}X_{45}X_{46}X_{47}X_{48}X_{49}$ (SEQ ID NO: 334), wherein $X_{42}$ is G, I, R, Or S; $X_{43}$ is H Or T; $X_{44}$ is F, L, S, or V; $X_{45}$ is L, P, or R; $X_{46}$ is F, L, or S; $X_{47}$ is A, C, or G; $X_{48}$ is I, M, or V; and $X_{49}$ is F or L.<br>Subgenus 3.6: $X_{42}X_{43}X_{44}X_{45}X_{46}X_{47}X_{48}X_{49}$ (SEQ ID NO: 335), wherein $X_{42}$ is S; $X_{43}$ is T; $X_{44}$ is F or V; $X_{45}$ is L or P; $X_{46}$ is F or L; $X_{47}$ is G; $X_{48}$ is I or M; and $X_{49}$ is F. |

TABLE 8D

| MMP9 Cleavable Core CM Consensus Sequence 4 | |
|---|---|
| Core CM Consensus 4 | Subgenus of Core CM Consensus 4 |
| $X_{52}X_{53}X_{54}X_{55}X_{56}X_{57}X_{58}X_{59}$ (SEQ ID NO: 340), wherein<br>$X_{52}$ is D, G, H, L, N, P, Q, R, S, W, or Y<br>$X_{53}$ is A, C, D, G, L, R, V, W, or Y;<br>$X_{54}$ is D, H, L, P, Q, R, S, or Y;<br>$X_{55}$ is D, F, H, I, L, M, P, S, or Y;<br>$X_{56}$ is A, C, E, F, G, K, M, R, S, V, or W;<br>$X_{57}$ is A, G, K L, M, N, P, R, S, or T;<br>$X_{58}$ is A, F, G, H, L, P, R, S, or T; and<br>$X_{59}$ is A, G, H, I, N, P, S, T, or Y. | Subgenus 4.1: $X_{52}X_{53}X_{54}X_{55}X_{56}X_{57}X_{58}X_{59}$ (SEQ ID NO: 341), wherein $X_{52}$ is D, G, H, L, P, Q, S or Y $X_{53}$ is D, W, or Y; $X_{54}$ is H, L, or R; $X_{55}$ is H, L, M, P, or Y; $X_{56}$ Is E, F, G, M, R, or W; $X_{57}$ is A, L, M, N, P, or R; $X_{58}$ is G, L, P, R, or S; and $X_{59}$ is G, I, P, S, T, or Y.<br>Subgenus 4.2: $X_{52}X_{53}X_{54}X_{55}X_{56}X_{57}X_{58}X_{59}$ (SEQ ID NO: 342), wherein $X_{52}$ is D or H; $X_{53}$ is W or Y; $X_{54}$ is H or L; $X_{55}$ is H, L, or Y; $X_{56}$ IS G or W; $X_{57}$ is P or R; $X_{58}$ is G, L, or P; and $X_{59}$ is G, I, S, or T.<br>Subgenus 4.3: $X_{52}X_{53}X_{54}X_{55}X_{56}X_{57}X_{58}X_{59}$ (SEQ ID NO: 343), wherein $X_{52}$ is H; $X_{53}$ is W; $X_{54}$ is H or L; $X_{55}$ is H, L, or Y; $X_{56}$ Is G or W; $X_{57}$ is P; $X_{58}$ is L or P; and $X_{59}$ is G, I, S or T.<br>Subgenus 4.4: $X_{52}X_{53}X_{54}X_{55}X_{56}X_{57}X_{58}X_{59}$ (SEQ ID NO: 344), wherein $X_{52}$ is H; $X_{53}$ is W; $X_{54}$ is H or L; $X_{55}$ is L or Y; $X_{56}$ Is G; $X_{57}$ is P; $X_{58}$ is L or P; and $X_{59}$ is G, I, S, or T.<br>Subgenus 4.5: $X_{52}X_{53}X_{54}X_{55}X_{56}X_{57}X_{58}X_{59}$ (SEQ ID NO: 345), wherein $X_{52}$ is H; $X_{53}$ is W; $X_{54}$ is H or L $X_{55}$ is L or Y $X_{56}$ Is G; $X_{57}$ is P; $X_{58}$ is P; and $X_{59}$ is T.<br>Subgenus 4.6: $X_{52}X_{53}X_{54}X_{55}X_{56}X_{57}X_{58}X_{59}$ (SEQ ID NO: 346), wherein $X_{52}$ is D, G, S, or Y; $X_{53}$ is W; $X_{54}$ is L or P; $X_{55}$ is D or Y; $X_{56}$ is C, E, G, or W; $X_{57}$ is M or P; $X_{58}$ is G, R, or S; and $X_{59}$ is H, I, or Y.<br>Subgenus 4.7: $X_{52}X_{53}X_{54}X_{55}X_{56}X_{57}X_{58}X_{59}$ (SEQ ID NO: 347), wherein $X_{52}$ is D, G, or S; $X_{53}$ is W; $X_{54}$ is L; $X_{55}$ is Y; $X_{56}$ is E or W; $X_{57}$ is M or P; $X_{58}$ is G or S; and $X_{59}$ is I or Y. |

TABLE 8E

| MMP14 Cleavable Core CM Consensus Sequence 5 | |
|---|---|
| Core CM Consensus 5 | Subgenus of Core CM Consensus 5 |
| $X_{62}X_{63}X_{64}X_{65}X_{66}X_{67}X_{68}X_{69}$ (SEQ ID NO: 352), wherein<br>$X_{62}$ is A, I, G, L, M, P, Q, S, T, or V;<br>$X_{63}$ is A, D, L, P, Q, S, T, V, or Y;<br>$X_{64}$ is A, C, E, F, G, H, K, L, P, Q, R, S, or V;<br>$X_{65}$ is D, E, G, S, or V;<br>$X_{66}$ is A, I, L, M, or V;<br>$X_{67}$ is C, E, G, I, K, L, M, | Subgenus 5.1: $X_{62}X_{63}X_{64}X_{65}X_{66}X_{67}X_{68}X_{69}$ (SEQ ID NO: 353), wherein $X_{62}$ is A, G, I, P, Q, S, T, or V; $X_{63}$ is A, L, Q, S, or V; $X_{64}$ is A, E, L, R, or S; $X_{65}$ is D or G; $X_{66}$ is I or L; $X_{67}$ is E, I, L, M, Q, R, or Y; $X_{68}$ is F, H, L, M, R, or S; and $X_{69}$ is A, G, H, L, N, P, Q, or S.<br>Subgenus 5.2: $X_{62}X_{63}X_{64}X_{65}X_{66}X_{67}X_{68}X_{69}$ (SEQ ID NO: 354), wherein $X_{62}$ is A, I, S or T; $X_{63}$ is L, Q, S, or V; $X_{64}$ is A, L, R, or S; $X_{65}$ is G; $X_{66}$ is I or L; $X_{67}$ is E, L, R, or Y; $X_{68}$ is F, H, L, R, or S; and $X_{69}$ is H, L, P, or S.<br>Subgenus 5.3: $X_{62}X_{63}X_{64}X_{65}X_{66}X_{67}X_{68}X_{69}$ (SEQ ID NO: 355), wherein $X_{62}$ is A, I, S or T; $X_{63}$ is L, S, or V; $X_{64}$ is A, R or S; |

TABLE 8E-continued

| MMP14 Cleavable Core CM Consensus Sequence 5 | |
|---|---|
| Core CM Consensus 5 | Subgenus of Core CM Consensus 5 |
| N, Q, R, or Y;<br>$X_{68}$ is A, F, H, I, L, M, N, P, R, S, or T; and<br>$X_{69}$ is A, C, G, H, I, L, N, P, Q, R, S, T, V, or W. | $X_{65}$ is G; $X_{66}$ is L; $X_{67}$ is E, L or R; $X_{68}$ is F, H, or S; and $X_{69}$ is L, P, or S.<br>Subgenus 5.4: $X_{62}X_{63}X_{64}X_{65}X_{66}X_{67}X_{68}X_{69}$ (SEQ ID NO: 356), wherein $X_{62}$ is A, I, S or T; $X_{63}$ is L, S, or V; $X_{64}$ is R or S; $X_{65}$ is G; $X_{66}$ is L; $X_{67}$ is L or R; $X_{68}$ is F, H, or S; and $X_{69}$ is P or S.<br>Subgenus 5.5: $X_{62}X_{63}X_{64}X_{65}X_{66}X_{67}X_{68}X_{69}$ (SEQ ID NO: 357), wherein $X_{62}$ is A, I, S or T; $X_{63}$ is L, S, or V; $X_{64}$ is R or S; $X_{65}$ is G; $X_{66}$ is L; $X_{67}$ is L or R; $X_{68}$ is S; and $X_{69}$ is P or S.<br>Subgenus 5.6: $X_{62}X_{63}X_{64}X_{65}X_{66}X_{67}X_{68}X_{69}$ (SEQ ID NO: 358), wherein $X_{62}$ is T; $X_{63}$ is L, S, or V; $X_{64}$ is S; $X_{65}$ is G; $X_{66}$ is L; $X_{67}$ is R; $X_{68}$ is S; and $X_{69}$ is P.<br>Subgenus 5.7: $X_{62}X_{63}X_{64}X_{65}X_{66}X_{67}X_{68}X_{69}$ (SEQ ID NO: 359), wherein $X_{62}$ is A, G, I, M, P, S, T, or V; $X_{63}$ is L, Q, S, or V; $X_{64}$ is A, C, F, K, L, Q, R or S; $X_{65}$ is D, G, S, or V; $X_{66}$ is L or M; $X_{67}$ is G, I, L, M, N, Q, or R; $X_{68}$ is I, N, P, or S; and $X_{69}$ is A, H, I, N, Q, or S.<br>Subgenus 5.8: $X_{62}X_{63}X_{64}X_{65}X_{66}X_{67}X_{68}X_{69}$ (SEQ ID NO: 360), wherein $X_{62}$ is A, I, or S; $X_{63}$ is L, Q, S, or V; $X_{64}$ is L, R or S; $X_{65}$ is G; $X_{66}$ is L; $X_{67}$ is L, M, or R; $X_{68}$ is S; and $X_{69}$ is A, H, N, Q, or S.<br>Subgenus 5.9: $X_{62}X_{63}X_{64}X_{65}X_{66}X_{67}X_{68}X_{69}$ (SEQ ID NO: 361), wherein $X_{62}$ is A, I, or S; $X_{63}$ is L, Q, S, or V; $X_{64}$ is L, R or S; $X_{65}$ is G; $X_{66}$ is L; $X_{67}$ is L, M, or R; $X_{68}$ is S; and $X_{69}$ is A, H, N, Q, or S.<br>Subgenus 5.10: $X_{62}X_{63}X_{64}X_{65}X_{66}X_{67}X_{68}X_{69}$ (SEQ ID NO: 362), wherein $X_{62}$ is A or S; $X_{63}$ is L or V; $X_{64}$ is L or S; $X_{65}$ is G; $X_{66}$ is L; $X_{67}$ is L or R; $X_{68}$ is S; and $X_{69}$ is H, or S.<br>Subgenus 5.11: $X_{62}X_{63}X_{64}X_{65}X_{66}X_{67}X_{68}X_{69}$ (SEQ ID NO: 363), wherein $X_{62}$ is A or S; $X_{63}$ is L or V; $X_{64}$ is S; $X_{65}$ is G; $X_{66}$ is L; $X_{67}$ is L or R; $X_{68}$ is S; and $X_{69}$ is H, or S. |

TABLE 8F-1

| MMP14 Cleavable Core CM Consensus Sequence 6 | |
|---|---|
| Core CM Consensus 6 | Subgenus of Core CM Consensus 6 |
| $X_{72}X_{73}X_{74}X_{75}X_{76}X_{77}X_{78}X_{79}$ (SEQ ID NO: 371), wherein<br>$X_{72}$ is A, C, D, E, F, G, H, I, K, L, M, N, P, Q, R, S, or V;<br>$X_{73}$ is A, C, E, F, H, L, N, R, S, or V;<br>$X_{74}$ is A, D, E, K, N, P Q, S, T, or Y;<br>$X_{75}$ is A, E, G, H, K, L, N, P, R, S, or T;<br>$X_{76}$ is I, K, L, M, N, R, T, V or Y;<br>$X_{77}$ is A, D, E, I, K, L, P, Q, R, S, T, V, or Y;<br>$X_{78}$ is A, C, D, E, G, I, L, M, Q, R, S, T, or V; and<br>$X_{79}$ is A, F, G, H, I, L, P, Q, R, S, T, or Y. | Subgenus 6.1: $X_{72}X_{73}X_{74}X_{75}X_{76}X_{77}X_{78}X_{79}$ (SEQ ID NO: 372), wherein $X_{72}$ is A, F, G, H, I, L, M, Q, R, or S; $X_{73}$ is A, F, H, L, or N; $X_{74}$ is A, E, N, Q, or S; $X_{75}$ is A, E, K, N, S, or T; $X_{76}$ is L or M; $X_{77}$ is A, I, K, L, P, R, or V; $X_{78}$ is A, D, I, L, M, R, T, or V; and $X_{79}$ is A, F, G, H, I, L, P, Q, R, or S.<br>Subgenus 6.2: $X_{72}X_{73}X_{74}X_{75}X_{76}X_{77}X_{78}X_{79}$ (SEQ ID NO: 373), wherein $X_{72}$ is G, L or R, or S; $X_{73}$ is A or L; $X_{74}$ is A, E, N, Q, or S; $X_{75}$ is A, E, N, S, or T; $X_{76}$ is L or M; $X_{77}$ is L or R; $X_{78}$ is A, L, or T; and $X_{79}$ is F, G, L, R, or S.<br>Subgenus 6.3: $X_{72}X_{73}X_{74}X_{75}X_{76}X_{77}X_{78}X_{79}$ (SEQ ID NO: 374), wherein $X_{72}$ is L; $X_{73}$ is A or L; $X_{74}$ is E, N, Q, or S; $X_{75}$ is A or S; $X_{76}$ is L or M; $X_{77}$ is R; $X_{78}$ is A or T; and $X_{79}$ is F, L, or R.<br>Subgenus 6.4: $X_{72}X_{73}X_{74}X_{75}X_{76}X_{77}X_{78}X_{79}$ (SEQ ID NO: 375), wherein $X_{72}$ is L; $X_{73}$ is A or L; $X_{74}$ is E, N, Q, or S; $X_{75}$ is A or S; $X_{76}$ is L or M; $X_{77}$ is R; $X_{78}$ is A; and $X_{79}$ is L or R. |

55

TABLE 8F-2

| MMP14 Cleavable Core CM Consensus Sequence 6A | |
|---|---|
| Core CM Consensus 6A | Subgenus of Core CM Consensus 6A |
| $X_{72}X_{73}X_{74}X_{75}X_{76}X_{77}X_{78}$ (SEQ ID NO: 485), wherein<br>$X_{72}$ is A, C, D, E, F, G, H, I, K, L, M, N, P, Q, R, S, or V; | Subgenus 6A.1: $X_{72}X_{73}X_{74}X_{75}X_{76}X_{77}X_{78}$ (SEQ ID NO: 376), wherein $X_{72}$ is A, E, L, N, P, or Q; $X_{73}$ is F, H, L, N, or S; $X_{74}$ is Q or Y; $X_{75}$ is A; $X_{76}$ is L, T, V or Y; $X_{77}$ is D, E, P, Q, or R; and $X_{78}$ is A, C, G, I, |

TABLE 8F-2-continued

| MMP14 Cleavable Core CM Consensus Sequence 6A | |
|---|---|
| Core CM Consensus 6A | Subgenus of Core CM Consensus 6A |
| $X_{73}$ is A, C, E, F, H, L, N, R, S, or V;<br>$X_{74}$ is A, D, E, K, N, P Q, S, T, or Y;<br>$X_{75}$ is A, E, G, H, K, L, N, P, R, S, or T;<br>$X_{76}$ is I, K, L, M, N, R, T, V or Y;<br>$X_{77}$ is A, D, E, I, K, L, P, Q, R, S, T, V, or Y; and<br>$X_{78}$ is A, C, D, E, G, I, L, M, Q, R, S, T, or V. | M, R, S, or T.<br>Subgenus 6A.2: $X_{72}X_{73}X_{74}X_{75}X_{76}X_{77}X_{78}$ (SEQ ID NO: 377), wherein $X_{72}$ is A, E, L, or Q; $X_{73}$ is F, H, or N; $X_{74}$ is Q; $X_{75}$ is A; $X_{76}$ is L or T; $X_{77}$ is Q or R; and $X_{78}$ is I or M.<br>Subgenus 6A.3: $X_{72}X_{73}X_{74}X_{75}X_{76}X_{77}X_{78}$ (SEQ ID NO: 378), wherein $X_{72}$ is A; $X_{73}$ is F, H, or N; $X_{74}$ is Q; $X_{75}$ is A; $X_{76}$ is L; $X_{77}$ is R; and $X_{78}$ is M. |

TABLE 8G

| MMP14 Cleavable Core CM Consensus Sequence 7 | |
|---|---|
| Core CM Consensus 7 | Subgenus of Core CM Consensus 7 |
| $X_{82}X_{83}X_{84}X_{85}X_{86}X_{87}X_{88}X_{89}$ (SEQ ID NO: 394), wherein<br>$X_{82}$ is A, F, L, Q, S, T, or V;<br>$X_{83}$ is A, E, G, H, K, Q, R, V, or Y;<br>$X_{84}$ is A, G, I, K, L, M, N, S, T, or V;<br>$X_{85}$ is A, D, F, G, I, L, N, P, R, S, T, or V;<br>$X_{86}$ is A, P, or R;<br>$X_{87}$ is A, D, G, L, M, P, R, S, T, V, W, or Y;<br>$X_{88}$ is A, C, E, F, H, I, L, N, R, S, T, W, or Y; and<br>$X_{89}$ is A, F, G, I, L, M, R, S, T, or V. | Subgenus 7.1: $X_{82}X_{83}X_{84}X_{85}X_{86}X_{87}X_{88}X_{89}$ (SEQ ID NO: 395), wherein $X_{82}$ is L; $X_{83}$ is H, K, Q, R, or Y; $X_{84}$ is A, L, M, S, T, or V; $X_{85}$ is A, I, L, S, or V; $X_{86}$ is P; $X_{87}$ is A, G, R, S, V, or W; $X_{88}$ is I, R, T, or W; and $X_{89}$ is A, F, G, L, S, or V.<br>Subgenus 7.2: $X_{82}X_{83}X_{84}X_{85}X_{86}X_{87}X_{88}X_{89}$ (SEQ ID NO: 396), wherein $X_{82}$ is L; $X_{83}$ is H, K, R, or Y; $X_{84}$ is A, L, or V; $X_{85}$ is A, I, or L; $X_{86}$ is P; $X_{87}$ is G, R, or V; $X_{88}$ is T or W; and $X_{89}$ is A, F, L, or S.<br>Subgenus 7.3: $X_{82}X_{83}X_{84}X_{85}X_{86}X_{87}X_{88}X_{89}$ (SEQ ID NO: 397), wherein $X_{82}$ is L; $X_{83}$ is K, R, or Y; $X_{84}$ is A; $X_{85}$ is A or L; $X_{86}$ is P; $X_{87}$ is G, R, or V; $X_{88}$ is W; and $X_{89}$ is A or L.<br>Subgenus 7.4: $X_{82}X_{83}X_{84}X_{85}X_{86}X_{87}X_{88}X_{89}$ (SEQ ID NO: 398), wherein $X_{82}$ is A, F, L, Q, or S; $X_{83}$ is A, E, G, H, K, Q, or Y; $X_{84}$ is A, G, K, S, or V; $X_{85}$ is A, I, L, P, or T; $X_{86}$ is A, P, or R; $X_{87}$ is A, L, M, R, V, or Y; $X_{88}$ is C, H, R, T, or W; and $X_{89}$ is A, F, L, R, S, or T.<br>Subgenus 7.5: $X_{82}X_{83}X_{84}X_{85}X_{86}X_{87}X_{88}X_{89}$ (SEQ ID NO: 399), wherein $X_{82}$ is F or L; $X_{83}$ is G, K, Q, or Y; $X_{84}$ is A, G, S, or V; $X_{85}$ is A, I, or L; $X_{86}$ is P; $X_{87}$ is A, R, or V; $X_{88}$ is R or W; and $X_{89}$ is A, F, L, or R.<br>Subgenus 7.6: $X_{82}X_{83}X_{84}X_{85}X_{86}X_{87}X_{88}X_{89}$ (SEQ ID NO: 400), wherein $X_{82}$ is L; $X_{83}$ is K or Y; $X_{84}$ is A or S; $X_{85}$ is A, I, or L; $X_{86}$ is P; $X_{87}$ is A, R, or V; $X_{88}$ is W; and $X_{89}$ is A or F.<br>Subgenus 7.7: $X_{82}X_{83}X_{84}X_{85}X_{86}X_{87}X_{88}X_{89}$ (SEQ ID NO: 401), wherein $X_{82}$ is L; $X_{83}$ is K or Y; $X_{84}$ is A; $X_{85}$ is A or I; $X_{86}$ is P; $X_{87}$ is R or V; $X_{88}$ is W; and $X_{89}$ is A or F. |

TABLE 8H-1

| MMP14 Cleavable Core CM Consensus Sequence 8 | |
|---|---|
| Core CM Consensus 8 | Subgenus of Core CM Consensus 8 |
| $X_{92}X_{93}X_{94}X_{95}X_{96}X_{97}X_{98}$ (SEQ ID NO: 410), wherein<br>$X_{92}$ is A, D, F, G, H, I, L, M, N, P, Q, R, S, T, V, or W;<br>$X_{93}$ is A, P, R, or T;<br>$X_{94}$ is A, E, F, G, H, I, K, L, N, P, Q, R, S, T, or V;<br>$X_{95}$ is A, D, E, G, H, K, M, N, P, R, S, or T;<br>$X_{96}$ is C, F, H, I, L, M, P, R, S, V, W, or Y;<br>$X_{97}$ is A, C, F, G, H, I, K, L, M, R, S, T, V, W, or Y; and<br>$X_{98}$ is A, D, E, F, G, H, | Subgenus 8.1: $X_{92}X_{93}X_{94}X_{95}X_{96}X_{97}X_{98}$ (SEQ ID NO: 411), wherein $X_{92}$ is A, F, G, I, L, M, N, S, T, V, or W; $X_{93}$ is P; $X_{94}$ is A, E, F, H, I, K, N, P, Q, R, S, T, or V; $X_{95}$ is A, D, E, G, H, N, P, or S; $X_{96}$ is C, F, I, L, M, R, S, or V; $X_{97}$ is C, F, G, I, L, R, S, T, V, or Y; and $X_{98}$ is A, F, L, M, P, Q, R, S, T, V, or Y.<br>Subgenus 8.2: $X_{92}X_{93}X_{94}X_{95}X_{96}X_{97}X_{98}$ (SEQ ID NO: 412), wherein $X_{92}$ is F, G, L, S, T, or V; $X_{93}$ is P; $X_{94}$ is A, E, H, K, N, Q, R, S, T, or V; $X_{95}$ is A, G, H, N, P, or S; $X_{96}$ is I, L, M, or V; $X_{97}$ is F, I, L, R, S, T, V, or Y; and $X_{98}$ is A, F, L, R, T, V, or Y.<br>Subgenus 8.3: $X_{92}X_{93}X_{94}X_{95}X_{96}X_{97}X_{98}$ (SEQ ID NO: 413), wherein $X_{92}$ is F, L, or S; $X_{93}$ is P; $X_{94}$ is A, K, Q, R, or S; $X_{95}$ is A, G, H, or S; $X_{96}$ is I, L, M, or V; $X_{97}$ is F, L, R, S, T, V, or Y and; $X_{98}$ is F, L, T, or V.<br>Subgenus 8.4: $X_{92}X_{93}X_{94}X_{95}X_{96}X_{97}X_{98}$ (SEQ ID NO: 414), wherein $X_{92}$ is F, L, or S; $X_{93}$ is P; $X_{94}$ is A, Q, or S; $X_{95}$ is G or S; $X_{96}$ is I, L, or M; $X_{97}$ is L, S, or V; and $X_{98}$ is F, L, or T.<br>Subgenus 8.5: $X_{92}X_{93}X_{94}X_{95}X_{96}X_{97}X_{98}$ (SEQ ID NO: 415), wherein $X_{92}$ is F, L, or S; $X_{93}$ is P; $X_{94}$ is A, Q or S; $X_{95}$ is G; $X_{96}$ is I, L, or |

TABLE 8H-1-continued

| MMP14 Cleavable Core CM Consensus Sequence 8 | |
|---|---|
| Core CM Consensus 8 | Subgenus of Core CM Consensus 8 |
| I, K, L, M, N, P, Q, R, S, T, V, or Y. | M; $X_{97}$ is L or V; and $X_{98}$ is L.<br>Subgenus 8.6: $X_{92}X_{93}X_{94}X_{95}X_{96}X_{97}X_{98}$ (SEQ ID NO: 416), wherein $X_{92}$ is F, L, or S; $X_{93}$ is P; $X_{94}$ is A or S; $X_{95}$ is G; $X_{96}$ is I, L, or M; $X_{97}$ is L or V; and $X_{98}$ is L.<br>Subgenus 8.7: $X_{92}X_{93}X_{94}X_{95}X_{96}X_{97}X_{98}$ (SEQ ID NO: 417), wherein $X_{92}$ is F, G, L, M, P, S, V, or W; $X_{93}$ is P; $X_{94}$ is A, N, Q, or S; $X_{95}$ is A, D, G, H, M, N, P, or S; $X_{96}$ is F, I, L, M, or V; $X_{97}$ is A, I, L, M, S, or V; and $X_{98}$ is A, G, I, L, M, N, P, Q, R, S, T, or Y.<br>Subgenus 8.8: $X_{92}X_{93}X_{94}X_{95}X_{96}X_{97}X_{98}$ (SEQ ID NO: 418), wherein $X_{92}$ is L, S, or V; $X_{93}$ is P; $X_{94}$ is A, N, Q, or S; $X_{95}$ is H, N, P, or S; $X_{96}$ is F, I, L, or M; $X_{97}$ is I, L, S, or V; and $X_{98}$ is A, L, or Q.<br>Subgenus 8.9: $X_{92}X_{93}X_{94}X_{95}X_{96}X_{97}X_{98}$ (SEQ ID NO: 419), wherein $X_{92}$ is L; $X_{93}$ is P; $X_{94}$ is A, N, Q, or S; $X_{95}$ is H; $X_{96}$ is I or L; $X_{97}$ is V; and $X_{98}$ is L. |

TABLE 8H-2

| MMP14 Cleavable Extended Core CM Consensus Sequence 8 | |
|---|---|
| Extended Core CM Consensus 8A | Subgenus of Extended Core CM Consensus 8A |
| $X_{92}X_{93}X_{94}X_{95}X_{96}X_{97}X_{98}X_{99}$ (SEQ ID NO: 486), wherein<br>$X_{92}$ is A, D, F, G, H, I, L, M, N, P, Q, R, S, T, V, or W;<br>$X_{93}$ is A, P, R, or T;<br>$X_{94}$ is A, E, F, G, H, I, K, L, N, P, Q, R, S, T, or V;<br>$X_{95}$ is A, D, E, G, H, K, M, N, P, R, S, or T;<br>$X_{96}$ is C, F, H, I, L, M, P, R, S, V, W, or Y;<br>$X_{97}$ is A, C, F, G, H, I, K, L, M, R, S, T, V, W, or Y;<br>$X_{98}$ is A, D, E, F, G, H, I, K, L, M, N, P, Q, R, S, T, V, or Y; and<br>$X_{99}$ is A, D, E, F, G, H, I, K, L, N, P, Q, R, S, T, V, W, or Y. | Subgenus 8A.1: $X_{92}X_{93}X_{94}X_{95}X_{96}X_{97}X_{98}X_{99}$ (SEQ ID NO: 487), wherein $X_{92}$ is A, F, G, I, L, M, N, S, T, V, or W; $X_{93}$ is P; $X_{94}$ is A, E, F, H, I, K, N, P, Q, R, S, T, or V; $X_{95}$ is A, D, E, G, H, N, P, or S; $X_{96}$ is C, F, I, L, M, R, S, or V; $X_{97}$ is C, F, G, I, L, R, S, T, V, or Y; $X_{98}$ is A, F, L, M, P, Q, R, S, T, V, or Y; and $X_{99}$ is A, D, E, G, H, I, L, N, P, Q, R, S, T, V, W, or Y.<br>Subgenus 8A.2: $X_{92}X_{93}X_{94}X_{95}X_{96}X_{97}X_{98}X_{99}$ (SEQ ID NO: 488), wherein $X_{92}$ is F, G, L, S, T, or V; $X_{93}$ is P; $X_{94}$ is A, E, H, K, N, Q, R, S, T, or V; $X_{95}$ is A, G, H, N, P, or S; $X_{96}$ is I, L, M, or V; $X_{97}$ is F, I, L, R, S, T, V, or Y; $X_{98}$ is A, F, L, R, T, V, or Y; and $X_{99}$ is A, D, G, L, P, R, S, T, V, or Y.<br>Subgenus 8A.3: $X_{92}X_{93}X_{94}X_{95}X_{96}X_{97}X_{98}X_{99}$ (SEQ ID NO: 489), wherein $X_{92}$ is F, L, or S; $X_{93}$ is P; $X_{94}$ is A, K, Q, R, or S; $X_{95}$ is A, G, H, or S; $X_{96}$ is I, L, M, or V; $X_{97}$ is F, L, R, S, T, V, or Y; $X_{98}$ is F, L, T, or V; and $X_{99}$ is A, D, G, L, R, T, or V.<br>Subgenus 8A.4: $X_{92}X_{93}X_{94}X_{95}X_{96}X_{97}X_{98}X_{99}$ (SEQ ID NO: 490), wherein $X_{92}$ is F, L, or S; $X_{93}$ is P; $X_{94}$ is A, Q, or S; $X_{95}$ is G or S; $X_{96}$ is I, L, or M; $X_{97}$ is L, S, or V; $X_{98}$ is F, L, or T; and $X_{99}$ is A, R, or T.<br>Subgenus 8A.5: $X_{92}X_{93}X_{94}X_{95}X_{96}X_{97}X_{98}X_{99}$ (SEQ ID NO: 491), wherein $X_{92}$ is F, L, or S; $X_{93}$ is P; $X_{94}$ is A, Q or S; $X_{95}$ is G; $X_{96}$ is I, L, or M; $X_{97}$ is L or V; $X_{98}$ is L; and $X_{99}$ is R.<br>Subgenus 8A.6: $X_{92}X_{93}X_{94}X_{95}X_{96}X_{97}X_{98}X_{99}$ (SEQ ID NO: 492), wherein $X_{92}$ is F, L, or S; $X_{93}$ is P; $X_{94}$ is A or S; $X_{95}$ is G; $X_{96}$ is I, L, or M; $X_{97}$ is L or V; $X_{98}$ is L; and $X_{99}$ is R.<br>Subgenus 8A.7: $X_{92}X_{93}X_{94}X_{95}X_{96}X_{97}X_{98}X_{99}$ (SEQ ID NO: 493), wherein $X_{92}$ is F, G, L, M, P, S, V, or W; $X_{93}$ is P; $X_{94}$ is A, N, Q, or S; $X_{95}$ is A, D, G, H, M, N, P, or S; $X_{96}$ is F, I, L, M, or V; $X_{97}$ is A, I, L, M, S, or V; $X_{98}$ is A, G, I, L, M, N, P, Q, R, S, T, or Y; and $X_{99}$ is A, F, H, I, L, Q, R, T, V, W, or Y.<br>Subgenus 8A.8: $X_{92}X_{93}X_{94}X_{95}X_{96}X_{97}X_{98}X_{99}$ (SEQ ID NO: 494), wherein $X_{92}$ is L, S, or V; $X_{93}$ is P; $X_{94}$ is A, N, Q, or S; $X_{95}$ is H, N, P, or S; $X_{96}$ is F, I, L, or M; $X_{97}$ is I, L, S, or V; $X_{98}$ is A, L, or Q; and $X_{99}$ is L, T, V, or Y.<br>Subgenus 8A.9: $X_{92}X_{93}X_{94}X_{95}X_{96}X_{97}X_{98}X_{99}$ (SEQ ID NO: 495), wherein $X_{92}$ is L; $X_{93}$ is P; $X_{94}$ is A, N, Q, or S; $X_{95}$ is H; $X_{96}$ is I or L; $X_{97}$ is V; $X_{98}$ is L; and $X_{99}$ is L or V. |

TABLE 8I

| MMP14 Cleavable Core CM Consensus Sequence 9 | |
|---|---|
| Core CM Consensus 9 | Subgenus of Core CM Consensus 9 |
| $X_{102}X_{103}X_{104}X_{105}X_{106}X_{107}X_{108}X_{109}$ (SEQ ID NO: 425), wherein $X_{102}$ is A, D, F, G, H, I, L, M, P, | Subgenus 9.1: $X_{102}X_{103}X_{104}X_{105}X_{106}X_{107}X_{108}X_{109}$ (SEQ ID NO: 426), wherein $X_{102}$ is A, D, F, G, I, R, or S; $X_{103}$ is D, E, L, M, P, R, S, T, V, or Y; $X_{104}$ is A, H, P, or S; $X_{105}$ is |

TABLE 8I-continued

| MMP14 Cleavable Core CM Consensus Sequence 9 | |
|---|---|
| Core CM Consensus 9 | Subgenus of Core CM Consensus 9 |
| R, S, T, or V; $X_{103}$ is A, D, E, L, M, P, Q, R, S, T, V, or Y; $X_{104}$ is A, G, H, L, N, P, R, S, T, or V; $X_{105}$ is A, D, E, H, L, M, N, P, Q, R, S, T, or V; $X_{106}$ is A, G, R, S, or T; $X_{107}$ is C, F, L, M, S, V, W, or Y; $X_{108}$ is A, E, F, G, H, I, L, M, N, Q, R, S, V, W, or Y; and $X_{109}$ is A, E, G, L, P, R, S, or V. | A, D, E, H, L, M, N, R, T, or V; $X_{106}$ is A, G, or R; $X_{107}$ is F, L, M, S, V, or W; $X_{108}$ is A, E, H, L, M, R, S, or V; and $X_{109}$ is A, G, L, P, R, S, or V. Subgenus 9.2: $X_{102}X_{103}X_{104}X_{105}X_{106}X_{107}X_{108}X_{109}$ (SEQ ID NO: 427), wherein $X_{102}$ is F, G, I, R, or S; $X_{103}$ is L, P, R, or V; $X_{104}$ is A or H; $X_{105}$ is A, D, or R; $X_{106}$ is A or G; $X_{107}$ is L or V; $X_{108}$ is H, L, M, R, S, or V; and $X_{109}$ is A, L, S, or V. Subgenus 9.3: $X_{102}X_{103}X_{104}X_{105}X_{106}X_{107}X_{108}X_{109}$ (SEQ ID NO: 428), wherein $X_{102}$ is G, R or S; $X_{103}$ is R or V; $X_{104}$ is A or H; $X_{105}$ is A, D, or R; $X_{106}$ is A or G; $X_{107}$ is L or V; $X_{108}$ is H or R; and $X_{109}$ is A, L, S, or V. Subgenus 9.4: $X_{102}X_{103}X_{104}X_{105}X_{106}X_{107}X_{108}X_{109}$ (SEQ ID NO: 429), wherein $X_{102}$ is R; $X_{103}$ is R; $X_{104}$ is A or H; $X_{105}$ is A or D; $X_{106}$ is G; $X_{107}$ is L or V; $X_{108}$ is R; and $X_{109}$ is A, S, or V. Subgenus 9.5: $X_{102}X_{103}X_{104}X_{105}X_{106}X_{107}X_{108}X_{109}$ (SEQ ID NO: 430), wherein $X_{102}$ is D, F, G, I, L, R, S, or T; $X_{103}$ is E, L, M, R, S, T, or V; $X_{104}$ is H or N; $X_{105}$ is A, D, L, M, R, or T; $X_{106}$ is A, G, R, or T; $X_{107}$ is C, L, M, S, V, or W; $X_{108}$ is A, E, F, G, L, R, S, or W; and $X_{109}$ is A, G, L, P, R, S, or V. Subgenus 9.6: $X_{102}X_{103}X_{104}X_{105}X_{106}X_{107}X_{108}X_{109}$ (SEQ ID NO: 431), wherein $X_{102}$ is F, I, R, or S; $X_{103}$ is E, L, R, or V; $X_{104}$ is H; $X_{105}$ is D, M, R, or T; $X_{106}$ is A or G; $X_{107}$ is L, M, S, or V; $X_{108}$ is E, R, or S; and $X_{109}$ is A, P, S, or V. Subgenus 9.7: $X_{102}X_{103}X_{104}X_{105}X_{106}X_{107}X_{108}X_{109}$ (SEQ ID NO: 432), wherein $X_{102}$ is I or R; $X_{103}$ is E, R, or V; $X_{104}$ is H; $X_{105}$ is D, M, R, or T; $X_{106}$ is A or G; $X_{107}$ is L or V; $X_{108}$ is R or S; and $X_{109}$ is A, P, S, or V. Subgenus 9.8: $X_{102}X_{103}X_{104}X_{105}X_{106}X_{107}X_{108}X_{109}$ (SEQ ID NO: 433), wherein $X_{102}$ is I or R; $X_{103}$ is R; $X_{104}$ is H; $X_{105}$ is D; $X_{106}$ is A or G; $X_{107}$ is L or V; $X_{108}$ is R or S; and $X_{109}$ is A or S. |

TABLE 8J

| MMP14 Cleavable Core CM Consensus Sequence 10 | |
|---|---|
| Core CM Consensus 10 | Subgenus of Core CM Consensus 10 |
| $X_{112}X_{113}X_{114}X_{115}X_{116}X_{117}X_{118}X_{119}$ (SEQ ID NO: 436), wherein $X_{112}$ is A, D, G, H, I, L, N, P, R, S, T, V, W, or Y; $X_{113}$ is A, D, G, H, L, M, N, P, Q, R, S, V, or Y; $X_{114}$ is A, H, K, L, N, P, Q, R, S, T, or V; $X_{115}$ is A, D, F, G, H, I, L, P, R, S, V, or Y; $X_{116}$ is C, F, I, L, P, V, or Y; $X_{117}$ is A, D, E, F, G, I, K, M, N, R, S, T, V, or W; $X_{118}$ is A, D, E, F, H, K, L, M, N, Q, R, V, or Y; and $X_{119}$ is A, F, I, L, M, or V. | Subgenus 10.1: $X_{112}X_{113}X_{114}X_{115}X_{116}X_{117}X_{118}X_{119}$ (SEQ ID NO: 437), wherein $X_{112}$ is A, I, P, S, T, V, or Y; $X_{113}$ is A, D, G, L, M, Q, R, S, V, or Y; $X_{114}$ is A, H, K, L, N, S, or T; $X_{115}$ is G, H, I, L, S, or V; $X_{116}$ is I, L, or V; $X_{117}$ is A, F, G, K, R, S, or W; $X_{118}$ is D, H, L, M, N, Q, R, or V; and $X_{119}$ is A, I, L, or V. Subgenus 10.2: $X_{112}X_{113}X_{114}X_{115}X_{116}X_{117}X_{118}X_{119}$ (SEQ ID NO: 438), wherein $X_{112}$ is A, I, T, or V; $X_{113}$ is A, L, M, Q, R, V, or Y; $X_{114}$ is A, N, S, or T; $X_{115}$ is G, L, S, or V; $X_{116}$ is L or V; $X_{117}$ is A, F, G, K, or S; $X_{118}$ is M, N, Q, R, or V; and $X_{119}$ is I, L, or V. Subgenus 10.3: $X_{112}X_{113}X_{114}X_{115}X_{116}X_{117}X_{118}X_{119}$ (SEQ ID NO: 439), wherein $X_{112}$ is A, I, T, or V; $X_{113}$ is M, Q, or Y; $X_{114}$ is A, N, or S; $X_{115}$ is G, L, S, or V; $X_{116}$ is L or V; $X_{117}$ is A, F, G, or S; $X_{118}$ is M, N, Q, or R; and $X_{119}$ is I, L, or V. Subgenus 10.4: $X_{112}X_{113}X_{114}X_{115}X_{116}X_{117}X_{118}X_{119}$ (SEQ ID NO: 440), wherein $X_{112}$ is A, I, or V; $X_{113}$ is Y; $X_{114}$ is N or S; $X_{115}$ is G, L, or V; $X_{116}$ is L; $X_{117}$ is A, G, or S; $X_{118}$ is M, Q, or R; and $X_{119}$ is L or V. Subgenus 10.5: $X_{112}X_{113}X_{114}X_{115}X_{116}X_{117}X_{118}X_{119}$ (SEQ ID NO: 441), wherein $X_{112}$ is A, I, or V; $X_{113}$ is Y; $X_{114}$ is N or S; $X_{115}$ is G, L, or V; $X_{116}$ is L; $X_{117}$ is G or S; $X_{118}$ is M or R; and $X_{119}$ is L or V. Subgenus 10.6: $X_{112}X_{113}X_{114}X_{115}X_{116}X_{117}X_{118}X_{119}$ (SEQ ID NO: 442), wherein $X_{112}$ is A, I, or V; $X_{113}$ is Y; $X_{114}$ is N or S; $X_{115}$ is G, L, or V; $X_{116}$ is L; $X_{117}$ is S, $X_{118}$ is M or R; and $X_{119}$ is L or V. Subgenus 10.7: $X_{112}X_{113}X_{114}X_{115}X_{116}X_{117}X_{118}X_{119}$ (SEQ ID NO: 443), wherein $X_{112}$ is A; $X_{113}$ is Y; $X_{114}$ is N or S; $X_{115}$ is G or L; $X_{116}$ is L; $X_{117}$ is S; $X_{118}$ is R; and $X_{119}$ is L or V. Subgenus 10.8: $X_{112}X_{113}X_{114}X_{115}X_{116}X_{117}X_{118}X_{119}$ (SEQ |

TABLE 8J-continued

| MMP14 Cleavable Core CM Consensus Sequence 10 | |
|---|---|
| Core CM Consensus 10 | Subgenus of Core CM Consensus 10 |
| | ID NO: 444), wherein $X_{112}$ is A, D, G, I, L, N, P, S, T, V, W, or Y; $X_{113}$ is A, D, G, L, M, Q, S, or V; $X_{114}$ is H, K, N, P, Q, R, S, or T; $X_{115}$ is H, I, L, R, or V; $X_{116}$ is I, L, P, or V; $X_{117}$ is A, D, E, G, I, K, M, N, S, or T; $X_{118}$ is D, F, L, M, Q, R, or V; and $X_{119}$ is A, F, I, L, or V.<br>Subgenus 10.9: $X_{112}X_{113}X_{114}X_{115}X_{116}X_{117}X_{118}X_{119}$ (SEQ ID NO: 445), wherein $X_{112}$ is A, I, T, or V; $X_{113}$ is A, D, G, L, M, Q, S, or V; $X_{114}$ is H, K, N, S, or T; $X_{115}$ is H, I, L, or V; $X_{116}$ is L; $X_{117}$ is A, G, K, or S; $X_{118}$ is L, M, Q, R, or V; and $X_{119}$ is A, L, or V.<br>Subgenus 10.10: $X_{112}X_{113}X_{114}X_{115}X_{116}X_{117}X_{118}X_{119}$ (SEQ ID NO: 446), wherein $X_{112}$ is A or I; $X_{113}$ is A, L, or Q; $X_{114}$ is N, S, or T; $X_{115}$ is L or V; $X_{116}$ is L; $X_{117}$ is A, G, K, or S; $X_{118}$ is M, R, or V; and $X_{119}$ is L or V.<br>Subgenus 10.11: $X_{112}X_{113}X_{114}X_{115}X_{116}X_{117}X_{118}X_{119}$ (SEQ ID NO: 447), wherein $X_{112}$ is A or I; $X_{113}$ is A, L, or Q; $X_{114}$ is N or S; $X_{115}$ is L or V; $X_{116}$ is L; $X_{117}$ is A or S; $X_{118}$ is M or R; and $X_{119}$ is L or V.<br>Subgenus 10.12: $X_{112}X_{113}X_{114}X_{115}X_{116}X_{117}X_{118}X_{119}$ (SEQ ID NO: 448), wherein $X_{112}$ is I; $X_{113}$ is A, L, or Q; $X_{114}$ is N; $X_{115}$ is L or V; $X_{116}$ is L; $X_{117}$ is A or S; $X_{118}$ is M or R; and $X_{119}$ is L or V.<br>Subgenus 10.13: $X_{112}X_{113}X_{114}X_{115}X_{116}X_{117}X_{118}X_{119}$ (SEQ ID NO: 449), wherein $X_{112}$ is I; $X_{113}$ is A, L, or Q; $X_{114}$ is N; $X_{115}$ is L or V; $X_{116}$ is L; $X_{117}$ is S, $X_{118}$ is M; and $X_{119}$ is L or V. |

TABLE 8K

| MMP14 Cleavable Core CM Consensus Sequence 11 | |
|---|---|
| Core CM Consensus 11 | Subgenus of Core CM Consensus 11 |
| $X_{122}X_{123}X_{124}X_{125}X_{126}X_{127}X_{128}X_{129}$ (SEQ ID NO: 453), wherein<br>$X_{122}$ is A, G, H, L, P, R, S, or V;<br>$X_{123}$ is A, G, R, S, T or V;<br>$X_{124}$ is A, G, P, R, S, or T;<br>$X_{125}$ is H, I, L, P, R, or V;<br>$X_{126}$ is L or W;<br>$X_{127}$ is F, H, L, M, Q, S, V, or Y;<br>$X_{128}$ is A, D, E, I, K, P, R, S, T, or V; and<br>$X_{129}$ is A, E, F, G, H, I, L, N, P, Q, R, or V. | Subgenus 11.1: $X_{122}X_{123}X_{124}X_{125}X_{126}X_{127}X_{128}X_{129}$ (SEQ ID NO: 454), wherein $X_{122}$ is A, G, P, R, or S; $X_{123}$ is A, R, or S; $X_{124}$ is G, P, S, or T; $X_{125}$ is L or V; $X_{126}$ is W; $X_{127}$ is L, S, V, or Y; $X_{128}$ is D, E, P, or T; and $X_{129}$ is P, Q or V.<br>Subgenus 11.2: $X_{122}X_{123}X_{124}X_{125}X_{126}X_{127}X_{128}X_{129}$ (SEQ ID NO: 455), wherein $X_{122}$ is G, P, R, or S; $X_{123}$ is A or R; $X_{124}$ is G, P, or S; $X_{125}$ is L or V; $X_{126}$ is W; $X_{127}$ is L or Y; $X_{128}$ is E or T; and $X_{129}$ is Q.<br>Subgenus 11.3: $X_{122}X_{123}X_{124}X_{125}X_{126}X_{127}X_{128}X_{129}$ (SEQ ID NO: 456), wherein $X_{122}$ is P; $X_{123}$ is A; $X_{124}$ is P or S; $X_{125}$ is L or V; $X_{126}$ is W; $X_{127}$ is Y; $X_{128}$ is T; and $X_{129}$ is Q. |

TABLE 8L

| MMP14 Cleavable Core CM Consensus Sequence 12 | |
|---|---|
| Core CM Consensus 12 | Subgenus of Core CM Consensus 12 |
| $X_2X_3X_4X_5X_6X_7X_8X_9$ (SEQ ID NO: 458), wherein<br>$X_2$ is A, D, E, F, G, H, I, L, M, N, P, Q, R, S, T, V, or Y;<br>$X_3$ is A, E, F, G, H, I, K, L, M, P, Q, R, S, T, V, W, or Y;<br>$X_4$ is A, E, G, H, K, N, P, R, S, T, V, or Y;<br>$X_5$ is A, G, H, I, L, N, P, R, S, T, or V;<br>$X_6$ is I, L, M, Q, T, V, W, or Y; | Subgenus 12.1: $X_2X_3X_4X_5X_6X_7X_8X_9$ (SEQ ID NO: 459), wherein $X_2$ is A, G, L, P, or S; $X_3$ is A, E, G, H, L, P, Q, S, T, or V; $X_4$ is G, N, R, or S; $X_5$ is L, P, or S; $X_6$ is I or L; $X_7$ is A, G, N, Q, R, or S; $X_8$ is D, F, G, I, L, M, P, S, or V; and $X_9$ is F, G, L, P, Q, R, or S.<br>Subgenus 12.2: $X_2X_3X_4X_5X_6X_7X_8X_9$ (SEQ ID NO: 460), wherein $X_2$ is A, P, or S; $X_3$ is L, S or V; $X_4$ is G, N, R, or S; $X_5$ is L, P, or S; $X_6$ is L; $X_7$ is A, G, R, or S; $X_8$ is L, P, or V; and $X_9$ is F, L, P, or S.<br>Subgenus 12.3: $X_2X_3X_4X_5X_6X_7X_8X_9$ (SEQ ID NO: 461), wherein $X_2$ is A, P, or S; $X_3$ is L, S, or V; $X_4$ is G, N, R, or S; $X_5$ is L, P, or S; $X_6$ is L; $X_7$ is A, G, R, or S; $X_8$ is L or P; and $X_9$ is F, P, or S.<br>Subgenus 12.4: $X_2X_3X_4X_5X_6X_7X_8X_9$ (SEQ ID NO: 462), wherein $X_2$ is A, P, or S; $X_3$ is L or V; $X_4$ is G, N, or S; $X_5$ is L or S; $X_6$ is L; $X_7$ is A, G, R, or S; $X_8$ is L or P; and $X_9$ is P or S.<br>Subgenus 12.5: $X_2X_3X_4X_5X_6X_7X_8X_9$ (SEQ ID NO: 463), wherein $X_2$ is A or S; $X_3$ is L; $X_4$ is G, N, or S; $X_5$ is L or S; $X_6$ is L; $X_7$ is R |

TABLE 8L-continued

| MMP14 Cleavable Core CM Consensus Sequence 12 | |
|---|---|
| Core CM Consensus 12 | Subgenus of Core CM Consensus 12 |
| $X_7$ is A, D, G, H, K, L, N, P, Q, R, S, T, or V; $X_8$ is A, D, E, F, G, I, K, L, M, P, Q, R, S, V, W, or Y; and $X_9$ is A, F, G, I, L, M, N, P, Q, R, S, T, V or Y. | or S; $X_8$ is L; and $X_9$ is P. Subgenus 12.6: $X_2X_3X_4X_5X_6X_7X_8X_9$ (SEQ ID NO: 464), wherein $X_2$ is A, E, G, H, I, L, M, P, or S; $X_3$ is A, E, G, H, I, K, L, P, Q, R, S, T, V, W, or Y; $X_4$ is A, G, N, R, S, T, or V; $X_5$ is A, G, H, L, N, P, R, S, T, or V; $X_6$ is I, L, M, or Q; $X_7$ is A, D, G, K, L, N, Q, R, S, or V; $X_8$ is A, D, E, F, G, I, K, L, M, P, R, V, W, or Y; and $X_9$ is A, F, G, M, P, Q, R, S, V, or Y. Subgenus 12.7: $X_2X_3X_4X_5X_6X_7X_8X_9$ (SEQ ID NO: 465), wherein $X_2$ is A, P, or S; $X_3$ is A, H, Q, S, or V; $X_4$ is G, N, or S; $X_5$ is L, P, or S; $X_6$ is L; $X_7$ is A, D, G, R, or S; $X_8$ is F, I, L, M, or P; and $X_9$ is F, P, Q, or R. Subgenus 12.8: $X_2X_3X_4X_5X_6X_7X_8X_9$ (SEQ ID NO: 466), wherein $X_2$ is A, P, or S; $X_3$ is H, S, or V; $X_4$ is G, N, or S; $X_5$ is L, P, or S; $X_6$ is L; $X_7$ is A, G, R, or S; $X_8$ is F, I, M, or P; and $X_9$ is P or R. Subgenus 12.9: $X_2X_3X_4X_5X_6X_7X_8X_9$ (SEQ ID NO: 467), wherein $X_2$ is A, P, or S; $X_3$ is S or V; $X_4$ is G, N, or S; $X_5$ is L; $X_6$ is L; $X_7$ is A, G or R; $X_8$ is F, I, or P; and $X_9$ is P. Subgenus 12.10: $X_2X_3X_4X_5X_6X_7X_8X_9$ (SEQ ID NO: 468), wherein $X_2$ is A, P, or S; $X_3$ is S or V; $X_4$ is G, N, or S; $X_5$ is L; $X_6$ is L; $X_7$ is A or R; $X_8$ is F or P; and $X_9$ is P. Subgenus 12.11: $X_2X_3X_4X_5X_6X_7X_8X_9$ (SEQ ID NO: 469), wherein $X_2$ is A or P; $X_3$ is S; $X_4$ is G or N; $X_5$ is L; $X_6$ is L; $X_7$ is R; $X_8$ is F; and $X_9$ is P. |

TABLE 8M

| MMP14 Cleavable Core CM Consensus Sequence 13 | |
|---|---|
| Core CM Consensus 13 | Subgenus of Core CM Consensus 13 |
| $X_{12}X_{13}X_{14}X_{15}X_{16}X_{17}X_{18}X_{19}$ (SEQ ID NO: 473), wherein $X_{12}$ is F, I, L, M, R, S, T, or V; $X_{13}$ is A, E, G, H, I, K, L, M, N, P, Q, R, S, T, V, W, or Y; $X_{14}$ is A, D, E, F, G, H, I, K, L, M, N, P, Q, R, S, T, V, or Y; $X_{15}$ is A, E, G, N, P, Q, S, T, V, or W; $X_{16}$ is A, F, G, H, I, K, L, M, N, P, Q, R, S, T, V, or Y; $X_{17}$ is A, D, E, F, G, H, I, L, M, N, P, Q, R, S, T, V, or Y; $X_{18}$ is A, C, D, E, F, G, H, I, L, M, N, P, Q, R, S, T, V, or Y; and $X_{19}$ is A, D, F, G, H, I, L, M, N, P, Q, R, S, T, V, W, or Y. | Subgenus 13.1: $X_{12}X_{13}X_{14}X_{15}X_{16}X_{17}X_{18}X_{19}$ (SEQ ID NO: 475), wherein $X_{12}$ is F, I, L, M, S, or V; $X_{13}$ is A, E, H, K, L, M, N, Q, S, T, V, or Y; $X_{14}$ is A, F, H, L, M, Q, S, T, or V; $X_{15}$ is A, G, or P; $X_{16}$ is A, F, G, H, I, L, M, N, R, S, V, or Y; $X_{17}$ is A, E, G, H, L, M, P, Q, R, S, T, or V; $X_{18}$ is A, D, E, F, G, H, L, M, N, R, S, V, or Y; and $X_{19}$ is A, F, G, I, L, M, P, Q, R, S, W, or Y. Subgenus 13.2: $X_{12}X_{13}X_{14}X_{15}X_{16}X_{17}X_{18}X_{19}$ (SEQ ID NO: 476), wherein $X_{12}$ is L, M, or V; $X_{13}$ is A, H, L, N, Q, S, or V; $X_{14}$ is A, L, M, Q, S, T, or V; $X_{15}$ is P; $X_{16}$ is A, F, G, I, L, R, S, V, or Y; $X_{17}$ is H, L, M, Q, or S; $X_{18}$ is A, D, G, H, R, or S; and $X_{19}$ is A, F, G, L, R, or S. Subgenus 13.3: $X_{12}X_{13}X_{14}X_{15}X_{16}X_{17}X_{18}X_{19}$ (SEQ ID NO: 477), wherein $X_{12}$ is L, M, or V; $X_{13}$ is A or L; $X_{14}$ is A, L, or S; $X_{15}$ is P; $X_{16}$ is L or V; $X_{17}$ is H, L, or Q; $X_{18}$ is G or S; and $X_{19}$ is G, R, or S. Subgenus 13.4: $X_{12}X_{13}X_{14}X_{15}X_{16}X_{17}X_{18}X_{19}$ (SEQ ID NO: 478), wherein $X_{12}$ is L or V; $X_{13}$ is A or L; $X_{14}$ is L or S; $X_{15}$ is P; $X_{16}$ is L or V; $X_{17}$ is H or L; $X_{18}$ is G or S; and $X_{19}$ is R or S. Subgenus 13.5: $X_{12}X_{13}X_{14}X_{15}X_{16}X_{17}X_{18}X_{19}$ (SEQ ID NO: 479), wherein $X_{12}$ is L or V; $X_{13}$ is A or L; $X_{14}$ is L or S; $X_{15}$ is P; $X_{16}$ is L; $X_{17}$ is H or L; $X_{18}$ is G; and $X_{19}$ is S. Subgenus 13.6: $X_{12}X_{13}X_{14}X_{15}X_{16}X_{17}X_{18}X_{19}$ (SEQ ID NO: 480), wherein $X_{12}$ is F, I, L, M, S, T, or V; $X_{13}$ is A, E, G, H, L, M, S, V, W, or Y; $X_{14}$ is A, D, E, G, K, L, M, N, Q, R, S, T, or V; $X_{15}$ is E, G, N, P, S, T, or V; $X_{16}$ is A, F, G, L, N, P, Q, R, S, V, or Y; $X_{17}$ is A, E, H, P, Q, or R; $X_{18}$ is D, E, G, N, R, S, or T; and $X_{19}$ is A, D, G, Q, S, T, or V. Subgenus 13.: $X_{12}X_{13}X_{14}X_{15}X_{16}X_{17}X_{18}X_{19}$ (SEQ ID NO: 481), wherein $X_{12}$ is L, M, or V; $X_{13}$ is A or L; $X_{14}$ is A, L, Q, or S; $X_{15}$ is G, P, or T; $X_{16}$ is A, S, or Y; $X_{17}$ is H or P; $X_{18}$ is D or G; and $X_{19}$ is A, G or S. Subgenus 13.7: $X_{12}X_{13}X_{14}X_{15}X_{16}X_{17}X_{18}X_{19}$ (SEQ ID NO: 482), wherein $X_{12}$ is L or M; $X_{13}$ is A or L; $X_{14}$ is L; $X_{15}$ is G or P; $X_{16}$ is A or S; $X_{17}$ is H; $X_{18}$ is G; and $X_{19}$ is A or G. |

In some embodiments, the CM comprises an amino acid sequence selected from the group consisting of Core CM Consensus 5, Core CM Consensus 6, Core CM Consensus 6A, Core CM Consensus 7, Core CM Consensus 8, Extended Core CM Consensus 8A, Core CM Consensus 9, Core CM Consensus 10, Core CM Consensus 11, Core CM Consensus 12 and Core CM Consensus 13. In some embodiments, the CM comprises an amino acid sequence selected from the group consisting of Subgenus 5.1-5.11 (ex. SEQ ID NOs: 358 and 363), Subgenus 6.1-6.4, Subgenus 6A.1-6.A.3

(ex. SEQ ID NO: 378), Subgenus 7.1-7.7 (ex. SEQ ID NOs: 397 and 401), Subgenus 8.1-8.9 (ex. SEQ ID NO: 419), Subgenus 9.1-9.8 (ex. SEQ ID NO: 429), Subgenus 10.1-10.13 (ex. SEQ ID NOs: 443 and 449), Subgenus 11.1-11.3 (ex. SEQ ID NO: 456), Subgenus 12.1-12.11 (ex. SEQ ID NOs: 463 and 469), Subgenus 13.1-13.7 (ex. SEQ ID NO: 479), and Subgenus 8A.1-8A.9 (ex. SEQ ID NOs: 491, 492 and 487). In some embodiments, the CM comprises an amino acid sequence selected from the group consisting of Subgenus 5.1-5.11. In some embodiments, the CM comprises an amino acid sequence selected from the group consisting of Subgenus 6.1-6.4. In some embodiments, the CM comprises an amino acid sequence selected from the group consisting of Subgenus 6A.1-6.A.3. In some embodiments, the CM comprises an amino acid sequence selected from the group consisting of Subgenus 7.1-7.7. In some embodiments, the CM comprises an amino acid sequence selected from the group consisting of Subgenus 8.1-8.9. In some embodiments, the CM comprises an amino acid sequence selected from the group consisting of Subgenus 9.1-9.8. In some embodiments, the CM comprises an amino acid sequence selected from the group consisting of Subgenus 10.1-10.13. In some embodiments, the CM comprises an amino acid sequence selected from the group consisting of Subgenus 11.1-11.3. In some embodiments, the CM comprises an amino acid sequence selected from the group consisting of Subgenus 12.1-12.11. In some embodiments, the CM comprises an amino acid sequence selected from the group consisting of Subgenus 13.1-13.7. In some embodiments, the CM comprises an amino acid sequence selected from the group consisting of Subgenus 8A.1-8A.9.

In some embodiments, the CM comprises an amino sequence selected from the group consisting of Core CM Consensus 1, Core CM Consensus 2, Core CM Consensus 3 and Core CM Consensus 4. In some embodiments, the CM comprises an amino acid sequence selected from the group consisting of Subgenus 1.1-1.6 (ex. SEQ ID NO: 322), Subgenus 2.1-2.3 (ex. SEQ ID NO: 327), Subgenus 3.1-3.6 (ex. SEQ ID NO: 335), and Subgenus 4.1-4.7 (ex. SEQ ID NOs: 344 and 345). In some embodiments, the CM comprises an amino acid sequence selected from the group consisting of Subgenus 1.1-1.6. In some embodiments, the CM comprises an amino acid sequence selected from the group consisting of Subgenus 2.1-2.3. In some embodiments, the CM comprises an amino acid sequence selected from the group consisting of Subgenus 3.1-3.6. In some embodiments, the CM comprises an amino acid sequence selected from the group consisting of Subgenus 4.1-4.7.

In some embodiments, the CM comprises a core CM consensus 1 sequence comprising the amino acid sequence RPSPMWAY (SEQ ID NO: 21).

In some embodiments, the CM comprises a core CM consensus 2 sequence comprising the amino acid sequence WDHPISLL (SEQ ID NO: 328). In some embodiments, the CM comprises a core CM consensus 2 sequence comprising the amino acid sequence WATPRPMR (SEQ ID NO: 22).

In some embodiments, the CM comprises a core CM consensus 3 sequence comprising the amino acid sequence LTFPTYIF (SEQ ID NO: 336). In some embodiments, the CM comprises a core CM consensus 3 sequence comprising the amino acid sequence MTFPTYIF (SEQ ID NO: 337). In some embodiments, the CM comprises a core CM consensus 3 sequence comprising the amino acid sequence LTFPTYWF (SEQ ID NO: 338). In some embodiments, the CM comprises a core CM consensus 3 sequence comprising the amino acid sequence MTFPTYWF (SEQ ID NO: 339). In some embodiments, the CM comprises a core CM consensus 3 sequence comprising the amino acid sequence STFPFGMF (SEQ ID NO: 17).

In some embodiments, the CM comprises a core CM consensus 4 sequence comprising the amino acid sequence DWLYWMGI (SEQ ID NO: 348). In some embodiments, the CM comprises a core CM consensus 4 sequence comprising the amino acid sequence DWLYWPGI (SEQ ID NO: 19). In some embodiments, the CM comprises a core CM consensus 4 sequence comprising the amino acid sequence DWLYWMSI (SEQ ID NO: 349). In some embodiments, the CM comprises a core CM consensus 4 sequence comprising the amino acid sequence DWLYWPSI (SEQ ID NO: 350). In some embodiments, the CM comprises a core CM consensus 4 sequence comprising the amino acid sequence HWHLGPPT (SEQ ID NO: 351).

In some embodiments, the CM comprises a core CM consensus 5 sequence comprising the amino acid sequence ISSGLLSS (SEQ ID NO: 14). In some embodiments, the CM comprises a core CM consensus 5 sequence comprising the amino acid sequence SVSGLLSH (SEQ ID NO: 364). In some embodiments, the CM comprises a core CM consensus 5 sequence comprising the amino acid sequence SVSGLLSS (SEQ ID NO: 365). In some embodiments, the CM comprises a core CM consensus 5 sequence comprising the amino acid sequence SVSGLRSH (SEQ ID NO: 366). In some embodiments, the CM comprises a core CM consensus 5 sequence comprising the amino acid sequence SVSGLRSS (SEQ ID NO: 367). In some embodiments, the CM comprises a core CM consensus 5 sequence comprising the amino acid sequence TLSGLRSP (SEQ ID NO: 368). In some embodiments, the CM comprises a core CM consensus 5 sequence comprising the amino acid sequence TSSGLRSP (SEQ ID NO: 369). In some embodiments, the CM comprises a core CM consensus 5 sequence comprising the amino acid sequence TVSGLRSP (SEQ ID NO: 370).

In some embodiments, the CM comprises a core CM consensus 6 sequence comprising the amino acid sequence AFQALRM (SEQ ID NO: 379). In some embodiments, the CM comprises a core CM consensus 6 sequence comprising the amino acid sequence AHQALRM (SEQ ID NO: 380). In some embodiments, the CM comprises a core CM consensus 6 sequence comprising the amino acid sequence ANQALRM (SEQ ID NO: 381). In some embodiments, the CM comprises a core CM consensus 6 sequence comprising the amino acid sequence ANQALRMA (SEQ ID NO: 382). In some embodiments, the CM comprises a core CM consensus 6 sequence comprising the amino acid sequence LLEALRAL (SEQ ID NO: 383). In some embodiments, the CM comprises a core CM consensus 6 sequence comprising the amino acid sequence LLNALRAL (SEQ ID NO: 384). In some embodiments, the CM comprises a core CM consensus 6 sequence comprising the amino acid sequence LLQALRAL (SEQ ID NO: 385). In some embodiments, the CM comprises a core CM consensus 6 sequence comprising the amino acid sequence LLSALRAL (SEQ ID NO: 386). In some embodiments, the CM comprises a core CM consensus 6 sequence comprising the amino acid sequence LLESLRAL (SEQ ID NO: 387). In some embodiments, the CM comprises a core CM consensus 6 sequence comprising the amino acid sequence LLNSLRAL (SEQ ID NO: 388). In some embodiments, the CM comprises a core CM consensus 6 sequence comprising the amino acid sequence LLQSLRAL (SEQ ID NO: 389). In some embodiments, the CM comprises a core CM consensus 6 sequence comprising the amino acid sequence LLSSLRAL (SEQ ID NO: 390). In some embodiments, the CM comprises a core CM consensus 6 sequence comprising the amino acid sequence QFQALRM (SEQ ID NO: 391). In some embodiments, the CM comprises a core CM consensus 6 sequence comprising the amino acid sequence QHQALRM (SEQ ID NO: 392). In some embodiments, the CM comprises a core CM consensus 6 sequence comprising the amino acid sequence QNQALRM (SEQ ID NO: 393). In some embodiments, the CM comprises a core CM consensus 6 sequence comprising the amino acid sequence QNQALRMA (SEQ ID NO: 15).

In some embodiments, the CM comprises a core CM consensus 7 sequence comprising the amino acid sequence LKAAPRWA (SEQ ID NO: 24). In some embodiments, the CM comprises a core CM consensus 7 sequence comprising the amino acid sequence LKAAPVWA (SEQ ID NO: 403). In some embodiments, the CM comprises a core CM consensus 7 sequence comprising the amino acid sequence LKAAPRWF (SEQ ID NO: 404). In some embodiments, the CM comprises a core CM consensus 7 sequence comprising the amino acid sequence LKAAPVWF (SEQ ID NO: 405). In some embodiments, the CM comprises a core CM consensus 7 sequence comprising the amino acid sequence LYAAPRWA (SEQ ID NO: 406). In some embodiments, the CM comprises a core CM consensus 7 sequence comprising the amino acid sequence LYAAPVWA (SEQ ID NO: 407). In some embodiments, the CM comprises a core CM consensus 7 sequence comprising the amino acid sequence LYAAPRWF (SEQ ID NO: 408). In some embodiments, the CM comprises a core CM consensus 7 sequence comprising the amino acid sequence LYAAPVWF (SEQ ID NO: 409).

In some embodiments, the CM comprises a core CM consensus 8 sequence comprising the amino acid sequence GPSHLVLT (SEQ ID NO: 25). In some embodiments, the CM comprises a core CM consensus 8 sequence comprising the amino acid sequence LPAGLLL (SEQ ID NO: 402). In some embodiments, the CM comprises a core CM consensus 8 sequence comprising the amino acid sequence LPAGLLLR (SEQ ID NO: 420). In some embodiments, the CM comprises a core CM consensus 8 sequence comprising the amino acid sequence LPAHLVLL (SEQ ID NO: 421). In some embodiments, the CM comprises a core CM consensus 8 sequence comprising the amino acid sequence LPSHLVLL (SEQ ID NO: 422). In some embodiments, the CM comprises a core CM consensus 8 sequence comprising the amino acid sequence LPAHLVLV (SEQ ID NO: 423). In some embodiments, the CM comprises a core CM consensus 8 sequence comprising the amino acid sequence LPSHLVLV (SEQ ID NO: 424).

In some embodiments, the CM comprises a core CM consensus 9 sequence comprising the amino acid sequence RMHLRSLG (SEQ ID NO: 29). In some embodiments, the CM comprises a core CM consensus 9 sequence comprising the amino acid sequence RRHDGLRA (SEQ ID NO: 434). In some embodiments, the CM comprises a core CM consensus 9 sequence comprising the amino acid sequence RRHDGLRS (SEQ ID NO: 435).

In some embodiments, the CM comprises a core CM consensus 10 sequence comprising the amino acid sequence AQNLLGMV (SEQ ID NO: 16). In some embodiments, the CM comprises a core CM consensus 10 sequence comprising the amino acid sequence IANLLSMV (SEQ ID NO: 450). In some embodiments, the CM comprises a core CM consensus 10 sequence comprising the amino acid sequence ILNLLSMV (SEQ ID NO: 451). In some embodiments, the CM comprises a core CM consensus 10 sequence comprising the amino acid sequence IQNLLSMV (SEQ ID NO: 452).

In some embodiments, the CM comprises a core CM consensus 11 sequence comprising the amino acid sequence PAGLWLDP (SEQ ID NO: 33). In some embodiments, the CM comprises a core CM consensus 11 sequence comprising the amino acid sequence PASLWYTQ (SEQ ID NO: 457).

In some embodiments, the CM comprises a core CM consensus 12 sequence comprising the amino acid sequence ALGLLRLP (SEQ ID NO: 470). In some embodiments, the CM comprises a core CM consensus 12 sequence comprising the amino acid sequence ALGLLSLP (SEQ ID NO: 471). In some embodiments, the CM comprises a core CM consensus 12 sequence comprising the amino acid sequence ASGLLRFP (SEQ ID NO: 472). In some embodiments, the CM comprises a core CM consensus 12 sequence comprising the amino acid sequence AVGLLAPP (SEQ ID NO: 31).

In some embodiments, the CM comprises a core CM consensus 13 sequence comprising the amino acid sequence LAAPLGLL (SEQ ID NO: 30). In some embodiments, the CM comprises a core CM consensus 13 sequence comprising the amino acid sequence LLAPSHRA (SEQ ID NO: 32).

In some embodiments, the CM comprises a core CM consensus 13 sequence comprising the amino acid sequence LLLPAHGG (SEQ ID NO: 474). In some embodiments, the CM comprises a core CM consensus 13 sequence comprising the amino acid sequence LLLPLLGS (SEQ ID NO: 483).

In some embodiments, the CM is a substrate for at least two proteases. In some embodiments, at least one protease is an MMP and at least one protease is selected from the group consisting of those shown in Table 7.

TABLE 7

| Exemplary Proteases and/or Enzymes |
|---|
| ADAMS, ADAMTS, e.g. |
| ADAM8 |
| ADAM9 |
| ADAM10 |
| ADAM12 |
| ADAM15 |
| ADAM17/TACE |
| ADAMDEC1 |
| ADAMTS1 |
| ADAMTS4 |
| ADAMTS5 |
| Aspartate proteases, e.g., |
| BACE |
| Renin |
| Aspartic cathepsins, e.g., |
| Cathepsin D |
| Cathepsin E |
| Caspases, e.g., |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |

TABLE 7-continued

| Exemplary Proteases and/or Enzymes |
|---|
| Otubain-2 |
| KLKs, e.g., |
| KLK4 |
| KLK5 |
| KLK6 |
| KLK7 |
| KLK8 |
| KLK10 |
| KLK11 |
| KLK13 |
| KLK14 |
| Metallo proteinases, e.g., |
| Meprin |
| Neprilysin |
| PSMA |
| BMP-1 |
| MMPs, e.g., |
| MMP1 |
| MMP2 |
| MMP3 |
| MMP7 |
| MMP8 |
| MMP9 |
| MMP10 |
| MMP11 |
| MMP12 |
| MMP13 |
| MMP14 |
| MMP15 |
| MMP16 |
| MMP17 |
| MMP19 |
| MMP20 |
| MMP23 |
| MMP24 |
| MMP26 |
| MMP27 |
| Serine proteases, e.g., |
| activated protein C |
| Cathepsin A |
| Cathepsin G |
| Chymase |
| coagulation factor proteases (e.g., FVIIa, FIXa, FXa, FXIa, FXIIa) |
| Elastase |
| Granzyme B |
| Guanidinobenzoatase |
| HtrA1 |
| Human Neutrophil Elastase |
| Lactoferrin |
| Marapsin |
| NS3/4A |
| PACE4 |
| Plasmin |
| PSA |
| tPA |
| Thrombin |
| Tryptase |
| uPA |
| Type II Transmembrane Serine Proteases (TTSPs), e.g., |
| DESC1 |
| DPP-4 |
| FAP |
| Hepsin |
| Matriptase-2 |
| MT-SP1/Matriptase |
| TMPRSS2 |
| TMPRSS3 |
| TMPRSS4 |

In some embodiments, the antibody includes at least a first CM and a second CM. In some embodiments, the first CM and the second CM are each polypeptides of no more than 15 amino acids long. In some embodiments, the first CM and the second CM in the antibody in the uncleaved state have the structural arrangement from N-terminus to C-terminus as follows: Agent-CM1-CM2-AB, AB-CM2-CM1-Agent, Agent-CM2-CM1-AB, or AB-CM1-CM2-Agent. In some embodiments, the activatable antibody includes a linking peptide between the agent and CM1. In some embodiments, the activatable antibody includes a linking peptide between CM1 and CM2. In some embodiments, the activatable antibody includes a linking peptide between CM2 and AB. In some embodiments, the activatable antibody includes a linking peptide between the agent and CM1 and a linking peptide between CM2 and AB. In some embodiments, the activatable antibody includes a linking peptide between agent and CM1 and a linking peptide between CM1 and CM2. In some embodiments, the activatable antibody includes a linking peptide between CM1 and CM2 and a linking peptide between CM2 and AB. In some embodiments, the activatable antibody includes a linking peptide between agent and CM1, a linking peptide between CM1 and CM2, and a linking peptide between CM2 and AB.

In some embodiments, the activatable antibody includes at least a first CM that includes a substrate for at least one matrix metalloprotease (MMP) and a second CM that includes a substrate sequence. Exemplary substrates for the second CM (CM2) include but are not limited to substrates cleavable by one or more of the following enzymes or proteases listed in Table 7.

In some embodiments, the CM2 is selected for use with a specific protease. In some embodiments, the CM2 is a substrate for at least one protease selected from the group consisting of a matrix metalloprotease (MMP), a neutrophil elastase, u-type plasminogen activator (uPA, also referred to as urokinase), legumain, matriptase (also referred to herein as MT-SP1 or MTSP1), thrombin, a cysteine protease such as a cathepsin, ADAM17, BMP-1, HtrA1, and a TMPRSS such as TMPRSS3 or TMPRSS4.

In some embodiments, the CM2 is a substrate for a neutrophil elastase. In some embodiments, the CM2 is a substrate for uPA. In some embodiments, the CM2 is a substrate for legumain. In some embodiments, the CM2 is a substrate for matriptase. In some embodiments, the CM2 is a substrate for thrombin. In some embodiments, the CM2 is a substrate for a cysteine protease. In some embodiments, the CM2 is a substrate for a cathepsin. In some embodiments, the CM2 is a substrate for ADAM17. In some embodiments, the CM2 is a substrate for BMP-1. In some embodiments, the CM2 is a substrate for HtrA1. In some embodiments, the CM2 is a substrate for a TMPRSS. In some embodiments, the CM2 is a substrate for TMPRSS3. In some embodiments, the CM2 is a substrate for TMPRSS4.

For example, suitable CM2 are cleaved by at least one protease and include the sequence TGRGPSWV (SEQ ID NO: 34); SARGPSRW (SEQ ID NO: 35); TARGPSFK (SEQ ID NO: 36); LSGRSDNH (SEQ ID NO: 37); GGWHTGRN (SEQ ID NO: 38); HTGRSGAL (SEQ ID NO: 39); PLTGRSGG (SEQ ID NO: 40); AARGPAIH (SEQ ID NO: 41); RGPAFNPM (SEQ ID NO: 42); SSRGPAYL (SEQ ID NO: 43); RGPATPIM (SEQ ID NO: 44); RGPA (SEQ ID NO: 45); GGQPSGMWGW (SEQ ID NO: 46); FPRPLGITGL (SEQ ID NO: 47); VHMPLGFLGP (SEQ ID NO: 48); SPLTGRSG (SEQ ID NO: 49); SAGFSLPA (SEQ ID NO: 126); LAPLGLQRR (SEQ ID NO: 50); SGG-PLGVR (SEQ ID NO: 51); PLGL (SEQ ID NO: 52); GPRSFGL (SEQ ID NO: 315) and/or GPRSFG (SEQ ID NO: 316).

In some embodiments, the CM2 comprises the amino acid sequence TGRGPSWV (SEQ ID NO: 34). In some embodiments, the CM2 comprises the amino acid sequence SARGPSRW (SEQ ID NO: 35). In some embodiments, the CM2 comprises the amino acid sequence TARGPSFK (SEQ ID NO: 36). In some embodiments, the CM2 comprises the amino acid sequence LSGRSDNH (SEQ ID NO: 37). In some embodiments, the CM2 comprises the amino acid sequence GGWHTGRN (SEQ ID NO: 38). In some embodiments, the CM2 comprises the amino acid sequence HTGRSGAL (SEQ ID NO: 39). In some embodiments, the CM2 comprises the amino acid sequence PLTGRSGG (SEQ ID NO: 40). In some embodiments, the CM2 comprises the amino acid sequence AARGPAIH (SEQ ID NO: 41). In some embodiments, the CM2 comprises the amino acid sequence RGPAFNPM (SEQ ID NO: 42). In some embodiments, the CM2 comprises the amino acid sequence SSRGPAYL (SEQ ID NO: 43). In some embodiments, the CM2 comprises the amino acid sequence RGPATPIM (SEQ ID NO: 44). In some embodiments, the CM2 comprises the amino acid sequence RGPA (SEQ ID NO: 45). In some embodiments, the CM2 comprises the amino acid sequence GGQPSGMWGW (SEQ ID NO: 46). In some embodiments, the CM2 comprises the amino acid sequence FPRPLGITGL (SEQ ID NO: 47). In some embodiments, the CM2 comprises the amino acid sequence VHMPLGFLGP (SEQ ID NO: 48). In some embodiments, the CM2 comprises the amino acid sequence SPLTGRSG (SEQ ID NO: 49). In some embodiments, the CM2 comprises the amino acid sequence LAPLGLQRR (SEQ ID NO: 50). In some embodiments, the CM2 comprises the amino acid sequence SGGPLGVR (SEQ ID NO: 51). In some embodiments, the CM2 comprises the amino acid sequence PLGL (SEQ ID NO: 52). In some embodiments, the CM2 comprises the amino acid sequence GPRSFGL (SEQ ID NO: 315). In some embodiments, the CM2 comprises the amino acid sequence GPRSFG (SEQ ID NO: 316).

In some embodiments, the CM2 is a substrate for at least one MMP. In some embodiments, the CM2 is a substrate for at least one MMP listed in the Table 7. In some embodiments, the CM2 is a substrate for MMP9. In some embodiments, the CM2 is a substrate for MMP14. In some embodiments, CM1 is substrate for a first MMP, and CM2 is a substrate for a second MMP, where the first MMP and the second MMP are different MMPs. In some embodiments, CM1 is a first substrate sequence for a MMP, and CM2 is a second substrate for the same MMP, where the CM1 and CM2 have different substrate sequences. In some embodiments, the CM2 is a substrate for two or more MMPs. In some embodiments, the CM2 is a substrate for at least MMP9 or MMP14. In some embodiments, the CM2 is a substrate for two or more MMPs. In some embodiments, the CM2 is a substrate for at least MMP9 and MMP14. In some embodiments, CM1 and CM2 are both substrates for MMP9. In some embodiments, CM1 and CM2 are both substrates for MMP14. In some embodiments, CM1 is a substrate for MMP9 and CM2 is a substrate for MMP14. In some embodiments, CM1 is a substrate for MMP14 and CM2 is a substrate for MMP9.

In some embodiments, at least one of CM1 and/or CM2 is a substrate for an MMP and includes the sequence ISSGLLSS (SEQ ID NO: 14); QNQALRMA (SEQ ID NO: 15); AQNLLGMV (SEQ ID NO: 16); STFPFGMF (SEQ ID NO: 17); PVGYTSSL (SEQ ID NO: 18); DWLYWPGI (SEQ ID NO: 19); MIAPVAYR (SEQ ID NO: 20); RPSPMWAY (SEQ ID NO: 21); WATPRPMR (SEQ ID NO: 22); FRLLDWQW (SEQ ID NO: 23); LKAAPRWA (SEQ ID NO: 24); GPSHLVLT (SEQ ID NO: 25); LPGGLSPW (SEQ ID NO: 26); MGLFSEAG (SEQ ID NO: 27); SPLPLRVP (SEQ ID NO: 28); RMHLRSLG (SEQ ID NO: 29); LAAPLGLL (SEQ ID NO: 30); AVGLLAPP (SEQ ID NO: 31); LLAPSHRA (SEQ ID NO: 32), PAGLWLDP (SEQ ID NO: 33); and/or ISSGLSS (SEQ ID NO: 159).

In some embodiments, the first cleaving agent and the second cleaving agent are the same protease, and the first CM and the second CM are different substrates for the enzyme. In some embodiments, the first cleaving agent and the second cleaving agent are different proteases. In some embodiments, the first cleaving agent and the second cleaving agent are co-localized in the target tissue. In some embodiments, the first CM and the second CM are cleaved by at least one cleaving agent in the target tissue.

In some embodiments, the agent conjugated to the AB is a therapeutic agent. In some embodiments, the agent is an antineoplastic agent. In some embodiments, the agent is a toxin or fragment thereof. As used herein, a fragment of a toxin is a fragment that retains toxic activity. In some embodiments, the agent is conjugated to the AB via a cleavable linker. In some embodiments, the agent is conjugated to the AB via a linker that includes at least one MMP-cleavable substrate sequence. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the agent is an anti-inflammatory agent.

In some embodiments, the antibody also includes a detectable moiety. In some embodiments, the detectable moiety is a diagnostic agent.

In some embodiments, the conjugated antibody and/or conjugated activatable antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or β-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the AB of the antibody naturally contains one or more disulfide bonds. In some embodiments, the AB can be engineered to include one or more disulfide bonds.

In some embodiments, the antibody and/or conjugated antibody is monospecific. In some embodiments, the antibody and/or conjugated antibody is multispecific, referred to herein as multispecific antibodies and/or conjugated multispecific antibodies. In some embodiments, the multispecific antibody and/or conjugated multispecific antibody is bispecific or trifunctional. In some embodiments, the antibody and/or conjugated antibody is formulated as part of a pro-Bispecific T Cell Engager (pro-BITE) molecule. In some embodiments, the antibody and/or conjugated antibody is formulated as part of a pro-Chimeric Antigen Receptor (pro-CAR) modified T cell or other engineered receptor.

In some embodiments, the activatable antibody and/or conjugated activatable antibody is monospecific. In some embodiments, the activatable antibody and/or conjugated activatable antibody is multispecific, referred to herein as multispecific activatable antibodies and/or conjugated multispecific activatable antibodies. As used herein, terms such as "activatable antibody" and all grammatical variations thereof, unless otherwise noted, are intended to encompass, but are not limited to embodiments where the activatable antibody is a multispecific activatable antibody of the disclosure. As used herein, terms such as "conjugated activatable antibody" and all grammatical variations thereof, unless otherwise noted, are intended to encompass, but are not limited to embodiments where the conjugated activatable antibody is a conjugated multispecific activatable antibody of the disclosure. In some embodiments, the multispecific activatable antibody and/or conjugated multispecific activatable antibody is bispecific or trifunctional. In some embodiments, the activatable antibody and/or conjugated activatable antibody is formulated as part of a pro-Bispecific T Cell Engager (pro-BITE) molecule. In some embodiments, the activatable antibody and/or conjugated activatable antibody is formulated as part of a pro-Chimeric Antigen Receptor (pro-CAR) modified T cell or other engineered receptor.

In some embodiments, the activatable antibodies, conjugated activatable antibodies, multispecific activatable antibodies, and/or conjugated multispecific activatable antibodies described herein are used in conjunction with one or more additional agents or a combination of additional agents. Suitable additional agents include current pharmaceutical and/or surgical therapies for an intended application, such as, for example, cancer. For example, the activatable antibodies, conjugated activatable antibodies, multispecific activatable antibodies, and/or conjugated multispecific activatable antibodies can be used in conjunction with an additional chemotherapeutic or anti-neoplastic agent.

The activatable antibodies described herein in an activated state bind a given target and include (i) an antibody or an antigen binding fragment thereof (AB) that specifically binds to the target; (ii) a masking moiety (MM) that inhibits the binding of the AB to the target in an uncleaved state; and (c) a cleavable moiety (CM) coupled to the AB, wherein the CM is a polypeptide that functions as a substrate for a matrix metalloprotease.

In some embodiments, the activatable antibody in the uncleaved state has the structural arrangement from N-terminus to C-terminus as follows: MM-CM-AB or AB-CM-MM.

In some embodiments, the activatable antibody comprises a linking peptide between the MM and the CM.

In some embodiments, the activatable antibody comprises a linking peptide between the CM and the AB.

In some embodiments, the activatable antibody comprises a first linking peptide (LP1) and a second linking peptide (LP2), and the activatable antibody in the uncleaved state has the structural arrangement from N-terminus to C-terminus as follows: MM-LP1-CM-LP2-AB or AB-LP2-CM-LP1-MM.

In some embodiments, each of LP1 and LP2 is a peptide of about 1 to 20 amino acids in length.

In some embodiments, the two linking peptides need not be identical to each other.

In some embodiments, at least one of LP1 or LP2 comprises an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one.

In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8).

In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 155), GSSGGSGGSG (SEQ ID NO: 156), or GSSGGSGGSGS (SEQ ID NO: 157).

In some embodiments, LP2 comprises the amino acid sequence GSS, GGS, GGGS (SEQ ID NO: 158), GSSGT (SEQ ID NO: 12) or GSSG (SEQ ID NO: 13).

In some embodiments, the AB has an equilibrium dissociation constant of about 100 nM or less for binding to the target.

In some embodiments, the activatable antibody includes an antibody or antigen-binding fragment thereof that specifically binds a target. In some embodiments, the antibody or immunologically active fragment thereof that binds the target is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an antibody or immunologically active fragment thereof that binds the target is a mouse, other rodent, chimeric, humanized or fully human monoclonal antibody.

In some embodiments, the activatable antibody is a multispecific activatable antibody. The multispecific activatable antibodies provided herein are multispecific antibodies that recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a cleavable moiety (CM) that functions as a substrate for at least one MMP protease. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 that sequence includes at least the amino acid sequence SYAMS (SEQ ID NO: 498); a VH CD2 sequence that includes at least the amino acid sequence SIDPEGRQTYYADSVKG (SEQ ID NO: 499); a VH CDR3 sequence that includes at least the amino acid sequence DIGGRSAFDY (SEQ ID NO: 500), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RASQSISSY (SEQ ID NO: 501); a VL CDR2 sequence that includes at least the amino acid sequence AASSLQS (SEQ ID NO: 502); a VL CDR3 sequence that includes at least the amino acid sequence QQTVVAPPL (SEQ ID NO: 503), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 498); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 499); a VH CDR3 sequence that includes a sequence that is at least 90%, 91%, 92%, 93%, 94%, 95%, 96%, 97%, 98%, 99% or more identical to the amino acid sequence DIGGRSAFDY (SEQ ID NO: 500), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 501); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 502); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 503), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes at least the amino acid sequence SYAMS (SEQ ID NO: 498); the VH CD2 sequence includes at least the amino acid sequence SIDPEGRQTYYADSVKG (SEQ ID NO: 499); the VH CDR3 sequence includes at least the amino acid sequence DIGGRSAFDY (SEQ ID NO: 500); the VL CDR1 sequence includes at least the amino acid sequence RASQSISSY (SEQ ID NO: 501); the VL CDR2 sequence includes at least the amino acid sequence AASSLQS (SEQ ID NO: 502); and the VL CDR3 sequence includes at least the amino acid sequence QQTVVAPPL (SEQ ID NO: 503).

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes a sequence that is at least 90%, 91%, 92%, 93%, 94%, 95%, 96%, 97%, 98%, 99% or more identical to the amino acid sequence SYAMS (SEQ ID NO: 498); the VH CD2 sequence includes a sequence that is at least 90%, 91%, 92%, 93%, 94%, 95%, 96%, 97%, 98%, 99% or more identical to the amino acid sequence SIDPEGRQTYYADSVKG (SEQ ID NO: 499); the VH CDR3 sequence includes a sequence that is at least 90%, 91%, 92%, 93%, 94%, 95%, 96%, 97%, 98%, 99% or more identical to the amino acid sequence DIGGRSAFDY (SEQ ID NO: 500); the VL CDR1 sequence includes a sequence that is at least 90%, 91%, 92%, 93%, 94%, 95%, 96%, 97%, 98%, 99% or more identical to the amino acid sequence RASQSISSY (SEQ ID NO: 501); the VL CDR2 sequence includes a sequence that is at least 90%, 91%, 92%, 93%, 94%, 95%, 96%, 97%, 98%, 99% or more identical to the amino acid sequence AASSLQS (SEQ ID NO: 502); and the VL CDR3 sequence includes a sequence that is at least 90%, 91%, 92%, 93%, 94%, 95%, 96%, 97%, 98%, 99% or more identical to the amino acid sequence QQTVVAPPL (SEQ ID NO: 503).

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds Epidermal Growth Factor Receptor (EGFR) and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes at least the amino acid sequence NYGVH (SEQ ID NO: 504); a VH CD2 sequence that includes at least the amino acid sequence VIWSGGNTDYNTPFTS (SEQ ID NO: 505); a VH CDR3 sequence that includes at least the amino acid sequence ALTYYDYEFAY (SEQ ID NO: 506); and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RASQSIGTNIH (SEQ ID NO: 507); a VL CDR2 sequence that includes at least the amino acid sequence KYASESIS (SEQ ID NO: 508); and a VL CDR3 sequence that includes at least the amino acid sequence QQNNNWPTT (SEQ ID NO: 509), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence NYGVH (SEQ ID NO: 504); a VH CD2 sequence that includes a sequence that is at least 90%, 91%, 92%, 93%, 94%, 95%, 96%, 97%, 98%, 99% or more identical to the amino acid sequence VIWSGGNTDYNTPFTS (SEQ ID NO: 505); a VH CDR3 sequence that includes a sequence that is at least 90%, 91%, 92%, 93%, 94%, 95%, 96%, 97%, 98%, 99% or more identical to the amino acid sequence ALTYYDYEFAY (SEQ ID NO: 506); and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RASQSIGTNIH (SEQ ID NO: 507); a VL CDR2 sequence that includes a sequence that is at least 90%, 91%, 92%, 93%, 94%, 95%, 96%, 97%, 98%, 99% or more identical to the amino acid sequence KYASESIS (SEQ ID NO: 508); and a VL CDR3 sequence that includes a sequence that is at least 90%, 91%, 92%, 93%, 94%, 95%, 96%, 97%, 98%, 99% or more identical to the amino acid sequence QQNNNWPTT (SEQ ID NO: 509), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes at least the amino acid sequence NYGVH (SEQ ID NO: 504); the VH CD2 sequence includes at least the amino acid sequence VIWSGGNTDYNTPFTS (SEQ ID NO: 505); the VH CDR3 sequence includes at least the amino acid sequence ALTYYDYEFAY (SEQ ID NO: 506); the VL CDR1 sequence includes at least the amino acid sequence RASQSIGTNIH (SEQ ID NO: 507); the VL CDR2 sequence includes at least the amino acid sequence KYASESIS (SEQ ID NO: 508); and the VL CDR3 sequence includes at least the amino acid sequence QQNNNWPTT (SEQ ID NO: 509).

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes a sequence that is at least 90%, 91%, 92%, 93%, 94%, 95%, 96%, 97%, 98%, 99% or more identical to the amino acid sequence NYGVH (SEQ ID NO: 504); the VH CD2 sequence includes a sequence that is at least 90%, 91%, 92%, 93%, 94%, 95%, 96%, 97%, 98%, 99% or more identical to the amino acid sequence VIWSGGNTDYNTPFTS (SEQ ID NO: 505); the VH CDR3 sequence includes a sequence that is at least 90%, 91%, 92%, 93%, 94%, 95%, 96%, 97%, 98%, 99% or more identical to the amino acid sequence ALTYYDYEFAY (SEQ ID NO: 506); the VL CDR1 sequence includes a sequence that is at least 90%, 91%, 92%, 93%, 94%, 95%, 96%, 97%, 98%, 99% or more identical to the amino acid sequence RASQSIGTNIH (SEQ ID NO: 507); the VL CDR2 sequence includes a sequence that is at least 90%, 91%, 92%, 93%, 94%, 95%, 96%, 97%, 98%, 99% or more identical to the amino acid sequence KYASESIS (SEQ ID NO: 508); and the VL CDR3 sequence includes a sequence that is at least 90%, 91%, 92%, 93%, 94%, 95%, 96%, 97%, 98%, 99% or more identical to the amino acid sequence QQNNNWPTT (SEQ ID NO: 509).

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence selected from the group consisting of SEQ ID NOs: 54, 56, 57, 58, 61, 63, 65, 68, 70, 72, 76, 78, 80, 82, 84, 86, 88, 90, 92, 94, 96, 98, 100, 102, 104, 106, 108, 110, 112, and 114. In some embodiments, the activatable antibody and/or conjugated activatable antibody provided herein, including but not limited to a multispecific activatable antibody and/or conjugated multispecific activatable antibody of the disclosure, includes at least a light chain amino acid sequence selected from the group consisting of SEQ ID NOs: 55, 59, 60, 62, 64, 67, 69, 71, 73, 75, 77, 79, 81, 83, 85, 87, 89, 91, 93, 95, 97, 99, 101, 103, 105, 107, 109, 111, and 113. In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence selected from the group consisting of SEQ ID NOs: 54, 56, 57, 58, 61, 63, 65, 68, 70, 72, 76, 78, 80, 82, 84, 86, 88, 90, 92, 94, 96, 98, 100, 102, 104, 106, 108, 110, 112, and 114 and a light chain amino acid sequence selected from the group consisting of SEQ ID NOs: 55, 59, 60, 62, 64, 67, 69, 71, 73, 75, 77, 79, 81, 83, 85, 87, 89, 91, 93, 95, 97, 99, 101, 103, 105, 107, 109, 111, and 113.

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence that is at least 90%, 91%, 92%, 93%, 94%, 95%, 96%, 97%, 98%, 99% or more identical to an amino acid sequence selected from the group consisting of SEQ ID NOs: 54, 56, 57, 58, 61, 63, 65, 68, 70, 72, 76, 78, 80, 82, 84, 86, 88, 90, 92, 94, 96, 98, 100, 102, 104, 106, 108, 110, 112, and 114. In some embodiments, the activatable antibody and/or conjugated activatable antibody provided herein, including but not limited to a multispecific activatable antibody and/or conjugated multispecific activatable antibody of the disclosure, includes at least a light chain amino acid sequence that is at least 90%, 91%, 92%, 93%, 94%, 95%, 96%, 97%, 98%, 99% or more identical to an amino acid sequence selected from the group consisting of SEQ ID NOs: 55, 59, 60, 62, 64, 67, 69, 71, 73, 75, 77, 79, 81, 83, 85, 87, 89, 91, 93, 95, 97, 99, 101, 103, 105, 107, 109, 111, and 113. In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence that is at least 90%, 91%, 92%, 93%, 94%, 95%, 96%, 97%, 98%, 99% or more identical to an amino acid sequence selected from the group consisting of SEQ ID NOs: 54, 56, 57, 58, 61, 63, 65, 68, 70, 72, 76, 78, 80, 82, 84, 86, 88, 90, 92, 94, 96, 98, 100, 102, 104, 106, 108, 110, 112, and 114 and a light chain amino acid sequence that is at least 90%, 91%, 92%, 93%, 94%, 95%, 96%, 97%, 98%, 99% or more identical to an amino acid sequence selected from the group consisting of SEQ ID NOs: 55, 59, 60, 62, 64, 67, 69, 71, 73, 75, 77, 79, 81, 83, 85, 87, 89, 91, 93, 95, 97, 99, 101, 103, 105, 107, 109, 111, and 113.

In some embodiments, the MM has an equilibrium dissociation constant for binding to the AB that is greater than the equilibrium dissociation constant of the AB to the target.

In some embodiments, the MM has an equilibrium dissociation constant for binding to the AB that is no more than the equilibrium dissociation constant of the AB to the target.

In some embodiments, the MM does not interfere or compete with the AB for binding to the target in a cleaved state.

In some embodiments, the MM is a polypeptide of about 2 to 40 amino acids in length. For example, the MM is a polypeptide of up to about 40 amino acids in length.

In some embodiments, the MM polypeptide sequence is different from that of any natural binding partner of the AB. In some embodiments, the MM polypeptide sequence is no more than 50% identical to any natural binding partner of the AB. In some embodiments, the MM polypeptide sequence is no more than 40%, 30%, 25%, 20%, 15%, or 10% identical to any natural binding partner of the AB.

In some embodiments, the coupling of the MM to the AB reduces the ability of the AB to bind its target such that the dissociation constant ($K_d$) of the AB when coupled to the MM towards the target is at least two times greater than the $K_d$ of the AB when not coupled to the MM towards the target.

In some embodiments, the coupling of the MM to the AB reduces the ability of the AB to bind its target such that the dissociation constant ($K_d$) of the AB when coupled to the MM towards the target is at least three times greater than the $K_d$ of the AB when not coupled to the MM towards the target.

In some embodiments, the coupling of the MM to the AB reduces the ability of the AB to bind its target such that the dissociation constant ($K_d$) of the AB when coupled to the MM towards the target is at least five times greater than the $K_d$ of the AB when not coupled to the MM towards the target.

In some embodiments, the coupling of the MM to the AB reduces the ability of the AB to bind its target such that the dissociation constant ($K_d$) of the AB when coupled to the MM towards the target is at least 10 times greater than the $K_d$ of the AB when not coupled to the MM towards the target.

In some embodiments, the coupling of the MM to the AB reduces the ability of the AB to bind its target such that the dissociation constant ($K_d$) of the AB when coupled to the MM towards the target is at least 20 times greater than the $K_d$ of the AB when not coupled to the MM towards the target.

In some embodiments, the coupling of the MM to the AB reduces the ability of the AB to bind the target such that the dissociation constant ($K_d$) of the AB when coupled to the MM towards the target is at least 40 times greater than the $K_d$ of the AB when not coupled to the MM towards the target.

In some embodiments, the coupling of the MM to the AB reduces the ability of the AB to bind the target such that the dissociation constant ($K_d$) of the AB when coupled to the MM towards the target is at least 100 times greater than the $K_d$ of the AB when not coupled to the MM towards the target.

In some embodiments, the coupling of the MM to the AB reduces the ability of the AB to bind the target such that the dissociation constant ($K_d$) of the AB when coupled to the MM towards the target is at least 1000 times greater than the $K_d$ of the AB when not coupled to the MM towards the target.

In some embodiments, the coupling of the MM to the AB reduces the ability of the AB to bind the target such that the dissociation constant ($K_d$) of the AB when coupled to the MM towards the target is at least 10,000 times greater than the $K_d$ of the AB when not coupled to the MM towards the target.

In some embodiments, the MMP protease is co-localized with the target in a tissue, and the MMP cleaves the CM in the activatable antibody when the activatable antibody is exposed to the MMP.

In some embodiments, in the presence of the target, the MM reduces the ability of the AB to bind the target by at least 90% when the CM is uncleaved, as compared to when the CM is cleaved when assayed in vitro using a target displacement assay such as, for example, the assay described in PCT Publication Nos. WO 2009/025846 and WO 2010/081173.

In some embodiments, the CM is positioned in the activatable antibody such that in the uncleaved state, binding of the activatable antibody to the target is reduced to occur with an equilibrium dissociation constant that is at least twofold greater than the equilibrium dissociation constant of an unmodified AB binding to the target, whereas in the cleaved state (i.e., when the activatable antibody is in the cleaved state), the AB binds the target.

In some embodiments, the CM is positioned in the activatable antibody such that in the uncleaved state, binding of the activatable antibody to the target is reduced to occur with an equilibrium dissociation constant that is at least five-fold greater than the equilibrium dissociation constant of an unmodified AB binding to the target, whereas in the cleaved state (i.e., when the activatable antibody is in the cleaved state), the AB binds the target.

In some embodiments, the CM is positioned in the activatable antibody such that in the uncleaved state, binding of the activatable antibody to the target is reduced to occur with an equilibrium dissociation constant that is at least ten-fold greater than the equilibrium dissociation constant of an unmodified AB binding to the target, whereas in the cleaved state (i.e., when the activatable antibody is in the cleaved state), the AB binds the target.

In some embodiments, the CM is positioned in the activatable antibody such that in the uncleaved state, binding of the activatable antibody to the target is reduced to occur with an equilibrium dissociation constant that is at least 20-fold greater than the equilibrium dissociation constant of an unmodified AB binding to the target, whereas in the cleaved state (i.e., when the activatable antibody is in the cleaved state), the AB binds the target.

In some embodiments, the CM is positioned in the activatable antibody such that in the uncleaved state, binding of the activatable antibody to the target is reduced to occur with an equilibrium dissociation constant that is at least 40-fold greater than the equilibrium dissociation constant of an unmodified AB binding to the target, whereas in the cleaved state, the AB binds the target.

In some embodiments, the CM is positioned in the activatable antibody such that in the uncleaved state, binding of the activatable antibody to the target is reduced to occur with an equilibrium dissociation constant that is at least 50-fold greater than the equilibrium dissociation constant of an unmodified AB binding to the target, whereas in the cleaved state, the AB binds the target.

In some embodiments, the CM is positioned in the activatable antibody such that in the uncleaved state, binding of the activatable antibody to the target is reduced to occur with an equilibrium dissociation constant that is at least 100-fold greater than the equilibrium dissociation constant of an unmodified AB binding to the target, whereas in the cleaved state, the AB binds the target.

In some embodiments, the CM is positioned in the activatable antibody such that in the uncleaved state, binding of the activatable antibody to the target is reduced to occur with an equilibrium dissociation constant that is at least 200-fold greater than the equilibrium dissociation constant of an unmodified AB binding to the target, whereas in the cleaved state, the AB binds the target.

In some embodiments, the CM is a polypeptide of up to 15 amino acids in length.

In some embodiments, the CM is a substrate for at least one matrix metalloprotease (MMP). Examples of MMPs include MMP1; MMP2; MMP3; MMP7; MMP8; MMP9; MMP10; MMP11; MMP12; MMP13; MMP14; MMP15; MMP16; MMP17; MMP19; MMP20; MMP23; MMP24; MMP26; and MMP27. In some embodiments, the CM is a substrate for MMP9, MMP14, MMP1, MMP3, MMP13, MMP17, MMP11, and MMP19. In some embodiments, the CM is a substrate for MMP9. In some embodiments, the CM is a substrate for MMP14. In some embodiments, the CM is a substrate for two or more MMPs. In some embodiments, the CM is a substrate for at least MMP9 and MMP14. In some embodiments, the CM comprises two or more substrates for the same MMP. In some embodiments, the CM comprises at least two or more MMP9 substrates. In some embodiments, the CM comprises at least two or more MMP14 substrates.

In some embodiments, the CM is a substrate for an MMP and includes the sequence ISSGLLSS (SEQ ID NO: 14); QNQALRMA (SEQ ID NO: 15); AQNLLGMV (SEQ ID NO: 16); STFPFGMF (SEQ ID NO: 17); PVGYTSSL (SEQ ID NO: 18); DWLYWPGI (SEQ ID NO: 19); MIAPVAYR (SEQ ID NO: 20); RPSPMWAY (SEQ ID NO: 21); WATPRPMR (SEQ ID NO: 22); FRLLDWQW (SEQ ID NO: 23); LKAAPRWA (SEQ ID NO: 24); GPSHLVLT (SEQ ID NO: 25); LPGGLSPW (SEQ ID NO: 26); MGLFSEAG (SEQ ID NO: 27); SPLPLRVP (SEQ ID NO: 28); RMHLRSLG (SEQ ID NO: 29); LAAPLGLL (SEQ ID NO: 30); AVGLLAPP (SEQ ID NO: 31); LLAPSHRA (SEQ ID NO: 32), PAGLWLDP (SEQ ID NO: 33); and/or ISSGLSS (SEQ ID NO: 159).

In some embodiments, the CM comprises the amino acid sequence ISSGLLSS (SEQ ID NO: 14). In some embodiments, the CM comprises the amino acid sequence QNQALRMA (SEQ ID NO: 15). In some embodiments, the CM comprises the amino acid sequence AQNLLGMV (SEQ ID NO: 16). In some embodiments, the CM comprises the amino acid sequence STFPFGMF (SEQ ID NO: 17). In some embodiments, the CM comprises the amino acid sequence PVGYTSSL (SEQ ID NO: 18). In some embodiments, the CM comprises the amino acid sequence DWLYWPGI (SEQ ID NO: 19). In some embodiments, the CM comprises the amino acid sequence MIAPVAYR (SEQ ID NO: 20). In some embodiments, the CM comprises the amino acid sequence RPSPMWAY (SEQ ID NO: 21). In some embodiments, the CM comprises the amino acid sequence WATPRPMR (SEQ ID NO: 22). In some embodiments, the CM comprises the amino acid sequence FRLLDWQW (SEQ ID NO: 23). In some embodiments, the CM comprises the amino acid sequence LKAAPRWA (SEQ ID NO: 24). In some embodiments, the CM comprises the amino acid sequence GPSHLVLT (SEQ ID NO: 25). In some embodiments, the CM comprises the amino acid sequence LPGGLSPW (SEQ ID NO: 26). In some embodiments, the CM comprises the amino acid sequence MGLFSEAG (SEQ ID NO: 27). In some embodiments, the CM comprises the amino acid sequence SPLPLRVP (SEQ ID NO: 28). In some embodiments, the CM comprises the amino acid sequence RMHLRSLG (SEQ ID NO: 29). In some embodiments, the CM comprises the amino acid sequence LAAPLGLL (SEQ ID NO: 30). In some embodiments, the CM comprises the amino acid sequence AVGLLAPP (SEQ ID NO: 31). In some embodiments, the CM comprises the amino acid sequence LLAPSHRA (SEQ ID NO: 32). In some embodiments, the CM comprises the amino acid sequence PAGLWLDP (SEQ ID NO: 33). In some embodiments, the CM comprises the amino acid sequence ISSGLSS (SEQ ID NO: 159).

In some embodiments, the CM is a substrate for at least two proteases. In some embodiments, at least one protease is an MMP and at least one protease is selected from the group consisting of those shown in Table 7.

In some embodiments, the activatable antibody includes at least a first CM and a second CM. In some embodiments, the first CM and the second CM are each polypeptides of no more than 15 amino acids long. In some embodiments, the first CM and the second CM in the activatable antibody have the structural arrangement from N-terminus to C-terminus as follows in the uncleaved state: MM-CM1-CM2-AB, AB-CM2-CM1-MM, MM-CM2-CM1-AB, or AB-CM1-CM2-MM. In some embodiments, the activatable antibody includes a linking peptide between MM and CM1. In some embodiments, the activatable antibody includes a linking peptide between CM1 and CM2. In some embodiments, the activatable antibody includes a linking peptide between CM2 and AB. In some embodiments, the activatable antibody includes a linking peptide between MM and CM1 and a linking peptide between CM2 and AB. In some embodiments, the activatable antibody includes a linking peptide between MM and CM1 and a linking peptide between CM1 and CM2. In some embodiments, the activatable antibody includes a linking peptide between CM1 and CM2 and a linking peptide between CM2 and AB. In some embodiments, the activatable antibody includes a linking peptide between MM and CM1, a linking peptide between CM1 and CM2, and a linking peptide between CM2 and AB.

In some embodiments, the activatable antibody includes at least a first CM that includes a substrate for at least one matrix metalloprotease (MMP) and a second CM that includes a substrate sequence. Exemplary substrates for the second CM (CM2) include but are not limited to substrates cleavable by one or more of the following enzymes or proteases listed in Table 7.

In some embodiments, the CM2 is selected for use with a specific protease. In some embodiments, the CM2 is a substrate for at least one protease selected from the group consisting of a matrix metalloprotease (MMP), a neutrophil elastase, u-type plasminogen activator (uPA, also referred to as urokinase), legumain, matriptase (MT-SP1), thrombin, a cysteine protease such as a cathepsin, ADAM17, BMP-1, HtrA1, and a TMPRSS such as TMPRSS3 or TMPRSS4.

In some embodiments, the CM2 is a substrate for a neutrophil elastase. In some embodiments, the CM2 is a substrate for uPA. In some embodiments, the CM2 is a substrate for legumain. In some embodiments, the CM2 is a substrate for matriptase. In some embodiments, the CM2 is a substrate for thrombin. In some embodiments, the CM2 is a substrate for a cysteine protease. In some embodiments, the CM2 is a substrate for a cathepsin. In some embodiments, the CM2 is a substrate for ADAM17. In some embodiments, the CM2 is a substrate for BMP-1. In some embodiments, the CM2 is a substrate for HtrA1. In some embodiments, the CM2 is a substrate for a TMPRSS. In some embodiments, the CM2 is a substrate for TMPRSS3. In some embodiments, the CM2 is a substrate for TMPRSS4.

For example, suitable CM2 are cleaved by at least one protease and include the sequence TGRGPSWV (SEQ ID NO: 34); SARGPSRW (SEQ ID NO: 35); TARGPSFK (SEQ ID NO: 36); LSGRSDNH (SEQ ID NO: 37); GGWHTGRN (SEQ ID NO: 38); HTGRSGAL (SEQ ID NO: 39); PLTGRSGG (SEQ ID NO: 40); AARGPAIH (SEQ ID NO: 41); RGPAFNPM (SEQ ID NO: 42); SSRGPAYL (SEQ ID NO: 43); RGPATPIM (SEQ ID NO: 44); RGPA (SEQ ID NO: 45); GGQPSGMWGW (SEQ ID NO: 46); FPRPLGITGL (SEQ ID NO: 47); VHMPLGFLGP (SEQ ID NO: 48); SPLTGRSG (SEQ ID NO: 49); SAGFSLPA (SEQ ID NO: 126); LAPLGLQRR (SEQ ID NO: 50); SGGPLGVR (SEQ ID NO: 51); PLGL (SEQ ID NO: 52); GPRSFGL (SEQ ID NO: 315) and/or GPRSFG (SEQ ID NO: 316).

In some embodiments, the CM2 comprises the amino acid sequence TGRGPSWV (SEQ ID NO: 34). In some embodiments, the CM2 comprises the amino acid sequence SARGPSRW (SEQ ID NO: 35). In some embodiments, the CM2 comprises the amino acid sequence TARGPSFK (SEQ ID NO: 36). In some embodiments, the CM2 comprises the amino acid sequence LSGRSDNH (SEQ ID NO: 37). In some embodiments, the CM2 comprises the amino acid sequence GGWHTGRN (SEQ ID NO: 38). In some embodiments, the CM2 comprises the amino acid sequence HTGRSGAL (SEQ ID NO: 39). In some embodiments, the CM2 comprises the amino acid sequence PLTGRSGG (SEQ ID NO: 40). In some embodiments, the CM2 comprises the amino acid sequence AARGPAIH (SEQ ID NO: 41). In some embodiments, the CM2 comprises the amino acid sequence RGPAFNPM (SEQ ID NO: 42). In some embodiments, the CM2 comprises the amino acid sequence SSRGPAYL (SEQ ID NO: 43). In some embodiments, the CM2 comprises the amino acid sequence RGPATPIM (SEQ ID NO: 44). In some embodiments, the CM2 comprises the amino acid sequence RGPA (SEQ ID NO: 45). In some embodiments, the CM2 comprises the amino acid sequence GGQPSGMWGW (SEQ ID NO: 46). In some embodiments, the CM2 comprises the amino acid sequence FPRPLGITGL (SEQ ID NO: 47). In some embodiments, the CM2 comprises the amino acid sequence VHMPLGFLGP (SEQ ID NO: 48). In some embodiments, the CM2 comprises the amino acid sequence SPLTGRSG (SEQ ID NO: 49). In some embodiments, the CM2 comprises the amino acid sequence LAPLGLQRR (SEQ ID NO: 50). In some embodiments, the CM2 comprises the amino acid sequence SGGPLGVR (SEQ ID NO: 51). In some embodiments, the CM2 comprises the amino acid sequence PLGL (SEQ ID NO: 52). In some embodiments, the CM2 comprises the amino acid sequence GPRSFGL (SEQ ID NO: 315). In some embodiments, the CM2 comprises the amino acid sequence GPRSFG (SEQ ID NO: 316)

In some embodiments, the CM2 is a substrate for at least one MMP. In some embodiments, the CM2 is a substrate for at least one MMP listed in the Table 7. In some embodiments, the CM2 is a substrate for MMP9. In some embodiments, the CM2 is a substrate for MMP14. In some embodiments, CM1 is substrate for a first MMP, and CM2 is a substrate for a second MMP, where the first MMP and the second MMP are different MMPs. In some embodiments, CM1 is a first substrate sequence for a MMP, and CM2 is a second substrate for the same MMP, where the CM1 and CM2 have different substrate sequences. In some embodiments, the CM2 is a substrate for two or more MMPs. In some embodiments, the CM2 is a substrate for at least MMP9 or MMP14. In some embodiments, the CM2 is a substrate for two or more MMPs. In some embodiments, the CM2 is a substrate for at least MMP9 and MMP14. In some embodiments, CM1 and CM2 are both substrates for MMP9. In some embodiments, CM1 and CM2 are both substrates for MMP14. In some embodiments, CM1 is a substrate for MMP9 and CM2 is a substrate for MMP14. In some embodiments, CM1 is a substrate for MMP14 and CM2 is a substrate for MMP9.

In some embodiments, at least one of CM1 and/or CM2 is a substrate for an MMP and includes the sequence ISSGLLSS (SEQ ID NO: 14); QNQALRMA (SEQ ID NO: 15); AQNLLGMV (SEQ ID NO: 16); STFPFGMF (SEQ ID NO: 17); PVGYTSSL (SEQ ID NO: 18); DWLYWPGI (SEQ ID NO: 19); MIAPVAYR (SEQ ID NO: 20); RPSPMWAY (SEQ ID NO: 21); WATPRPMR (SEQ ID NO: 22); FRLLDWQW (SEQ ID NO: 23); LKAAPRWA (SEQ ID NO: 24); GPSHLVLT (SEQ ID NO: 25); LPGGLSPW (SEQ ID NO: 26); MGLFSEAG (SEQ ID NO: 27); SPLPLRVP (SEQ ID NO: 28); RMHLRSLG (SEQ ID NO: 29); LAAPLGLL (SEQ ID NO: 30); AVGLLAPP (SEQ ID NO: 31); LLAPSHRA (SEQ ID NO: 32), PAGLWLDP (SEQ ID NO: 33); and/or ISSGLSS (SEQ ID NO: 159).

In some embodiments, the first cleaving agent and the second cleaving agent are the same matrix metalloprotease, and the first CM and the second CM are different substrates for the enzyme. In some embodiments, the first cleaving agent and the second cleaving agent are different proteases, where at least one protease is an MMP. In some embodiments, the first cleaving agent and the second cleaving agent are co-localized in the target tissue. In some embodiments, the first CM and the second CM are cleaved by at least one cleaving agent in the target tissue.

In some embodiments, the activatable antibody is exposed to and cleaved by a MMP such that, in the activated or cleaved state, the activated antibody includes a light chain amino acid sequence that includes at least a portion of LP2 and/or CM sequence after the MMP has cleaved the CM.

In some embodiments, the CM comprises the non-prime side of the protease cleavage site; that is, the CM comprises at least the P1 and P2 amino acids, and in some embodiments, comprises the P1, P2 and P3 amino acids and in some embodiments, comprises the P1, P2, P3, and P4 amino acids. In some embodiments, the CM comprises the non-prime side and the prime side of the protease cleavage site. In some embodiments, the CM comprises the non-prime side but lacks at least part of the prime side of the protease cleavage site. In some embodiments, the CM comprises the non-prime side but lacks the prime side of the protease cleavage site. Such a CM can be linked directly or through a linker to an antibody or other molecule as disclosed herein, such as, but not limited to, a detection moiety.

In some embodiments, the activatable antibody is an anti-EGFR activatable antibody that includes at least an AB that is or is derived from cetuximab or panitumumab; a MM comprising an amino acid sequence selected from the group consisting of SEQ ID NOS: 160, 167-200, and 497; and a CM comprising an amino acid sequence selected from the group consisting of SEQ ID NO: 14-33, and 159. In some embodiments, the activatable antibody is an anti-EGFR activatable antibody that includes at least an AB that is or is derived from cetuximab or panitumumab; a MM comprising an amino acid sequence selected from the group consisting of SEQ ID NOs: 160, 167-200, and 497; and a CM comprising an amino acid sequence selected from the group consisting of the sequences presented in Tables 8A-8M. In some embodiments, the anti-EGFR activatable antibody also includes a first linking peptide (LP1) and a second linking peptide (LP2), and the activatable antibody in the uncleaved state has the structural arrangement from N-terminus to C-terminus as follows: MM-LP1-CM-LP2-AB or AB-LP2-CM-LP1-MM. In some embodiments, each of LP1 and LP2 is a peptide of about 1 to 20 amino acids in length. In some embodiments, the two linking peptides need not be identical to each other. In some embodiments, at least one of LP1 or LP2 comprises an amino acid sequence selected from the group consisting of (GS), $(GGS)_n$, $(GSGGS)_n$ (SEQ ID NO: 1) and $(GGGS)_n$ (SEQ ID NO: 2), where n is an integer of at least one. In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8). In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 155), GSSGGSGGSG (SEQ ID NO: 156), or GSSGGSGGSGS (SEQ ID NO: 157). In some embodiments, LP2 comprises the amino acid sequence GSS, GGS, GGGS (SEQ ID NO: 158), GSSGT (SEQ ID NO: 12) or GSSG (SEQ ID NO: 13).

In some embodiments, the activatable antibody is an anti-EGFR activatable antibody that includes at least an AB comprising a heavy chain amino acid sequence comprising the VH CDR1 sequence of SEQ ID NO: 504, the VH CDR2 sequence of SEQ ID NO: 505, the VH CDR3 sequence of SEQ ID NO: 506, the VL CDR1 sequence of SEQ ID NO: 507, the VL CDR2 sequence of SEQ ID NO: 508, and the VL CDR2 sequence of SEQ ID NO: 509; a MM comprising an amino acid sequence selected from the group consisting of SEQ ID NOs: 160, 167-200, and 497; and a CM comprising an amino acid sequence selected from the group consisting of SEQ ID NO: 14-33, and 159. In some embodiments, the activatable antibody is an anti-EGFR activatable antibody that includes at least an AB comprising a heavy chain amino acid sequence comprising the VH CDR1 sequence of SEQ ID NO: 504, the VH CDR2 sequence of SEQ ID NO: 505, the VH CDR3 sequence of SEQ ID NO: 506, the VL CDR1 sequence of SEQ ID NO: 507, the VL CDR2 sequence of SEQ ID NO: 508, and the VL CDR2 sequence of SEQ ID NO: 509; a MM comprising an amino acid sequence selected from the group consisting of SEQ ID NOs: 160, 167-200, and 497; and a CM comprising an amino acid sequence selected from the group consisting of the sequences presented in Tables 8A-8M. In some embodiments, the anti-EGFR activatable antibody also includes a first linking peptide (LP1) and a second linking peptide (LP2), and the activatable antibody in the uncleaved state has the structural arrangement from N-terminus to C-terminus as follows: MM-LP1-CM-LP2-AB or AB-LP2-CM-LP1-MM. In some embodiments, each of LP1 and LP2 is a peptide of about 1 to 20 amino acids in length. In some embodiments, the two linking peptides need not be identical to each other. In some embodiments, at least one of LP1 or LP2 comprises an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one. In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8). In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 155), GSSGGSGGSG (SEQ ID NO: 156), or GSSGGSGGSGS (SEQ ID NO: 157). In some embodiments, LP2 comprises the amino acid sequence GSS, GGS, GGGS (SEQ ID NO: 158), GSSGT (SEQ ID NO: 12) or GSSG (SEQ ID NO: 13).

In some embodiments, the activatable antibody is an anti-EGFR activatable antibody that includes at least an AB comprising the heavy chain amino acid sequence of SEQ ID NO: 56, 57 or 58 and the light chain amino acid sequence of SEQ ID NO: 59; a MM comprising an amino acid sequence selected from the group consisting of SEQ ID NOs: 160, 167-200, and 497; and a CM comprising an amino acid sequence selected from the group consisting of SEQ ID NO: 14-33, and 159. In some embodiments, the activatable antibody is an anti-EGFR activatable antibody that includes at least an AB comprising the heavy chain amino acid sequence of SEQ ID NO: 56, 57 or 58 and the light chain amino acid sequence of SEQ ID NO: 59; a MM comprising an amino acid sequence selected from the group consisting of SEQ ID NOs: 160, 167-200, and 497; and a CM comprising an amino acid sequence selected from the group consisting of the sequences presented in Tables 8A-8M. In some embodiments, the anti-EGFR activatable antibody also includes a first linking peptide (LP1) and a second linking peptide (LP2), and the activatable antibody in the uncleaved state has the structural arrangement from N-terminus to C-terminus as follows: MM-LP1-CM-LP2-AB or AB-LP2-CM-LP1-MM. In some embodiments, each of LP1 and LP2 is a peptide of about 1 to 20 amino acids in length. In some embodiments, the two linking peptides need not be identical to each other. In some embodiments, at least one of LP1 or LP2 comprises an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one. In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8). In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 155), GSSGGSGGSG (SEQ ID NO: 156), or GSSGGSGGSGS (SEQ ID NO: 157). In some embodiments, LP2 comprises the amino acid sequence GSS, GGS, GGGS (SEQ ID NO: 158), GSSGT (SEQ ID NO: 12) or GSSG (SEQ ID NO: 13).

In some embodiments, the activatable antibody is an anti-EGFR activatable antibody that includes at least an AB comprising the heavy chain amino acid sequence of SEQ ID NO: 56 and the light chain amino acid sequence of SEQ ID NO: 59; a MM comprising the amino acid sequence of SEQ ID NO: 160; and a CM comprising an amino acid sequence selected from the group consisting of SEQ ID NO: 14-33, and 159. In some embodiments, the activatable antibody is an anti-EGFR activatable antibody that includes at least an AB comprising the heavy chain amino acid sequence of SEQ ID NO: 56 and the light chain amino acid sequence of SEQ ID NO: 59; a MM comprising the amino acid sequence of SEQ ID NO: 160; and a CM comprising an amino acid sequence selected from the group consisting of the sequences presented in Tables 8A-8M. In some embodiments, the anti-EGFR activatable antibody also includes a first linking peptide (LP1) and a second linking peptide (LP2), and the activatable antibody in the uncleaved state has the structural arrangement from N-terminus to C-terminus as follows: MM-LP1-CM-LP2-AB or AB-LP2-CM-LP1-MM. In some embodiments, each of LP1 and LP2 is a peptide of about 1 to 20 amino acids in length. In some embodiments, the two linking peptides need not be identical to each other. In some embodiments, at least one of LP1 or LP2 comprises an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one. In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8). In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 155), GSSGGSGGSG (SEQ ID NO: 156), or GSSGGSGGSGS (SEQ ID NO: 157). In some embodiments, LP2 comprises the amino acid sequence GSS, GGS, GGGS (SEQ ID NO: 158), GSSGT (SEQ ID NO: 12) or GSSG (SEQ ID NO: 13).

In some embodiments, the activatable antibody is an anti-EGFR activatable antibody that includes at least an AB comprising a heavy chain amino acid sequence comprising the VH CDR1 sequence of SEQ ID NO: 504, the VH CDR2 sequence of SEQ ID NO: 505, the VH CDR3 sequence of SEQ ID NO: 506, the VL CDR1 sequence of SEQ ID NO: 507, the VL CDR2 sequence of SEQ ID NO: 508, and the VL CDR2 sequence of SEQ ID NO: 509; a MM comprising the amino acid sequence of SEQ ID NO: 160; and a CM comprising an amino acid sequence selected from the group consisting of SEQ ID NO: 14-33, and 159. In some embodiments, the activatable antibody is an anti-EGFR activatable antibody that includes at least an AB comprising a heavy chain amino acid sequence comprising the VH CDR1 sequence of SEQ ID NO: 504, the VH CDR2 sequence of SEQ ID NO: 505, the VH CDR3 sequence of SEQ ID NO: 506, the VL CDR1 sequence of SEQ ID NO: 507, the VL CDR2 sequence of SEQ ID NO: 508, and the VL CDR2 sequence of SEQ ID NO: 509; a MM comprising the amino acid sequence of SEQ ID NO: 160; and a CM comprising an amino acid sequence selected from the group consisting of the sequences presented in Tables 8A-8M. In some embodiments, the anti-EGFR activatable antibody also includes a first linking peptide (LP1) and a second linking peptide (LP2), and the activatable antibody in the uncleaved state has the structural arrangement from N-terminus to C-terminus as follows: MM-LP1-CM-LP2-AB or AB-LP2-CM-LP1-MM. In some embodiments, each of LP1 and LP2 is a peptide of about 1 to 20 amino acids in length. In some embodiments, the two linking peptides need not be identical to each other. In some embodiments, at least one of LP1 or LP2 comprises an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one. In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8). In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 155), GSSGGSGGSG (SEQ ID NO: 156), or GSSGGSGGSGS (SEQ ID NO: 157). In some embodiments, LP2 comprises the amino acid sequence GSS, GGS, GGGS (SEQ ID NO: 158), GSSGT (SEQ ID NO: 12) or GSSG (SEQ ID NO: 13).

In some embodiments, the activatable antibody is an anti-Jagged activatable antibody that includes at least an AB comprising the heavy chain amino acid sequence of SEQ ID NO: 61, 63, 65, 68, 70, 72, 76, 78, 80, 82, 84, 86, 88, 90, 92, 94, 96, 98, 100, 102, 104, 106, 108, 110, 112, or 114 and the light chain amino acid sequence of SEQ ID NO: 60, 62, 64, 67, 69, 71, 73, 75, 77, 79, 81, 83, 85, 87, 89, 91, 93, 95, 97, 99, 101, 103, 105, 107, 109, 111, or 113; a MM comprising an amino acid sequence selected from the group consisting of SEQ ID NOs: 201-263, and 496; and a CM comprising an amino acid sequence selected from the group consisting of SEQ ID NO: 14-33, and 159. In some embodiments, the activatable antibody is an anti-Jagged activatable antibody that includes at least an AB comprising the heavy chain amino acid sequence of SEQ ID NO: 61, 63, 65, 68, 70, 72, 76, 78, 80, 82, 84, 86, 88, 90, 92, 94, 96, 98, 100, 102, 104, 106, 108, 110, 112, or 114 and the light chain amino acid sequence of SEQ ID NO: 60, 62, 64, 67, 69, 71, 73, 75, 77, 79, 81, 83, 85, 87, 89, 91, 93, 95, 97, 99, 101, 103, 105, 107, 109, 111, or 113; a MM comprising an amino acid sequence selected from the group consisting of SEQ ID NOs: 201-263, and 496; and a CM comprising an amino acid sequence selected from the group consisting of the sequences presented in Tables 8A-8M. In some embodiments, the anti-Jagged activatable antibody also includes a first linking peptide (LP1) and a second linking peptide (LP2), and the activatable antibody in the uncleaved state has the structural arrangement from N-terminus to C-terminus as follows: MM-LP1-CM-LP2-AB or AB-LP2-CM-LP1-MM. In some embodiments, each of LP1 and LP2 is a peptide of about 1 to 20 amino acids in length. In some embodiments, the two linking peptides need not be identical to each other. In some embodiments, at least one of LP1 or LP2 comprises an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one. In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8). In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 155), GSSGGSGGSG (SEQ ID NO: 156), or GSSGGSGGSGS (SEQ ID NO: 157). In some embodiments, LP2 comprises the amino acid sequence GSS, GGS, GGGS (SEQ ID NO: 158), GSSGT (SEQ ID NO: 12) or GSSG (SEQ ID NO: 13).

In some embodiments, the activatable antibody is an anti-Jagged activatable antibody that includes at least an AB comprising the heavy chain amino acid sequence of SEQ ID NO: 112 and the light chain amino acid sequence of SEQ ID NO: 111; a MM comprising the amino acid sequence selected of SEQ ID NO: 217; and a CM comprising an amino acid sequence selected from the group consisting of SEQ ID NO: 14-33, and 159. In some embodiments, the activatable antibody is an anti-Jagged activatable antibody that includes at least an AB comprising the heavy chain amino acid sequence of SEQ ID NO: 112 and the light chain amino acid sequence of SEQ ID NO: 111; a MM comprising the amino acid sequence selected of SEQ ID NO: 217; and a CM comprising an amino acid sequence selected from the group consisting of the sequences presented in Tables 8A-8M. In some embodiments, the anti-Jagged activatable antibody also includes a first linking peptide (LP1) and a second linking peptide (LP2), and the activatable antibody in the uncleaved state has the structural arrangement from N-terminus to C-terminus as follows: MM-LP1-CM-LP2-AB or AB-LP2-CM-LP1-MM. In some embodiments, each of LP1 and LP2 is a peptide of about 1 to 20 amino acids in length. In some embodiments, the two linking peptides need not be identical to each other. In some embodiments, at least one of LP1 or LP2 comprises an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one. In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8). In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 155), GSSGGSGGSG (SEQ ID NO: 156), or GSSGGSGGSGS (SEQ ID NO: 157). In some embodiments, LP2 comprises the amino acid sequence GSS, GGS, GGGS (SEQ ID NO: 158), GSSGT (SEQ ID NO: 12) or GSSG (SEQ ID NO: 13).

In some embodiments, the activatable antibody is an anti-Jagged activatable antibody that includes at least an AB comprising a heavy chain amino acid sequence comprising the VH CDR1 sequence of SEQ ID NO: 498, the VH CDR2 sequence of SEQ ID NO: 499, the VH CDR3 sequence of SEQ ID NO: 500, the VL CDR1 sequence of SEQ ID NO: 501, the VL CDR2 sequence of SEQ ID NO: 502, and the VL CDR2 sequence of SEQ ID NO: 503; a MM comprising the amino acid sequence selected from the group consisting of SEQ ID NO: 217; and a CM comprising an amino acid sequence selected from the group consisting of SEQ ID NO: 14-33, and 159. In some embodiments, the activatable antibody is an anti-Jagged activatable antibody that includes at least an AB comprising a heavy chain amino acid sequence comprising the VH CDR1 sequence of SEQ ID NO: 498, the VH CDR2 sequence of SEQ ID NO: 499, the VH CDR3 sequence of SEQ ID NO: 500, the VL CDR1 sequence of SEQ ID NO: 501, the VL CDR2 sequence of SEQ ID NO: 502, and the VL CDR2 sequence of SEQ ID NO: 503; a MM comprising the amino acid sequence selected from the group consisting of SEQ ID NO: 217; and a CM comprising an amino acid sequence selected from the group consisting of the sequences presented in Tables 8A-8M. In some embodiments, the anti-Jagged activatable antibody also includes a first linking peptide (LP1) and a second linking peptide (LP2), and the activatable antibody in the uncleaved state has the structural arrangement from N-terminus to C-terminus as follows: MM-LP1-CM-LP2-AB or AB-LP2-CM-LP1-MM. In some embodiments, each of LP1 and LP2 is a peptide of about 1 to 20 amino acids in length. In some embodiments, the two linking peptides need not be identical to each other. In some embodiments, at least one of LP1 or LP2 comprises an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one. In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8). In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 155), GSSGGSGGSG (SEQ ID NO: 156), or GSSGGSGGSGS (SEQ ID NO: 157). In some embodiments, LP2 comprises the amino acid sequence GSS, GGS, GGGS (SEQ ID NO: 158), GSSGT (SEQ ID NO: 12) or GSSG (SEQ ID NO: 13).

In some embodiments, the activatable antibody also includes an agent conjugated to the AB. In some embodiments, the agent is a therapeutic agent. In some embodiments, the agent is an antineoplastic agent. In some embodiments, the agent is a toxin or a fragment thereof. In some embodiments, the agent is conjugated to the AB via a linker.

In some embodiments, the linker is a cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is conjugated to the AB via a linker that includes at least one MMP-cleavable substrate sequence. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the agent is an anti-inflammatory agent.

In some embodiments, the activatable antibody also includes a detectable moiety. In some embodiments, the detectable moiety is a diagnostic agent.

In some embodiments, the conjugated antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or β-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM-AB. An example of a spacer joined directly to the N-terminus of MM of the activatable antibody is QGQSGQ (SEQ ID NO: 53). In some embodiments, the spacer includes at least the amino acid sequence QGQSGQ (SEQ ID NO: 53).

In some embodiments, the AB of the activatable antibody naturally contains one or more disulfide bonds. In some embodiments, the AB can be engineered to include one or more disulfide bonds.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

In some embodiments, the activatable antibody and/or conjugated activatable antibody is monospecific. In some embodiments, the activatable antibody and/or conjugated activatable antibody is multispecific, e.g., by way of non-limiting example, bispecific or trifunctional. In some embodiments, the activatable antibody and/or conjugated activatable antibody is formulated as part of a pro-Bispecific T Cell Engager (pro-BITE) molecule. In some embodiments, the activatable antibody and/or conjugated activatable antibody is formulated as part of a pro-Chimeric Antigen Receptor (pro-CAR) modified T cell or other engineered receptor.

The disclosure also provides compositions and methods that include an activatable antibody that includes an antibody or antibody fragment (AB) that specifically binds a given target, where the AB is coupled to a masking moiety (MM) that decreases the ability of the AB to bind its target. In some embodiments, the activatable antibody further includes a cleavable moiety (CM) that is a substrate for at least one MMP. The compositions and methods provided herein enable the attachment of one or more agents to one or more cysteine residues in the AB without compromising the activity (e.g., the masking, activating or binding activity) of the activatable antibody. In some embodiments, the compositions and methods provided herein enable the attachment of one or more agents to one or more cysteine residues in the AB without reducing or otherwise disturbing one or more disulfide bonds within the MM. The compositions and methods provided herein produce an activatable antibody that is conjugated to one or more agents, e.g., any of a variety of therapeutic, diagnostic and/or prophylactic agents, for example, in some embodiments, without any of the agent(s) being conjugated to the MM of the activatable antibody. The compositions and methods provided herein produce conjugated activatable antibodies in which the MM retains the ability to effectively and efficiently mask the AB of the activatable antibody in an uncleaved state. The compositions and methods provided herein produce conjugated activatable antibodies in which the activatable antibody is still activated, i.e., cleaved, in the presence of a MMP that can cleave the CM.

The activatable antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of an activatable antibody having one or more interchain disulfide bonds in the AB and one or more intrachain disulfide bonds in the MM, and a drug reactive with free thiols is provided. The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In some embodiments, a method of reducing and conjugating an agent, e.g., a drug, to an activatable antibody resulting in selectivity in the placement of the agent is provided. The method generally includes partially reducing the activatable antibody with a reducing agent such that any conjugation sites in the masking moiety or other non-AB portion of the activatable antibody are not reduced, and conjugating the agent to interchain thiols in the AB. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable antibody will vary depending on the activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

In some embodiments, a method of reducing interchain disulfide bonds in the AB of an activatable antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration.

In some embodiments, the reduced antibody is not purified after partial reduction and prior to conjugation.

The disclosure also provides partially reduced activatable antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to the target, a masking moiety (MM) that inhibits the binding of the AB of the activatable antibody in an uncleaved state to the target, and a cleavable moiety (CM) coupled to the AB, wherein the CM is a polypeptide that functions as a substrate for at least one MMP. In some embodiments, the MM is coupled to the AB via the CM. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

The disclosure also provides partially reduced activatable antibodies, including but not limited to multispecific activatable antibodies of the disclosure, in which at least one interchain disulfide bond in the activatable antibody has been reduced with a reducing agent without disturbing or otherwise compromising the activity and/or efficacy of the activatable antibody, wherein the activatable antibody includes an antibody or an antigen binding fragment thereof (AB) that specifically binds to a target, a masking moiety (MM) that inhibits the binding of the AB of the activatable antibody in an uncleaved state to the target, and a cleavable moiety (CM) coupled to the AB, and the CM is a polypeptide that functions as a substrate for a protease. The activity and/or efficacy of the activatable antibody is, by way of nonlimiting example, masking activity, activation of the activatable antibody, and/or binding activity of the activated activatable antibody. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

The disclosure also provides conjugated activatable antibodies that include an activatable antibody linked to monomethyl auristatin D (MMAD) payload, wherein the activatable antibody includes an antibody or an antigen binding fragment thereof (AB) that specifically binds to a target, a masking moiety (MM) that inhibits the binding of the AB of the activatable antibody in an uncleaved state to the target, and cleavable moiety (CM) coupled to the AB, and the CM is a polypeptide that functions as a substrate for at least one MMP protease.

In some embodiments, the MMAD-conjugated activatable antibody can be conjugated using any of several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB.

In some embodiments, the MMAD payload is conjugated to the AB via a linker. In some embodiments, the MMAD payload is conjugated to a cysteine in the AB via a linker. In some embodiments, the MMAD payload is conjugated to a lysine in the AB via a linker. In some embodiments, the MMAD payload is conjugated to another residue of the AB via a linker, such as those residues disclosed herein. In some embodiments, the linker is a thiol-containing linker. In some embodiments, the linker is a cleavable linker. In some embodiments, the linker is a non-cleavable linker. In some embodiments, the linker is selected from the group consisting of the linkers shown in Tables 5 and 6. In some embodiments, the activatable antibody and the MMAD payload are linked via a maleimide caproyl-valine-citrulline linker. In some embodiments, the activatable antibody and the MMAD payload are linked via a maleimide PEG-valine-citrulline linker. In some embodiments, the activatable antibody and the MMAD payload are linked via a maleimide caproyl-valine-citrulline-para-aminobenzyloxycarbonyl linker. In some embodiments, the activatable antibody and the MMAD payload are linked via a maleimide PEG-valine-citrulline-para-aminobenzyloxycarbonyl linker. In some embodiments, the MMAD payload is conjugated to the AB using the partial reduction and conjugation technology disclosed herein.

In some embodiments, the target is selected from the group of targets listed in Table 1. In some embodiments, the target is EGFR. In some embodiments, the target is a Jagged protein, e.g., Jagged 1 and/or Jagged 2. In some embodiments, the target is interleukin 6 receptor (IL-6R). In some embodiments, the AB is or is derived from an antibody selected from the group of antibodies listed in Table 2. In some embodiments, the antigen binding fragment thereof is selected from the group consisting of a Fab fragment, a $F(ab')_2$ fragment, a scFv, a scAb, a dAb, a single domain heavy chain antibody, and a single domain light chain antibody. In some embodiments, the AB has an equilibrium dissociation constant of about 100 nM or less for binding to the target. In some embodiments, the MM has an equilibrium dissociation constant for binding to the AB that is greater than the equilibrium dissociation constant of the AB to the target. In some embodiments, the MM does not interfere or compete with the AB of the activatable antibody in a cleaved state for binding to the target. In some embodiments, the MM is a polypeptide of no more than 40 amino acids in length. In some embodiments, the MM polypeptide sequence is different from that of the target, and the MM polypeptide sequence is no more than 50% identical to any natural binding partner of the AB. In some embodiments, the MM does not include more than 25% amino acid sequence identity to the target. In some embodiments, the MM does not include more than 10% amino acid sequence identity to the target. In some embodiments, the CM is a polypeptide of up to 15 amino acids in length. In some embodiments, the MMP protease is co-localized with the target in a tissue, and the MMP protease cleaves the CM in the activatable antibody when the activatable antibody is exposed to the MMP protease. In some embodiments, the MMP protease is a MMP9 protease. In some embodiments, the MMP protease is a MMP14 protease. In some embodiments, the activatable antibody includes a linking peptide between the MM and the CM. In some embodiments, the activatable antibody includes a linking peptide between the CM and the AB. In some embodiments, the activatable antibody includes a first linking peptide (LP1) and a second linking peptide (LP2), and the activatable antibody in an uncleaved state has the structural arrangement from N-terminus to C-terminus as follows: MM-LP1-CM-LP2-AB or AB-LP2-CM-LP1-MM. In some embodiments, the two linking peptides need not be identical to each other. In some embodiments, each of LP1 and LP2 is a peptide of about 1 to 20 amino acids in length. In some embodiments, at least one of LP1 or LP2 includes an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one. In some embodiments, at least one of LP1 or LP2 includes an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8). In some embodiments, the activatable antibody includes a second CM; in some embodiments, the second CM is a substrate for an enzyme selected from the group consisting of those shown in Table 7.

The disclosure also provides polypeptides and other larger molecules that include one or more of the MMP-cleavable substrate sequences presented herein. By way of non-limiting example, the MMP-cleavable substrate sequences presented herein are useful in prodrug compositions and methods of use thereof. These MMP-cleavable substrate sequences presented herein are also useful in probes and other detection agents and methods of use thereof. For example, the MMP-cleavable substrate sequences presented herein can be used in conjunction with fluors and other quenchers to produce detection agents, such as imaging agents and/or other diagnostic agents. Those of ordinary skill in the art will appreciate that the MMP-cleavable substrate sequences presented herein are useful in any composition and/or method in the art that would use a substrate that is cleavable by one or more MMPs, such as MMP9 and/or MMP14.

The disclosure also provides an isolated nucleic acid molecule encoding an antibody and/or an activatable antibody described herein, as well as vectors that include these isolated nucleic acid sequences. The disclosure provides methods of producing an antibody and/or activatable antibody by culturing a cell under conditions that lead to expression of the antibody and/or activatable antibody, wherein the cell comprises such a vector.

The disclosure provides a method of manufacturing a conjugated antibody of the disclosure that bind a given target by (a) culturing a cell comprising a nucleic acid construct that encodes the antibody under conditions that lead to expression of the antibody, (i) wherein the antibody includes a cleavable moiety (CM), and (ii) wherein the CM is a polypeptide that functions as a substrate for a matrix metalloprotease; (b) recovering the antibody; and (c) conjugating the recovered antibody to one or more additional agents.

The disclosure also provides a method of manufacturing the activatable antibodies of the disclosure that bind in an activated state a given target by (a) culturing a cell comprising a nucleic acid construct that encodes the activatable antibody under conditions that lead to expression of the activatable antibody, wherein the activatable antibody comprises a masking moiety (MM), a cleavable moiety (CM), and an antibody or an antigen binding fragment thereof (AB) that specifically binds the target, (i) wherein the CM is a polypeptide that functions as a substrate for a MMP; and (ii) wherein the CM is positioned in the activatable antibody such that, in an uncleaved state, the MM interferes with specific binding of the AB to the target and in a cleaved state the MM does not interfere or compete with specific binding of the AB to the target; and (b) recovering the activatable antibody.

The disclosure provides methods of preventing, delaying the progression of, treating, alleviating a symptom of, or otherwise ameliorating a target-related disease in a subject by administering a therapeutically effective amount of a conjugated antibody, an activatable antibody and/or a conjugated activatable antibody described herein to a subject in need thereof.

The disclosure provides methods of preventing, delaying the progression of, treating, alleviating a symptom of, or otherwise ameliorating inflammation and/or an inflammatory disorder in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating cancer in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating an autoimmune disease in a subject by administering a therapeutically effective amount a conjugated antibody, an activatable antibody and/or a conjugated activatable antibody described herein to a subject in need thereof.

A conjugated antibody, an activatable antibody and/or a conjugated activatable antibody used in any of the embodiments of these methods and uses can be administered at any stage of the disease. For example, such a conjugated antibody, activatable antibody and/or conjugated activatable antibody can be administered to a patient suffering cancer of any stage, from early to metastatic. The terms subject and patient are used interchangeably herein.

In some embodiments, the subject is a mammal, such as a human, non-human primate, companion animal (e.g., cat, dog, horse), farm animal, work animal, or zoo animal. In some embodiments, the subject is a rodent. In some embodiments, the subject is a human. In some embodiments, the subject is a companion animal. In some embodiments, the subject is an animal in the care of a veterinarian.

The conjugated antibody, activatable antibody and/or conjugated activatable antibody and therapeutic formulations thereof are administered to a subject suffering from or susceptible to a disease or disorder associated with aberrant target expression and/or activity. A subject suffering from or susceptible to a disease or disorder associated with aberrant target expression and/or activity is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of a conjugated antibody, an activatable antibody and/or a conjugated activatable antibody to a patient suffering from a disease or disorder associated with aberrant target expression and/or activity is considered successful if any of a variety of laboratory or clinical objectives is achieved. For example, administration of a conjugated antibody, an activatable antibody and/or a conjugated activatable antibody to a patient suffering from a disease or disorder associated with aberrant target expression and/or activity is considered successful if one or more of the symptoms associated with the disease or disorder is alleviated, reduced, inhibited or does not progress to a further, i.e., worse, state. Administration of a conjugated antibody, an activatable antibody and/or a conjugated activatable antibody to a patient suffering from a disease or disorder associated with aberrant target expression and/or activity is considered successful if the disease or disorder enters remission or does not progress to a further, i.e., worse, state.

In some embodiments, the conjugated antibody, activatable antibody and/or conjugated activatable antibody is administered during and/or after treatment in combination with one or more additional agents such as, by way of non-limiting example, an anti-inflammatory agent, an immunosuppressive agent, a chemotherapeutic agent, such as an alkylating agent, an anti-metabolite, an anti-microtubule agent, a topoisomerase inhibitor, a cytotoxic antibiotic, and/or any other nucleic acid damaging agent. In some embodiments, the additional agent is a taxane, such as paclitaxel (e.g., Abraxane®). In some embodiments, the additional agent is an anti-metabolite, such as gemcitabine. In some embodiments, the additional agent is an alkylating agent, such as platinum-based chemotherapy, such as carboplatin or cisplatin. In some embodiments, the additional agent is a targeted agent, such as a kinase inhibitor, e.g., sorafenib or erlotinib. In some embodiments, the additional agent is a targeted agent, such as another antibody, e.g., a monoclonal antibody (e.g., bevacizumab), a bispecific antibody, or a multispecific antibody. In some embodiments, the additional agent is a proteosome inhibitor, such as bortezomib or carfilzomib. In some embodiments, the additional agent is an immune modulating agent, such as lenalidomide or IL-2. In some embodiments, the additional agent is radiation. In some embodiments, the additional agent is an agent considered standard of care by those skilled in the art. In some embodiments, the additional agent is a chemotherapeutic agent well known to those skilled in the art.

In some embodiments, the additional agent is an antibody, another conjugated antibody, another activatable antibody and/or another conjugated activatable antibody. In some embodiments, the conjugated antibody, activatable antibody and/or conjugated activatable antibody and the additional agent(s) are administered simultaneously. For example, the conjugated antibody, activatable antibody and/or conjugated activatable antibody and the additional agent(s) can be formulated in a single composition or administered as two or more separate compositions. In some embodiments, the conjugated antibody, activatable antibody and/or conjugated activatable antibody and the additional agent(s) are administered sequentially, or the antibody and/or conjugated antibodies and the additional agent are administered at different times during a treatment regimen. For example, the antibody and/or conjugated antibodies is administered prior to the administration of the additional agent, the antibody and/or conjugated antibodies is administered subsequent to the administration of the additional agent, or the antibody and/or conjugated antibodies and the additional agent are administered in an alternating fashion. As described herein, the antibody and/or conjugated antibodies and additional agent are administered in single doses or in multiple doses.

In some embodiments, the CM is linked or otherwise attached to an activatable antibody that includes an antibody or antigen-binding fragment thereof that specifically binds a given target coupled to a masking moiety (MM), such that coupling of the MM to the AB reduces the ability of the antibody or antigen-binding fragment thereof to bind the target. In some embodiments, the MM is coupled via the CM. Exemplary targets include, but are not limited to the targets shown in Table 1. Exemplary ABs include, but are not limited to, the targets shown in Table 2. The activatable antibodies provided herein are stable in circulation, activated at intended sites of therapy and/or diagnosis but not in normal, e.g., healthy tissue or other tissue not targeted for treatment and/or diagnosis, and, when activated, exhibit binding to the target that is at least comparable to the corresponding, unmodified antibody.

The disclosure also provides methods and kits for using the conjugated antibodies, activatable antibodies and/or conjugated activatable antibodies in a variety of diagnostic and/or prophylactic indications.

In some embodiments, the disclosure provides methods and kits for detecting presence or absence of a cleaving agent and a target of interest in a subject or a sample by (i) contacting a subject or sample with an activatable antibody, wherein the activatable antibody comprises a masking moiety (MM), a cleavable moiety (CM) that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent and the target are present in the subject or sample and wherein no detectable level of activated activatable antibody in the subject or sample indicates that the cleaving agent, the target or both the cleaving agent and the target are absent in the subject or sample.

In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

In some embodiments of these methods and kits, the activatable antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods, the subject is a human. In some embodiments, the subject is a non-human mammal, such as a non-human primate, companion animal (e.g., cat, dog, horse), farm animal, work animal, or zoo animal. In some embodiments, the subject is a rodent. In some embodiments, the subject is a human. In some embodiments, the subject is a companion animal. In some embodiments, the subject is an animal in the care of a veterinarian.

In some embodiments of these methods and kits, the method is an in vivo method. In some embodiments of these methods, the method is an in situ method. In some embodiments of these methods, the method is an ex vivo method. In some embodiments of these methods, the method is an in vitro method.

In some embodiments of the methods and kits, the method is used to identify or otherwise refine a patient population suitable for treatment with an activatable antibody of the disclosure, followed by treatment by administering that activatable antibody and/or conjugated activatable antibody to a subject in need thereof. For example, patients that test positive for both the target and at least one MMP that cleaves the substrate in the cleavable moiety (CM) of the activatable antibody being tested in these methods are identified as suitable candidates for treatment with such an activatable antibody comprising such a CM, and the patient is then administered a therapeutically effective amount of the activatable antibody and/or conjugated activatable antibody that was tested. Likewise, patients that test negative for either or both of the target and the MMP that cleaves the substrate in the CM in the activatable antibody being tested using these methods might be identified as suitable candidates for another form of therapy. In some embodiments, such patients can be tested with other activatable antibodies until a suitable activatable antibody for treatment is identified (e.g., an activatable antibody comprising a CM that is cleaved by the patient at the site of disease). In some embodiments, the patient is then administered a therapeutically effective amount of the activatable antibody and/or conjugated for which the patient tested positive.

Pharmaceutical compositions according to the disclosure can include an antibody of the disclosure and a carrier. These pharmaceutical compositions can be included in kits, such as, for example, diagnostic kits.

BRIEF DESCRIPTION OF THE DRAWINGS

FIG. 7A is a schematic representation of the sequence of the display platform referred to herein as "Display Platform CYTX-DP-XXXXXXXX" or "CYTX-DP-XXXXXXXX" (SEQ ID NO: 512). FIG. 7B is a schematic representation of the sequence of the display platform referred to herein as "Display Platform SP-CYTX-DP-XXXXXXXX" or "SP-CYTX-DP-XXXXXXXX" (SEQ ID NO: 513), where SP-CYTX-DP-XXXXXXXX is the CYTX-DP-XXXXXXXX platform with a signal peptide.

DETAILED DESCRIPTION OF THE INVENTION

Figure 1A:
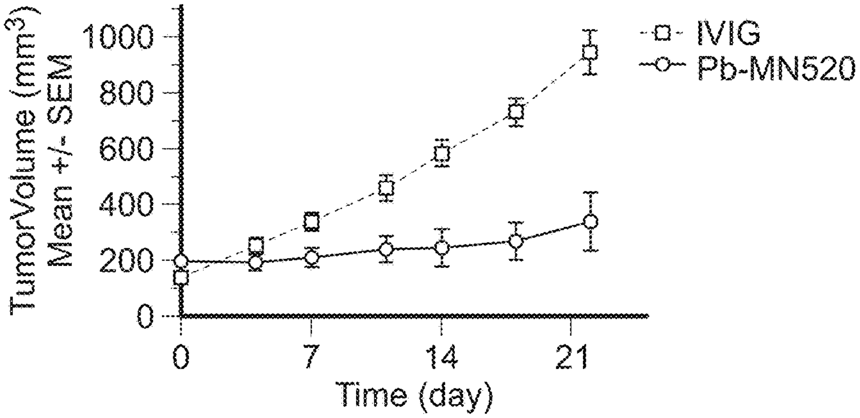
FIGS. 1A and 1B are a series of graphs depicting the ability of the activatable anti-EGFR antibody containing a masking moiety comprising amino acid sequence CISPRGCPDGPYVMY (SEQ ID NO: 160), a cleavage moiety comprising the MMP14 substrate 520 (also referred to herein as MN520) ISSGLLSS (SEQ ID NO: 14), and the heavy and light chains of the anti-EGFR antibody C225v5, where the entire activatable antibody construct is referred to herein as Pb-MN520, to inhibit tumor growth in the H292 xenograft lung cancer model.

The disclosure provides amino acid sequences that include a cleavable moiety (CM) that is a substrate for at least one matrix metalloprotease (MMP). These CMs are useful in a variety of therapeutic, diagnostic and prophylactic indications.

The working examples provided herein demonstrate that these CM, when displayed in a peptide display platform, exhibit a number of desirable cleavage characteristics when exposed to an MMP protease under specified conditions. For example, Table 9 depicts (a) the percentage of MMP9-selected substrates tested in the CYTX-DP display platform that exhibited at least 20% cleavage when incubated with 50 nM human MMP9 for 1 hour at 37° C. in 50 mM Tris-HCl, pH 7.4, supplemented with 150 mM NaCl, 10 mM $CaCl_2$, and 0.05% (w/v) Brij-35 (>20% Cleavage with 50 nM MMP9); (b) the percentage of MMP14-selected substrates tested in the CYTX-DP display platform that exhibited at least 20% cleavage when incubated with 50 nM human MMP14 for 1 hour at 37° C. in 50 mM HEPES, pH 6.8, supplemented with 10 mM $CaCl_2$, and 0.5 mM $MgCl_2$ (>20% Cleavage with 50 nM MMP14); and (c) the percentage of MMP9-selected or MMP-14-selected substrates tested in the CYTX-DP display platform that exhibited less than 20% cleavage when incubated with 500 μM human plasmin for 1 hour at 37° C. in 50 mM Tris-HCl, pH 7.4, supplemented with 100 mM NaCl, 0.01% Tween20 and 1 mM EDTA (<20% cleavage with 500 μM plasmin).

In some embodiments, a MMP9 substrate when displayed in the CYTX-DP platform exhibits at least 20% cleavage when incubated with 50 nM human MMP9 for 1 hour at 37° C. in 50 mM Tris-HCl, pH 7.4, supplemented with 150 mM NaCl, 10 mM $CaCl_2$, and 0.05% (w/v) Brij-35. In some embodiments, a MMP9 substrate when displayed in the CYTX-DP platform exhibits less than 20% cleavage when incubated with 500 μM human plasmin for 1 hour at 37° C. in 50 mM Tris-HCl, pH 7.4, supplemented with 100 mM NaCl, 0.01% Tween20 and 1 mM EDTA. In some embodiments, a MMP9 substrate when displayed in the CYTX-DP platform exhibits at least 20% cleavage when incubated with 50 nM human MMP9 for 1 hour at 37° C. in 50 mM Tris-HCl, pH 7.4, supplemented with 150 mM NaCl, 10 mM $CaCl_2$, and 0.05% (w/v) Brij-35 and exhibits less than 20% cleavage when incubated with 500 μM human plasmin for 1 hour at 37° C. in 50 mM Tris-HCl, pH 7.4, supplemented with 100 mM NaCl, 0.01% Tween20 and 1 mM EDTA.

In some embodiments a MMP14 substrate exhibits at least 20% cleavage when incubated with 50 nM human MMP14 for 1 hour at 37° C. in 50 mM HEPES, pH 6.8, supplemented with 10 mM $CaCl_2$, and 0.5 mM $MgCl_2$. In some embodiments, a MMP14 substrate when displayed in the CYTX-DP platform exhibits less than 20% cleavage when incubated with 500 μM human plasmin for 1 hour at 37° C. in 50 mM Tris-HCl, pH 7.4, supplemented with 100 mM NaCl, 0.01% Tween20 and 1 mM EDTA. In some embodiments a MMP14 substrate exhibits at least 20% cleavage when incubated with 50 nM human MMP14 for 1 hour at 37° C. in 50 mM HEPES, pH 6.8, supplemented with 10 mM $CaCl_2$, and 0.5 mM $MgCl_2$ and exhibits less than 20% cleavage when incubated with 500 μM human plasmin for 1 hour at 37° C. in 50 mM Tris-HCl, pH 7.4, supplemented with 100 mM NaCl, 0.01% Tween20 and 1 mM EDTA.

In some embodiments, the observed $k_{cat}/K_M$ value of a substrate in an activatable antibody for MMP9 is greater than 100 $M^{-1}s^{-1}$. In some embodiments, the observed $k_{cat}/K_M$ value of a substrate in an activatable antibody for MMP9 is greater than 1,000 $M^{-1}s^{-1}$. In some embodiments, the observed $k_{cat}/K_M$ value of a substrate in an activatable antibody for MMP9 is greater than 10,000 $M^{-1}s^{-1}$.

In some embodiments, the observed $k_{cat}/K_M$ value of a substrate in an activatable antibody for MMP14 is greater than 100 $M^{-1}s^{-1}$. In some embodiments, the observed $k_{cat}/K_M$ value of a substrate in an activatable antibody for MMP14 is greater than 1,000 $M^{-1}s^{-1}$. In some embodiments, the observed $k_{cat}/K_M$ value of a substrate in an activatable antibody for MMP14 is greater than 10,000 $M^{-1}s^{-1}$.

The disclosure also provides antibodies that include one or more of these MMP-cleavable substrates. For example, these MMP-cleavable substrates are useful when conjugating antibodies to one or more additional agents to produce conjugated antibodies. These MMP-cleavable are useful in activatable antibody constructs.

The conjugated antibodies and/or activatable antibodies include an antibody or antigen-binding fragment thereof (AB) that specifically binds a target. Exemplary classes of targets of an AB include, but are not necessarily limited to, cell surface receptors and secreted binding proteins (e.g., growth factors), soluble enzymes, structural proteins (e.g. collagen, fibronectin) and the like. In some embodiments, conjugated antibodies and/or activatable antibodies have an AB that binds an extracellular target, usually an extracellular protein target. In some embodiments, conjugated antibodies and/or activatable antibodies are designed for cellular uptake and are switchable inside a cell.

As a non-limiting example, the AB is a binding partner for any target listed in Table 1.

TABLE 1

| Exemplary Targets | | | | | |
|---|---|---|---|---|---|
| 1-92-LFA-3 | CD52 | DL44 | HVEM | LIF-R | STEAP1 |
| Alpha-4 integrin | CD56 | DLK1 | Hyaluronidase | Lewis X | STEAP2 |
| Alpha-V integrin | CD64 | DLL4 | ICOS | LIGHT | TAG-72 |
| alpha4beta1 integrin | CD70 | DPP-4 | IFNalpha | LRP4 | TAPA1 |
| alpha4beta7 integrin | CD71 | DSG1 | IFNbeta | LRRC26 | TGFbeta |
| AGR2 | CD74 | EGFR | IFNgamma | MCSP | TIGIT |
| Anti-Lewis-Y | | EGFRviii | IgE | Mesothelin | TIM-3 |
| Apelin J receptor | CD80 | Endothelin B receptor (ETBR) | IgE Receptor (FceRI) | MRP4 | TLR2 |
| APRIL | CD81 | ENPP3 | IGF | MUC1 | TLR4 |
| B7-H4 | CD86 | EpCAM | IGF1R | Mucin-16 (MUC16, CA-125) | TLR6 |
| BAFF | CD95 | EPHA2 | IL1B | Na/K ATPase | TLR7 |
| BTLA | CD117 | EPHB2 | IL1R | Neutrophil elastase | TLR8 |
| C5 complement | CD125 | ERBB3 | IL2 | NGF | TLR9 |
| C-242 | CD132 (IL-2RG) | F protein of RSV | IL11 | Nicastrin | TMEM31 |
| CA9 | CD133 | FAP | IL12 | Notch Receptors | TNFalpha |
| CA19-9 (Lewis a) | CD137 | FGF-2 | IL12p40 | Notch 1 | TNFR |
| Carbonic anhydrase 9 | CD138 | FGF8 | IL-12R, IL-12Rbeta1 | Notch 2 | TNFRS12A |
| CD2 | CD166 | FGFR1 | IL13 | Notch 3 | TRAIL-R1 |
| CD3 | CD172A | FGFR2 | IL13R | Notch 4 | TRAIL-R2 |
| CD6 | CD248 | FGFR3 | IL15 | NOV | Transferrin |
| CD9 | CDH6 | FGFR4 | IL17 | OSM-R | Transferrin receptor |
| CD11a | CEACAM5 (CEA) | Folate receptor | IL18 | OX-40 | TRK-A |
| CD19 | CEACAM6 (NCA-90) | GAL3ST1 | IL21 | PAR2 | TRK-B |
| CD20 | CLAUDIN-3 | G-CSF | IL23 | PDGF-AA | uPAR |

TABLE 1-continued

| Exemplary Targets | | | | | |
|---|---|---|---|---|---|
| CD22 | CLAUDIN-4 | G-CSFR | IL23R | PDGF-BB | VAP1 |
| CD24 | cMet | GD2 | IL27/IL27R (wsx1) | PDGFRalpha | VCAM-1 |
| CD25 | Collagen | GITR | IL29 | PDGFRbeta | VEGF |
| CD27 | Cripto | GLUT1 | IL-31R | PD-1 | VEGF-A |
| CD28 | CSFR | GLUT4 | IL31/IL31R | PD-L1 | VEGF-B |
| CD30 | CSFR-1 | GM-CSF | IL2R | PD-L2 | VEGF-C |
| CD33 | CTLA-4 | GM-CSFR | IL4 | Phosphatidyl-serine | VEGF-D |
| CD38 | CTGF | GP IIb/IIIa receptors | IL4R | P1GF | VEGFR1 |
| CD40 | CXCL10 | Gp130 | IL6, IL6R | PSCA | VEGFR2 |
| CD40L | CXCL13 | GPIIB/IIIA | Insulin Receptor | PSMA | VEGFR3 |
| CD41 | CXCR1 | GPNMB | Jagged Ligands | RAAG12 | VISTA |
| CD44 | CXCR2 | GRP78 | Jagged 1 | RAGE | WISP-1 |
| CD44v6 | | HER2/neu | Jagged 2 | SLC44A4 | WISP-2 |
| CD47 | CXCR4 | HGF | LAG-3 | Sphingosine 1 Phosphate | WISP-3 |
| CD51 | CYR61 | hGH | | | |

As a non-limiting example, the AB is or is derived from an antibody listed in Table 2.

TABLE 2

| Exemplary sources for Abs | |
|---|---|
| Antibody Trade Name (antibody name) | Target |
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocrelizumab | CD20 |
| Arzerra ™ (ofatumumab) | CD20 |
| Obinutuzumab | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |

TABLE 2-continued

| Exemplary sources for Abs | |
|---|---|
| Antibody Trade Name (antibody name) | Target |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
| | Notch, e.g., Notch 1 |
| | Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

Exemplary conjugated antibodies and/or activatable antibodies of the disclosure include, for example, antibodies that bind interleukin 6 receptor (IL-6R) and that include a heavy chain and a light chain that are, or are derived from, the antibody referred to herein as the "Av1" antibody, which binds interleukin-6 receptor (IL-6R). The amino acid sequences for the Av1 heavy chain and the Av1 light chain are shown below in SEQ ID NO: 54 and SEQ ID NO: 55, respectively.

```
Av1 Antibody Heavy Chain Amino Acid Sequence:
                                          (SEQ ID NO: 54)
QVQLQESGPGLVRPSQTLSLTCTVSGYSITSDHAWSWVRQPPGRGLEWIG

YISYSGITTYNPSLKSRVTISRDNSKNTLYLQMNSLRAEDTAVYYCARSL

ARTTAMDYWGQGSLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTIPPVL

DSDGSFFLYSKLTVDKSRWQQGNVFSCSVMHEALHNHYTQKSLSLSPGK
```

-continued

Av1 Antibody Light Chain Amino Acid Sequence:
(SEQ ID NO: 55)
DIQMTQSPSSLSASVGDRVTITCRASQDISSYLNWYQQKPGKAPKLLIYY

TSRLHSGVPSRFSGSGSGTDFTFTISSLQPEDIATYYCQQGNTLPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Exemplary conjugated antibodies and/or activatable antibodies of the disclosure include, for example, antibodies that bind interleukin 6 receptor (IL-6R) and that include a heavy chain and a light chain that are, or are derived from, the Av1 antibody and a masking moiety. Exemplary conjugated antibodies and/or activatable antibodies of the disclosure include an amino acid sequence attached to the N-terminus of the AV1 light chain. These N-terminal amino acid sequences include, for example, YGSCSWNYVHIFMDC (SEQ ID NO: 161); QGDFDIPFPAHWVPIT (SEQ ID NO: 162); MGVPAGCVWNYAHIFMDC (SEQ ID NO: 163); QGQSGQYGSCSWNYVHIFMDC (SEQ ID NO: 164); QGQSGQGDFDIPFPAHWVPIT (SEQ ID NO: 165); or QGQSGQMGVPAGCVWNYAHIFMDC (SEQ ID NO: 166). It is also to be appreciated that such amino acid sequences can be attached to the N-terminus of the AV1 heavy chain or to the C-terminus of the AV1 heavy or light chain.

Exemplary activatable antibodies of the disclosure include, for example, antibodies that bind Epidermal Growth Factor Receptor (EGFR) and that include a heavy chain and a light chain that are, or are derived from, an antibody selected from the group consisting of the antibody referred to herein as the "c225v5" antibody, the antibody referred to herein as the "c225v4" antibody, and the antibody referred to herein as the "c225v6" antibody, each of which binds EGFR. The c225v5 antibody, the c225v4 antibody, and the c225v6 antibody share the same light chain sequence, referred to herein as "c225 light chain." The amino acid sequences for the c225v5 heavy chain, the c225v4 antibody, the c225v6 antibody, and the c225 light chain are shown below.

C225v5 Antibody Heavy Chain Amino Acid Sequence:
(SEQ ID NO: 56)
QVQLKQSGPGLVQPSQSLSITCTVSGFSLTNYGVHWVRQSPGKGLEWLGV

IWSGGNTDYNTPFTSRLSINKDNSKSQVFFKMNSLQSQDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

-continued

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK*

C225v4 Antibody Heavy Chain Amino Acid Sequence:
(SEQ ID NO: 57)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK*

C225v6 Antibody Heavy Chain Amino Acid Sequence:
(SEQ ID NO: 58)
QVQLKQSGPGLVQPSQSLSITCTVSGFSLTNYGVHWVRQSPGKGLEWLGV

IWSGGNTDYNTPFTSRLSINKDNSKSQVFFKMNSLQSQDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYAS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTIPPVL

DSDGSFFLYSKLTVDKSRWQQGNVFSCSVMHEALHNHYTQKSLSLSPGK*

C225 Antibody Light Chain Amino Acid Sequence:
(SEQ ID NO: 59)
QILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC*

Exemplary conjugated antibodies and/or activatable antibodies of the disclosure include, for example, antibodies that bind a Jagged target, e.g., Jagged-1, Jagged-2 and/or both Jagged-1 and Jagged-2, and that include a combination of a variable heavy chain region and a variable light chain region that are, or are derived from, the variable heavy chain and variable light chain sequences shown below.

Variable Light Chain Amino Sequence Lc4
(SEQ ID NO: 60)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc4
(SEQ ID NO: 61)
EVQLLESGGGLVQPGGSLRLSCAASGFTFSSYAMSWVRQAPGKGLEWVSSIEQMGWQTYYADSV -continued

KGRFTISRDNSKNTLYLQMNSLRAEDTAVYYCAKDIGGRSAFDYWGQGTLVTVSS

Variable Light Chain Amino Sequence Lc5
(SEQ ID NO: 62)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc5
(SEQ ID NO: 63)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPYHGQFDYWGQGTLVTVSS

Variable Light Chain Amino Sequence Lc7
(SEQ ID NO: 64)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc7
(SEQ ID NO: 65)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc8
(SEQ ID NO: 67)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc8
(SEQ ID NO: 68)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKHIGRTNPFDYWGQGTLVTVSS

Variable Light Chain Amino Sequence Lc13
(SEQ ID NO: 69)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc13
(SEQ ID NO: 70)
EVQLLESGGGLVQPGGSLRLSCAASGFTFSSYAMSWVRQAPGKGLEWVSSIEQMGWQTEYADSV

KGRFTISRDNSKNTLYLQMNSLRAEDTAVYYCAKSAAAFDYWGQGTLVTVSS

Variable Light Chain Amino Sequence Lc16
(SEQ ID NO: 71)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc16
(SEQ ID NO: 72)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPYYGQFDYWGQGTLVTVSS

Variable Light Chain Amino Sequence Lc19
(SEQ ID NO: 73)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc19
(SEQ ID NO: 74)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc21
(SEQ ID NO: 75)
DIQMTQSPSSLSASVGDRVTITCRASQSISSYLNWYQQKPGKAPKLLIYAASSLQSGVPSRFSG -continued

SGSGTDFTLTISSLQPEDFATYYCQQSVVAPLTFGQGTKVEIKR

Variable Heavy Chain Amino Sequence Hc21
(SEQ ID NO: 76)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc24
(SEQ ID NO: 77)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc24
(SEQ ID NO: 78)
EVQLLESGGGLVQPGGSLRLSCAASGFTFSSYAMSWVRQAPGKGLEWVSSIEEMGWQTLYADSV

KGRFTISRDNSKNTLYLQMNSLRAEDTAVYYCAKSAAAFDYWGQGTLVTVSS

Variable Light Chain Amino Sequence Lc26
(SEQ ID NO: 79)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc26
(SEQ ID NO: 80)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc27
(SEQ ID NO: 81)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc27
(SEQ ID NO: 82)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFYGQFDYWGQGTLVTVSS

Variable Light Chain Amino Sequence Lc28
(SEQ ID NO: 83)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc28
(SEQ ID NO: 84)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc30
(SEQ ID NO: 85)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc30
(SEQ ID NO: 86)
EVQLLESGGGLVQPGGSLRLSCAASGFTFSSYAMSWVRQAPGKGLEWVSSIEEMGWQTLYADSV

KGRFTISRDNSKNTLYLQMNSLRAEDTAVYYAKSAAAFDYWGQGTLVTVSS

Variable Light Chain Amino Sequence Lc31
(SEQ ID NO: 87)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

-continued

Variable Heavy Chain Amino Sequence Hc31

(SEQ ID NO: 88)

EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc32

(SEQ ID NO: 89)

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc32

(SEQ ID NO: 90)

EVQLLESGGGLVQPGGSLRLSCAASGFTFSSYAMSWVRQAPGKGLEWVSSIDPEGWQTYYADSV

KGRFTISRDNSKNTLYLQMNSLRAEDTAVYYCAKSAAAFDYWGQGTLVTVSS

Variable Light Chain Amino Sequence Lc37

(SEQ ID NO: 91)

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc37

(SEQ ID NO: 92)

EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPHNGQFDYWGQGTLVTVSS

Variable Light Chain Amino Sequence Lc39

(SEQ ID NO: 93)

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc39

(SEQ ID NO: 94)

EVQLLESGGGLVQPGGSLRLSCAASGFTFSSYAMSWVRQAPGKGLEWVSSIEQMGWQTEYADSV

KGRFTISRDNSKNTLYLQMNSLRAEDTAVYYCAKSAAAFDYWGQGTLVTVSS

Variable Light Chain Amino Sequence Lc40

(SEQ ID NO: 95)

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Heavy Chain Amino Sequence Hc40

(SEQ ID NO: 96)

EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc47

(SEQ ID NO: 97)

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc47

(SEQ ID NO: 98)

EVQLLESGGGLVQPGGSLRLSCAASGFTFSSYAMSWVRQAPGKGLEWVSSIDEMGWQTEYADSV

KGRFTISRDNSKNTLYLQMNSLRAEDTAVYYCAKSAAAFDYWGQGTLVTVSS

Variable 4B2 Light Chain (SEQ ID NO: 99)

IQMTQSPSSLSASVGDRVTITCRASQSISSYLNWYQQKPGKAPKLLIYAASSLQSGVPSRFSG

SGSGTDFTLTISSLQPEDFATYYCQQTLDAPPQFGQGTKVEIKR

Variable 4B2 Heavy Chain (SEQ ID NO: 100)

EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

-continued

Variable 4D11 Light Chain
(SEQ ID NO: 101)
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKR

Variable 4D11 Heavy Chain
(SEQ ID NO: 102)
EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSS

Variable 4E7 Light Chain
(SEQ ID NO: 103)
DIQMTQSPSSLSASVGDRVTITCRASQSISSYLNWYQQKPGKAPKLLIYAASSLQSGVPSRFSG

SGSGTDFTLTISSLQPEDFATYYCQQSLVAPLTFGQGTKVEIKR

Variable 4E7 Heavy Chain
(SEQ ID NO: 104)
EVQLLESGGGLVQPGGSLRLSCAASGFTFSSYAMSWVRQAPGKGLEWVSSIEEMGWQTKYADSV

KGRFTISRDNSKNTLYLQMNSLRAEDTAVYYCAKSAAAFDYWGQGTLVTVSS

Variable 4E11 Light Chain
(SEQ ID NO: 105)
DIQMTQSPSSLSASVGDRVTITCRASQSISSYLNWYQQKPGKAPKLLIYAASSLQSGVPSRFSG

SGSGTDFTLTISSLQPEDFATYYCQQALDAPLMFGQGTKVEIKR

Variable 4E11 Heavy Chain
(SEQ ID NO: 106)
EVQLLESGGGLVQPGGSLRLSCAASGFTFSSYAMSWVRQAPGKGLEWVSSIEPMGQLTEYADSV

KGRFTISRDNSKNTLYLQMNSLRAEDTAVYYCAKDIGGRSAFDYWGQGTLVTVSS

Variable 6B7 Light Chain
(SEQ ID NO: 107)
DIQMTQSPSSLSASVGDRVTITCRASQSISSYLNWYQQKPGKAPKLLIYAASSLQSGVPSRFSG

SGSGTDFTLTISSLQPEDFATYYCQQALVAPLTFGQGTKVEIKR

Variable 6B7 Heavy Chain
(SEQ ID NO: 108)
EVQLLESGGGLVQPGGSLRLSCAASGFTFSSYAMSWVRQAPGKGLEWVSSIDEMGWQTYYADSV

KGRFTISRDNSKNTLYLQMNSLRAEDTAVYYCAKSAAAFDYWGQGTLVTVSS

Variable 6F8 Light Chain
(SEQ ID NO: 109)
DIQMTQSPSSLSASVGDRVTITCRASQSISSYLNWYQQKPGKAPKLLIYAASSLQSGVPSRFSG

SGSGTDFTLTISSLQPEDFATYYCQQALVAPLTFGQGTKVEIKR

Variable 6F8 Heavy Chain
(SEQ ID NO: 110)
EVQLLESGGGLVQPGGSLRLSCAASGFTFSSYAMSWVRQAPGKGLEWVSSIDEMGWQTYYADSV

KGRFTISRDNSKNTLYLQMNSLRAEDTAVYYCAKSAAAFDYWGQGTLVTVSS

Exemplary conjugated antibodies and/or activatable antibodies of the disclosure include, for example, antibodies that bind a Jagged target, e.g., Jagged-1, Jagged-2 and/or both Jagged-1 and Jagged-2, and that include a combination of a heavy chain region and a light chain region that are, or are derived from, the heavy chain and light chain sequences shown below.

4D11 Light Chain sequence:
(SEQ ID NO: 111)
DIQMTQSPSSLSASVGDRVTITCRASQSISSYLNWYQQKPGKAPKLLIY

AASSLQSGVPSRFSGSGSGTDFTLTISSLQPEDFATYYCQQTVVAPPLF

GQGTKVEIKRTVAAPSVFIFPPSDEQLKSGTASVVCLLNNFYPREAKVQ

-continued

WKVDNALQSGNSQESVTEQDSKDSTYSLSSTLTLSKADYEKHKVYACEV

THQGLSSPVTKSFNRGEC

4D11 Heavy Chain sequence:
(SEQ ID NO: 112)
EVQLLESGGGLVQPGGSLRLSCAASGFTFSSYAMSWVRQAPGKGLEWVS

SIDPEGRQTYYADSVKGRFTISRDNSKNTLYLQMNSLRAEDTAVYYCAK

DIGGRSAFDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

-continued

```
EEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQK

SLSLSPGK

4D11v2 Heavy Chain sequence
                                    (SEQ ID NO: 113)
EVHLLESGGGLVQPGGSLRLSCAASGFTFSSYAMSWVRQAPGKGLEWVS

SIDPEGRQTYYADSVKGRFTISRDNSKNTLYLQMNSLRAEDTAVYYCAK

DIGGRSAFDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQK

SLSLSPGK

4D11v2 Light Chain Sequence
                                    (SEQ ID NO: 114)
DIQMTQSPSSLSASVGDRVTITCRASQSISSYLNWYQQKPGKAPKLLIY

AASSLQSGVPSRFSGSGSGTDFTLTISSLQPEDFATYYCQQTVVAPPLF

GQGTKVEIKRTVAAPSVFIFPPSDEQLKSGTASVVCLLNNFYPREAKVQ

WKVDNALQSGNSQESVTEQDSKDSTYSLSSTLTLXKADYEKHKVYACEV

THQGLSSPVTKSFNRGEC
```

The activatable antibodies and activatable antibody compositions provided herein contain at least an antibody or antibody fragment thereof (collectively referred to as AB throughout the disclosure) that specifically binds a target, e.g., a human target, wherein the AB is modified by a masking moiety (MM).

In some embodiments, the masking moiety is selected for use with a specific antibody or antibody fragment. For example, suitable masking moieties for use with antibodies that bind EGFR include MMs that include the sequence CISPRG (SEQ ID NO: 167). By way of non-limiting examples, the MM can include a sequence such as CISPRGC (SEQ ID NO: 497); CISPRGCG (SEQ ID NO: 168); CISPRGCPDGPYVMY (SEQ ID NO: 160); CISPRGCPDGPYVM (SEQ ID NO: 169), CISPRGCEPGTYVPT (SEQ ID NO: 170) and CISPRGCPGQIWHPP (SEQ ID NO: 171). Other suitable masking moieties include any of the EGFR-specific masks disclosed in PCT Publication No. WO 2010/081173, such as, by way of non-limiting example, GSHCLIPINMGAPSC (SEQ ID NO: 172); CISPRGCGGSSASQSGQGSHCLIPINMGAPSC (SEQ ID NO: 173); CNHHYFYTCGCISPRGCPG (SEQ ID NO: 174); ADHVFWGSYGCISPRGCPG (SEQ ID NO: 175); CHHVYWGHCGCISPRGCPG (SEQ ID NO: 176); CPHFTTTSCGCISPRGCPG (SEQ ID NO: 177); CNHHYHYYCGCISPRGCPG (SEQ ID NO: 178); CPHVSFGSCGCISPRGCPG (SEQ ID NO: 179); CPYYTLSYCGCISPRGCPG (SEQ ID NO: 180); CNHVYFGTCGCISPRGCPG (SEQ ID NO: 181); CNHFTLTTCGCISPRGCPG (SEQ ID NO: 182); CHHFTLTTCGCISPRGCPG (SEQ ID NO: 183); YNPCATPMCCISPRGCPG (SEQ ID NO: 184); CNHHYFYTCGCISPRGCG (SEQ ID NO: 185); CNHHYHYYCGCISPRGCG (SEQ ID NO: 186); CNHVYFGTCGCISPRGCG (SEQ ID NO: 187); CHHVYWGHCGCISPRGCG (SEQ ID NO: 188); CPHFTTTSCGCISPRGCG (SEQ ID NO: 189); CNHFTLTTCGCISPRGCG (SEQ ID NO: 190); CHHFTLTTCGCISPRGCG (SEQ ID NO: 191); CPYYTLSYCGCISPRGCG (SEQ ID NO: 192); CPHVSFGSCGCISPRGCG (SEQ ID NO: 193); ADHVFWGSYGCISPRGCG (SEQ ID NO: 194); YNPCATPMCCISPRGCG (SEQ ID NO: 195); CHHVYWGHCGCISPRGCG (SEQ ID NO: 196); C(N/P)H(H/V/F)(Y/T)(F/W/T/L)(Y/G/T/S)(T/S/Y/H) CGCISPRGCG (SEQ ID NO: 197); CISPRGCGQPIPSVK (SEQ ID NO: 198); CISPRGCTQPYHVSR (SEQ ID NO: 199); and/or CISPRGCNAVSGLGS (SEQ ID NO: 200).

Suitable masking moieties for use with antibodies that bind a Jagged target, e.g., Jagged 1 and/or Jagged 2, include, by way of non-limiting example, masking moieties that include a sequence such as QGQSGQCNIWLVGGDCRGWQG (SEQ ID NO: 496); QGQSGQGQQQWCNIWINGGDCRGWNG (SEQ ID NO: 201); PWCMQRQDFLRCPQP (SEQ ID NO: 202); QLGLPAYMCTFECLR (SEQ ID NO: 203); CNLWVSGGDCGGLQG (SEQ ID NO: 204); SCSLWTSGSCLPHSP (SEQ ID NO: 205); YCLQLPHYMQAMCGR (SEQ ID NO: 206); CFLYSCTDVSYWNNT (SEQ ID NO: 207); PWCMQRQDYLRCPQP (SEQ ID NO: 208); CNLWISGGDCRGLAG (SEQ ID NO: 209); CNLWVSGGDCRGVQG (SEQ ID NO: 210); CNLWVSGGDCRGLRG (SEQ ID NO: 211); CNLWISGGDCRGLPG (SEQ ID NO: 212); CNLWVSGGDCRDAPW (SEQ ID NO: 213); CNLWVSGGDCRDLLG (SEQ ID NO: 214); CNLWVSGGDCRGLQG (SEQ ID NO: 215); CNLWLHGGDCRGWQG (SEQ ID NO: 216); CNIWLVGGDCRGWQG (SEQ ID NO: 217); CTTWFCGGDCGVMRG (SEQ ID NO: 218); CNIWGPSVDCGALLG (SEQ ID NO: 219); CNIWVNGGDCRSFEG (SEQ ID NO: 220); YCLNLPRYMQDMCWA (SEQ ID NO: 221); YCLALPHYMQADCAR (SEQ ID NO: 222); CFLYSCGDVSYWGSA (SEQ ID NO: 223); CYLYSCTDSAFWNNR (SEQ ID NO: 224); CYLYSCNDVSYWSNT (SEQ ID NO: 225); CFLYSCTDVSYW (SEQ ID NO: 226); CFLYSCTDVAYWNSA (SEQ ID NO: 227); CFLYSCTDVSYWGDT (SEQ ID NO: 228); CFLYSCTDVSYWGNS (SEQ ID NO: 229); CFLYSCTDVAYWNNT (SEQ ID NO: 230); CFLYSCGDVSYWGNPGLS (SEQ ID NO: 231); CFLYSCTDVAYWSGL (SEQ ID NO: 232); CYLYSCTDGSYWNST (SEQ ID NO: 233); CFLYSCSDVSYWGNI (SEQ ID NO: 234); CFLYSCTDVAYW (SEQ ID NO: 235); CFLYSCTDVSYWGST (SEQ ID NO: 236); CFLYSCTDVAYWGDT (SEQ ID NO: 237); GCNIWLNGGDCRGWVDPLQG (SEQ ID NO: 238); GCNIWLVGGDCRGWIGDTNG (SEQ ID NO: 239); GCNIWLVGGDCRGWIEDSNG (SEQ ID NO: 240); GCNIWANGGDCRGWIDNIDG (SEQ ID NO: 241); GCNIWLVGGDCRGWLGEAVG (SEQ ID NO: 242); GCNIWLVGGDCRGWLEEAVG (SEQ ID NO: 243); GGPALCNIWLNGGDCRGWSG (SEQ ID NO: 244); GAPVFCNIWLNGGDCRGWMG (SEQ ID NO: 245); GQQQWCNIWINGGDCRGWNG (SEQ ID NO: 246); GKSEFCNIWLNGGDCRGWIG (SEQ ID NO: 247); GTPGGCNIWANGGDCRGWEG (SEQ ID NO: 248);

GASQYCNLWINGGDCRGWRG (SEQ ID NO: 249); GCNIWLVGGDCRPWVEGG (SEQ ID NO: 250); GCNIWAVGGDCRPFVDGG (SEQ ID NO: 251); GCNIWLNGGDCRAWVDTG (SEQ ID NO: 252); GCNIWIVGGDCRPFINDG (SEQ ID NO: 253); GCNIWLNGGDCRPVVFGG (SEQ ID NO: 254); GCNIWLSGGDCRMFMNEG (SEQ ID NO: 255); GCNIWVNGGDCRSFVYSG (SEQ ID NO: 256); GCNIWLNGGDCRGWEASG (SEQ ID NO: 257); GCNIWAHGGDCRGFIEPG (SEQ ID NO: 258); GCNIWLNGGDCRTFVASG (SEQ ID NO: 259); GCNIWAHGGDCRGFIEPG (SEQ ID NO: 260); GFLENCNIWLNGGDCRTG (SEQ ID NO: 261); GIYENCNIWLNGGDCRMG (SEQ ID NO: 262); and/or GIPDNCNIWINGGDCRYG (SEQ ID NO: 263).

Suitable masking moieties for use with antibodies that bind an interleukin 6 target, e.g., interleukin 6 receptor (IL-6R), include, by way of non-limiting example, masking moieties that include a sequence such as QGQSGQYGSCSWNYVHIFMDC (SEQ ID NO: 264); QGQSGQGDFDIPFPAHWVPIT (SEQ ID NO: 265); QGQSGQMGVPAGCVWNYAHIFMDC (SEQ ID NO: 266); YRSCNWNYVSIFLDC (SEQ ID NO: 267); PGAFDIPFPAHWVPNT (SEQ ID NO: 268); ESSCVWNYVHIYMDC (SEQ ID NO: 269); YPGCKWNYDRIFLDC (SEQ ID NO: 270); YRTCSWNYVGIFLDC (SEQ ID NO: 271); YGSCSWNYVHIFMDC (SEQ ID NO: 161); YGSCSWNYVHIFLDC (SEQ ID NO: 272); YGSCNWNYVHIFLDC (SEQ ID NO: 273); YTSCNWNYVHIFMDC (SEQ ID NO: 274); YPGCKWNYDRIFLDC (SEQ ID NO: 275); WRSCNWNYAHIFLDC (SEQ ID NO: 276); WSNCHWNYVHIFLDC (SEQ ID NO: 277); DRSCTWNYVRISYDC (SEQ ID NO: 278); SGSCKWDYVHIFLDC (SEQ ID NO: 279); SRSCIWNYAHIHLDC (SEQ ID NO: 280); SMSCYWQYERIFLDC (SEQ ID NO: 281); YRSCNWNYVSIFLDC (SEQ ID NO: 282); SGSCKWDYVHIFLDC (SEQ ID NO: 283); YKSCHWDYVHIFLDC (SEQ ID NO: 284); YGSCTWNYVHIFMEC (SEQ ID NO: 285); FSSCNWNYVHIFLDC (SEQ ID NO: 286); WRSCNWNYAHIFLDC (SEQ ID NO: 287); YGSCQWNYVHIFLDC (SEQ ID NO: 288); YRSCNWNYVHIFLDC (SEQ ID NO: 289); NMSCHWDYVHIFLDC (SEQ ID NO: 290); FGPCTWNYARISWDC (SEQ ID NO: 291); XXsCXWXYvhIfXdC (SEQ ID NO: 292); MGVPAGCVWNYAHIFMDC (SEQ ID NO: 163); RDTGGQCRWDYVHIFMDC (SEQ ID NO: 293); AGVPAGCTWNYVHIFMEC (SEQ ID NO: 294); VGVPNGCVWNYAHIFMEC (SEQ ID NO: 295); DGGPAGCSWNYVHIFMEC (SEQ ID NO: 296); AVGPAGCWWNYVHIFMEC (SEQ ID NO: 297); CTWNYVHIFMDCGEGEGP (SEQ ID NO: 298); GGVPEGCTWNYAHIFMEC (SEQ ID NO: 299); AEVPAGCWWNYVHIFMEC (SEQ ID NO: 300); AGVPAGCTWNYVHIFMEC (SEQ ID NO: 301); SGASGGCKWNYVHIFMDC (SEQ ID NO: 302); TPGCRWNYVHIFMECEAL (SEQ ID NO: 303); VGVPNGCVWNYAHIFMEC (SEQ ID NO: 304); PGAFDIPFPAHWVPNT (SEQ ID NO: 305); RGACDIPFPAHWIPNT (SEQ ID NO: 306); QGDFDIPFPAHWVPIT (SEQ ID NO: 162); XGafDIPFPAHWvPnT (SEQ ID NO: 307); RGDGNDSDIPFPAHWVPRT (SEQ ID NO: 308); SGVGRDRDIPFPAHWVPRT (SEQ ID NO: 309); WAGGNDCDIPFPAHWIPNT (SEQ ID NO: 310); WGDGMDVDIPFPAHWVPVT (SEQ ID NO: 311); AGSGNDSDIPFPAHWVPRT (SEQ ID NO: 312); ESRSGYADIPFPAHWVPRT (SEQ ID NO: 313); and/or RECGRCGDIPFPAHWVPRT (SEQ ID NO: 314).

When the AB is modified with a MM and is in the presence of the target, specific binding of the AB to its target is reduced or inhibited, as compared to the specific binding of the AB not modified with an MM or the specific binding of the parental AB to the target.

The $K_d$ of the AB modified with a MM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM or of the parental AB towards the target. Conversely, the binding affinity of the AB modified with a MM towards the target is at least 2, 3, 4, 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM or of the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

When the AB is modified with a MM and is in the presence of the target specific binding of the AB to its target is reduced or inhibited, as compared to the specific binding of the AB not modified with an MM or the specific binding of the parental AB to the target. When compared to the binding of the AB not modified with an MM or the binding of the parental AB to the target the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of the AB to the target. The MM binds the antigen binding domain of the AB and inhibits binding of the AB to the target. The MM can sterically inhibit the binding of the AB to the target. The MM can allosterically inhibit the binding of the AB to its target. In these embodiments when the AB is modified or coupled to a MM and in the presence of target there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified by a MM, the MM 'masks' or reduces or otherwise inhibits the specific binding of the AB to the target. When an AB is coupled to or modified by a MM, such coupling or modification can effect a structural change that reduces or inhibits the ability of the AB to specifically bind its target.

An AB coupled to or modified with an MM can be represented by the following formulae (in order from an amino (N) terminal region to carboxyl (C) terminal region:

(MM)—(AB) (AB)—(MM) (MM)—L—(AB)

(AB)—L—(MM)

where MM is a masking moiety, the AB is an antibody or antibody fragment thereof, and the L is a linker. In many embodiments, it may be desirable to insert one or more linkers, e.g., flexible linkers, into the composition so as to provide for flexibility.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 20% identical to any natural binding partner of the AB. In some embodiments, the MM is no more than 10% identical to any natural binding partner of the AB.

In some embodiments, the activatable antibodies include an AB that is modified by an MM and also includes one or more cleavable moieties (CM). Such activatable antibodies exhibit activatable/switchable binding, to the AB's target. Activatable antibodies generally include an antibody or antibody fragment (AB), modified by or coupled to a masking moiety (MM) and a modifiable or cleavable moiety (CM). In some embodiments, the CM contains an amino acid sequence that serves as a substrate for at least one matrix metalloprotease of interest.

The elements of the activatable antibodies are arranged so that the MM and CM are positioned such that in a cleaved (or relatively active) state and in the presence of a target, the AB binds a target while in an uncleaved (or relatively inactive) state in the presence of the target, specific binding of the AB to its target is reduced or inhibited. The specific binding of the AB to its target can be reduced due to the inhibition or masking of the AB's ability to specifically bind its target by the MM.

The $K_d$ of the AB modified with a MM and a CM towards the target is at least 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM and a CM or of the parental AB towards the target. Conversely, the binding affinity of the AB modified with a MM and a CM towards the target is at least 2, 3, 4, 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM or of the parental AB towards the target.

When the AB is modified with a MM and a CM and is in the presence of the target but not in the presence of a modifying agent (for example a MMP), specific binding of the AB to its target is reduced or inhibited, as compared to the specific binding of the AB not modified with an MM and a CM or of the parental AB to the target. When compared to the binding of the parental AB or the binding of an AB not modified with an MM and a CM to its target, the AB's ability to bind the target when modified with an MM and a CM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the activatable antibodies following modification of the CM by at least one matrix metalloprotease. The term uncleaved state, as used herein, refers to the condition of the activatable antibodies in the absence of cleavage of the CM by a MMP. As discussed above, the term "activatable antibodies" is used herein to refer to an activatable antibody in both its uncleaved (native) state, as well as in its cleaved state. It will be apparent to the ordinarily skilled artisan that in some embodiments, a cleaved activatable antibody may lack an MM due to cleavage of the CM by protease, resulting in release of at least the MM (e.g., where the MM is not joined to the activatable antibodies by a covalent bond (e.g., a disulfide bond between cysteine residues).

By activatable or switchable is meant that the activatable antibody exhibits a first level of binding to a target when in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM and AB of the activatable antibodies are selected so that the AB represents a binding moiety for a given target, and the CM represents a substrate for a MMP that is co-localized with the target at a treatment site or diagnostic site in a subject. The activatable antibodies disclosed herein find particular use where, for example, a MMP capable of cleaving a site in the CM is present at relatively higher levels in target-containing tissue of a treatment site or diagnostic site than in tissue of non-treatment sites (for example in healthy tissue).

In some embodiments, activatable antibodies provide for reduced toxicity and/or adverse side effects that could otherwise result from binding of the AB at non-treatment sites if the AB were not masked or otherwise inhibited from binding to the target.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

Activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an activatable antibody, the dynamic range refers to the ratio of (a) a maximum detected level of target protein binding to an activatable antibody in the presence of a MMP capable of cleaving the CM of the activatable antibodies to (b) a minimum detected level of target protein binding to an activatable antibody in the absence of the protease. The dynamic range of an activatable antibody can be calculated as the ratio of the equilibrium dissociation constant of an activatable antibody cleaving agent (e.g., enzyme) treatment to the equilibrium dissociation constant of the activatable antibodies cleaving agent treatment. The greater the dynamic range of an activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM of the activatable antibodies than in the absence of a cleaving agent.

Activatable antibodies can be provided in a variety of structural configurations. Exemplary formulae for activatable antibodies are provided below. It is specifically contemplated that the N- to C-terminal order of the AB, MM and CM may be reversed within an activatable antibody. It is also specifically contemplated that the CM and MM may overlap in amino acid sequence, e.g., such that the CM is contained within the MM.

For example, activatable antibodies can be represented by the following formula (in order from an amino (N) terminal region to carboxyl (C) terminal region:

(MM)-(CM)-(AB) (AB)-(CM)-(MM)

where MM is a masking moiety, CM is a cleavable moiety, and AB is an antibody or fragment thereof. It should be noted that although MM and CM are indicated as distinct components in the formulae above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that may be positioned N-terminal or C-terminal to the activatable antibodies elements.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In many embodiments, it may be desirable to insert one or more linkers, e.g., flexible linkers, into the activatable antibody construct so as to provide for flexibility at one or more of the MM-CM junction, the CM-AB junction, or both. For example, the AB, MM, and/or CM may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments, an activatable antibody comprises one of the following formulae (where the formula below represent an amino acid sequence in either N- to C-terminal direction or C- to N-terminal direction):

(MM)-L1-(CM)-(AB) (MM)-(CM)-L2-(AB)

(MM)-L1-(CM)-L2-(AB)

wherein MM, CM, and AB are as defined above; wherein L1 and L2 are each independently and optionally present or absent, are the same or different flexible linkers that include at least 1 flexible amino acid (e.g., Gly). In addition, the formulae above provide for additional amino acid sequences that may be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

The CM is specifically cleaved by at least one MMP at a rate of about $0.001\text{-}1500\times10^4$ $M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4$ $M^{-1}S^{-1}$.

For specific cleavage by an enzyme, contact between the enzyme and CM is made. When the activatable antibody comprising an AB coupled to a MM and a CM is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers (G)n, glycine-serine polymers (including, for example, (GS) n, (GSGGS)n (SEQ ID NO: 1) and (GGGS)n (SEQ ID NO: 2), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 3), Gly-Gly-Ser-Gly-Gly (SEQ ID NO: 4), Gly-Ser-Gly-Ser-Gly (SEQ ID NO: 5), Gly-Ser-Gly-Gly-Gly (SEQ ID NO: 6), Gly-Gly-Gly-Ser-Gly (SEQ ID NO: 7), Gly-Ser-Ser-Ser-Gly (SEQ ID NO: 8), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

In some embodiments, the activatable antibodies described herein also include an agent conjugated to the activatable antibody. In some embodiments, the conjugated agent is a therapeutic agent, such as an anti-inflammatory and/or an antineoplastic agent. In such embodiments, the agent is conjugated to a carbohydrate moiety of the activatable antibody, for example, in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

The disclosure also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE, MMAD, DMAF, DMAE). For example, the agent is monomethyl auristatin E (MMAE) or monomethyl auristatin D (MMAD). In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the agent is linked to the AB using a maleimide caproyl-valine-citrulline linker or a maleimide PEG-valine-citrulline linker. In some embodiments, the agent is linked to the AB using a maleimide caproyl-valine-citrulline linker. In some embodiments, the agent is linked to the AB using a maleimide PEG-valine-citrulline linker In some embodiments, the agent is monomethyl auristatin D (MMAD) linked to the AB using a maleimide PEG-valine-citrulline-para-aminobenzyloxycarbonyl linker, and this linker payload construct is referred to herein as "vc-MMAD." In some embodiments, the agent is monomethyl auristatin E (MMAE) linked to the AB using a maleimide PEG-valine-citrulline-para-aminobenzyloxycarbonyl linker, and this linker payload construct is referred to herein as "vc-MMAE." The structures of vc-MMAD and vc-MMAE are shown below:

vc-MMAD:

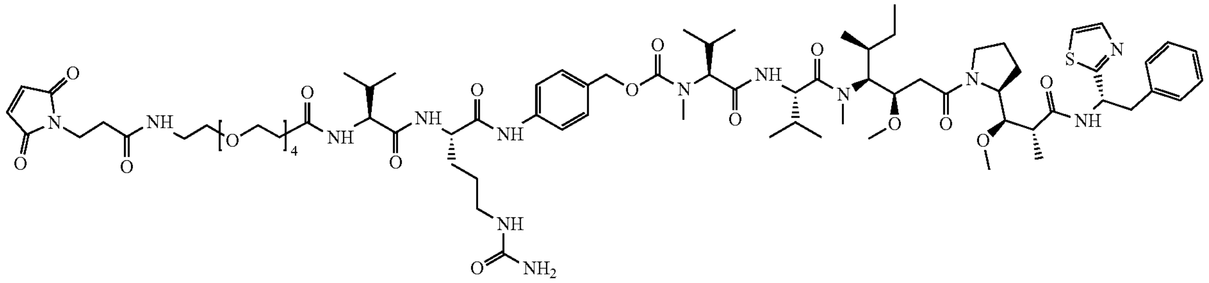

-continued vc-MMAE:

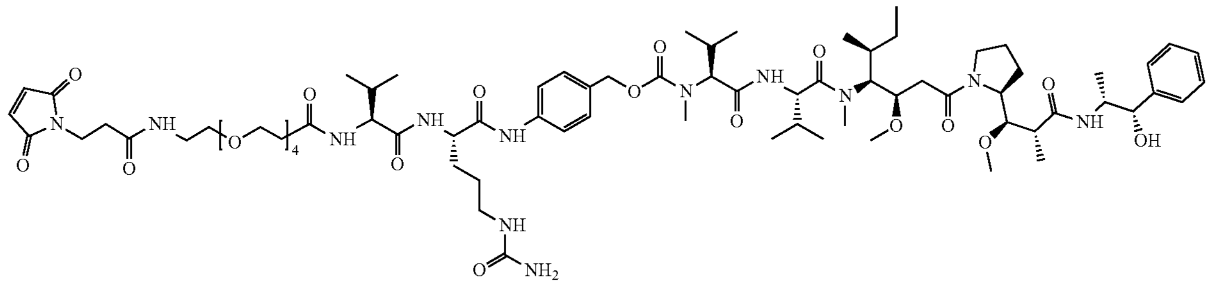

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutarelde-hyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triamine-pentaacetic acid (MX-DTPA) is an exemplary chelating agent for conjugation of radionucleotide to the antibody. (See WO94/11026).

Table 3 lists some of the exemplary pharmaceutical agents that may be employed in the herein described disclosure but in no way is meant to be an exhaustive list.

TABLE 3

| Exemplary Pharmaceutical Agents for Conjugation |
|---|
| CYTOTOXIC AGENTS |
| Auristatins |
| Auristatin E |
| Monomethyl auristatin D (MMAD) |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinoline |
| Dolastatins |
| Dolastatin derivatives |
| Dolastatin 16 DmJ |
| Dolastatin 16 Dpv |

TABLE 3-continued

| Exemplary Pharmaceutical Agents for Conjugation |
|---|
| Maytansinoids, e.g. DM-1; DM-4 |
| Maytansinoid derivatives |
| Duocarmycin |
| Duocarmycin derivatives |
| Alpha-amanitin |
| Anthracyclines |
| Doxorubicin |
| Daunorubicin |
| Bryostatins |
| Camptothecin |
| Camptothecin derivatives |
| 7-substituted Camptothecin |
| 10,11-Difluoromethylenedioxycamptothecin |
| Combretastatins |
| Debromoaplysiatoxin |
| Kahalalide-F |
| Discodermolide |
| Ecteinascidins |
| ANTIVIRALS |
| Acyclovir |
| Vira A |
| Symmetrel |
| ANTIFUNGALS |
| Nystatin |
| ADDITIONAL ANTI-NEOPLASTICS |
| Adriamycin |
| Cerubidine |
| Bleomycin |
| Alkeran |
| Velban |
| Oncovin |
| Fluorouracil |
| Methotrexate |
| Thiotepa |
| Bisantrene |
| Novantrone |
| Thioguanine |
| Procarabizine |
| Cytarabine |
| ANTI-BACTERIALS |
| Aminoglycosides |
| Streptomycin |
| Neomycin |
| Kanamycin |
| Amikacin |
| Gentamicin |
| Tobramycin |
| Streptomycin B |
| Spectinomycin |
| Ampicillin |
| Sulfanilamide |
| Polymyxin |
| Chloramphenicol |

TABLE 3-continued

| Exemplary Pharmaceutical Agents for Conjugation |
| --- |
| Turbostatin |
| Phenstatins |
| Hydroxyphenstatin |
| Spongistatin 5 |
| Spongistatin 7 |
| Halistatin 1 |
| Halistatin 2 |
| Halistatin 3 |
| Modified Bryostatins |
| Halocomstatins |
| Pyrrolobenzimidazoles (PBI) |
| Cibrostatin6 |
| Doxaliform |
| Anthracyclins analogues |
| Cemadotin analogue (CemCH2-SH) |
| Pseudomonas toxin A (PE38) variant |
| Pseudomonas toxin A (ZZ-PE38) variant |
| ZJ-101 |
| OSW-1 |
| 4-Nitrobenzyloxycarbonyl Derivatives of O6-Benzylguanine |
| Topoisomerase inhibitors |
| Hemiasterlin |
| Cephalotaxine |
| Homoharringtonine |
| Pyrrolobenzodiazepine dimers (PBDs) |
| Functionalized pyrrolobenzodiazepenes |
| Calicheamicins |
| Podophyllotoxins |
| Taxanes |
| Vinca alkaloids |
| CONJUGATABLE DETECTION REAGENTS |
| Fluorescein and derivatives thereof |
| Fluorescein isothiocyanate (FITC) |
| RADIOPHARMACEUTICALS |
| $^{125}I$ |
| $^{131}I$ |
| $^{89}Zr$ |
| $^{111}In$ |
| $^{123}I$ |
| $^{131}I$ |
| $^{99}mTc$ |
| $^{201}Tl$ |
| $^{133}Xe$ |
| $^{11}C$ |
| $^{62}Cu$ |
| $^{18}F$ |
| $^{68}Ga$ |
| $^{13}N$ |
| $^{15}O$ |
| $^{38}K$ |
| $^{82}Rb$ |
| $^{99}mTc$ (Technetium) |
| HEAVY METALS |
| Barium |
| Gold |
| Platinum |
| ANTI-MYCOPLASMALS |
| Tylosine |
| Spectinomycin |

Those of ordinary skill in the art will recognize that a large variety of possible moieties can be coupled to the resultant antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

In some embodiments, in addition to the compositions and methods provided herein, the conjugated activatable antibody can also be modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. In some embodiments, suitable linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propionamide] hexanoate (Pierce Chem. Co. Cat. #2165-G); and (v) sulfo-NHS (N-hydroxysulfo-succinimide: Pierce Chem. Co., Cat. #24510) conjugated to EDC. Additional linkers include, but are not limited to, SMCC, sulfo-SMCC, SPDB, or sulfo-SPDB.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, the linkers are cleavable. In some embodiments, the linkers are non-cleavable. In some embodiments, two or more linkers are present. The two or more linkers are all the same, i.e., cleavable or non-cleavable, or the two or more linkers are different, i.e., at least one cleavable and at least one non-cleavable.

The present disclosure utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the disclosure, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present disclosure, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101:3097-3110).

According to the present disclosure, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present disclosure, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In some embodiments, the AB is first attached to the MM, CM and associated linkers and then attached to the linker for conjugation purposes.

Branched Linkers: In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

In some embodiments, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers: Peptide linkers that are susceptible to cleavage by enzymes of the complement system, such as but not limited to urokinase, tissue plasminogen activator, trypsin, plasmin, or another enzyme having proteolytic activity may be used in one embodiment of the present disclosure. According to one method of the present disclosure, an agent is attached via a linker susceptible to cleavage by complement. The antibody is selected from a class that can activate complement. The antibody-agent conjugate, thus, activates the complement cascade and releases the agent at the target site. According to another method of the present disclosure, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 3.

Non-limiting examples of cleavable linker sequences are provided in Table 4.

TABLE 4

Exemplary Linker Sequences for Conjugation

| Types of Cleavable Sequences | Amino Acid Sequence |
|---|---|
| Plasmin cleavable sequences | |
| Pro-urokinase | PRFKIIGG (SEQ ID NO: 127) |
| | PRFRIIGG (SEQ ID NO: 128) |

TABLE 4-continued

Exemplary Linker Sequences for Conjugation

| Types of Cleavable Sequences | Amino Acid Sequence |
|---|---|
| TGFβ | SSRHRRALD (SEQ ID NO: 129) |
| Plasminogen | RKSSIIIRMRDVVL (SEQ ID NO: 130) |
| Staphylokinase | SSSFDKGKYKKGDDA (SEQ ID NO: 131)<br>SSSFDKGKYKRGDDA (SEQ ID NO: 132) |
| Factor Xa cleavable sequences | IEGR (SEQ ID NO: 133)<br>IDGR (SEQ ID NO: 134)<br>GGSIDGR (SEQ ID NO: 135) |
| MMP cleavable sequences | |
| Gelatinase A | PLGLWA (SEQ ID NO: 136) |
| Collagenase cleavable sequences | |
| Calf skin collagen (α1(I) chain) | GPQGIAGQ (SEQ ID NO: 137) |
| Calf skin collagen (α2(I) chain) | GPQGLLGA (SEQ ID NO: 138) |
| Bovine cartilage collagen (α1(II) chain) | GIAGQ (SEQ ID NO: 139) |
| Human liver collagen (α1(III) chain) | GPLGIAGI (SEQ ID NO: 140) |
| Human $\alpha_2$M | GPEGLRVG (SEQ ID NO: 141) |
| Human PZP | YGAGLGVV (SEQ ID NO: 142)<br>AGLGVVER (SEQ ID NO: 143)<br>AGLGISST (SEQ ID NO: 144) |
| Rat $\alpha_1$M | EPQALAMS (SEQ ID NO: 145)<br>QALAMSAI (SEQ ID NO: 146) |
| Rat $\alpha_2$M | AAYHLVSQ (SEQ ID NO: 147)<br>MDAFLESS (SEQ ID NO: 148) |
| Rat $\alpha_1I_3$(2J) | ESLPVVAV (SEQ ID NO: 149) |
| Rat $\alpha_1I_3$(27J) | SAPAVESE (SEQ ID NO: 150) |
| Human fibroblast collagenase (autolytic cleavages) | DVAQFVLT (SEQ ID NO: 151)<br>VAQFVLTE (SEQ ID NO: 152)<br>AQFVLTEG (SEQ ID NO: 153)<br>PVQPIGPQ (SEQ ID NO: 154) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments, the reducing agent that would modify a CM would also modify the linker of the conjugated activatable antibody.

Spacers and Cleavable Elements: In some embodiments, it may be necessary to construct the linker in such a way as to optimize the spacing between the agent and the AB of the activatable antibody. This may be accomplished by use of a linker of the general structure:

$$W-(CH_2)n-Q$$

wherein

W is either —NH—$CH_2$— or —$CH_2$—;

Q is an amino acid, peptide; and n is an integer from 0 to 20.

In some embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers: According to one method of the present disclosure, when release of an agent is desired, an AB that is an antibody of a class that can activate complement is used. The resulting conjugate retains both the ability to bind antigen and activate the complement cascade. Thus, according to this embodiment of the present disclosure, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 3.

Linkers for Release without Complement Activation: In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers: In some embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 5.

TABLE 5

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines | Stable maleimide reactive group | 11.6 Å |
| | Sulfhydryls | Enzyme-antibody conjugation Hapten-carrier proteinconjugation | |
| Sulfo-SMCC | Primary amines | Stable maleimide reactive group | 11.6 Å |
| | Sulfhydryls | Water-soluble Enzyme-antibody conjugation | |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment: In some embodiments of the disclosure, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A-general formula for such an organic linker could be $$W—(CH_2)n—Q$$

wherein

W is either —NH—$CH_2$— or —$CH_2$—;

Q is an amino acid, peptide; and n is an integer from 0 to 20.

Non-Cleavable Conjugates: In some embodiments, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82:3688 (1985); Hwang et al., Proc. Natl Acad. Sci. USA, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257:286-288 (1982) via a disulfide-interchange reaction.

Definitions

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d>10^{-6}$). Antibodies include, but are not limited to, polyclonal, monoclonal, chimeric, domain antibody, single chain, Fab, and $F(ab')_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 μM; in some embodiments, ≤100 nM and in some embodiments, ≤10 nM.

As used herein, the terms "specific binding," "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to the target, when the equilibrium binding constant ($K_d$) is ≤1 μM, in some embodiments ≤100 nM, in some embodiments ≤10 nM, and in some embodiments ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology-A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to the target, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Activatable antibodies of the disclosure specifically bind a given target, e.g., a human target protein. Also included in the disclosure are activatable antibodies that bind to the same epitope as the activatable antibodies described herein.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to the target. If the monoclonal antibody being tested competes with the monoclonal antibody of the disclosure, as shown by a decrease in binding by the monoclonal antibody of the disclosure, then the two monoclonal antibodies bind to the same, or a closely related, epitope. A method for determining whether a monoclonal antibody has the specificity of a monoclonal antibody of the disclosure is to pre-incubate the monoclonal antibody of the disclosure with the target and then add the monoclonal antibody being tested to determine if the monoclonal antibody being tested is inhibited in its ability to bind the target. If the monoclonal antibody being tested is inhibited then, in all likelihood, it has the same, or functionally equivalent, epitopic specificity as the monoclonal antibody of the disclosure.

Multispecific Activatable Antibodies

The disclosure also provides multispecific activatable antibodies. The multispecific activatable antibodies provided herein are multispecific antibodies that recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a cleavable moiety (CM) that functions as a substrate for at least one MMP protease. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the multispecific activatable antibodies are designed to engage immune effector cells, also referred to herein as immune-effector cell engaging multispecific activatable antibodies. In some embodiments, the multispecific activatable antibodies are designed to engage leukocytes, also referred to herein as leukocyte engaging multispecific activatable antibodies. In some embodiments, the multispecific activatable antibodies are designed to engage T cells, also referred to herein as T-cell engaging multispecific activatable antibodies. In some embodiments, the multispecific activatable antibodies engage a surface antigen on a leukocyte, such as on a T cell, on a natural killer (NK) cell, on a myeloid mononuclear cell, on a macrophage, and/or on another immune effector cell. In some embodiments, the immune effector cell is a leukocyte. In some embodiments, the immune effector cell is a T cell. In some embodiments, the immune effector cell is a NK cell. In some embodiments, the immune effector cell is a mononuclear cell, such as a myeloid mononuclear cell. In some embodiments, the multispecific activatable antibodies are designed to bind or otherwise interact with more than one target and/or more than one epitope, also referred to herein as multi-antigen targeting activatable antibodies. As used herein, the terms "target" and "antigen" are used interchangeably.

In some embodiments, immune effector cell engaging multispecific activatable antibodies of the disclosure include a targeting antibody or antigen-binding fragment thereof and an immune effector cell engaging antibody or antigen-binding portion thereof, where at least one of the targeting antibody or antigen-binding fragment thereof and/or the immune effector cell engaging antibody or antigen-binding portion thereof is masked. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the non-immune effector cell engaging antibody is a cancer targeting antibody. In some embodiments the non-immune cell effector antibody is an IgG. In some embodiments the immune effector cell engaging antibody is a scFv. In some embodiments the targeting antibody (e.g., non-immune cell effector antibody) is an IgG and the immune effector cell engaging antibody is a scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments, T-cell engaging multispecific activatable antibodies of the disclosure include a targeting antibody or antigen-binding fragment thereof and a T-cell engaging antibody or antigen-binding portion thereof, where at least one of the targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibodies include a cancer targeting antibody or antigen-binding fragment thereof and a T-cell engaging antibody or antigen-binding portion thereof, where at least one of the cancer targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibodies include a cancer targeting IgG antibody or antigen-binding fragment thereof and a T-cell engaging scFv, where at least one of the cancer targeting IgG antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments of an immune effector cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA. In some embodiments, the antigen is a stimulatory receptor present on the surface of a T cell or NK cell; examples of such stimulatory receptors include, but are not limited to, CD3, CD27, CD28, CD137 (also referred to as 4-1BB), GITR, HVEM, ICOS, NKG2D, and OX40. In some embodiments, the antigen is an inhibitory receptor present on the surface of a T-cell; examples of such inhibitory receptors include, but are not limited to, BTLA, CTLA-4, LAG3, PD-1, TIGIT, TIM3, and NK-expressed KIRs. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9.

One embodiment of the disclosure is a multispecific activatable antibody that is activatable in a cancer microenvironment and that includes an antibody, for example a IgG or scFv, directed to a tumor target and an agonist antibody, for example an IgG or scFv, directed to a co-stimulatory receptor expressed on the surface of an activated T cell or NK cell, wherein at least one of the cancer target antibody and/or agonist antibody is masked. Examples of co-stimulatory receptors include, but are not limited to, CD27, CD137, GITR, HVEM, NKG2D, and OX40. In this embodiment, the multispecific activatable antibody, once activated by tumor-associated proteases, would effectively crosslink and activate the T cell or NK cell expressed co-stimulatory receptors in a tumor-dependent manner to enhance the activity of T cells that are responding to any tumor antigen via their endogenous T cell antigen or NK-activating receptors. The activation-dependent nature of these T cell or NK cell costimulatory receptors would focus the activity of the activated multispecific activatable antibody to tumor-specific T cells, without activating all T cells independent of their antigen specificity. In one embodiment, at least the co-stimulatory receptor antibody of the multispecific activatable antibody is masked to prevent activation of autoreactive T cells that may be present in tissues that also express the antigen recognized by the tumor target-directed antibody in the multispecific activatable antibody, but whose activity is restricted by lack of co-receptor engagement.

One embodiment of the disclosure is a multispecific activatable antibody that is activatable in a disease characterized by T cell overstimulation, such as, but not limited to, an autoimmune disease or inflammatory disease microenvironment. Such a multispecific activatable antibody includes an antibody, for example a IgG or scFv, directed to a target comprising a surface antigen expressed in a tissue targeted by a T cell in autoimmune or inflammatory disease and an antibody, for example a IgG or scFv, directed to an inhibitory receptor expressed on the surface of a T cell or NK cell, wherein at least one of the disease tissue target antibody and/or T cell inhibitory receptor antibody is masked. Examples of inhibitory receptors include, but are not limited to, BTLA, CTLA-4, LAG3, PD-1, TIGIT, TIM3, and NK-expressed KIRs. Examples of a tissue antigen targeted by T cells in autoimmune disease include, but are not limited to, a surface antigen expressed on myelin or nerve cells in multiple sclerosis or a surface antigen expressed on pancreatic islet cells in Type 1 diabetes. In this embodiment, the multispecific activatable antibody when localized in the tissue under autoimmune attack or inflammation is activated and co-engages the T cell or NK cell inhibitory receptor to suppress the activity of autoreactive T cells responding to any disease tissue-targeted antigens via their endogenous TCR or activating receptors. In one embodiment, at least one or multiple antibodies are masked to prevent suppression of T cell responses in non-disease tissues where the target antigen may also be expressed.

In some embodiments, the T-cell engaging multispecific activatable antibody includes an anti-CD3 epsilon (CD3ε, also referred to herein as CD3e and CD3) scFv and a targeting antibody or antigen-binding fragment thereof, where at least one of the anti-CD3ε scFv and/or the targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CD3ε scFv and a cancer targeting antibody or antigen-binding fragment thereof, where at least one of the anti-CD3ε scFv and/or the cancer targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3ε scFv and a cancer targeting IgG antibody or antigen-binding fragment thereof, where at least one of the anti-CD3ε scFv and/or the cancer targeting IgG antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3 epsilon (CD3ε) scFv that is derived from OKT3, where at least one of the targeting antibody or antigen-binding fragment thereof and/or the OKT3 scFv or OKT3-derived scFv is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an OKT3 scFv or OKT3-derived scFv and a cancer targeting antibody or antigen-binding fragment thereof, where at least one of the OKT3 scFv or OKT3-derived scFv and/or the cancer targeting antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an OKT3 scFv or OKT3-derived scFv and a cancer targeting IgG antibody or antigen-binding fragment thereof, where at least one of the OKT3 scFv or OKT3-derived scFv and/or the cancer targeting IgG antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CTLA-4 scFv, where at least one of the targeting antibody or antigen-binding fragment thereof and/or the anti-CTLA-4 scFv is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CTLA-4 scFv and a targeting IgG antibody or antigen-binding fragment thereof, where at least one of the anti-CTLA-4 scFv and/or the targeting IgG antibody or antigen-binding portion thereof is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting IgG antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody IgG or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the multi-antigen targeting antibodies and/or multi-antigen targeting activatable antibodies include at least a first antibody or antigen-binding fragment thereof that binds a first target and/or first epitope and a second antibody or antigen-binding fragment thereof that binds a second target and/or a second epitope. In some embodiments, the multi-antigen targeting antibodies and/or multi-antigen targeting activatable antibodies bind two or more different targets. In some embodiments, the multi-antigen targeting antibodies and/or multi-antigen targeting activatable antibodies bind two or more different epitopes on the same target. In some embodiments, the multi-antigen targeting antibodies and/or multi-antigen targeting activatable antibodies bind a combination of two or more different targets and two or more different epitopes on the same target.

In some embodiments, a multispecific activatable antibody comprising an IgG has the IgG variable domains masked. In some embodiments, a multispecific activatable antibody comprising a scFv has the scFv domains masked. In some embodiments, a multispecific activatable antibody has both IgG variable domains and scFv domains, where at least one of the IgG variable domains is coupled to a masking moiety. In some embodiments, a multispecific activatable antibody has both IgG variable domains and scFv domains, where at least one of the scFv domains is coupled to a masking moiety. In some embodiments, a multispecific activatable antibody has both IgG variable domains and scFv domains, where at least one of the IgG variable domains is coupled to a masking moiety and at least one of the scFv domains is coupled to a masking moiety. In some embodiments, a multispecific activatable antibody has both IgG variable domains and scFv domains, where each of the IgG variable domains and the scFv domains is coupled to its own masking moiety. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

In a multispecific activatable antibody, a scFv can be fused to the carboxyl terminus of the heavy chain of an IgG activatable antibody, to the carboxyl terminus of the light chain of an IgG activatable antibody, or to the carboxyl termini of both the heavy and light chains of an IgG activatable antibody. In a multispecific activatable antibody, a scFv can be fused to the amino terminus of the heavy chain of an IgG activatable antibody, to the amino terminus of the light chain of an IgG activatable antibody, or to the amino termini of both the heavy and light chains of an IgG activatable antibody. In a multispecific activatable antibody, a scFv can be fused to any combination of one or more carboxyl termini and one or more amino termini of an IgG activatable antibody. In some embodiments, a masking moiety (MM) linked to a cleavable moiety (CM) is attached to and masks an antigen binding domain of the IgG. In some embodiments, a masking moiety (MM) linked to a cleavable moiety (CM) is attached to and masks an antigen binding domain of at least one scFv. In some embodiments, a masking moiety (MM) linked to a cleavable moiety (CM) is attached to and masks an antigen binding domain of an IgG and a masking moiety (MM) linked to a cleavable moiety (CM) is attached to and masks an antigen binding domain of at least one scFv.

The disclosure provides examples of multispecific activatable antibody structures which include, but are not limited to, the following: $(VL-CL)_2$: $(VH-CH1-CH2-CH3-L4-VH^*-L3-VL^*-L2-CM-L1-MM)_2$; $(VL-CL)_2$: $(VH-CH1-CH2-CH3-L4-VL^*-L3-VH^*-L2-CM-L1-MM)_2$; $(MM-L1-CM-L2-VL-CL)_2$: $(VH-CH1-CH2-CH3-L4-VH^*-L3-VL^*)_2$; $(MM-L1-CM-L2-VL-CL)_2$: $(VH-CH1-CH2-CH3-L4-VL^*-L3-VH^*)_2$; $(VL-CL)_2$: $(MM-L1-CM-L2-VL^*-L3-VH^*-L4-VH-CH1-CH2-CH3)_2$; $(VL-CL)_2$: $(MM-L1-CM-L2-VH^*-L3-VL^*-L4-VH-CH1-CH2-CH3)_2$; $(MM-L1-CM-L2-VL-CL)_2$: $(VL^*-L3-VH^*-L4-VH-CH1-CH2-CH3)_2$; $(MM-L1-CM-L2-VL-CL)_2$: $(VH^*-L3-VL^*-L4-VH-CH1-CH2-CH3)_2$; $(VL-CL-L4-VH^*-L3-VL^*-L2-CM-L1-MM)_2$: $(VH-CH1-CH2-CH3)_2$; $(VL-CL-L4-VL^*-L3-VH^*-L2-CM-L1-MM)_2$: $(VH-CH1-CH2-CH3)_2$; $(MM-L1-CM-L2-VL^*-L3-VH^*-L4-VL-CL)_2$: $(VH-CH1-CH2-CH3)_2$; $(MM-L1-CM-L2-VH^*-L3-VL^*-L4-VL-CL)_2$: $(VH-CH1-CH2-CH3)_2$; $(VL-CL-L4-VH^*-L3-VL^*-L2-CM-L1-MM)_2$: $(MM-L1-CM-L2-VL^*-L3-VH^*-L4-VH-CH1-CH2-CH3)_2$; $(VL-CL-L4-VH^*-L3-VL^*-L2-CM-L1-MM)_2$: $(MM-L1-CM-L2-VH^*-L3-VL^*-L4-VH-CH1-CH2-CH3)_2$; $(VL-CL-L4-VL^*-L3-VH^*-L2-CM-L1-MM)_2$: $(MM-L1-CM-L2-VL^*-L3-VH^*-L4-VH-CH1-CH2-CH3)_2$; $(VL-CL-L4-VL^*-L3-VH^*-L2-CM-L1-MM)_2$: $(MM-L1-CM-L2-VH^*-L3-VL^*-L4-VH-CH1-CH2-CH3)_2$; $(VL-CL-L4-VH^*-L3-VL^*)_2$: $(MM-L1-CM-L2-VL^*-L3-VH^*-L4-VH-CH1-CH2-CH3)_2$; $(VL-CL-L4-VH^*-L3-VL^*)_2$: $(MM-L1-CM-L2-VH^*-L3-VL^*-L4-VH-CH1-CH2-CH3)_2$; $(VL-CL-L4-VL^*-L3-VH^*)_2$: $(MM-L1-CM-L2-VL^*-L3-VH^*-L4-VH-CH1-CH2-CH3)_2$; $(VL-CL-L4-VL^*-L3-VH^*)_2$: $(MM-L1-CM-L2-VH^*-L3-VL^*-L4-VH-CH1-CH2-CH3)_2$; $(VL-CL-L4-VH^*-L3-VL^*-L2-CM-L1-MM)_2$: $(VL^*-L3-VH^*-L4-VH-CH1-CH2-CH3)_2$; $(VL-CL-L4-VH^*-L3-VL^*-L2-CM-L1-MM)_2$: $(VH^*-L3-VL^*-L4-VH-CH1-CH2-CH3)_2$; $(VL-CL-L4-VL^*-L3-VH^*-L2-CM-L1-MM)_2$: $(VL^*-L3-VH^*-L4-VH-CH1-CH2-CH3)_2$; or $(VL-CL-L4-VL^*-L3-VH^*-L2-CM-L1-MM)_2$: (VH*-L3-VL*-L4-VH-CH1-CH2-CH3) 2, wherein: VL and VH represent the light and heavy variable domains of the first specificity, contained in the IgG; VL* and VH* represent the variable domains of the second specificity, contained in the scFv; L1 is a linker peptide connecting the masking moiety (MM) and the cleavable moiety (CM); L2 is a linker peptide connecting the cleavable moiety (CM), and the antibody; L3 is a linker peptide connecting the variable domains of the scFv; L4 is a linker peptide connecting the antibody of the first specificity to the antibody of the second specificity; CL is the light-chain constant domain; and CH1, CH2, CH3 are the heavy chain constant domains. The first and second specificities may be toward any antigen or epitope.

In some embodiments of a T-cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory (also referred to herein as activating) or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137 (also referred to as TNFRSF9), CTLA-4, GITR, HVEM, ICOS, LAG3, NKG2D, OX40, PD-1, TIGIT, TIM3, or VISTA. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9. In some embodiments of a multi-antigen targeting activatable antibody, one antigen is selected from the group of targets listed in Table 1, and another antigen is selected from the group of targets listed in Table 1.

In some embodiments, the targeting antibody is an anti-EGFR antibody. In some embodiments, the targeting antibody is C225v5, which is specific for binding to EGFR. In some embodiments, the targeting antibody is C225, which is specific for binding to EGFR. In some embodiments, the targeting antibody is C225v4, which is specific for binding to EGFR. In some embodiments, the targeting antibody is C225v6, which is specific for binding to EGFR. In some embodiments, the targeting antibody is an anti-Jagged antibody. In some embodiments, the targeting antibody is 4D11, which is specific for binding to human and mouse Jagged 1 and Jagged 2. In some embodiments, the targeting antibody is 4D11v2, which is specific for binding to human and mouse Jagged 1 and Jagged 2.

In some embodiments, the targeting antibody can be in the form an activatable antibody. In some embodiments, the scFv(s) can be in the form of a Pro-scFv (see, e.g., WO 2009/025846, WO 2010/081173).

In some embodiments, the scFv is specific for binding CD3ε, and is or is derived from an antibody or fragment thereof that binds CD3ε, e.g., CH2527, FN18, H2C, OKT3, 2C11, UCHT1, or V9. In some embodiments, the scFv is specific for binding CTLA-4 (also referred to herein as CTLA and CTLA4).

In some embodiments, the anti-CTLA-4 scFv includes the amino acid sequence:

(SEQ ID NO: 510)
GGGSGGGGSGSGGGSGGGGSGGGEIVLTQSPGTLSLSPGERATLSCRASQ

-continued

SVSSSYLAWYQQKPGQAPRLLIYGASSRATGIPDRFSGSGSGTDFTLTIS

RLEPEDFAVYYCQQYGSSPLTFGGGTKVEIKRSGGSTITSYNVYYTKLSS

SGTQVQLVQTGGGVVQPGRSLRLSCAASGSTFSSYAMSWVRQAPGKGLEW

VSAISGSGGSTYYADSVKGRFTISRDNSKNTLYLQMNSLRAEDTAVYYCA

TNSLYWYFDLWGRGTLVTVSSAS

In some embodiments, the anti-CTLA-4 scFv includes the amino acid sequence that is at least 90%, 91%, 92%, 93%, 94%, 95%, 96%, 97%, 98%, 99% or more identical to the amino acid sequence of SEQ ID NO: 510.

In some embodiments, the anti-CD3ε scFv includes the amino acid sequence:

(SEQ ID NO: 511)
GGGSGGGGSGSGGGSGGGGSGGGQVQLQQSGAELARPGASVKMSCKASGY

TFTRYTMHWVKQRPGQGLEWIGYINPSRGYTNYNQKFKDKATLTTDKSSS

TAYMQLSSLTSEDSAVYYCARYYDDHYCLDYWGQGTTLTVSSGGGGSGGG

GSGGGGSQIVLTQSPAIMSASPGEKVTMTCSASSSVSYMNWYQQKSGTSP

KRWIYDTSKLASGVPAHFRGSGSGTSYSLTISGMEAEDAATYYCQQWSSN

PFTFGSGTKLEINR

In some embodiments, the anti-CD3ε scFv includes the amino acid sequence that is at least 90%, 91%, 92%, 93%, 94%, 95%, 96%, 97%, 98%, 99% or more identical to the amino acid sequence of SEQ ID NO: 511.

In some embodiments, the scFv is specific for binding one or more T-cells, one or more NK-cells and/or one or more macrophages. In some embodiments, the scFv is specific for binding a target selected from the group consisting of B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA.

In some embodiments, the multispecific activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the multispecific activatable antibody via a linker. In some embodiments, the agent is conjugated to the AB via a cleavable linker. In some embodiments, the agent is conjugated to the AB via a linker that includes at least one MMP-cleavable substrate sequence. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the multispecific activatable antibody also includes a detectable moiety. In some embodiments, the detectable moiety is a diagnostic agent.

In some embodiments, the multispecific activatable antibody naturally contains one or more disulfide bonds. In some embodiments, the multispecific activatable antibody can be engineered to include one or more disulfide bonds.

The disclosure also provides an isolated nucleic acid molecule encoding a multispecific activatable antibody described herein, as well as vectors that include these isolated nucleic acid sequences. The disclosure provides methods of producing a multispecific activatable antibody by culturing a cell under conditions that lead to expression of the activatable antibody, wherein the cell comprises such a nucleic acid molecule. In some embodiments, the cell comprises such a vector.

The disclosure also provides a method of manufacturing multispecific activatable antibodies of the disclosure by (a) culturing a cell comprising a nucleic acid construct that encodes the multispecific activatable antibody under conditions that lead to expression of the multispecific activatable, and (b) recovering the multispecific activatable antibody.

The disclosure also provides multispecific activatable antibodies and/or multispecific activatable antibody compositions that include at least a first antibody or antigen-binding fragment thereof (AB1) that specifically binds a first target or first epitope and a second antibody or antigen-biding fragment thereof (AB2) that binds a second target or a second epitope, where at least AB1 is coupled or otherwise attached to a masking moiety (MM1), such that coupling of the MM1 reduces the ability of AB1 to bind its target. In some embodiments, the MM1 is coupled to AB1 via a first cleavable moiety (CM1) sequence that includes a substrate for a protease, for example, a protease that is co-localized with the target of AB1 at a treatment site or a diagnostic site in a subject. The multispecific activatable antibodies provided herein are stable in circulation, activated at intended sites of therapy and/or diagnosis but not in normal, i.e., healthy tissue, and, when activated, exhibit binding to the target of AB1 that is at least comparable to the corresponding, unmodified multispecific antibody.

In some embodiments, the multispecific activatable antibody comprises a linking peptide between the MM1 and the CM1.

In some embodiments, the multispecific activatable antibody comprises a linking peptide between the CM1 and the AB1.

In some embodiments, the activatable antibody comprises a first linking peptide (LP1) and a second linking peptide (LP2), and at least a portion of the multispecific activatable antibody has the structural arrangement from N-terminus to C-terminus as follows in the uncleaved state: MM1-LP1-CM1-LP2-AB1 or AB1-LP2-CM1-LP1-MM1. In some embodiments, the two linking peptides need not be identical to each other.

In some embodiments, at least one of LP1 or LP2 includes an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one. In some embodiments, at least one of LP1 or LP2 includes an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8).

In some embodiments, the multispecific activatable antibody includes at least a first antibody or antigen-binding fragment thereof (AB1) that specifically binds a first target or first epitope and a second antibody or antigen-binding fragment thereof (AB2) that specifically binds a second target or second epitope. In some embodiments, each of the AB in the multispecific activatable antibody is independently selected from the group consisting of a monoclonal antibody, domain antibody, single chain, Fab fragment, a $F(ab')_2$ fragment, a scFv, a scAb, a dAb, a single domain heavy chain antibody, and a single domain light chain antibody. In some embodiments, each of the AB in the multispecific activatable antibody is a rodent (e.g., mouse or rat), chimeric, humanized or fully human monoclonal antibody.

In some embodiments, each of the AB in the multispecific activatable antibody has an equilibrium dissociation constant of about 100 nM or less for binding to its corresponding target or epitope.

In some embodiments, MM1 has an equilibrium dissociation constant for binding to its corresponding AB that is greater than the equilibrium dissociation constant of the AB to its corresponding target or epitope.

In some embodiments, MM1 has an equilibrium dissociation constant for binding to its corresponding AB that is no more than the equilibrium dissociation constant of the AB to its corresponding target or epitope.

In some embodiments, MM1 does not interfere or compete with its corresponding AB for binding to the corresponding target or epitope when the multispecific activatable antibody is in a cleaved state.

In some embodiments, MM1 is a polypeptide of about 2 to 40 amino acids in length. In some embodiments, each of the MM in the multispecific activatable antibody is a polypeptide of no more than 40 amino acids in length.

In some embodiments, MM1 has a polypeptide sequence that is different from that of target of the corresponding AB.

In some embodiments, MM1 has a polypeptide sequence that is no more than 50% identical to any natural binding partner of the corresponding AB. In some embodiments, MM1 has a polypeptide sequence that is no more than 25% identical to any natural binding partner of the corresponding AB. In some embodiments, MM1 has a polypeptide sequence that is no more than 10% identical to any natural binding partner of the corresponding AB.

In some embodiments, the coupling of MM1 reduces the ability of the corresponding AB to bind its target or epitope such that the dissociation constant ($K_d$) of the AB when coupled to the MM1 towards its corresponding target or epitope is at least 20 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 40 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 100 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 1000 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 10,000 times greater than the $K_d$ of the AB when not coupled to the MM1 towards its corresponding target or epitope.

In some embodiments, MM1 is an amino acid sequence selected from a MM disclosed herein.

In some embodiments, the multispecific activatable antibody includes at least a second masking moiety (MM2) that inhibits the binding of the AB2 to its target when the multispecific activatable antibody is in an uncleaved state, and a second cleavable moiety (CM2) coupled to the AB2, wherein the CM2 is a polypeptide that functions as a substrate for a second protease. In some embodiments, CM2 is a polypeptide of no more than 15 amino acids long. In some embodiments, the second protease is co-localized with the second target or epitope in a tissue, and wherein the second protease cleaves the CM2 in the multispecific activatable antibody when the multispecific activatable antibody is exposed to the second protease. In some embodiments, the first protease and the second protease are co-localized with the first target or epitope and the second target or epitope in a tissue. In some embodiments, the first protease and the second protease are the same protease. In some embodiments, CM1 and CM2 are different substrates for the same protease. In some embodiments, the protease is selected from the group consisting of those shown in Table 7. In some embodiments, the first protease and the second protease are different proteases. In some embodiments, the first protease and the second protease are different proteases selected from the group consisting of those shown in Table 7.

In some embodiments, each of the MM in the multispecific activatable antibody, e.g., MM1 and at least MM2, has an equilibrium dissociation constant for binding to its corresponding AB that is greater than the equilibrium dissociation constant of the AB to its corresponding target or epitope.

In some embodiments, each of the MM in the multispecific activatable antibody has an equilibrium dissociation constant for binding to its corresponding AB that is no more than the equilibrium dissociation constant of the AB to its corresponding target or epitope.

In some embodiments, each of the MM in the multispecific activatable antibody does not interfere or compete with its corresponding AB for binding to the corresponding target or epitope when the multispecific activatable antibody is in a cleaved state.

In some embodiments, each of the MM in the multispecific activatable antibody is a polypeptide of about 2 to 40 amino acids in length. In some embodiments, each of the MM in the multispecific activatable antibody is a polypeptide of no more than 40 amino acids in length.

In some embodiments, each of the MM in the multispecific activatable antibody has a polypeptide sequence that is different from that of target of the corresponding AB.

In some embodiments, each of the MM in the multispecific activatable antibody has a polypeptide sequence that is no more than 50% identical to any natural binding partner of the corresponding AB. In some embodiments, each of the MM in the multispecific activatable antibody has a polypeptide sequence that is no more than 25% identical to any natural binding partner of the corresponding AB. In some embodiments, each of the MM in the multispecific activatable antibody has a polypeptide sequence that is no more than 10% identical to any natural binding partner of the corresponding AB.

In some embodiments, the coupling of each of the MM reduces the ability of the corresponding AB to bind its target or epitope such that the dissociation constant ($K_d$) of the AB when coupled to the MM towards its corresponding target or epitope is at least 20 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 40 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 100 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 1000 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 10,000 times greater than the $K_d$ of the AB when not coupled to the MM towards its corresponding target or epitope.

In some embodiments, each of the MM is an amino acid sequence selected from a MM disclosed herein.

In some embodiments, at least one of CM1 and/or CM2 is cleaved by at least one MMP protease. In some embodiments, at least one of CM1 and/or CM2 includes an amino acid sequence selected from the group consisting of ISSGLLSS (SEQ ID NO: 14); QNQALRMA (SEQ ID NO: 15); AQNLLGMV (SEQ ID NO: 16); STFPFGMF (SEQ ID NO: 17); PVGYTSSL (SEQ ID NO: 18); DWLYWPGI (SEQ ID NO: 19); MIAPVAYR (SEQ ID NO: 20); RPSPMWAY (SEQ ID NO: 21); WATPRPMR (SEQ ID NO: 22); FRLLDWQW (SEQ ID NO: 23); LKAAPRWA (SEQ ID NO: 24); GPSHLVLT (SEQ ID NO: 25); LPGGLSPW (SEQ ID NO: 26); MGLFSEAG (SEQ ID NO: 27); SPLPLRVP (SEQ ID NO: 28); RMHLRSLG (SEQ ID NO: 29); LAAPLGLL (SEQ ID NO: 30); AVGLLAPP (SEQ ID NO: 31); LLAPSHRA (SEQ ID NO: 32); PAGLWLDP (SEQ ID NO: 33); and ISSGLSS (SEQ ID NO: 159).

In some embodiments, at least one of CM1 and/or CM2 includes an amino acid sequence selected from the group consisting of SEQ ID NOs: 364-370, 379-393, 402-409, 420-424, 434, 435, 450-452, 457, 470-472, 474, and 483.

In some embodiments, at least one of CM1 and/or CM2 includes an amino acid sequence selected from the group consisting of SEQ ID NOs: 328, 336-339, and 348-351.

In some embodiments, the protease that cleaves the first cleavable moiety (CM1) sequence is co-localized with the target of the AB1 in the multispecific activatable antibody in a tissue, and the protease cleaves the CM1 in the multispecific activatable antibody when the multispecific activatable antibody is exposed to the protease.

In some embodiments, the multispecific activatable antibody includes more than one cleavable moiety sequence, and the protease that cleaves at least one cleavable moiety sequence is co-localized with the target of at least one of the AB regions in the multispecific activatable antibody in a tissue, and the protease cleaves the CM in the multispecific activatable antibody when the multispecific activatable antibody is exposed to the protease.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least twofold greater than the equilibrium dissociation constant of an unmodified AB binding to its target, and whereas in the cleaved state, the AB binds its target.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least threefold greater than the equilibrium dissociation constant of an unmodified AB binding to its target, and whereas in the cleaved state, the AB binds its target.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least fourfold greater than the equilibrium dissociation constant of an unmodified AB binding to its target, and whereas in the cleaved state, the AB binds its target.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least fivefold greater than the equilibrium dissociation constant of an unmodified AB binding to its target, and whereas in the cleaved state, the AB binds its target.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least tenfold greater than the equilibrium dissociation constant of an unmodified AB binding to its target, and whereas in the cleaved state, the AB binds its target.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least 20-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 40-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 50-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 100-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 200-fold greater than the equilibrium dissociation constant of an unmodified AB binding to its target, and whereas in the cleaved state, the AB binds its target.

In some embodiments, each CM in the multispecific activatable antibody is a polypeptide of up to 15 amino acids in length.

In some embodiments, at least one CM in the multispecific activatable antibody includes an amino acid sequence selected from the group consisting of SEQ ID NOs: 14-33 and 159 and the other CM includes the amino acid sequence LSGRSDNH (SEQ ID NO: 26). In some embodiments, at least one CM includes the amino acid sequence LSGRSDNH (SEQ ID NO: 26). In some embodiments, at least one cleavable moiety is selected for use with a specific protease, for example a protease that is known to be co-localized with at least one target of the multispecific activatable antibody. For example, suitable cleavable moieties for use in the multispecific activatable antibodies of the disclosure are cleaved by at least a protease such as urokinase, legumain, and/or matriptase (also referred to herein as MT-SP1 or MTSP1). In some embodiments, a suitable cleavable moiety includes at least one of the following sequences: TGRGPSWV (SEQ ID NO: 27); SARGPSRW (SEQ ID NO: 28); TARGPSFK (SEQ ID NO: 29); LSGRSDNH (SEQ ID NO: 26); GGWHTGRN (SEQ ID NO: 30); HTGRSGAL (SEQ ID NO: 31); PLTGRSGG (SEQ ID NO: 32); AARGPAIH (SEQ ID NO: 33); RGPAFNPM (SEQ ID NO: 34); SSRGPAYL (SEQ ID NO: 35); RGPATPIM (SEQ ID NO: 36); RGPA (SEQ ID NO: 37); GGQPSGMWGW (SEQ ID NO: 38); FPRPLGITGL (SEQ ID NO: 39); VHMPLGFLGP (SEQ ID NO: 40); SPLTGRSG (SEQ ID NO: 41); SAGFSLPA (SEQ ID NO: 42); LAPLGLQRR (SEQ ID NO: 43); SGGPLGVR (SEQ ID NO: 44); and/or PLGL (SEQ ID NO: 45).

In some embodiments, one CM is a substrate for at least one MMP protease and the other CM in the multispecific activatable antibody is a substrate for a protease selected from the group consisting of those shown in Table 7. In some embodiments, the protease is selected from the group consisting of uPA, legumain, matriptase, ADAM17, BMP-1, TMPRSS3, TMPRSS4, neutrophil elastase, MMP-7, MMP-9, MMP-12, MMP-13, and MMP-14. In some embodiments, the protease is a cathepsin, such as, but not limited to, cathepsin S. In some embodiments, each CM in the multispecific activatable antibody is a substrate for a protease selected from the group consisting of uPA (urokinase plasminogen activator), legumain and matriptase. In some embodiments, the protease comprises uPA. In some embodiments, the protease comprises legumain. In some embodiments, the protease comprises matriptase. In some embodiments, the protease comprises a matrix metalloproteinase (MMP).

In some embodiments, at least one CM in the multispecific activatable antibody is a substrate for at least two proteases. In some embodiments, each protease is selected from the group consisting of those shown in Table 7. In some embodiments, at least one CM in the multispecific activatable antibody is a substrate for at least two proteases, wherein one of the proteases is selected from the group consisting of uPA, legumain and matriptase and the other protease is selected from the group consisting of those shown in Table 7. In some embodiments, at least one CM in the multispecific activatable antibody is a substrate for at least two proteases selected from the group consisting of uPA, legumain and matriptase.

In some embodiments, the multispecific activatable antibody includes at least a first CM (CM1) and a second CM (CM2). In some embodiments, CM1 and CM2 are part of a single cleavable linker that joins an MM to an AB. In some embodiments, CM1 is part of a cleavable linker that joins MM1 to AB1, and CM2 is part of a separate cleavable linker that joins an MM2 to AB2. In some embodiments, a multispecific activatable antibody comprises more than two CMs. In some embodiments, such a multispecific activatable antibody comprises more than two CMs and more than two MMs. In some embodiments, CM1 and CM2 are each polypeptides of no more than 15 amino acids long. In some embodiments, at least one of the first CM and the second CM is a polypeptide that functions as a substrate for a protease selected from the group consisting of those listed in Table 7. In some embodiments, at least one of the first CM and the second CM is a polypeptide that functions as a substrate for a protease selected from the group consisting of uPA, legumain, and matriptase. In some embodiments, the first CM is cleaved by a first cleaving agent selected from the group consisting of uPA, legumain, and matriptase in a target tissue and the second CM is cleaved by a second cleaving agent in a target tissue. In some embodiments, the other protease is selected from the group consisting of those shown in Table 7. In some embodiments, the first cleaving agent and the second cleaving agent are the same protease selected from the group consisting of those listed in Table 7, and the first CM and the second CM are different substrates for the enzyme. In some embodiments, the first cleaving agent and the second cleaving agent are the same protease selected from the group consisting of uPA, legumain, and matriptase, and the first CM and the second CM are different substrates for the enzyme. In some embodiments, the first cleaving agent and the second cleaving agent are the same protease selected from the group listed in Table 7, and the first CM and the second CM are the same substrate. In some embodiments, the first cleaving agent and the second cleaving agent are different proteases. In some embodiments, the first cleaving agent and the second cleaving agent are different proteases selected from the group consisting of those shown in Table 7. In some embodiments, the first cleaving agent and the second cleaving agent are co-localized in the target tissue. In some embodiments, the first CM and the second CM are cleaved by at least one cleaving agent in the target tissue.

In some embodiments, the multispecific activatable antibody is exposed to and cleaved by a protease such that, in the activated or cleaved state, the activated multispecific activatable antibody includes a light chain amino acid sequence that includes at least a portion of LP2 and/or CM sequence after the protease has cleaved the CM.

The disclosure also provides compositions and methods that include a multispecific activatable antibody that includes at least a first antibody or antibody fragment (AB1) that specifically binds a target and a second antibody or antibody fragment (AB2), where at least the first AB in the multispecific activatable antibody is coupled to a masking moiety (MM1) that decreases the ability of AB1 to bind its target. In some embodiments, each AB is coupled to a MM that decreases the ability of its corresponding AB to each target. For example, in bispecific activatable antibody embodiments, AB1 is coupled to a first masking moiety (MM1) that decreases the ability of AB1 to bind its target, and AB2 is coupled to a second masking moiety (MM2) that decreases the ability of AB2 to bind its target. In some embodiments, the multispecific activatable antibody comprises more than two AB regions; in such embodiments, AB1 is coupled to a first masking moiety (MM1) that decreases the ability of AB1 to bind its target, AB2 is coupled to a second masking moiety (MM2) that decreases the ability of AB2 to bind its target, AB3 is coupled to a third masking moiety (MM3) that decreases the ability of AB3 to bind its target, and so on for each AB in the multispecific activatable antibody.

In some embodiments, the multispecific activatable antibody further includes at least one cleavable moiety (CM) that is a substrate for a protease, where the CM links a MM to an AB. For example, in some embodiments, the multispecific activatable antibody includes at least a first antibody or antibody fragment (AB1) that specifically binds a target and a second antibody or antibody fragment (AB2), where at least the first AB in the multispecific activatable antibody is coupled via a first cleavable moiety (CM1) to a masking moiety (MM1) that decreases the ability of AB1 to bind its target. In some bispecific activatable antibody embodiments, AB1 is coupled via CM1 to MM1, and AB2 is coupled via a second cleavable moiety (CM2) to a second masking moiety (MM2) that decreases the ability of AB2 to bind its target. In some embodiments, the multispecific activatable antibody comprises more than two AB regions; in some of these embodiments, AB1 is coupled via CM1 to MM1, AB2 is coupled via CM2 to MM2, and AB3 is coupled via a third cleavable moiety (CM3) to a third masking moiety (MM3) that decreases the ability of AB3 to bind its target, and so on for each AB in the multispecific activatable antibody.

Activatable Antibodies Having Non-Binding Steric Moieties or Binding Partners for Non-Binding Steric Moieties The disclosure also provides activatable antibodies that include non-binding steric moieties (NB) or binding partners (BP) for non-binding steric moieties, where the BP recruits or otherwise attracts the NB to the activatable antibody. The activatable antibodies provided herein include, for example, an activatable antibody that includes a non-binding steric moiety (NB), a cleavable linker (CL) and antibody or antibody fragment (AB) that binds a target; an activatable antibody that includes a binding partner for a non-binding steric moiety (BP), a CL and an AB; and an activatable antibody that includes a BP to which an NB has been recruited, a CL and an AB that binds the target. Activatable antibodies in which the NB is covalently linked to the CL and AB of the activatable antibody or is associated by interaction with a BP that is covalently linked to the CL and AB of the activatable antibody are referred to herein as "NB-containing activatable antibodies." By activatable or switchable is meant that the activatable antibody exhibits a first level of binding to a target when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

In some embodiments, activatable antibodies provide for reduced toxicity and/or adverse side effects that could otherwise result from binding of the at non-treatment sites and/or non-diagnostic sites if the AB were not masked or otherwise inhibited from binding to such a site.

In one embodiment, the activatable antibody includes a non-binding steric moiety (NB); a cleavable linker (CL); and an antibody or antibody fragment (AB) that binds specifically to the target, wherein the NB is a polypeptide that does not bind specifically to the AB; the CL is a polypeptide that includes a substrate(S) for an enzyme; the CL is positioned such that in an uncleaved state, the NB interferes with binding of the AB to the target and in a cleaved state, the NB does not interfere with binding of the AB to the target; and the NB does not inhibit cleavage of the CL by the enzyme. As used herein and throughout, the term polypeptide refers to any polypeptide that includes at least two amino acid residues, including larger polypeptides, full-length proteins and fragments thereof, and the term polypeptide is not limited to single-chain polypeptides and can include multi-unit, e.g., multi-chain, polypeptides. In cases where the polypeptide is of a shorter length, for example, less than 50 amino acids total, the terms peptide and polypeptide are used interchangeably herein, and in cases where the polypeptide is of a longer length, e.g., 50 amino acids or greater, the terms polypeptide and protein are used interchangeably herein.

In one embodiment, the activatable antibody includes a non-binding steric moiety (NB); a cleavable linker (CL); and an antibody or antibody fragment (AB) that binds specifically to the target, wherein (i) the NB includes a polypeptide that does not bind specifically to the AB; (ii) CL is a polypeptide of up to 50 amino acids in length that includes a substrate(S) for an enzyme; (iii) the CL is positioned such that in an uncleaved state, the NB interferes with binding of the AB to the target and in a cleaved state, the NB does not interfere with binding of the AB to the target; and (iv) the NB does not inhibit cleavage of the CL by the enzyme. For example, the CL has a length of up to 15 amino acids, a length of up to 20 amino acids, a length of up to 25 amino acids, a length of up to 30 amino acids, a length of up to 35 amino acids, a length of up to 40 amino acids, a length of up to 45 amino acids, a length of up to 50 amino acids, a length in the range of 10-50 amino acids, a length in the range of 15-50 amino acids, a length in the range of 20-50 amino acids, a length in the range of 25-50 amino acids, a length in the range of 30-50 amino acids, a length in the range of 35-50 amino acids, a length in the range of 40-50 amino acids, a length in the range of 45-50 amino acids, a length in the range of 10-40 amino acids, a length in the range of 15-40 amino acids, a length in the range of 20-40 amino acids, a length in the range of 25-40 amino acids, a length in the range of 30-40 amino acids, a length in the range of 35-40 amino acids, a length in the range of 10-30 amino acids, a length in the range of 15-30 amino acids, a length in the range of 20-30 amino acids, a length in the range of 25-30 amino acids, a length in the range of 10-20 amino acids, or a length in the range of 10-15 amino acids.

In one embodiment, the activatable antibody includes a non-binding steric moiety (NB); a cleavable linker (CL); and an antibody or antibody fragment (AB) that binds specifically to the target, wherein (i) the NB includes a polypeptide that does not bind specifically to the AB; (ii) the CL is a polypeptide that includes a substrate(S) for an enzyme; (iii) the CL is positioned such that in an uncleaved state, the NB interferes with binding of the AB to the target and in a cleaved state, the NB does not interfere with binding of the AB to the target; (iv) the NB does not inhibit cleavage of the CL by the enzyme; and (v) the activatable antibody has the structural arrangement from N-terminus to C-terminus as follows in the uncleaved state: NB-CL-AB or AB-CL-NB.

In one embodiment, the activatable antibody includes a non-binding steric moiety (NB); a cleavable linker (CL); and an antibody or antibody fragment (AB) that binds specifically to the target, wherein (i) the NB includes a polypeptide that does not bind specifically to the AB; (ii) the CL is a polypeptide that includes a substrate(S) for an enzyme; (iii) the CL is positioned such that in an uncleaved state, the NB interferes with binding of the AB to the target and in a cleaved state, the NB does not interfere with binding of the AB to the target, and wherein the NB in the uncleaved activatable antibody reduces the ability of the AB to bind the target by at least 50%, for example, by at least 60%, by at least 70%, by at least 75%, by at least 80%, by at least 85%, by at least 90%, by at least 95%, by at least 96%, by at least 97%, by at least 98%, by at least 99%, by at least 100% as compared to the ability of the cleaved AB to bind the target; and (iv) the NB does not inhibit cleavage of the CL by the enzyme. The reduction in the ability of the AB to bind the target is determined, e.g., using an assay as described herein or an in vitro target displacement assay such as, for example, the assay described in PCT Publication Nos. WO 2009/025846 and WO 2010/081173.

In one embodiment, the activatable antibody includes a binding partner (BP) for a non-binding steric moiety (NB); a cleavable linker (CL); and an antibody or antibody fragment (AB) that binds specifically to the target, wherein the BP is a polypeptide that binds to the NB when exposed thereto; the NB does not bind specifically to the AB; the CL is a polypeptide that includes a substrate(S) for an enzyme; the CL is positioned such that in an uncleaved state in the presence of the NB, the NB interferes with binding of the AB to the target and in a cleaved state, the NB does not interfere with binding of the AB to the target and the BP does not interfere with binding of the AB to the target; and the NB and the BP do not inhibit cleavage of the CL by the enzyme. In some examples of this embodiment, the BP of the activatable antibody is optionally bound to the NB. In one embodiment, the NB is recruited by the BP of the activatable antibody in vivo.

In some examples of any of these activatable antibody embodiments, the activatable antibody is formulated as a composition. In some of these embodiments, the composition also includes the NB, where the NB is co-formulated with the activatable antibody that includes the BP, the CL, and the AB. In some examples of this embodiment, the BP is selected from the group consisting of an albumin binding peptide, a fibrinogen binding peptide, a fibronectin binding peptide, a hemoglobin binding peptide, a transferrin binding peptide, an immunoglobulin domain binding peptide, and other serum protein binding peptides.

In some examples of any of these activatable antibody embodiments, the NB is a soluble, globular protein. In some examples of any of these activatable antibody embodiments, the NB is a protein that circulates in the bloodstream. In some examples of any of these activatable antibody embodiments, the NB is selected from the group consisting of albumin, fibrinogen, fibronectin, hemoglobin, transferrin, an immunoglobulin domain, and other serum proteins.

In some examples of any of these activatable antibody embodiments, the CL is a polypeptide that includes a substrate(S) for a protease. In some examples of any of these activatable antibody embodiments, the protease is co-localized with the in a tissue, and the protease cleaves the CL in the activatable antibody when the activatable antibody is exposed to the protease. In some examples of any of these activatable antibody embodiments, the CL is a polypeptide of up to 50 amino acids in length. In some examples of any of these activatable antibody embodiments, the CL is a polypeptide that includes a substrate(S) having a length of up to 15 amino acids, e.g., 3 amino acids long, 4 amino acids long, 5 amino acids long, 6 amino acids long, 7 amino acids long, 8 amino acids long, 9 amino acids long, 10 amino acids long, 11 amino acids long, 12 amino acids long, 13 amino acids long, 14 amino acids long, or 15 amino acids long.

In some examples of any of these activatable antibody embodiments, the activatable antibody has the structural arrangement from N-terminus to C-terminus as follows in the uncleaved state: NB-CL-AB, AB-CL-NB, BP-CL-AB or AB-CL-BP. In embodiments where the activatable antibody includes a BP and the activatable antibody is in the presence of the corresponding NB, the activatable antibody has a structural arrangement from N-terminus to C-terminus as follows in the uncleaved state: NB: BP-CM-AB or AB-CM-BP: NB, where ":" represents an interaction, e.g., binding, between the NB and BP.

In some examples of any of these activatable antibody embodiments, the activatable antibody includes an antibody or antigen-binding fragment thereof that specifically binds a given target and is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an antibody or immunologically active fragment thereof that binds the target a mouse, other rodent, chimeric, humanized or fully human monoclonal antibody.

In some examples of any of these activatable antibody embodiments, the activatable antibody includes a combination of a variable heavy chain region comprising an amino acid sequence presented herein and a variable light chain region comprising an amino acid sequence presented herein. In some embodiments, the activatable antibody includes a combination of a variable heavy chain region comprising an amino acid sequence that is at least 90%, 91%, 92%, 93%, 94%, 95%, 96%, 97%, 98%, 99% or more identical to an amino acid sequence presented herein, and a variable light chain region comprising an amino acid sequence that is at least 90%, 91%, 92%, 93%, 94%, 95%, 96%, 97%, 98%, 99% or more identical to an amino acid sequence presented herein.

In some examples of any of these activatable antibody embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is conjugated to the AB via a noncleavable linker. In some embodiments, the agent is an agent selected from the group listed in Table 3. In some embodiments, the agent is a microtubule inhibitor. In some embodiments, the agent is a nucleic acid damaging agent, such as a DNA alkylator or DNA intercalator, or other DNA damaging agent. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some examples of any of these activatable antibody embodiments, the activatable antibody also includes a detectable moiety. In some embodiments, the detectable moiety is a diagnostic agent.

In some examples of any of these activatable antibody embodiments, the activatable antibody also includes a spacer. In some examples of any of these activatable antibody embodiments, the activatable antibody also includes a signal peptide. In some embodiments, the signal peptide is conjugated to the activatable antibody via a spacer. In some examples of any of these activatable antibody embodiments, the spacer is joined directly to the MM of the activatable antibody.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some examples of any of these activatable antibody embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The disclosure also provides an isolated nucleic acid molecule encoding any of these activatable antibodies, as well as vectors that include these isolated nucleic acid sequences. The disclosure provides methods of producing an activatable antibody by culturing a cell under conditions that lead to expression of the activatable antibody, wherein the cell comprises such a nucleic acid sequence. In some embodiments, the cell comprises such a vector.

The dissociation constant ($K_d$) of the NB-containing activatable antibody toward the target is greater than the $K_d$ of the AB towards the target when it is not associated with the NB or NB: BP. The dissociation constant ($K_d$) of the NB-containing activatable antibody toward the target is greater than the $K_d$ of the parental AB towards the target. For example, the $K_d$ of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB when it is not associated with the NB or NB: BP or the $K_d$ of the parental AB towards the target. Conversely, the binding affinity of the NB-containing activatable antibody towards the target is lower than the binding affinity of the AB when it is not associated with the NB or NB: BP or lower than the binding affinity of the parental AB towards the target. For example, the binding affinity of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB when it is not associated with the NB or NB: BP or lower than the binding affinity of the parental AB towards the target.

When the NB-containing activatable antibody is in the presence of the target, specific binding of the AB to the target is reduced or inhibited, as compared to the specific binding of the AB when it is not associated with the NB or NB: BP. When the NB-containing activatable antibody is in the presence of the target, specific binding of the AB to the target is reduced or inhibited, as compared to the specific binding of the parental AB to the target. When compared to the binding of the AB not associated with an NB or NB: BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

When the NB-containing activatable antibody is in the presence of the target but not in the presence of a modifying agent (for example a protease or other enzyme), specific binding of the AB to the target is reduced or inhibited, as compared to the specific binding of the AB when it is not associated with the NB or NB: BP. When the NB-containing activatable antibody is in the presence of the target but not in the presence of a modifying agent (for example a protease, other enzyme, reduction agent, or light), specific binding of the AB to the target is reduced or inhibited, as compared to the specific binding of the parental AB to the target. When compared to the binding of the AB not associated with an NB or NB: BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

In some examples of any of these activatable antibody embodiments, the activatable antibody includes an agent conjugated to the AB to produce an activatable antibody conjugate. In some embodiments of the activatable antibody conjugate, the agent is a therapeutic agent. In some embodiments, the agent is a diagnostic agent. In some embodiments, the agent is a detectable marker. In some embodiments of the activatable antibody conjugate, the agent is an antineoplastic agent. In some embodiments of the activatable antibody conjugate, the agent is a toxin or fragment thereof. In some embodiments of the activatable antibody conjugate, the agent is conjugated to the AB via a linker. In some embodiments of the activatable antibody conjugate, the linker is a cleavable linker. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some examples of any of these activatable antibody embodiments, the activatable antibodies are dual-target binding activatable antibodies. Such dual target binding activatable antibodies contain two Abs that may bind the same or different targets. In specific embodiments, dual-targeting activatable antibodies contain bispecific antibodies or antibody fragments.

Dual target binding activatable antibodies are designed so as to have a CL cleavable by a cleaving agent that is co-localized in a target tissue with one or both of the targets capable of binding to the ABs of the activatable antibodies. Dual target binding activatable antibodies with more than one AB to the same or different targets can be designed so as to have more than one CL, wherein the first CL is cleavable by a cleaving agent in a first target tissue and wherein the second CL is cleavable by a cleaving agent in a second target tissue, with one or more of the targets binding to the ABs of the activatable antibodies. In one embodiment, the first and second target tissues are spatially separated, for example, at different sites in the organism. In one embodiment, the first and second target tissues are the same tissue temporally separated, for example the same tissue at two different points in time, for example the first time point is when the tissue is an early stage tumor, and the second time point is when the tissue is a late stage tumor.

The disclosure also provides nucleic acid molecules encoding the activatable antibodies described herein. The disclosure also provides vectors that include these nucleic acids. The activatable antibodies described herein are produced by culturing a cell under conditions that lead to expression of the activatable antibody, wherein the cell includes these nucleic acid molecules or vectors.

The disclosure also provides methods of manufacturing activatable antibodies. In one embodiment, the method includes the steps of (a) culturing a cell that includes a nucleic acid construct that encodes the activatable antibody under conditions that lead to expression of the activatable antibody, wherein the activatable antibody includes (i) a non-binding steric moiety (NB); (ii) a cleavable linker (CL); and (iii) an antibody or an antigen binding fragment thereof (AB) that specifically binds a target, wherein (1) the NB does not bind specifically to the AB; (2) the CL is a polypeptide that includes a substrate(S) for an enzyme; (3) the CL is positioned such that in an uncleaved state, the NB interferes with binding of the AB to the target and in a cleaved state, the NB does not interfere with binding of the AB to the target; and (4) the NB does not inhibit cleavage of the CL by the enzyme; and (b) recovering the activatable antibody.

In some embodiments, the method includes the steps of (a) culturing a cell that includes a nucleic acid construct that encodes the activatable antibody under conditions that lead to expression of the activatable antibody, wherein the activatable antibody includes (i) a binding partner (BP) for a non-binding steric moiety (NB); (ii) a cleavable linker (CL); and (iii) an antibody or an antigen binding fragment thereof (AB) that specifically binds a target, wherein (1) the NB does not bind specifically to the AB; (2) the CL is a polypeptide that includes a substrate(S) for an enzyme; (3) the CL is positioned such that in an uncleaved state in the presence of the NB, the NB interferes with binding of the AB to the target and in a cleaved state, the NB does not interfere with binding of the AB to the target and the BP does not interfere with binding of the AB to the target; and (4) the NB and the BP do not inhibit cleavage of the CL by the enzyme; and (b) recovering the activatable antibody. In some examples of this embodiment, the BP of the activatable antibody is bound to the NB.

Use of Activatable Antibodies and Conjugated Activatable Antibodies

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the disclosure, which include a conjugated antibody, an activatable antibody and/or a conjugated activatable antibody, are used to prevent, treat or otherwise ameliorate a disease or disorder associated with aberrant target expression and/or activity. For example, therapeutic formulations of the disclosure, which include a conjugated antibody, an activatable antibody and/or a conjugated activatable antibody, are used to treat or otherwise ameliorate inflammation, an inflammatory disorder, an autoimmune disease and/or a cancer or other neoplastic condition. In some embodiments, the cancer is a solid tumor or a hematologic malignancy where the target is expressed. In some embodiments, the cancer is a solid tumor where the target is expressed. In some embodiments, the cancer is a hematologic malignancy where the target is expressed. In some embodiments, the target is expressed on parenchyma (e.g., in cancer, the portion of an organ or tissue that often carries out function(s) of the organ or tissue). In some embodiments, the target is expressed on a cell, tissue, or organ. In some embodiments, the target is expressed on stroma (i.e., the connective supportive framework of a cell, tissue, or organ). In some embodiments, the target is expressed on an osteoblast. In some embodiments, the target is expressed on the endothelium (vasculature). In some embodiments, the target is expressed on a cancer stem cell. In some embodiments, the agent to which the activatable antibody is conjugated is a microtubule inhibitor. In some embodiments, the agent to which the activatable antibody is conjugated is a nucleic acid damaging agent.

Efficaciousness of prevention, amelioration or treatment is determined in association with any known method for diagnosing or treating the disease or disorder associated with target expression and/or activity, such as, for example, aberrant target expression and/or activity. Prolonging the survival of a subject or otherwise delaying the progression of the disease or disorder associated with target expression and/or activity, e.g., aberrant target expression and/or activity, in a subject indicates that the conjugated antibody, activatable antibody and/or conjugated activatable antibody confers a clinical benefit.

A conjugated antibody, an activatable antibody and/or a conjugated activatable antibody can be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

In some embodiments where antibody fragments are used, the smallest fragment that specifically binds to the binding domain of the target protein is selected. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compounds as necessary for the particular indication being treated, for example, in some embodiments, those with complementary activities that do not adversely affect each other. In some embodiments, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the conjugated antibody, activatable antibody and/or conjugated activatable antibody contains a detectable label. An intact antibody, or a fragment thereof (e.g., Fab, scFv, or $F(ab)_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, NJ, 1995; "Immunoassay", E. Diamandis and T. Christopoulus, Academic Press, Inc., San Diego, CA, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The conjugated antibodies, activatable antibodies and/or conjugated activatable antibodies of the disclosure are also useful in a variety of diagnostic and prophylactic formulations. In one embodiment, a conjugated antibody, an activatable antibody and/or a conjugated activatable antibody is administered to patients that are at risk of developing one or more of the aforementioned disorders. A patient's or organ's predisposition to one or more of the aforementioned disorders can be determined using genotypic, serological or biochemical markers.

In some embodiments, a conjugated antibody, an activatable antibody and/or a conjugated activatable antibody is administered to human individuals diagnosed with a clinical indication associated with one or more of the aforementioned disorders. Upon diagnosis, a conjugated antibody, an activatable antibody and/or a conjugated activatable antibody is administered to mitigate or reverse the effects of the clinical indication.

A conjugated antibody, an activatable antibody and/or a conjugated activatable antibody of the disclosure is also useful in the detection of a target in patient samples and accordingly are useful as diagnostics. For example, the antibodies and/or activatable antibodies, and conjugated versions thereof, of the disclosure are used in in vitro assays, e.g., ELISA, to detect target levels in a patient sample.

In one embodiment, a conjugated antibody, an activatable antibody and/or a conjugated activatable antibody of the disclosure is immobilized on a solid support (e.g., the well(s) of a microtiter plate). The immobilized conjugated antibody, activatable antibody and/or conjugated activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure, and conjugated versions thereof, in an in vitro diagnostic assay, it is possible to stage a disease in a subject based on expression levels of the target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

A conjugated antibody, an activatable antibody and/or a conjugated activatable antibody can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM can be used to detect the presence or absence of an enzyme that is capable of cleaving the CM. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM) but also that the tissue expresses target to which the activated antibody binds.

For example, the CM can be selected to be substrate for a matrix metalloprotease (MMP) found at the site of a tumor, at the site of a viral or bacterial infection at a biologically confined site (e.g., such as in an abscess, in an organ, and the like), and the like. The AB can be one that binds a target antigen. Using methods as disclosed herein, or when appropriate, methods familiar to one skilled in the art, a detectable label (e.g., a fluorescent label or radioactive label or radiotracer) can be conjugated to an AB or other region of an antibody and/or activatable antibody. Suitable detectable labels are discussed in the context of the above screening methods and additional specific examples are provided below. Using an AB specific to a protein or peptide of the disease state, along with an MMP whose activity is elevated in the disease tissue of interest, activatable antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM susceptible to cleavage by an enzyme, the activatable antibodies can be used to detect (either qualitatively or quantitatively) the presence of an enzyme in the sample. In another example, where the activatable antibodies contain a CM susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a matrix metalloprotease (MMP) that is specific for the CM of the activatable antibody. In some embodiments, the presence of the MMP can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a MMP specific for the CM of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a MMP that is specific for the CM of the activatable antibody.

These techniques are also useful in kits and/or as reagents for the detection, identification or characterization of protease activity in a variety of cells, tissues, and organisms based on the protease-specific CM in the activatable antibody.

The disclosure provides methods of using the antibodies and/or activatable antibodies in a variety of diagnostic and/or prophylactic indications. For example, the disclosure provides methods of detecting presence or absence of a cleaving agent and a target of interest in a subject or a sample by (i) contacting a subject or sample with an activatable antibody, wherein the activatable antibody comprises a masking moiety (MM), a cleavable moiety (CM) that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent and the target are present in the subject or sample and wherein no detectable level of activated activatable antibody in the subject or sample indicates that the cleaving agent, the target or both the cleaving agent and the target are absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody in the presence of a target of interest, e.g., the target, wherein the activatable antibody comprises a masking moiety (MM), a cleavable moiety (CM) that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody comprises a masking moiety (MM), a cleavable moiety (CM) that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody, wherein the activatable antibody comprises a masking moiety (MM), a cleavable moiety (CM) that is cleaved by the cleaving agent, an antigen binding domain (AB) that specifically binds the target, and a detectable label, wherein the activatable antibody in an uncleaved, non-activated state comprises a structural arrangement from N-terminus to C-terminus as follows: MM-CM-AB or AB-CM-MM; wherein the MM is a peptide that inhibits binding of the AB to the target, and wherein the MM does not have an amino acid sequence of a naturally occurring binding partner of the AB and is not a modified form of a natural binding partner of the AB; wherein, in an uncleaved, non-activated state, the MM interferes with specific binding of the AB to the target, and in a cleaved, activated state the MM does not interfere or compete with specific binding of the AB to the target; and wherein the detectable label is positioned on a portion of the activatable antibody that is released following cleavage of the CM; and (ii) measuring a level of detectable label in the subject or sample, wherein a detectable level of the detectable label in the subject or sample indicates that the cleaving agent is absent and/or not sufficiently present in the subject or sample and wherein no detectable level of the detectable label in the subject or sample indicates that the cleaving agent is present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody (e.g., an activatable antibody to which a therapeutic agent is conjugated) described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent and the target are present in the subject or biological sample and wherein no detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample.

The disclosure also provides methods of detecting presence or absence of a cleaving agent in a subject or a sample by (i) contacting a subject or biological sample with an activatable antibody in the presence of the target, and (ii) measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a cleavable moiety (CM) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments, all antigen binding sites are masked. In some embodiments, the measuring step includes use of a secondary reagent comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample with an activatable antibody in the presence of the target, and measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a cleavable moiety (CM) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments, all antigen binding sites are masked. In some embodiments, the measuring step includes use of a secondary reagent comprising a detectable label.

The disclosure also provides kits for use in methods of detecting presence or absence of a cleaving agent in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM, wherein a detectable level of activated activatable antibody in the subject or biological sample indicates that the cleaving agent is absent and/or not sufficiently present in the subject or biological sample such that the target binding and/or protease cleavage of the activatable antibody cannot be detected in the subject or biological sample, and wherein no detectable level of activated activatable antibody in the subject or biological sample indicates that the cleaving agent is present in the subject or biological sample at a detectable level.

The disclosure provides methods of detecting presence or absence of a cleaving agent and the target in a subject or a sample by (i) contacting a subject or biological sample with an activatable antibody, wherein the activatable antibody includes a detectable label that is positioned on a portion of the activatable antibody that is released following cleavage of the CM and (ii) measuring a level of activated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a cleavable moiety (CM) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The disclosure also provides methods of detecting presence or absence of a cleaving agent in a subject or a sample by (i) contacting a subject or biological sample with an activatable antibody, wherein the activatable antibody includes a detectable label that is positioned on a portion of the activatable antibody that is released following cleavage of the CM; and (ii) measuring a level of detectable label in the subject or biological sample, wherein a detectable level of the detectable label in the subject or biological sample indicates that the cleaving agent is absent and/or not sufficiently present in the subject or biological sample at a detectable level, such that protease cleavage of the activatable antibody cannot be detected in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a cleavable moiety (CM) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM, wherein a detectable level of the detectable label in the subject or biological sample indicates that the cleaving agent, the target, or both the cleaving agent and the target are absent and/or not sufficiently present in the subject or biological sample, such that the target binding and/or protease cleavage of the activatable antibody cannot be detected in the subject or biological sample, and wherein a reduced detectable level of the detectable label in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

In some embodiments of these methods and kits, the activatable antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments, in situ imaging is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative for either or both of the target (e.g., the target) and the protease that cleaves the substrate in the CM in the activatable antibody being tested using these methods might be identified as suitable candidates for another form of therapy. In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease). In some embodiments, the patient is then administered a therapeutically effective amount of the conjugated activatable antibody for which the patient tested positive.

In some embodiments, in vivo imaging is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative might be identified as suitable candidates for another form of therapy. In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease). In some embodiments, the patient is then administered a therapeutically effective amount of the conjugated activatable antibody for which the patient tested positive.

In some embodiments of the methods and kits, the method or kit is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested in these methods are identified as suitable candidates for treatment with such an activatable antibody comprising such a CM. Likewise, patients that test negative for both of the targets (e.g., the target) and the protease that cleaves the substrate in the CM in the activatable antibody being tested using these methods might be identified as suitable candidates for another form of therapy. In some embodiments, such patients can be tested with other activatable antibodies until a suitable activatable antibody for treatment is identified (e.g., an activatable antibody comprising a CM that is cleaved by the patient at the site of disease). In some embodiments, patients that test negative for either of the target (e.g., the target) are identified as suitable candidates for treatment with such an activatable antibody comprising such a CM. In some embodiments, patients that test negative for either of the target (e.g., the target) are identified as not being suitable candidates for treatment with such an activatable antibody comprising such a CM. In some embodiments, such patients can be tested with other activatable antibodies until a suitable activatable antibody for treatment is identified (e.g., an activatable antibody comprising a CM that is cleaved by the patient at the site of disease). In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

In some embodiments, a method or kit is used to identify or otherwise refine a patient population suitable for treatment with an anti-the target activatable antibody and/or conjugated activatable antibody (e.g., activatable antibody to which a therapeutic agent is conjugated) of the disclosure, followed by treatment by administering that activatable antibody and/or conjugated activatable antibody to a subject in need thereof. For example, patients that test positive for both the targets (e.g., the target) and a protease that cleaves the substrate in the cleavable moiety (CM) of the activatable antibody and/or conjugated activatable antibody being tested in these methods are identified as suitable candidates for treatment with such antibody and/or such a conjugated activatable antibody comprising such a CM, and the patient is then administered a therapeutically effective amount of the activatable antibody and/or conjugated activatable antibody that was tested. Likewise, patients that test negative for either or both of the target (e.g., the target) and the protease that cleaves the substrate in the CM in the activatable antibody being tested using these methods might be identified as suitable candidates for another form of therapy. In some embodiments, such patients can be tested with other antibody and/or conjugated activatable antibody until a suitable antibody and/or conjugated activatable antibody for treatment is identified (e.g., an activatable antibody and/or conjugated activatable antibody comprising a CM that is cleaved by the patient at the site of disease). In some embodiments, the patient is then administered a therapeutically effective amount of the activatable antibody and/or conjugated for which the patient tested positive.

In some embodiments of these methods and kits, the MM is a peptide having a length from about 4 to 40 amino acids. In some embodiments of these methods and kits, the activatable antibody comprises a linker peptide, wherein the linker peptide is positioned between the MM and the CM. In some embodiments of these methods and kits, the activatable antibody comprises a linker peptide, where the linker peptide is positioned between the AB and the CM. In some embodiments of these methods and kits, the activatable antibody comprises a first linker peptide (L1) and a second linker peptide (L2), wherein the first linker peptide is positioned between the MM and the CM and the second linker peptide is positioned between the AB and the CM. In some embodiments of these methods and kits, each of L1 and L2 is a peptide of about 1 to 20 amino acids in length, and wherein each of L1 and L2 need not be the same linker. In some embodiments of these methods and kits, one or both of L1 and L2 comprises a glycine-serine polymer. In some embodiments of these methods and kits, at least one of L1 and L2 comprises an amino acid sequence selected from the group consisting of (GS)n, (GSGGS)n (SEQ ID NO: 1) and (GGGS)n (SEQ ID NO: 2), where n is an integer of at least one. In some embodiments of these methods and kits, at least one of L1 and L2 comprises an amino acid sequence having the formula $(GGS)_n$, where n is an integer of at least one. In some embodiments of these methods and kits, at least one of L1 and L2 comprises an amino acid sequence selected from the group consisting of Gly-Gly-Ser-Gly (SEQ ID NO: 3), Gly-Gly-Ser-Gly-Gly (SEQ ID NO: 4), Gly-Ser-Gly-Ser-Gly (SEQ ID NO: 5), Gly-Ser-Gly-Gly-Gly (SEQ ID NO: 6), Gly-Gly-Gly-Ser-Gly (SEQ ID NO: 7), and Gly-Ser-Ser-Ser-Gly (SEQ ID NO: 8).

In some embodiments of these methods and kits, the AB comprises an antibody or antibody fragment sequence selected from the cross-reactive antibody sequences presented herein. In some embodiments of these methods and kits, the AB comprises a Fab fragment, a scFv or a single chain antibody (scAb).

In some embodiments of these methods and kits, the cleaving agent is a protease that is co-localized in the subject or sample with the target and the CM is a polypeptide that functions as a substrate for the protease, wherein the protease cleaves the CM in the activatable antibody when the activatable antibody is exposed to the protease. In some embodiments of these methods and kits, the CM is a polypeptide of up to 15 amino acids in length. In some embodiments of these methods and kits, the CM is coupled to the N-terminus of the AB. In some embodiments of these methods and kits, the CM is coupled to the C-terminus of the AB. In some embodiments of these methods and kits, the CM is coupled to the N-terminus of a VL chain of the AB.

The activatable antibodies and/or conjugated activatable antibodies of the disclosure are used in diagnostic and prophylactic formulations. In one embodiment, an activatable antibody is administered to patients that are at risk of developing one or more of the aforementioned inflammation, inflammatory disorders, cancer or other disorders.

A patient's or organ's predisposition to one or more of the aforementioned disorders can be determined using genotypic, serological or biochemical markers.

In some embodiments, an activatable antibody and/or conjugated activatable antibodies is administered to human individuals diagnosed with a clinical indication associated with one or more of the aforementioned disorders. Upon diagnosis, an activatable antibody and/or conjugated activatable antibodies is administered to mitigate or reverse the effects of the clinical indication.

Activatable antibodies and/or conjugated activatable antibodies of the disclosure are also useful in the detection of the target in patient samples and accordingly are useful as diagnostics. For example, the activatable antibodies and/or conjugated activatable antibodies of the disclosure are used in in vitro assays, e.g., ELISA, to detect target levels in a patient sample.

In one embodiment, an activatable antibody of the disclosure is immobilized on a solid support (e.g., the well(s) of a microtiter plate). The immobilized activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure in an in vitro diagnostic assay, it is possible to stage a disease in a subject based on expression levels of the Target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Activatable antibodies and/or conjugated activatable antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM can be used to detect the presence or absence of an enzyme that is capable of cleaving the CM. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM) but also that the tissue expresses target to which the activated antibody binds.

For example, the CM can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an activatable antibody. Suitable detectable labels are discussed in the context of the above screening methods and additional specific examples are provided below. Using an AB specific to a protein or peptide of the disease state, along with a protease whose activity is elevated in the disease tissue of interest, activatable antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM susceptible to cleavage by an enzyme, the activatable antibodies can be used to detect (either qualitatively or quantitatively) the presence of an enzyme in the sample. In another example, where the activatable antibodies contain a CM susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. Fluorescein Isothiocyanate (FITC), Rhodamine Isothiocyanate (TRITC), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a protease that is specific for the CM of the activatable antibody. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM of the activatable antibody.

These techniques are also useful in kits and/or as reagents for the detection, identification or characterization of protease activity in a variety of cells, tissues, and organisms based on the protease-specific CM in the activatable antibody.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments, in situ imaging is used to identify or otherwise refine a patient population suitable for treatment with an activatable antibody of the disclosure. For example, patients that test positive for both the target and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative for either or both of the target and the protease that cleaves the substrate in the CM in the activatable antibody being tested using these methods are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease).

In some embodiments, in vivo imaging is used to identify or otherwise refine a patient population suitable for treatment with an activatable antibody of the disclosure. For example, patients that test positive for both the target and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease).

Pharmaceutical Compositions

The conjugated antibodies, activatable antibodies and/or conjugated activatable antibodies of the disclosure (also referred to herein as "active compounds"), and derivatives, fragments, analogs and homologs thereof, can be incorporated into pharmaceutical compositions suitable for administration. Such compositions typically comprise the conjugated antibody, activatable antibody and/or conjugated activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1. Ability of Synovial Fluid to Activate Quenched Probes Comprising Substrates of the Disclosure This Example demonstrates the ability of synovial fluid samples to cleave MMP substrate sequences of the disclosure. In particular, the MMP cleavable sequences were tested in the context of an activatable antibody construct comprising a masking moiety linked to an anti-IL-6R antibody sequence via a linker region that includes the MMP cleavable sequence being evaluated.

The following MMP-cleavable activatable antibodies were incubated with synovial fluid:

$4792^{10419}$AV1 amino acid (SEQ ID NO: 115)

```
QGQSGQYGSCSWNYVHIFMDCGSSGGSGGSGGSGISSGLSSGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC
```

$4792^{10419}$AV1 nucleotide (SEQ ID NO: 116)

```
Caaggccagtctggccagtatgggtcctgcagttggaactatgtacacatattcatggattgcg
gctcgagcggtggcagcggtggctctggtggctcaggtattagtagtggtcttagcagtggcgg
ttctgacatccagatgactcagtctcctagctccctgtccgcctctgtgggggaccgagtcacc
atcacatgcagagccagccaggatatttctagttacctgaactggtatcagcagaagcccggaa
aagcacctaagctgctgatctactatacctccaggctgcactctggcgtgcccagtcggttcag
tggctcagggagcggaaccgacttcacttttaccatctcaagcctgcagccagaggatattgcc
acatactattgtcagcagggcaatacactgccctacacttttggccaggggaccaaggtggaaa
tcaaacgtacggtggctgcaccatctgtcttcatcttcccgccatctgatgagcagttgaaatc
tggaactgcctctgttgtgtgcctgctgaataacttctatcccagagaggccaaagtacagtgg
aaggtggataacgccctccaatcgggtaactcccaggagagtgtcacagagcaggacagcaagg
acagcacctacagcctcagcagcaccctgacgctgagcaaagcagactacgagaaacacaaagt
ctacgcctgcgaagtcacccatcagggcctgagctcgcccgtcacaaagagcttcaacagggga
gagtgt
```

$4792^{559}$AV1 amino acid (SEQ ID NO: 117)

```
QGQSGQYGSCSWNYVHIFMDCGSSGGSGGSGGSQNQALRMAGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC
```

$4792^{559}$AV1 nucleotide (SEQ ID NO: 118)

```
caaggccagtctggccagtatgggtcctgcagttggaactatgtacacatattcatggattgcg
gctcgagcggtggcagcggtggctctggtggctcacagaatcaggcattacgtatggcaggcgg
ttctgacatccagatgactcagtctcctagctccctgtccgcctctgtgggggaccgagtcacc
```

-continued atcacatgcagagccagccaggatatttctagttacctgaactggtatcagcagaagcccggaa
aagcacctaagctgctgatctactatacctccaggctgcactctggcgtgcccagtcggttcag
tggctcagggagcggaaccgacttcacttttaccatctcaagcctgcagccagaggatattgcc
acatactattgtcagcagggcaatacactgccctacacttttggccaggggaccaaggtggaaa
tcaaacgtacggtggctgcaccatctgtcttcatcttcccgccatctgatgagcagttgaaatc
tggaactgcctctgttgtgtgcctgctgaataacttctatcccagagaggccaaagtacagtgg
aaggtggataacgccctccaatcgggtaactcccaggagagtgtcacagagcaggacagcaagg
acagcacctacagcctcagcagcaccctgacgctgagcaaagcagactacgagaaacacaaagt
ctacgcctgcgaagtcacccatcagggcctgagctcgcccgtcacaaagagcttcaacagggga
gagtgt $4792^{601}$AV1 amino acid (SEQ ID NO: 119)

QGQSGQYGSCSWNYVHIFMDCGSSGGSGGSGGSAQNLLGMVGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC $4792^{601}$AV1 nucleotide (SEQ ID NO: 120)

Caaggccagtctggccagtatgggtcctgcagttggaactatgtacacatattcatggattgcg
gctcgagcggtggcagcggtggctctggtggctcagcacagaatctgttaggtatggtaggcgg
ttctgacatccagatgactcagtctcctagctccctgtccgcctctgtgggggaccgagtcacc
atcacatgcagagccagccaggatatttctagttacctgaactggtatcagcagaagcccggaa
aagcacctaagctgctgatctactatacctccaggctgcactctggcgtgcccagtcggttcag
tggctcagggagcggaaccgacttcacttttaccatctcaagcctgcagccagaggatattgcc
acatactattgtcagcagggcaatacactgccctacacttttggccaggggaccaaggtggaaa
tcaaacgtacggtggctgcaccatctgtcttcatcttcccgccatctgatgagcagttgaaatc
tggaactgcctctgttgtgtgcctgctgaataacttctatcccagagaggccaaagtacagtgg
aaggtggataacgccctccaatcgggtaactcccaggagagtgtcacagagcaggacagcaagg
acagcacctacagcctcagcagcaccctgacgctgagcaaagcagactacgagaaacacaaagt
ctacgcctgcgaagtcacccatcagggcctgagctcgcccgtcacaaagagcttcaacagggga
gagtgt $4792^{3457}$AV1 amino acid (SEQ ID NO: 121)

QGQSGQYGSCSWNYVHIFMDCGSSGGSGGSGGSSTFPFGMFGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC $4792^{3457}$AV1 nucleotide (SEQ ID NO: 122)

Caaggccagtctggccagtatgggtcctgcagttggaactatgtacacatattcatggattgcg
gctcgagcggtggcagcggtggctctggtggctcaagtacatttccattcggtatgttcggcgg
ttctgacatccagatgactcagtctcctagctccctgtccgcctctgtgggggaccgagtcacc
atcacatgcagagccagccaggatatttctagttacctgaactggtatcagcagaagcccggaa -continued aagcacctaagctgctgatctactatacctccaggctgcactctggcgtgcccagtcggttcag
tggctcagggagcggaaccgacttcacttttaccatctcaagcctgcagccagaggatattgcc
acatactattgtcagcagggcaatacactgccctacacttttggccaggggaccaaggtggaaa
tcaaacgtacggtggctgcaccatctgtcttcatcttcccgccatctgatgagcagttgaaatc
tggaactgcctctgttgtgtgcctgctgaataacttctatcccagagaggccaaagtacagtgg
aaggtggataacgccctccaatcgggtaactcccaggagagtgtcacagagcaggacagcaagg
acagcacctacagcctcagcagcaccctgacgctgagcaaagcagactacgagaaacacaaagt
ctacgcctgcgaagtcacccatcagggcctgagctcgcccgtcacaaagagcttcaacagggga
gagtgt 4792 3458 AV1 amino acid (SEQ ID NO: 123)

QGQSGQYGSCSWNYVHIFMDCGSSGGSGGSGGSPVGYTSSLGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC 4792 3458 AV1 nucleotide (SEQ ID NO: 124)

Caaggccagtctggccagtatgggtcctgcagttggaactatgtacacatattcatggattgcg
gctcgagcggtggcagcggtggctctggtggctcacctgttggatatacgagtagtctgggcgg
ttctgacatccagatgactcagtctcctagctccctgtccgcctctgtgggggaccgagtcacc
atcacatgcagagccagccaggatatttctagttacctgaactggtatcagcagaagcccggaa
aagcacctaagctgctgatctactatacctccaggctgcactctggcgtgcccagtcggttcag
tggctcagggagcggaaccgacttcacttttaccatctcaagcctgcagccagaggatattgcc
acatactattgtcagcagggcaatacactgccctacacttttggccaggggaccaaggtggaaa
tcaaacgtacggtggctgcaccatctgtcttcatcttcccgccatctgatgagcagttgaaatc
tggaactgcctctgttgtgtgcctgctgaataacttctatcccagagaggccaaagtacagtgg
aaggtggataacgccctccaatcgggtaactcccaggagagtgtcacagagcaggacagcaagg
acagcacctacagcctcagcagcaccctgacgctgagcaaagcagactacgagaaacacaaagt
ctacgcctgcgaagtcacccatcagggcctgagctcgcccgtcacaaagagcttcaacagggga
gagtgt 4792 3463 AV1 amino acid (SEQ ID NO: 125)

QGQSGQYGSCSWNYVHIFMDCGSSGGSGGSGGSDWLYWPGIGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC 4792 3463 AV1 nucleotide (SEQ ID NO: 66)

Caaggccagtctggccagtatgggtcctgcagttggaactatgtacacatattcatggattgcg
gctcgagcggtggcagcggtggctctggtggctcagactggttatactggcctggtattggcgg
ttctgacatccagatgactcagtctcctagctccctgtccgcctctgtgggggaccgagtcacc
atcacatgcagagccagccaggatatttctagttacctgaactggtatcagcagaagcccggaa -continued

```
aagcacctaagctgctgatctactatacctccaggctgcactctggcgtgcccagtcggttcag

tggctcagggagcggaaccgacttcacttttaccatctcaagcctgcagccagaggatattgcc

acatactattgtcagcagggcaatacactgccctacacttttggccaggggaccaaggtggaaa

tcaaacgtacggtggctgcaccatctgtcttcatcttcccgccatctgatgagcagttgaaatc

tggaactgcctctgttgtgtgcctgctgaataacttctatcccagagaggccaaagtacagtgg

aaggtggataacgccctccaatcgggtaactcccaggagagtgtcacagagcaggacagcaagg

acagcacctacagcctcagcagcaccctgacgctgagcaaagcagactacgagaaacacaaagt

ctacgcctgcgaagtcacccatcagggcctgagctcgcccgtcacaaagagcttcaacagggga

gagtgt
```

The extent of activatable antibody activation was determined by an ELISA format that measured the ability of the activatable antibody, following incubation in synovial fluid, to bind to human IL6R as compared to the binding of anti-IL6R parental antibody to IL6R. Briefly, Nunc Maxisorp plates were coated overnight at 4° C. with 100 μl/well (microliters/well) of a 500-ng/mL solution of human IL6R (R and D Systems, Cat No. 227-SR/CF) in PBS, pH 7.4. Plates were washed 3 times with PBST (PBS, pH 7.4, 0.05% Tween-20). Wells were then blocked with 200 μl/well, 2% NFDM (non-fat dry milk) in PBST for 2 hours at room temperature. The IL6R-coated plates were washed 3 times with PBST (PBS, pH 7.4, 0.05% Tween-20). A dilution series of each activatable antibody-synovial fluid reaction mixture, as well as a dilution series of the parental anti-IL6R antibody, was added to appropriate wells of the IL6R-coated ELISA plate. The plates were incubated 1 hour at room temperature, and then washed 3 times with PBST (PBS, pH 7.4, 0.05% Tween-20). One hundred μl/well 1:3000 dilution goat-anti-human IgG (Fab specific, Sigma Cat No. A0293) in 2% NFDM-PBST was added, and the plate incubated for 1 hour at room temperature. The plates were washed 6 times with PBST (PBS, pH 7.4, 0.05% Tween-20) and then developed with TMB and 1N HCl.

Table 6 provides the results of this experiment. The data indicate that anti-IL6R activatable antibodies comprising the substrates in Table 6 are cleaved by at least some synovial fluid samples (SyF) obtained from RA patients.

TABLE 6

| Activatable Antibody Activation | | | |
|---|---|---|---|
| Substrate/ Sequence | Activation in vivo | Activation in SyF | Incidence in SyF |
| 10419 ISSGLSS (SEQ ID NO: 159) | <5% | >30% | 3/3 |
| 559 QNQALRMA (SEQ ID NO: 15) | <5% | 20% | 3/3 |
| 601 AQNLLGMV (SEQ ID NO: 16) | <5% | >30% | 3/3 |
| 3457 STFPFGMF (SEQ ID NO: 17) | 10% | >50% | 3/3 |
| 3458 PVGYTSSL (SEQ ID NO: 18) | 10% | 20% | 3/3 |
| 3463 DWLYWPGI (SEQ ID NO: 19) | <5% | >30% | 3/3 |

Example 2. Activatable Anti-EGFR Antibody with MMP-Cleavable Substrate to Inhibit Tumor Growth This Example demonstrates the ability of an activatable anti-EGFR antibody that contains a masking moiety comprising the amino acid sequence CISPRGCPDGPYVMY (SEQ ID NO: 160), a cleavage moiety comprising the MMP14 substrate 520 (also referred to herein as MN520) ISSGLLSS (SEQ ID NO: 14), and the heavy chain (SEQ ID NO: 56) and light chain (SEQ ID NO: 59) of the anti-EGFR antibody C225v5, where the entire activatable antibody construct is referred to herein as Pb-MN520, to inhibit tumor growth in the H292 xenograft lung cancer model. The configuration of the light chain of the activatable antibody was masking moiety-MMP substrate-light chain of C225v5.

Figure 1B:
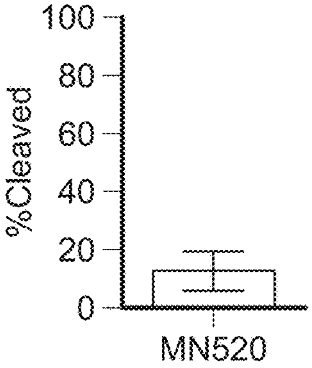

FIG. 1A is a graph depicting the effects seen in H292 xenograft tumor-bearing mice that were treated using Pb-520 (12.5 mg/kg, solid blue line) and IVIG (12.5 mg/kg, green dashed line) dosed at different times. Data are presented as mean tumor volume±SEM. FIG. 1B is a graph depicting systemic stability of the Pb-520 activatable antibody in H292 tumor bearing mice. Blood samples were taken through retro-orbital bleeds at Day 7 and the circulating stability of substrate 520 was determined by analysis of IgG pull-downs with capillary electrophoresis (GXII; Caliper LifeSciences). Concentrations of cleaved and uncleaved light chain were determined using LabChip GX software (Caliper LifeSciences).

Example 3. Materials and Methods

Reagents and Strains: Streptavidin-conjugated phycoerythrin (SA-PE) (Invitrogen, Life Technologies) was used without modifications. Human MMP9 (Research & Diagnostics Systems, Inc.) was activated following the supplied protocol and used without modifications. Human MMP14

(Research & Diagnostics Systems, Inc.) was activated following the supplied protocol and used without modifications. Human Plasmin (Haematologic Technologies Inc.) was used without modifications. Human tPA (Molecular Innovations) was used without modifications. YPet fused to the SH3 domain of Mona (monocytic adaptor protein) was produced at CytomX Therapeutics and used without modifications. MMP14 Buffer HCM (50 mM HEPES (pH 6.8), 10 mM $CaCl_2$, 0.5 mM $MgCl_2$), was used. MMP9 Buffer TCNB (50 mM Tris-HCl, 10 mM $CaCl_2$, 150 mM NaCl, 0.05% (w/v) Brij-35, pH 7.5) was used. Plasmin Buffer (50 mM Tris-Cl pH 7.5, 100 mM NaCl, 0.01% Tween20 and 1 mM EDTA was used. TBST (50 mM Tris-HCl, 150 mM NaCl, 0.05% Tween20, pH 7.4) was used. *E. coli* MC1061 (Casadaban et al., JMB 138(2):179-207 (1980) was used. All bacterial growth was performed at 37° C. with vigorous shaking in Luria-Bertani broth (LB) supplemented with 34 μg/mL chloramphenicol, unless another antibiotic is specified.

Substrate Cleavage and Scaffold Stability Analysis: For screening and clone analysis, overnight cultures were subcultured by dilution into fresh medium (1:50) and grown for 1.5-2 hours. The subculture was then induced with 0.04% arabinose and incubated with shaking at 37° C. for 45 minutes to 1 hour. To stop further growth cells were incubated on ice for 15 minutes to 1 hour. Cell aliquots were harvested and washed with PBS (pH 7.4). Cells were pelleted by centrifugation, the supernatant removed and the cells resuspended in reaction buffer containing the enzyme; the reaction mixture was incubated at 37° C. static. To stop the reaction, cells were removed and diluted 10-fold in PBS, pelleted by centrifugation, and resuspended in PBS containing either (CLIPS) SA-PE (20 μg/mL) or YPet-MONA (50 nM). After incubation on ice (30 min), cells were washed with PBS and analyzed using a FACSAria™ cell sorter.

For MMP9 protease cleavage assays, cultures were induced for 45 minutes to 1 hour. The reaction buffer for MMP9 was TCNB. Assays for MMP9 hydrolysis were performed after fresh cells were incubated with 5 nM-25 nM MMP9 for 1 hr. Background hydrolysis of the regions flanking the substrate site (using platform eCLiPS3.0-NSUB_SP described in PCT patent application PCT/US13/54378, filed Aug. 9, 2013, which was published as International Publication No. WO 2014/026136 on 13 Feb. 2014, the contents of which are hereby incorporated by reference in their entirety) was measured under each reaction condition to ensure that hydrolysis occurred in the designated substrate region.

For MMP14 protease cleavage assays, cultures were induced for 45 minutes to 1 hour. The reaction buffer for MMP14 was HCM. Assays for MMP14 hydrolysis were performed after reactions with 3 nM-250 nM MMP14 or 1 hr. Background hydrolysis of the regions flanking the substrate site (using platform eCLiPS3.0-NSUB_SP described herein) was measured under each reaction condition to ensure that hydrolysis occurred in the designated substrate region.

For human plasmin stability assays, platform eCLIPS3.0-NSUB_SP is used; cultures are induced for 45 minutes to 1 hr. The reaction buffer for plasmin is 50 mM Tris-HCl pH 7.5 supplemented with 100 mM NaCl, 0.01% Tween20 and 1 mM EDTA. Assays for plasmin hydrolysis are performed after reactions with plasmin for 1 hr.

For human tPA stability assays, platform eCLiPS3.0-NSUB_SP is used; cultures are induced for 45 minutes to 1 hr. The reaction buffer for tPA is TBST. Assays for tPA hydrolysis are performed after reactions with tPA for 1 hr.

Amino and Carboxy terminus labeling conditions: Streptavidin conjugated phycoerythrin (SAPE) was used for labeling streptavidin binding affinity ligand on the N-termini of CPX. Fluorescent protein YPet fused to the SH3 domain of Mona was used for labeling the MONA binding affinity ligand on the C-termini of CPX. For optimum labeling of cells without protease reaction, the cells were incubated for 30 min at 4° C. with SAPE (20 μg/mL) or YPet-MONA (50 nM). For the described example below 30 min incubation was used.

Kinetic Data Analysis: The extent of conversion of cell surface displayed peptide substrates was measured directly, using flow cytometry to measure changes in mean fluorescence of clonal cell populations upon protease treatment. Specifically, for each sample, conversion was determined by flow cytometry analyses using the relationship $$\text{Conversion} = \frac{FL_- - FL_+}{FL_- - FL_0} \quad \text{Conversion} = \frac{FL_- - FL_+}{FL_- - FL_0} \qquad [1]$$

where ($FL_-$) is the fluorescence after incubating without enzyme, ($FL_+$) is fluorescence after incubation with enzyme, and ($FL_0$) is fluorescence of unlabeled cells. Given that the expected substrate concentrations that were used are significantly below the expected $K_M$ of the substrate for the target protease, the Michaelis-Menten model simplifies to:

$$\frac{d[S]}{dt} = -\frac{k_{cat}}{k_M}[S][E] \qquad [2]$$

allowing substrate conversion to be expressed as $$\text{Conversion} = 1 - \exp\left(-\frac{k_{cat}}{k_M} \cdot [E] \cdot t\right) \qquad [3]$$

$$\text{Conversion} = 1 - \exp\left(-\frac{k_{cat}}{k_M} \cdot [E] \cdot t\right)$$

where [S] is the substrate concentration, [E] is enzyme concentration and t is time. To determine the second order rate constant ($k_{cat}/K_M$), equation [3] was simplified to:

$$\frac{k_{cat}}{K_m} = -\ln(1 - C)/(t * p)$$

where C is product conversion, t is time and p is protease concentration.

Sequence Data Analysis—Directed Families: Substrates were submitted to Ion Torrent™ sequencing (see, e.g., Rothenberg, J M, Nature 475, 348-352). Raw Ion Torrent reads were cropped by invariant vector sequences to obtain just the variable peptide insert. Insert sequences were translated, and sequences with stop codons were excluded from further analysis. The frequency of each sequence was obtained by number of times observed out of all viable peptide reads observed. Enrichment of sequences was obtained by comparison of observed frequency of each sequence post selection to the frequency of each sequence pre-selection. Individual sequences were identified and isolated from these data, and sequences were aligned in CLC main lab (CLC Main Workbench 6.6.2, available online). The alignment file was imported to Jalview (see, e.g., Waterhouse, A. M., et al., 2009, Bioinformatics 9, 1189-1191), and an average distance tree was assembled using the BLOSUM62 algorithm (S Henikoff S et al., 1992, Proc Natl Acad Sci USA. 89, 10915-10919). The restricted group of sequences includes members of the cluster closest to the sequence of interest. The extended group of sequences includes the restricted group of sequences plus members of the branch that shares the closest common ancestor (where applicable).

Figure 2A:
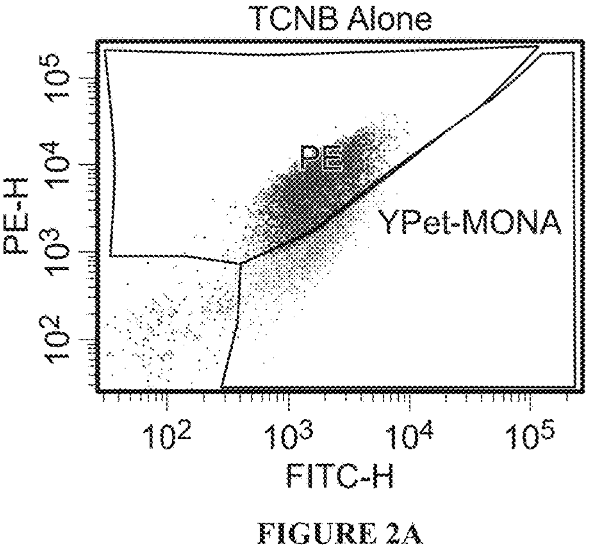
FIGS. 2A and 2B are a series of graphs depicting cleavage of the substrate pool referred to herein as SMP87 by 5 nM MMP9.
Figure 2B:
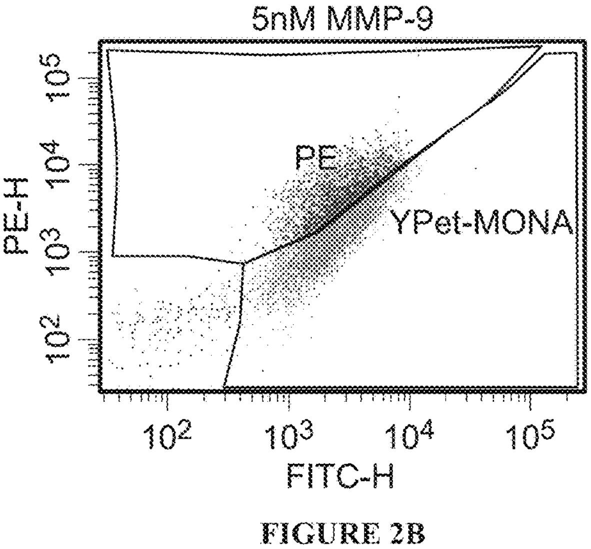

Example 4. Selection and Characterization of Substrate Pools in a Platform Scaffold The use of multi-copy substrate display on whole cells enabled selection of populations of substrates cleaved by MMP9. Selections were performed as described in U.S. Pat. No. 7,666,817 B2, issued Feb. 23, 2010, using recombinant human MMP9. Background hydrolysis of the regions flanking the substrate site (using platform eCLiPS3.0-NSUB_SP) was measured under each reaction condition to ensure that hydrolysis occurred in the designated substrate region. Selected pools were tested with MMP9 and MMP14. FIGS. 2A and 2B show cleavage of pool SMP87 by MMP9 at 5 nM in TCNB buffer.

Figure 3A:
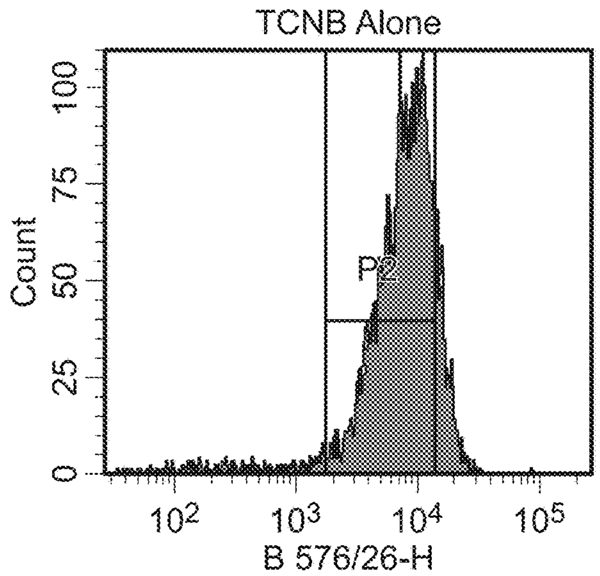
FIGS. 3A and 3B are a series of graphs depicting cleavage of substrate sequence VAGRSMRP (SEQ ID NO: 484) by 5 nM MMP9.
Figure 3B:
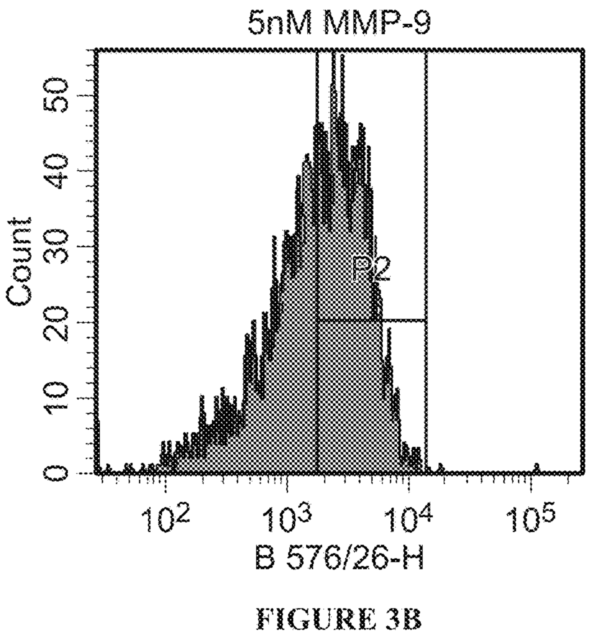

Example 5. Characterization of Substrate Cleavage Kinetics in the Platform Scaffold The use of multi-copy substrate display on whole cells enabled simple and direct quantitative characterization of cleavage kinetics. Consequently, flow cytometry was used to rank individual isolated clones on the basis of substrate conversion, and clones were identified by DNA sequencing. In this way, the extent of conversion for each clone could be determined at several different protease concentrations and fit to a Michaelis-Menten model (Kinetic Data Analysis Section). The observed second order rate constant ($k_{cat}/K_M$) was determined for each substrate versus MMP9. Background hydrolysis of the regions flanking the substrate site (using platform eCLiPS3.0-NSUB_SP), was measured under each reaction condition to ensure that hydrolysis occurred in the designated substrate region. For example, FIGS. 3A and 3B show cleavage of a substrate comprising amino acid sequence VAGRSMRP (SEQ ID NO: 484) by 5 nM MMP9 in TBST.

Figure 4:
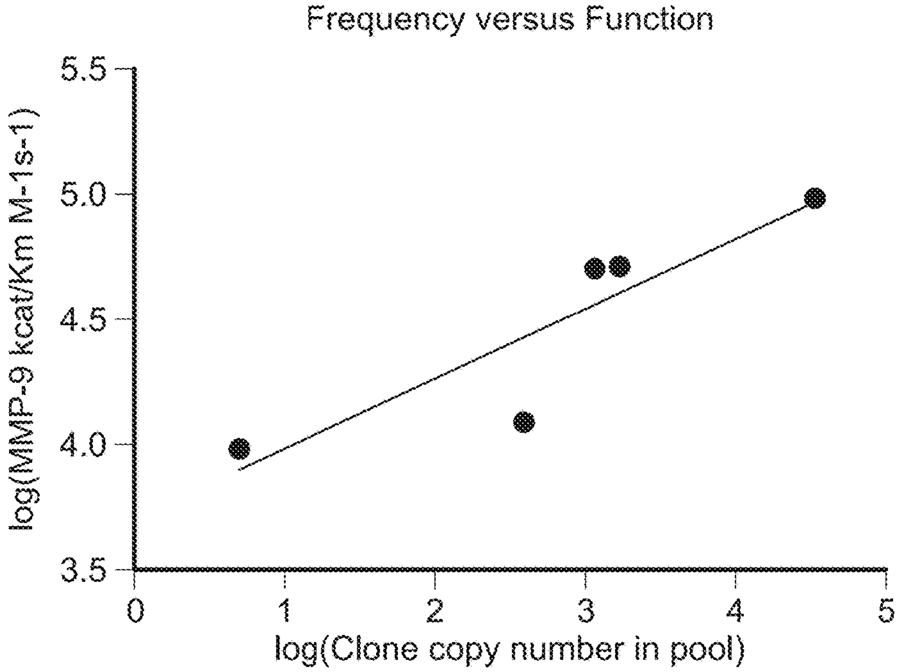
FIG. 4 is a graph depicting correlation of substrate sequence frequency and function.

Example 6. Correlation of Next Generation Sequencing Frequency and Substrate Cleavage Kinetics in the Platform Scaffold Final pools of enriched substrates were sequenced using Ion Torrent Next-Generation Sequencing. Raw Ion Torrent reads were cropped by invariant vector sequences to obtain just the variable peptide insert. Insert sequences were translated, and sequences with stop codons were excluded from further analysis. A selection of clones (displaying a range of frequencies) was selected for functional analysis. Selected clones were cleaved with human MMP9, and a $k_{cat}/K_M$ was determined for each. The log of the clone copy number in the pool was then plotted versus the log of the $k_{cat}/K_M$. FIG. 4 shows the correlation between frequency of particular cleavage moieties (Copy Number) and their abilities to be cleaved by MMP9 (MMP9 $k_{cat}/K_M$ $M^{-1}s^{-1}$).

Figure 5A:
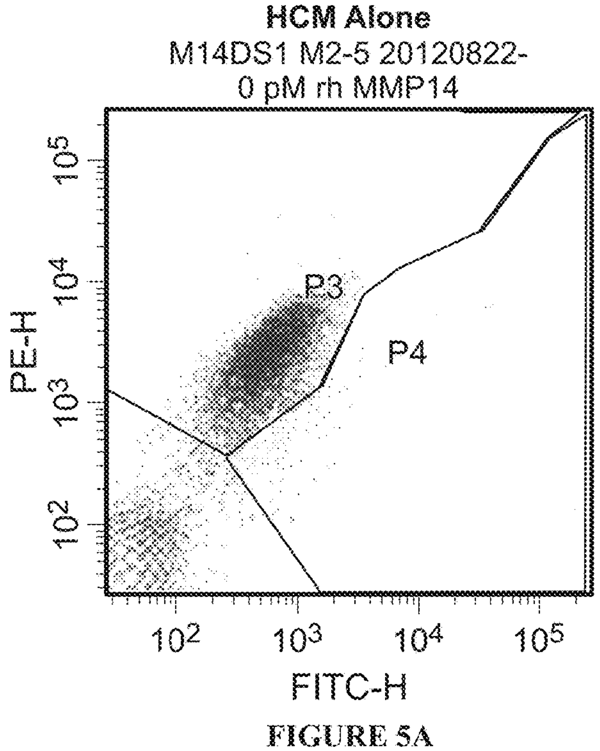
FIGS. 5A and 5B are a series of graphs depicting cleavage of the substrate pool SMP39 by 60 nM MMP14.
Figure 5B:
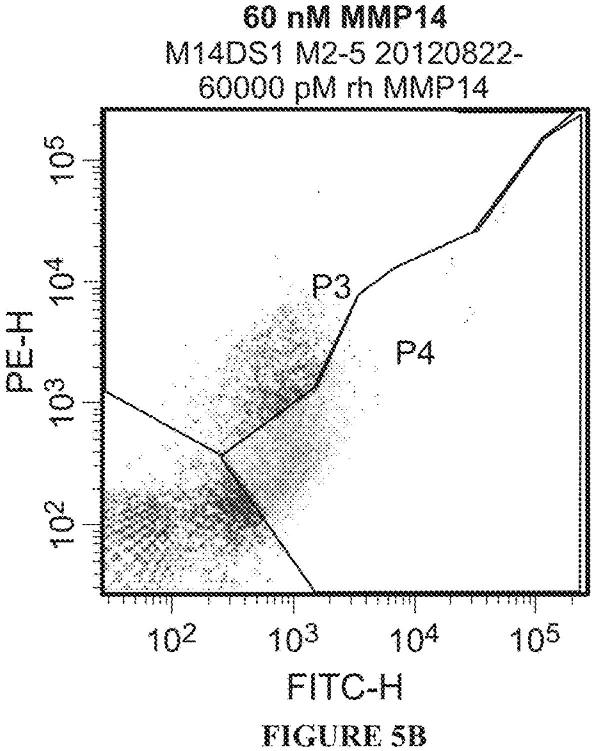

Example 7. Selection and Characterization of Substrate Pools in a Platform Scaffold The use of multi-copy substrate display on whole cells enabled selection of populations of substrates cleaved by MMP14. Selections were performed as described in U.S. Pat. No. 7,666,817 B2, using recombinant human MMP14. Background hydrolysis of the regions flanking the substrate site (using platform eCLiPS3.0-NSUB_SP) was measured under each reaction condition to ensure that hydrolysis occurred in the designated substrate region. Selected pools were tested with MMP9 and MMP14. FIGS. 5A and 5B show cleavage of pool SMP39 by MMP14 at 60 nM in HCM buffer.

Figure 6A:
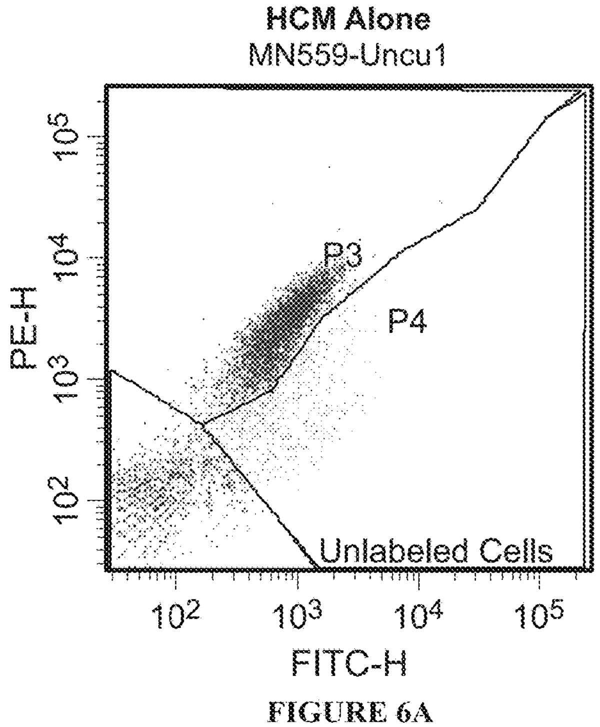
FIGS. 6A and 6B are a series of graphs depicting cleavage of the substrate sequence QNQALRMA (SEQ ID NO: 15) by 30 nM MMP14.
Figure 6B:
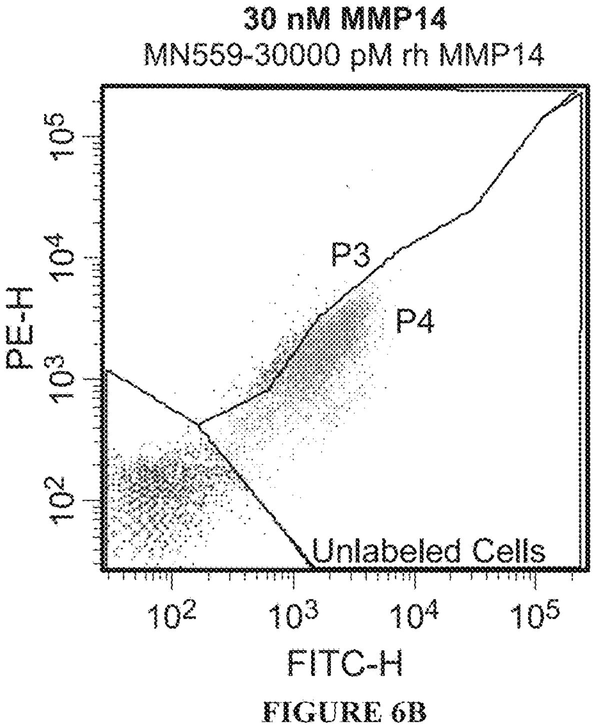

Example 8. Characterization of Substrate Cleavage Kinetics in the Platform Scaffold The use of multi-copy substrate display on whole cells enabled simple and direct quantitative characterization of cleavage kinetics. Consequently, flow cytometry was used to rank individual isolated clones on the basis of substrate conversion, and clones were identified by DNA sequencing. In this way, the extent of conversion for each clone could be determined at several different protease concentrations and fit to a Michaelis-Menten model (Kinetic Data Analysis Section). The observed second order rate constant ($k_{cat}/K_M$) was determined for each substrate versus MMP14. Background hydrolysis of the regions flanking the substrate site (using platform eCLiPS3.0-NSUB_SP), was measured under each reaction condition to ensure that hydrolysis occurred in the designated substrate region. For example, FIGS. 6A and 6B show cleavage of a substrate comprising amino acid sequence QNQALRMA (SEQ ID NO: 15) by 30 nM MMP14 in HCM buffer.

Example 9. In Vitro Substrate Activity in Activatable Antibodies

This Example demonstrates the in vitro activity of substrates of the disclosure when they are incorporated into activatable antibodies.

Several substrates identified in these studies were inserted into activatable antibodies having the 3954 mask and C225v5 variant of cetuximab, which is described in PCT Publication No. WO 2013/163631, and which is incorporated herein by reference in its entirety.

The ability of substrates in the resultant activatable antibodies to be cleaved by MMP9 or MMP14 was determined as follows. MMP9 protease digests were performed in TCNB, 50 mM Tris-HCl, 10 mM $CaCl_2$, 150 mM NaCl, 0.05% (w/v) Brij-35, pH 7.5. MMP14 digests were performed in 50 mM HEPES (pH 6.8), 10 mM $CaCl_2$, 0.5 mM $MgCl_2$. Varying concentrations of active site titrated MMP9 or MMP14 were combined with a fixed activatable antibody concentration to maintain a substrate to protease ratio of at least 50. Samples comprising MMP9 substrates were incubated at 37° C. for up to 24 hr. Samples comprising MMP14 substrates were incubated at 37° C. for 4 hr. To stop the reaction, 5 μl of the digest was added to 7 μl of HT Protein Express Sample Buffer (Caliper LifeSciences) containing 20 mM 2-Mercaptoethanol for 10 minutes at 95° C. After heat denaturation, 32 μl of $ddH_2O$ was added and samples analyzed on a LabChip GXII per manufacturer's instructions. The LabChip GXII software was used to quantify light chain peak area. Product conversion was calculated by plugging the light chain peak areas into the following equation: cleaved LC/(cleaved LC+uncleaved LC), LC=light chain. $k_{cat}/K_M$ values were determined with the following equation $$\frac{k_{cat}}{K_m} = -\ln(1-C)/(t*p)$$

where C is product conversion, t is time (s), and p is protease concentration (M), which assumes that the substrate concentration is below the $K_m$ and in excess of the protease concentration.

Resultant activatable antibodies comprising substrates selected for cleavage by MMP14 tested for cleavage by MMP14 had $k_{cat}/K_M$ values ranging from about 400 to 60,000 $M^{-1}s^{-1}$ for MMP14. Resultant activatable antibodies comprising substrates selected for cleavage by MMP9 tested for cleavage by MMP9 were cleaved by MMP9.

Example 10. Substrate Stability of Activatable Antibodies In Vivo

This Example demonstrates the in vivo stability of substrates of the disclosure when they are incorporated into activatable antibodies and injected into mice.

Three nude mice (Crl:NU-Foxn1nu) received a single IP dose of each activatable antibody at 12.5 mg/kg on Day 0. Mice were euthanized on day 4 (~96 h post-dose) by $CO_2$ asphyxiation, and blood was collected immediately as plasma-EDTA and stored at −80° C.

Activatable antibodies were purified from plasma by anti-human IgG immunoprecipitation using magnetic beads. Eluted activatable antibodies were prepared for analysis by capillary electrophoresis as described in the $k_{cat}/K_M$ section. Briefly, 5 μl of eluted IgG was added to 7 μl Protein Express Sample Buffer with 2-mercaptoethanol. Quantification of circulating stability was identical to quantification of product conversion.

Of ten activatable antibodies comprising substrates of the disclosure selected for cleavage by MMP14, seven demonstrated less than 20% cleavage in the collected plasma samples. Of seven activatable antibodies comprising substrates of the disclosure selected for cleavage by MMP9, four demonstrated no more than 20% cleavage in the collected plasma samples.

Example 11. Materials and Methods

Reagents and Strains: Human MMP9 (catalog no. 911-MP, Research & Diagnostics Systems, Inc.) was activated following the supplied protocol and used without modifications. Human MMP14 (catalog no. 918-M), Research & Diagnostics Systems, Inc.) was activated following the supplied protocol and used without modifications. Human Plasmin (catalog no. HCPM-0140, Haematologic Technologies Inc.) was used without modifications. Anti-EE monoclonal antibody (Covance, Princeton, NJ) was labeled with Alexa 647 (Life Sciences) and used with no other modifications (named EE647). *E. coli* MC1061 or MC1061 derived strains (DH10β) were used for all experiments (Casadaban et al., JMB 138(2):179-207 (1980)). All bacterial growth was performed at 37° C. with vigorous shaking in Luria-Bertani broth (LB) supplemented with 34 μg/mL chloramphenicol (cm), unless another antibiotic is specified.

Figure 7A:
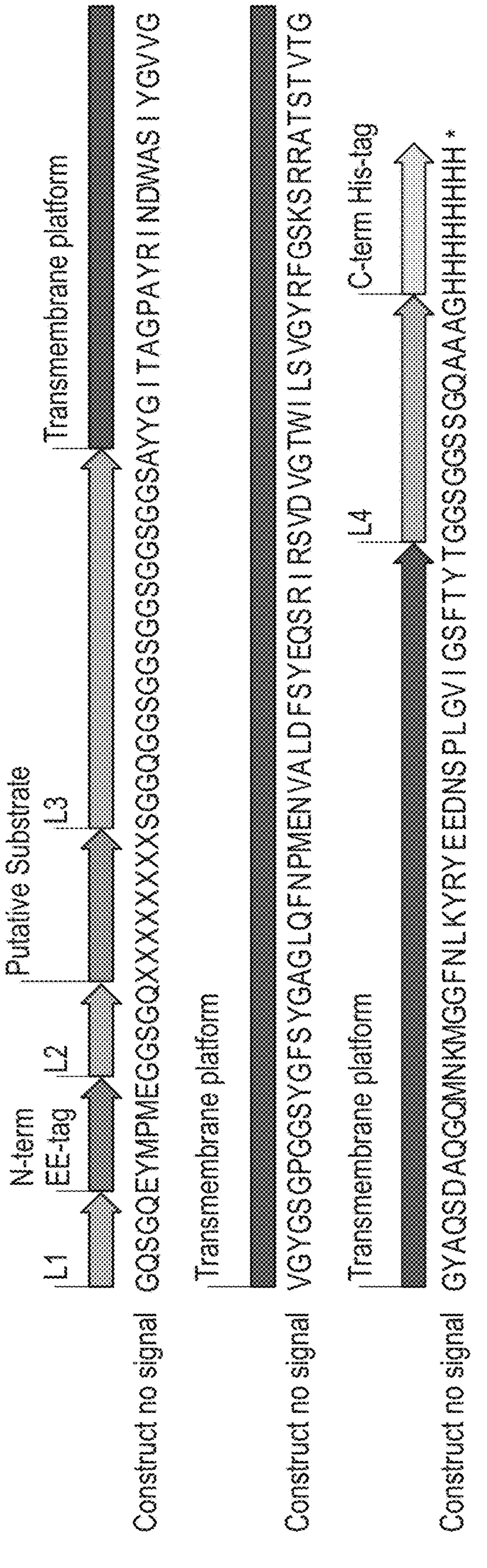
FIGS. 7A and 7B are a series of schematic representations of the peptide display platforms used in the working examples provided herein.
Figure 7B:
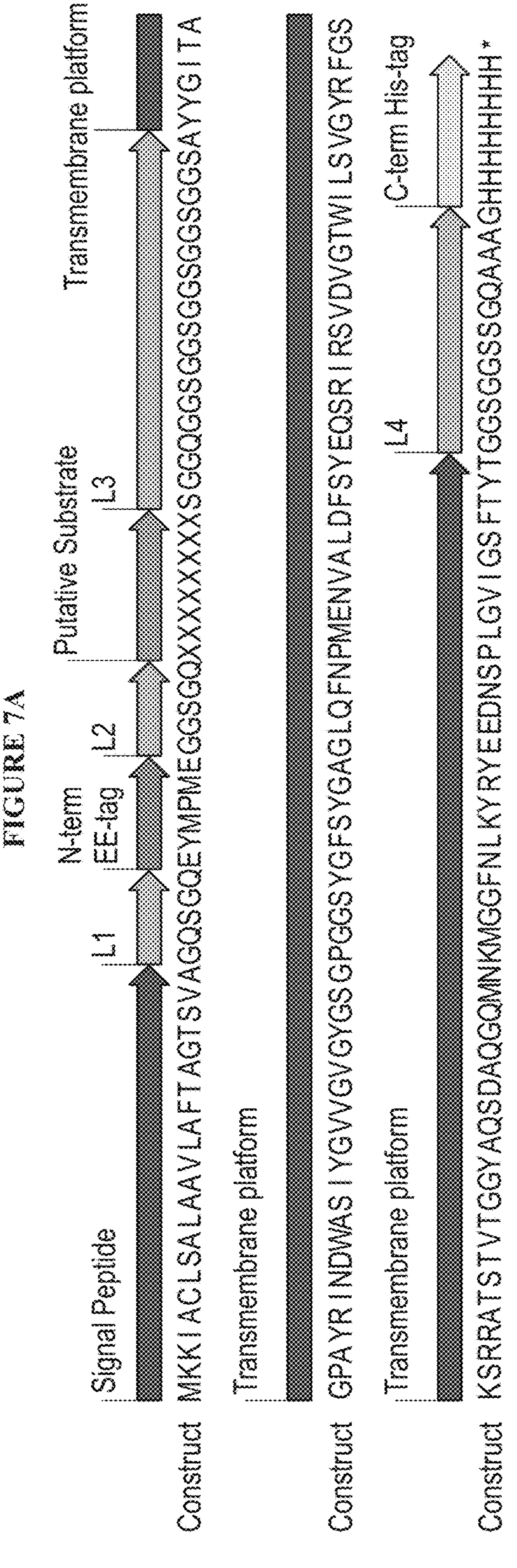

Display Platforms: Display platforms, each engineered to contain an 8-amino acid substrate of the embodiments, were produced and used as described in International Publication No. WO 2014/026136, published 13 Feb. 2014, the contents of which are hereby incorporated by reference in their entirety. The amino acid sequence of the mature (i.e., without a signal peptide) CYTX-DP-XXXXXXXX display platform (SEQ ID NO: 512) is shown in FIG. 7A. XXXXXXXX indicates the location into which each substrate is inserted. The amino acid sequence of CYTX-DP-XXXXXXXX display platform also including its signal peptide, i.e., SP-CYTX-DP-XXXXXXXX display platform (SEQ ID NO: 513) is shown in FIG. 7B.

```
CYTX-DP-XXXXXXXX Display Platform:
                                          (SEQ ID NO: 512)
GQSGQEYMPMEGGSGQXXXXXXXXSGGQGGSGGSGGSGGSGGSAYYGITA

GPAYRINDWASIYGVVGVGYGSGPGGSYGFSYGAGLQFNPMENVALDFSY

EQSRIRSVDVGTWILSVGYRFGSKSRRATSTVTGGYAQSDAQGQMNKMGG

ENLKYRYEEDNSPLGVIGSFTYTGGSGGSSGQAAAGHHHHHHHH

SP-CYTX-DP-XXXXXXXX Display Platform:
                                          (SEQ ID NO: 513)
MKKIACLSALAAVLAFTAGTSVAGQSGQEYMPMEGGSGQXXXXXXXXSGG

QGGSGGSGGSGGSGGSAYYGITAGPAYRINDWASIYGVVGVGYGSGPGGS

YGFSYGAGLQFNPMENVALDFSYEQSRIRSVDVGTWILSVGYRFGSKSRR

ATSTVTGGYAQSDAQGQMNKMGGFNLKYRYEEDNSPLGVIGSFTYTGGSG

GSSGQAAAGHHHHHHHH
```

Substrate Cleavage and Cleavage Kinetics Analysis: For clone analysis, overnight cultures were subcultured by dilution into fresh medium (1:40) and grown for 1.5-2 hours. The subculture was then induced with 0.04% arabinose and incubated with shaking at 37° C. for 40 minutes to 1 hour. To stop further growth, cells were then incubated on ice for 15 minutes to 1 hour. Cell aliquots were harvested and washed with PBS (pH 7.4). Cells were pelleted by centrifugation, the supernatant removed and the cells resuspended in reaction buffer containing the enzyme; the reaction mixture was incubated at 37° C. with shaking. To stop the reaction cells were removed and diluted 10-fold in PBS, pelleted by centrifugation, and resuspended in PBS containing EE647 (20 micrograms per ml (also referred to herein as ug/ml or ug/ml)). After incubation on ice (1 hour), cells were washed with PBS and analyzed using an Accuri C6 cell sorter.

For MMP9 protease cleavage assays, cultures were induced for 45 minutes. The reaction buffer for MMP9 was 50 mM Tris-HCl, pH 7.4, supplemented with 150 mM NaCl, 10 mM $CaCl_2$ and 0.05% (w/v) Brij-35. Assays for MMP9 hydrolysis, were performed after cleavage with 5 nM-150 nM MMP9 for 1 hour. Background hydrolysis of the regions flanking the substrate site (using, e.g., CYTX-DP-NSUB, a display platform in which the "Substrate" is non-cleavable linker GGGSGGGS) was measured under each reaction condition to ensure that hydrolysis occurred in the designated substrate region.

For MMP14 protease cleavage assays, cultures were induced for 45 minutes. The reaction buffer for MMP14 was 50 mM HEPES, pH 6.8, supplemented with 10 mM $CaCl_2$ and 0.5 mM $MgCl_2$. Assays for MMP14 hydrolysis, were performed after cleavage with 5 nM-150 nM MMP14 for 1 hr. Background hydrolysis of the regions flanking the substrate site (using, e.g., CYTX-DP-NSUB) was measured under each reaction condition to ensure that hydrolysis occurred in the designated substrate region.

For human plasmin stability assays, cultures were induced for 45 minutes. The reaction buffer for plasmin was 50 mM Tris-HCl pH 7.4, supplemented with 100 mM NaCl, 0.01% Tween20 and 1 mM EDTA. Assays for plasmin hydrolysis were performed after cleavage with 500 μM plasmin for 1 hr. Background hydrolysis of the regions flanking the substrate site (using, e.g., CYTX-DP-NSUB) was measured under each reaction condition to ensure that hydrolysis occurred in the designated substrate region.

Amino and Carboxyl terminus labeling conditions: Alexa-647 conjugated anti-EE antibody (EE647) was used for labeling EE binding affinity ligand on the N-termini of the CYTX-DP display platform. Alexa-647 conjugated anti-His antibody (His647) was used for labeling the 8His binding affinity ligand on the C-termini of the CYTX-DP display platform. For optimum labeling of cells without protease reaction, the cells were incubated for 1 hour at 4° C. with EE647 (20 μg/mL) or His647 (2 μg/mL). For the example described below, a 1-hour incubation was used.

Kinetic Data Analysis: The extent of conversion of cell surface displayed peptide substrates was measured directly, using flow cytometry to measure changes in mean fluorescence of clonal cell populations upon protease treatment. Specifically, for each sample, conversion was determined by flow cytometry analyses using the relationship $$\text{Conversion}_{CLiPS} = \frac{FL_{-} - FL_{+}}{FL_{-} - FL_{0}} \quad [1]$$

where ($FL_{-}$) is the fluorescence after incubating without enzyme, ($FL_{+}$) is fluorescence after incubation with enzyme, and ($FL_0$) is fluorescence of unlabeled cells. Given that the expected substrate concentrations that were used are significantly below the expected $K_M$ of the substrate for the target protease, the Michaelis-Menten model simplifies to $$\frac{d[S]}{dt} = -\frac{k_{cat}}{k_M}[S][E] \quad [2]$$

allowing substrate conversion to be expressed as $$\text{Conversion}_{MM} = 1 - \exp\left(-\frac{k_{cat}}{k_M}[E]\cdot t\right) \quad [3]$$

where [S] is the substrate concentration, [E] is enzyme concentration and t is time. To determine the second order rate constant ($k_{cat}/K_M$), the time dependent conversion for each substrate was fit to equation [3].

Example 12. Characterization of Substrate Cleavability in CYTX-DP Display Platform This Example demonstrates the ability of substrates of the embodiments to be cleaved by MMP but not by plasmin.

The use of multi-copy substrate display on whole cells enabled simple and direct quantitative characterization of cleavage kinetics. Clones encoding substrates were identified by DNA sequencing and subcloned into the CYTX-DP display platform such that the expressed display platform contained the 8-amino acid substrate in place of XXXXXXXX. Individual substrate displaying clones (127 independent substrate-containing display platforms in total) were assessed for cleavage by either MMP9 or MMP14 (target proteases, i.e., the proteases used to select the substrate) and plasmin (off-target protease); turnover was determined by flow cytometry. Thirty-one of the MMP9-selected substrates were selected from the same pool that was the source of substrates comprising amino acid sequences SEQ ID NOs: 17, 18, 19, 20, 21, 22, or 23 (MMP9 substrates from pool). Nine of the MMP9-selected substrates comprise consensus amino acid sequences SEQ ID NOs: 328, 336, 337, 338, 339, 348, 349, 350 or 351 (MMP9 consensus sequences). Thirty-eight of the MMP14-selected substrates were selected from the same pool that was the source of substrates comprising amino acid sequences SEQ ID NOs: 14, 15, 16, 24, 25, 26, 27, 28, 29, 30, or 33 (MMP14 substrates from 1st pool). Ten of the MMP14-selected substrates were selected from the same pool that was the source of substrates comprising amino acid sequences SEQ ID NOs: 31 or 32 (MMP14 substrates from 2nd pool). Thirty-nine of the MMP14-selected substrates were chosen from consensus amino acid sequences SEQ ID NOs: 364-370, 379-393, 402-409, 420-424, 434-435, 450-452, 457, 470-472, 474, or 483 (MMP14 consensus sequences).

In this way, the extent of cleavage for each clone could be determined and the data aggregated to determine a percent of clones that are cleaved by the target protease and not the off-target protease. Background hydrolysis of the regions flanking the substrate site (using, e.g., CYTX-DP-NSUB) was measured under each reaction condition to ensure that hydrolysis occurred in the designated substrate region. Results are presented in Table 9.

TABLE 9

Summary statistics of substrate cleavability

| Discovery effort | Substrate Group | >20% Cleavage with 50 nM MMP9 or MMP14 | <20% Cleavage with 500 pM Plasmin |
|---|---|---|---|
| MMP9-selected Substrates | All MMP9 substrates tested | 35% (14 of 40) | 85% (34 of 40) |
| | MMP9 substrates from pool | 39% (12 of 31) | 84% (26 of 31) |
| | MMP9 consensus substrates | 22% (2 of 9) | 89% (8 of 9) |
| MMP14-selected Substrates | All MMP14 substrates tested | 85% (74 of 87) | 94% (82 of 87) |
| | MMP14 substrates from 1st and 2nd pools | 79% (38 of 48) | 94% (45 of 48) |
| | MMP14 substrates from 1st pool | 79% (30 of 38) | 95% (36 of 38) |
| | MMP14 substrates from 2nd pool | 80% (8 of 10) | 100% (9 of 10) |
| | MMP14 consensus substrates | 92% (36 of 39) | 95% (37 of 39) |
| Combined MMP9 and MMP14 | Total | 69% (88 of 127) | 91% (116 of 127) |

Table 9 depicts (a) the percentage of MMP9-selected substrates tested in the CYTX-DP display platform that exhibited at least 20% cleavage when incubated with 50 nM human MMP9 (catalog no. 911-MP, Research & Diagnostics Systems, Inc., activated following the supplied protocol and used without modifications) for 1 hour at 37° C. in 50 mM Tris-HCl, pH 7.4, supplemented with 150 mM NaCl, 10 mM $CaCl_2$, and 0.05% (w/v) Brij-35 (>20% Cleavage with 50 nM MMP9); (b) the percentage of MMP14-selected substrates tested in the CYTX-DP display platform that exhibited at least 20% cleavage when incubated with 50 nM human MMP14 (catalog no. 918-MP, Research & Diagnostics Systems, Inc., activated following the supplied protocol and used without modifications) for 1 hour at 37° C. in 50 mM HEPES, pH 6.8, supplemented with 10 mM $CaCl_2$, and 0.5 mM $MgCl_2$ (>20% Cleavage with 50 nM MMP14); and (c) the percentage of MMP9-selected or MMP-14-selected substrates tested in the CYTX-DP display platform that exhibited less than 20% cleavage when incubated with 500 μM human plasmin (catalog number HCPM-0140, Haematologic Technologies, Inc., used without modifications) for 1 hour at 37° C. in 50 mM Tris-HCl, pH 7.4, supplemented with 100 mM NaCl, 0.01% Tween20 and 1 mM EDTA (<20% cleavage with 500 μM plasmin).

Example 13. Characterization of Substrate Cleavage Kinetics in CYTX-DP Display Platforms This Example demonstrates the cleavage kinetics of various substrates.

The use of multi-copy substrate display on whole cells enabled simple and direct quantitative characterization of cleavage kinetics. Clones were identified by DNA sequencing and subcloned into the CYTX-DP-XXXXXXXX display platform as described in the preceding example. Seventy-two individual substrate-displaying clones were assessed for cleavage and a subset were chosen to assess cleavage kinetics by their target protease. The extent of conversion for each clone could be determined at several different protease concentrations and fit to the Michaelis-Menten model described herein. Observed $k_{cat}/K_M$ values were then plotted versus frequency of the clone within the substrate pool and a correlation between frequency and $k_{cat}/K_M$ was seen. Background hydrolysis of the regions flanking the substrate site (using, e.g., CYTX-DP-NSUB) was measured under each reaction condition to ensure that hydrolysis occurred in the designated substrate region. Results are presented in Table 10.

TABLE 10

Summary statistics of substrate kinetics

| | Substrate Group | Target Protease $k_{cat}/K_M$ > 1 × 10E2 | Target Protease $k_{cat}/K_M$ > 1 × 10E3 | Target Protease $k_{cat}/K_M$ > 1 × 10E4 |
|---|---|---|---|---|
| MMP9 Substrates | All MMP9 substrates tested | 100% (16 of 16) | 100% (16 of 16) | 63% (10 of 16) |
| | MMP9 substrates from pool | 100% (15 of 15) | 100% (15 of 15) | 67% (10 of 15) |
| | MMP9 consensus substrates | 100% (1 of 1) | 100% (1 of 1) | 0% (0 of 1) |
| MMP14 Substrates | All MMP-14 | 100% (55 of 55) | 98% (54 of 55) | 36% (20 of 55) |
| | MMP14 substrates from 1st and 2nd pools | 100% (47 of 47) | 98% (46 of 47) | 36% (17 of 47) |
| | MMP14 substrates from 1st pool | 100% (38 of 38) | 100% (38 of 38) | 39% (15 of 38) |
| | MMP14 substrates from 2nd pool | 100% (9 of 9) | 89% (8 of 9) | 22% (2 of 9) |
| | MMP14 consensus substrates | 100% (8 of 8) | 100% (8 of 8) | 38% (3 of 8) |
| Combined MMP9 and MMP14 | Total | 100% (71 of 71) | 99% (70 of 71) | 42% (30 of 71) |

Example 14. In Vivo Efficacy and In Situ Activation of Activatable Antibodies Comprising a MMP Substrate This Example demonstrates that activatable antibodies comprising MMP substrates of the embodiments are efficacious in vivo. This Example also demonstrates that such activatable antibodies are activatable in an in situ imaging assay, such as that described in International Publication No. WO 2014/107559, published 10 Jul. 2014, the contents of which are hereby incorporated by reference in their entirety. Six activatable antibodies comprising different MMP substrates (one MMP9-selected and five MMP14-selected) of the embodiments were administered at 10 mg/kg or 12.5 mg/kg to H292 xenograft tumor-bearing (lung cancer) mice. All six activatable antibodies also comprised the masking moiety comprising the amino acid sequence CISPRGCPDGPYVMY (SEQ ID NO: 160) and anti-EGFR antibody C225v5 antibody comprising a light chain (SEQ ID NO: 59) and a heavy chain (SEQ ID NO: 56). The configuration of the light chain of the activatable antibody was masking moiety—MMP substrate—light chain of C225v5. All six activatable antibodies demonstrated tumor growth inhibition ranging from 22% to 81% as measured by mean % Δ inhibition. Mean % Δ inhibition is calculated as (mean(C)−mean(C0))−(mean(T)−mean(T0))/(mean(C)−mean(C0))*100%, wherein T is the current test group value, T0 is the current test group initial value, C is the control group value, and C0 is the control group initial value. The EGFR antibody cetuximab demonstrated 96-98% inhibition in this study.

The same six activatable antibodies were submitted to in situ imaging assays of H292 tumor tissue, using the conditions described in the examples of WO 2014/107559. All six activatable antibodies were activated, demonstrating that all six MMP substrates were cleaved and the released antibodies bound to EGFR on the tumor tissue. The staining signals ranged from 15% to 65% of the IHC signal intensity of cetuximab. In general, the percentage of activation of each activatable antibody demonstrated a positive correlation with the efficacy that activatable antibody demonstrated in the H292 mouse model.

Tissue from ten triple negative breast cancer patients was submitted to in situ imaging using an anti-Jagged activatable antibody (e.g., an anti-Jagged activatable antibody cited in International Publication No. WO 2013/192550, published 27 Dec. 2013, the contents of which are hereby incorporated by reference in their entirety) comprising an MMP14-selected substrate under the conditions described in the examples of WO 2014/107559. Nine of the ten tissue samples demonstrated activatable antibody activation staining scores ranging from 15% to 100% as compared to the IHC signal intensity of cetuximab: Eight of the ten tissue samples demonstrated activatable antibody activation staining scores ranging from 30% to 100% as compared to the IHC signal intensity of cetuximab.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following.

SEQUENCE LISTING

```
Sequence total quantity: 515
SEQ ID NO: 1           moltype = AA  length = 5
FEATURE                Location/Qualifiers
REGION                 1..5
                       note = linking peptide
REPEAT                 1..5
                       note = May be repeated
source                 1..5
                       mol_type = protein
                       organism = synthetic construct
SEQUENCE: 1
GSGGS                                                                   5

SEQ ID NO: 2           moltype = AA  length = 4
FEATURE                Location/Qualifiers
REGION                 1..4
                       note = linking peptide
REPEAT                 1..4
                       note = May be repeated
source                 1..4
                       mol_type = protein
                       organism = synthetic construct
SEQUENCE: 2
GGGS                                                                    4

SEQ ID NO: 3           moltype = AA  length = 4
FEATURE                Location/Qualifiers
REGION                 1..4
                       note = linking peptide
source                 1..4
                       mol_type = protein
                       organism = synthetic construct
SEQUENCE: 3
GGSG                                                                    4

SEQ ID NO: 4           moltype = AA  length = 5
FEATURE                Location/Qualifiers
REGION                 1..5
                       note = linking peptide
source                 1..5
                       mol_type = protein
                       organism = synthetic construct
SEQUENCE: 4
GGSGG                                                                   5

SEQ ID NO: 5           moltype = AA  length = 5
FEATURE                Location/Qualifiers
REGION                 1..5
                       note = linking peptide
source                 1..5
                       mol_type = protein
                       organism = synthetic construct
SEQUENCE: 5
GSGSG                                                                   5

SEQ ID NO: 6           moltype = AA  length = 5
FEATURE                Location/Qualifiers
```

-continued

```
REGION               1..5
                     note = linking peptide
source               1..5
                     mol_type = protein
                     organism = synthetic construct
SEQUENCE: 6
GSGGG                                                         5

SEQ ID NO: 7         moltype = AA  length = 5
FEATURE              Location/Qualifiers
REGION               1..5
                     note = linking peptide
source               1..5
                     mol_type = protein
                     organism = synthetic construct
SEQUENCE: 7
GGGSG                                                         5

SEQ ID NO: 8         moltype = AA  length = 5
FEATURE              Location/Qualifiers
REGION               1..5
                     note = linking peptide
source               1..5
                     mol_type = protein
                     organism = synthetic construct
SEQUENCE: 8
GSSSG                                                         5

SEQ ID NO: 9         moltype = AA  length = 13
FEATURE              Location/Qualifiers
REGION               1..13
                     note = linking peptide
source               1..13
                     mol_type = protein
                     organism = synthetic construct
SEQUENCE: 9
GSSGGSGGSG GSG                                                13

SEQ ID NO: 10        moltype = AA  length = 11
FEATURE              Location/Qualifiers
REGION               1..11
                     note = linking peptide
source               1..11
                     mol_type = protein
                     organism = synthetic construct
SEQUENCE: 10
GSSGGSGGSG G                                                  11

SEQ ID NO: 11        moltype = AA  length = 12
FEATURE              Location/Qualifiers
REGION               1..12
                     note = linking peptide
source               1..12
                     mol_type = protein
                     organism = synthetic construct
SEQUENCE: 11
GSSGGSGGSG GS                                                 12

SEQ ID NO: 12        moltype = AA  length = 5
FEATURE              Location/Qualifiers
REGION               1..5
                     note = linking peptide
source               1..5
                     mol_type = protein
                     organism = synthetic construct
SEQUENCE: 12
GSSGT                                                         5

SEQ ID NO: 13        moltype = AA  length = 4
FEATURE              Location/Qualifiers
REGION               1..4
                     note = linking peptide
source               1..4
                     mol_type = protein
                     organism = synthetic construct
SEQUENCE: 13
GSSG                                                          4

SEQ ID NO: 14        moltype = AA  length = 8
```

```
FEATURE                 Location/Qualifiers
REGION                  1..8
                        note = cleavable moiety
source                  1..8
                        mol_type = protein
                        organism = synthetic construct
SEQUENCE: 14
ISSGLLSS                                                                  8

SEQ ID NO: 15           moltype = AA  length = 8
FEATURE                 Location/Qualifiers
REGION                  1..8
                        note = cleavable moiety
source                  1..8
                        mol_type = protein
                        organism = synthetic construct
SEQUENCE: 15
QNQALRMA                                                                  8

SEQ ID NO: 16           moltype = AA  length = 8
FEATURE                 Location/Qualifiers
REGION                  1..8
                        note = cleavable moiety
source                  1..8
                        mol_type = protein
                        organism = synthetic construct
SEQUENCE: 16
AQNLLGMV                                                                  8

SEQ ID NO: 17           moltype = AA  length = 8
FEATURE                 Location/Qualifiers
REGION                  1..8
                        note = cleavable moiety
source                  1..8
                        mol_type = protein
                        organism = synthetic construct
SEQUENCE: 17
STFPFGMF                                                                  8

SEQ ID NO: 18           moltype = AA  length = 8
FEATURE                 Location/Qualifiers
REGION                  1..8
                        note = cleavable moiety
source                  1..8
                        mol_type = protein
                        organism = synthetic construct
SEQUENCE: 18
PVGYTSSL                                                                  8

SEQ ID NO: 19           moltype = AA  length = 8
FEATURE                 Location/Qualifiers
REGION                  1..8
                        note = cleavable moiety
source                  1..8
                        mol_type = protein
                        organism = synthetic construct
SEQUENCE: 19
DWLYWPGI                                                                  8

SEQ ID NO: 20           moltype = AA  length = 8
FEATURE                 Location/Qualifiers
REGION                  1..8
                        note = cleavable moiety
source                  1..8
                        mol_type = protein
                        organism = synthetic construct
SEQUENCE: 20
MIAPVAYR                                                                  8

SEQ ID NO: 21           moltype = AA  length = 8
FEATURE                 Location/Qualifiers
REGION                  1..8
                        note = cleavable moiety
source                  1..8
                        mol_type = protein
                        organism = synthetic construct
SEQUENCE: 21
RPSPMWAY                                                                  8
```

-continued

```
SEQ ID NO: 22           moltype = AA  length = 8
FEATURE                 Location/Qualifiers
REGION                  1..8
                        note = cleavable moiety
source                  1..8
                        mol_type = protein
                        organism = synthetic construct
SEQUENCE: 22
WATPRPMR                                                                    8

SEQ ID NO: 23           moltype = AA  length = 8
FEATURE                 Location/Qualifiers
REGION                  1..8
                        note = cleavable moiety
source                  1..8
                        mol_type = protein
                        organism = synthetic construct
SEQUENCE: 23
FRLLDWQW                                                                    8

SEQ ID NO: 24           moltype = AA  length = 8
FEATURE                 Location/Qualifiers
REGION                  1..8
                        note = cleavable moiety
source                  1..8
                        mol_type = protein
                        organism = synthetic construct
SEQUENCE: 24
LKAAPRWA                                                                    8

SEQ ID NO: 25           moltype = AA  length = 8
FEATURE                 Location/Qualifiers
REGION                  1..8
                        note = cleavable moiety
source                  1..8
                        mol_type = protein
                        organism = synthetic construct
SEQUENCE: 25
GPSHLVLT                                                                    8

SEQ ID NO: 26           moltype = AA  length = 8
FEATURE                 Location/Qualifiers
REGION                  1..8
                        note = cleavable moiety
source                  1..8
                        mol_type = protein
                        organism = synthetic construct
SEQUENCE: 26
LPGGLSPW                                                                    8

SEQ ID NO: 27           moltype = AA  length = 8
FEATURE                 Location/Qualifiers
REGION                  1..8
                        note = cleavable moiety
source                  1..8
                        mol_type = protein
                        organism = synthetic construct
SEQUENCE: 27
MGLFSEAG                                                                    8

SEQ ID NO: 28           moltype = AA  length = 8
FEATURE                 Location/Qualifiers
REGION                  1..8
                        note = cleavable moiety
source                  1..8
                        mol_type = protein
                        organism = synthetic construct
SEQUENCE: 28
SPLPLRVP                                                                    8

SEQ ID NO: 29           moltype = AA  length = 8
FEATURE                 Location/Qualifiers
REGION                  1..8
                        note = cleavable moiety
source                  1..8
                        mol_type = protein
                        organism = synthetic construct
SEQUENCE: 29
RMHLRSLG                                                                    8
```

```
SEQ ID NO: 30            moltype = AA  length = 8
FEATURE                  Location/Qualifiers
REGION                   1..8
                         note = cleavable moiety
source                   1..8
                         mol_type = protein
                         organism = synthetic construct
SEQUENCE: 30
LAAPLGLL                                                            8

SEQ ID NO: 31            moltype = AA  length = 8
FEATURE                  Location/Qualifiers
REGION                   1..8
                         note = cleavable moiety
source                   1..8
                         mol_type = protein
                         organism = synthetic construct
SEQUENCE: 31
AVGLLAPP                                                            8

SEQ ID NO: 32            moltype = AA  length = 8
FEATURE                  Location/Qualifiers
REGION                   1..8
                         note = cleavable moiety
source                   1..8
                         mol_type = protein
                         organism = synthetic construct
SEQUENCE: 32
LLAPSHRA                                                            8

SEQ ID NO: 33            moltype = AA  length = 8
FEATURE                  Location/Qualifiers
REGION                   1..8
                         note = cleavable moiety
source                   1..8
                         mol_type = protein
                         organism = synthetic construct
SEQUENCE: 33
PAGLWLDP                                                            8

SEQ ID NO: 34            moltype = AA  length = 8
FEATURE                  Location/Qualifiers
REGION                   1..8
                         note = cleavable moiety
source                   1..8
                         mol_type = protein
                         organism = synthetic construct
SEQUENCE: 34
TGRGPSWV                                                            8

SEQ ID NO: 35            moltype = AA  length = 8
FEATURE                  Location/Qualifiers
REGION                   1..8
                         note = cleavable moiety
source                   1..8
                         mol_type = protein
                         organism = synthetic construct
SEQUENCE: 35
SARGPSRW                                                            8

SEQ ID NO: 36            moltype = AA  length = 8
FEATURE                  Location/Qualifiers
REGION                   1..8
                         note = cleavable moiety
source                   1..8
                         mol_type = protein
                         organism = synthetic construct
SEQUENCE: 36
TARGPSFK                                                            8

SEQ ID NO: 37            moltype = AA  length = 8
FEATURE                  Location/Qualifiers
REGION                   1..8
                         note = cleavable moiety
source                   1..8
                         mol_type = protein
                         organism = synthetic construct
SEQUENCE: 37
```

-continued

```
LSGRSDNH                                                          8

SEQ ID NO: 38          moltype = AA  length = 8
FEATURE                Location/Qualifiers
REGION                 1..8
                       note = cleavable moiety
source                 1..8
                       mol_type = protein
                       organism = synthetic construct
SEQUENCE: 38
GGWHTGRN                                                          8

SEQ ID NO: 39          moltype = AA  length = 8
FEATURE                Location/Qualifiers
REGION                 1..8
                       note = cleavable moiety
source                 1..8
                       mol_type = protein
                       organism = synthetic construct
SEQUENCE: 39
HTGRSGAL                                                          8

SEQ ID NO: 40          moltype = AA  length = 8
FEATURE                Location/Qualifiers
REGION                 1..8
                       note = cleavable moiety
source                 1..8
                       mol_type = protein
                       organism = synthetic construct
SEQUENCE: 40
PLTGRSGG                                                          8

SEQ ID NO: 41          moltype = AA  length = 8
FEATURE                Location/Qualifiers
REGION                 1..8
                       note = cleavable moiety
source                 1..8
                       mol_type = protein
                       organism = synthetic construct
SEQUENCE: 41
AARGPAIH                                                          8

SEQ ID NO: 42          moltype = AA  length = 8
FEATURE                Location/Qualifiers
REGION                 1..8
                       note = cleavable moiety
source                 1..8
                       mol_type = protein
                       organism = synthetic construct
SEQUENCE: 42
RGPAFNPM                                                          8

SEQ ID NO: 43          moltype = AA  length = 8
FEATURE                Location/Qualifiers
REGION                 1..8
                       note = cleavable moiety
source                 1..8
                       mol_type = protein
                       organism = synthetic construct
SEQUENCE: 43
SSRGPAYL                                                          8

SEQ ID NO: 44          moltype = AA  length = 8
FEATURE                Location/Qualifiers
REGION                 1..8
                       note = cleavable moiety
source                 1..8
                       mol_type = protein
                       organism = synthetic construct
SEQUENCE: 44
RGPATPIM                                                          8

SEQ ID NO: 45          moltype = AA  length = 4
FEATURE                Location/Qualifiers
REGION                 1..4
                       note = cleavable moiety
source                 1..4
                       mol_type = protein
                       organism = synthetic construct
```

```
SEQUENCE: 45
RGPA                                                                4

SEQ ID NO: 46           moltype = AA  length = 10
FEATURE                 Location/Qualifiers
REGION                  1..10
                        note = cleavable moiety
source                  1..10
                        mol_type = protein
                        organism = synthetic construct
SEQUENCE: 46
GGQPSGMWGW                                                          10

SEQ ID NO: 47           moltype = AA  length = 10
FEATURE                 Location/Qualifiers
REGION                  1..10
                        note = cleavable moiety
source                  1..10
                        mol_type = protein
                        organism = synthetic construct
SEQUENCE: 47
FPRPLGITGL                                                          10

SEQ ID NO: 48           moltype = AA  length = 10
FEATURE                 Location/Qualifiers
REGION                  1..10
                        note = cleavable moiety
source                  1..10
                        mol_type = protein
                        organism = synthetic construct
SEQUENCE: 48
VHMPLGFLGP                                                          10

SEQ ID NO: 49           moltype = AA  length = 8
FEATURE                 Location/Qualifiers
REGION                  1..8
                        note = cleavable moiety
source                  1..8
                        mol_type = protein
                        organism = synthetic construct
SEQUENCE: 49
SPLTGRSG                                                            8

SEQ ID NO: 50           moltype = AA  length = 9
FEATURE                 Location/Qualifiers
REGION                  1..9
                        note = cleavable moiety
source                  1..9
                        mol_type = protein
                        organism = synthetic construct
SEQUENCE: 50
LAPLGLQRR                                                           9

SEQ ID NO: 51           moltype = AA  length = 8
FEATURE                 Location/Qualifiers
REGION                  1..8
                        note = cleavable moiety
source                  1..8
                        mol_type = protein
                        organism = synthetic construct
SEQUENCE: 51
SGGPLGVR                                                            8

SEQ ID NO: 52           moltype = AA  length = 4
FEATURE                 Location/Qualifiers
REGION                  1..4
                        note = cleavable moiety
source                  1..4
                        mol_type = protein
                        organism = synthetic construct
SEQUENCE: 52
PLGL                                                                4

SEQ ID NO: 53           moltype = AA  length = 6
FEATURE                 Location/Qualifiers
REGION                  1..6
                        note = spacer peptide
source                  1..6
                        mol_type = protein
```

-continued

```
                         organism = synthetic construct
SEQUENCE: 53
QGQSGQ                                                                  6

SEQ ID NO: 54            moltype = AA  length = 449
FEATURE                  Location/Qualifiers
REGION                   1..449
                         note = Av1 Antibody Heavy Chain
source                   1..449
                         mol_type = protein
                         organism = synthetic construct
SEQUENCE: 54
QVQLQESGPG LVRPSQTLSL TCTVSGYSIT SDHAWSWVRQ PPGRGLEWIG YISYSGITTY  60
NPSLKSRVTI SRDNSKNTLY LQMNSLRAED TAVYYCARSL ARTTAMDYWG QGSLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 55            moltype = AA  length = 214
FEATURE                  Location/Qualifiers
REGION                   1..214
                         note = Av1 Antibody Light Chain
source                   1..214
                         mol_type = protein
                         organism = synthetic construct
SEQUENCE: 55
DIQMTQSPSS LSASVGDRVT ITCRASQDIS SYLNWYQQKP GKAPKLLIYY TSRLHSGVPS  60
RFSGSGSGTD FTFTISSLQP EDIATYYCQQ GNTLPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 56            moltype = AA  length = 449
FEATURE                  Location/Qualifiers
REGION                   1..449
                         note = C225v5 Antibody Heavy Chain
source                   1..449
                         mol_type = protein
                         organism = synthetic construct
SEQUENCE: 56
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 57            moltype = AA  length = 449
FEATURE                  Location/Qualifiers
REGION                   1..449
                         note = C225v4 Antibody Heavy Chain
source                   1..449
                         mol_type = protein
                         organism = synthetic construct
SEQUENCE: 57
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSNDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 58            moltype = AA  length = 449
FEATURE                  Location/Qualifiers
REGION                   1..449
                         note = C225v6 Antibody Heavy Chain
source                   1..449
                         mol_type = protein
                         organism = synthetic construct
SEQUENCE: 58
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
```

-continued

```
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYAS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 59          moltype = AA  length = 214
FEATURE                Location/Qualifiers
REGION                 1..214
                       note = C225 Antibody Light Chain
source                 1..214
                       mol_type = protein
                       organism = synthetic construct
SEQUENCE: 59
QILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 60          moltype = AA  length = 108
FEATURE                Location/Qualifiers
REGION                 1..108
                       note = Variable Light Chain Lc4
source                 1..108
                       mol_type = protein
                       organism = synthetic construct
SEQUENCE: 60
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 61          moltype = AA  length = 119
FEATURE                Location/Qualifiers
REGION                 1..119
                       note = Variable Heavy Chain Hc4
source                 1..119
                       mol_type = protein
                       organism = synthetic construct
SEQUENCE: 61
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKDI GGRSAFDYWG QGTLVTVSS   119

SEQ ID NO: 62          moltype = AA  length = 108
FEATURE                Location/Qualifiers
REGION                 1..108
                       note = Variable Light Chain Lc5
source                 1..108
                       mol_type = protein
                       organism = synthetic construct
SEQUENCE: 62
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 63          moltype = AA  length = 119
FEATURE                Location/Qualifiers
REGION                 1..119
                       note = Variable Heavy Chain Hc5
source                 1..119
                       mol_type = protein
                       organism = synthetic construct
SEQUENCE: 63
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PYHGQFDYWG QGTLVTVSS   119

SEQ ID NO: 64          moltype = AA  length = 108
FEATURE                Location/Qualifiers
REGION                 1..108
                       note = Variable Light Chain Lc7
source                 1..108
                       mol_type = protein
                       organism = synthetic construct
SEQUENCE: 64
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 65          moltype = AA  length = 119
FEATURE                Location/Qualifiers
REGION                 1..119
                       note = Variable Heavy Chain Hc7
source                 1..119
```

```
                        mol_type = protein
                        organism = synthetic construct
SEQUENCE: 65
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PFFGQFDYWG QGTLVTVSS   119

SEQ ID NO: 66           moltype = DNA  length = 774
FEATURE                 Location/Qualifiers
misc_feature            1..774
                        note = 4792 3463 AV1
source                  1..774
                        mol_type = other DNA
                        organism = synthetic construct
SEQUENCE: 66
caaggccagt ctggccagta tgggtcctgc agttggaact atgtacacat attcatggat  60
tgcggctcga gcggtggcag cggtggctct ggtggctcag actggttata ctggcctggt  120
attggcggtt ctgacatcca gatgactcag tctcctagct ccctgtccgc ctctgtgggg  180
gaccgagtca ccatcacatg cagagccagc caggatattt ctagttacct gaactggtat  240
cagcagaagc ccggaaaagc acctaagctg ctgatctact atacctccag gctgcactct  300
ggcgtgccca gtcggttcag tggctcaggg agcggaaccg acttcacttt taccatctca  360
agcctgcagc cagaggatat tgccacatac tattgtcagc agggcaatac actgccctac  420
acttttggcc aggggaccaa ggtggaaatc aaacgtacgg tggctgcacc atctgtcttc  480
atcttcccgc catctgatga gcagttgaaa tctggaactg cctctgttgt gtgcctgctg  540
aataacttct atcccagaga ggccaaagta cagtggaagg tggataacgc cctccaatcg  600
ggtaactccc aggagagtgt cacagagcag gacagcaagg acagcaccta cagcctcagc  660
agcaccctga cgctgagcaa agcagactac gagaaacaca aagtctacgc ctgcgaagtc  720
acccatcagg gcctgagctc gcccgtcaca aagagcttca acaggggaga gtgt        774

SEQ ID NO: 67           moltype = AA  length = 108
FEATURE                 Location/Qualifiers
REGION                  1..108
                        note = Variable Light Chain Lc8
source                  1..108
                        mol_type = protein
                        organism = synthetic construct
SEQUENCE: 67
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 68           moltype = AA  length = 119
FEATURE                 Location/Qualifiers
REGION                  1..119
                        note = Variable Heavy Chain Hc8
source                  1..119
                        mol_type = protein
                        organism = synthetic construct
SEQUENCE: 68
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKHI GRTNPFDYWG QGTLVTVSS   119

SEQ ID NO: 69           moltype = AA  length = 108
FEATURE                 Location/Qualifiers
REGION                  1..108
                        note = Variable Light Chain Lc13
source                  1..108
                        mol_type = protein
                        organism = synthetic construct
SEQUENCE: 69
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 70           moltype = AA  length = 116
FEATURE                 Location/Qualifiers
REGION                  1..116
                        note = Variable Heavy Chain Hc13
source                  1..116
                        mol_type = protein
                        organism = synthetic construct
SEQUENCE: 70
EVQLLESGGG LVQPGGSLRL SCAASGFTFS SYAMSWVRQA PGKGLEWVSS IEQMGWQTEY  60
ADSVKGRFTI SRDNSKNTLY LQMNSLRAED TAVYYCAKSA AAFDYWGQGT LVTVSS      116

SEQ ID NO: 71           moltype = AA  length = 108
FEATURE                 Location/Qualifiers
REGION                  1..108
                        note = Variable Light Chain Lc16
source                  1..108
                        mol_type = protein
                        organism = synthetic construct
```

-continued

```
SEQUENCE: 71
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR              108

SEQ ID NO: 72          moltype = AA  length = 119
FEATURE                Location/Qualifiers
REGION                 1..119
                       note = Variable Heavy Chain Hc16
source                 1..119
                       mol_type = protein
                       organism = synthetic construct
SEQUENCE: 72
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PYYGQFDYWG QGTLVTVSS   119

SEQ ID NO: 73          moltype = AA  length = 108
FEATURE                Location/Qualifiers
REGION                 1..108
                       note = Variable Light Chain Lc19
source                 1..108
                       mol_type = protein
                       organism = synthetic construct
SEQUENCE: 73
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR              108

SEQ ID NO: 74          moltype = AA  length = 119
FEATURE                Location/Qualifiers
REGION                 1..119
                       note = Variable Heavy Chain Hc19
source                 1..119
                       mol_type = protein
                       organism = synthetic construct
SEQUENCE: 74
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PFFGQFDYWG QGTLVTVSS   119

SEQ ID NO: 75          moltype = AA  length = 108
FEATURE                Location/Qualifiers
REGION                 1..108
                       note = Variable Light Chain Lc21
source                 1..108
                       mol_type = protein
                       organism = synthetic construct
SEQUENCE: 75
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR              108

SEQ ID NO: 76          moltype = AA  length = 119
FEATURE                Location/Qualifiers
REGION                 1..119
                       note = Variable Heavy Chain Hc21
source                 1..119
                       mol_type = protein
                       organism = synthetic construct
SEQUENCE: 76
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKDI GGRSAFDYWG QGTLVTVSS   119

SEQ ID NO: 77          moltype = AA  length = 108
FEATURE                Location/Qualifiers
REGION                 1..108
                       note = Variable Light Chain Lc24
source                 1..108
                       mol_type = protein
                       organism = synthetic construct
SEQUENCE: 77
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR              108

SEQ ID NO: 78          moltype = AA  length = 116
FEATURE                Location/Qualifiers
REGION                 1..116
                       note = Variable Heavy Chain Hc24
source                 1..116
                       mol_type = protein
                       organism = synthetic construct
SEQUENCE: 78
EVQLLESGGG LVQPGGSLRL SCAASGFTFS SYAMSWVRQA PGKGLEWVSS IEEMGWQTLY  60
```

-continued

```
ADSVKGRFTI SRDNSKNTLY LQMNSLRAED TAVYYCAKSA AAFDYWGQGT LVTVSS      116

SEQ ID NO: 79          moltype = AA  length = 108
FEATURE                Location/Qualifiers
REGION                 1..108
                       note = Variable Light Chain Lc26
source                 1..108
                       mol_type = protein
                       organism = synthetic construct
SEQUENCE: 79
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 80          moltype = AA  length = 119
FEATURE                Location/Qualifiers
REGION                 1..119
                       note = Variable Heavy Chain Hc26
source                 1..119
                       mol_type = protein
                       organism = synthetic construct
SEQUENCE: 80
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKDI GGRSAFDYWG QGTLVTVSS   119

SEQ ID NO: 81          moltype = AA  length = 108
FEATURE                Location/Qualifiers
REGION                 1..108
                       note = Variable Light Chain Lc27
source                 1..108
                       mol_type = protein
                       organism = synthetic construct
SEQUENCE: 81
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 82          moltype = AA  length = 119
FEATURE                Location/Qualifiers
REGION                 1..119
                       note = Variable Heavy Chain Hc27
source                 1..119
                       mol_type = protein
                       organism = synthetic construct
SEQUENCE: 82
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PFYGQFDYWG QGTLVTVSS   119

SEQ ID NO: 83          moltype = AA  length = 108
FEATURE                Location/Qualifiers
REGION                 1..108
                       note = Variable Light Chain Lc28
source                 1..108
                       mol_type = protein
                       organism = synthetic construct
SEQUENCE: 83
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 84          moltype = AA  length = 119
FEATURE                Location/Qualifiers
REGION                 1..119
                       note = Variable Heavy Chain Hc28
source                 1..119
                       mol_type = protein
                       organism = synthetic construct
SEQUENCE: 84
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PFFGQFDYWG QGTLVTVSS   119

SEQ ID NO: 85          moltype = AA  length = 108
FEATURE                Location/Qualifiers
REGION                 1..108
                       note = Variable Light Chain Lc30
source                 1..108
                       mol_type = protein
                       organism = synthetic construct
SEQUENCE: 85
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108
```

-continued

```
SEQ ID NO: 86          moltype = AA  length = 115
FEATURE                Location/Qualifiers
REGION                 1..115
                       note = Variable Heavy Chain Hc30
source                 1..115
                       mol_type = protein
                       organism = synthetic construct
SEQUENCE: 86
EVQLLESGGG LVQPGGSLRL SCAASGFTFS SYAMSWVRQA PGKGLEWVSS IEEMGWQTLY  60
ADSVKGRFTI SRDNSKNTLY LQMNSLRAED TAVYYAKSAA AFDYWGQGTL VTVSS       115

SEQ ID NO: 87          moltype = AA  length = 108
FEATURE                Location/Qualifiers
REGION                 1..108
                       note = Variable Light Chain Lc31
source                 1..108
                       mol_type = protein
                       organism = synthetic construct
SEQUENCE: 87
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 88          moltype = AA  length = 119
FEATURE                Location/Qualifiers
REGION                 1..119
                       note = Variable Heavy Chain Hc31
source                 1..119
                       mol_type = protein
                       organism = synthetic construct
SEQUENCE: 88
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKDI GGRSAFDYWG QGTLVTVSS   119

SEQ ID NO: 89          moltype = AA  length = 108
FEATURE                Location/Qualifiers
REGION                 1..108
                       note = Variable Light Chain Lc32
source                 1..108
                       mol_type = protein
                       organism = synthetic construct
SEQUENCE: 89
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 90          moltype = AA  length = 116
FEATURE                Location/Qualifiers
REGION                 1..116
                       note = Variable Heavy Chain Hc32
source                 1..116
                       mol_type = protein
                       organism = synthetic construct
SEQUENCE: 90
EVQLLESGGG LVQPGGSLRL SCAASGFTFS SYAMSWVRQA PGKGLEWVSS IDPEGWQTYY  60
ADSVKGRFTI SRDNSKNTLY LQMNSLRAED TAVYYCAKSA AAFDYWGQGT LVTVSS      116

SEQ ID NO: 91          moltype = AA  length = 108
FEATURE                Location/Qualifiers
REGION                 1..108
                       note = Variable Light Chain Lc37
source                 1..108
                       mol_type = protein
                       organism = synthetic construct
SEQUENCE: 91
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 92          moltype = AA  length = 119
FEATURE                Location/Qualifiers
REGION                 1..119
                       note = Variable Heavy Chain Hc37
source                 1..119
                       mol_type = protein
                       organism = synthetic construct
SEQUENCE: 92
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PHNGQFDYWG QGTLVTVSS   119

SEQ ID NO: 93          moltype = AA  length = 108
FEATURE                Location/Qualifiers
```

```
REGION                  1..108
                        note = Variable Light Chain Lc39
source                  1..108
                        mol_type = protein
                        organism = synthetic construct
SEQUENCE: 93
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 94           moltype = AA  length = 116
FEATURE                 Location/Qualifiers
REGION                  1..116
                        note = Variable Heavy Chain Hc39
source                  1..116
                        mol_type = protein
                        organism = synthetic construct
SEQUENCE: 94
EVQLLESGGG LVQPGGSLRL SCAASGFTFS SYAMSWVRQA PGKGLEWVSS IEQMGWQTEY  60
ADSVKGRFTI SRDNSKNTLY LQMNSLRAED TAVYYCAKSA AAFDYWGQGT LVTVSS      116

SEQ ID NO: 95           moltype = AA  length = 108
FEATURE                 Location/Qualifiers
REGION                  1..108
                        note = Variable Light Chain Lc40
source                  1..108
                        mol_type = protein
                        organism = synthetic construct
SEQUENCE: 95
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 96           moltype = AA  length = 119
FEATURE                 Location/Qualifiers
REGION                  1..119
                        note = Heavy Chain Hc40
source                  1..119
                        mol_type = protein
                        organism = synthetic construct
SEQUENCE: 96
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PFFGQFDYWG QGTLVTVSS   119

SEQ ID NO: 97           moltype = AA  length = 108
FEATURE                 Location/Qualifiers
REGION                  1..108
                        note = Variable Light Chain Lc47
source                  1..108
                        mol_type = protein
                        organism = synthetic construct
SEQUENCE: 97
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 98           moltype = AA  length = 116
FEATURE                 Location/Qualifiers
REGION                  1..116
                        note = Variable Heavy Chain Hc47
source                  1..116
                        mol_type = protein
                        organism = synthetic construct
SEQUENCE: 98
EVQLLESGGG LVQPGGSLRL SCAASGFTFS SYAMSWVRQA PGKGLEWVSS IDEMGWQTEY  60
ADSVKGRFTI SRDNSKNTLY LQMNSLRAED TAVYYCAKSA AAFDYWGQGT LVTVSS      116

SEQ ID NO: 99           moltype = AA  length = 108
FEATURE                 Location/Qualifiers
REGION                  1..108
                        note = Variable 4B2 Light Chain
source                  1..108
                        mol_type = protein
                        organism = synthetic construct
SEQUENCE: 99
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ TLDAPPQFGQ GTKVEIKR               108

SEQ ID NO: 100          moltype = AA  length = 119
FEATURE                 Location/Qualifiers
REGION                  1..119
                        note = Variable 4B2 Heavy Chain
```

```
source                  1..119
                        mol_type = protein
                        organism = synthetic construct
SEQUENCE: 100
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKDI GGRSAFDYWG QGTLVTVSS   119

SEQ ID NO: 101          moltype = AA  length = 108
FEATURE                 Location/Qualifiers
REGION                  1..108
                        note = Variable 4D11 Light Chain
source                  1..108
                        mol_type = protein
                        organism = synthetic construct
SEQUENCE: 101
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ TVVAPPLFGQ GTKVEIKR              108

SEQ ID NO: 102          moltype = AA  length = 119
FEATURE                 Location/Qualifiers
REGION                  1..119
                        note = Variable 4D11 Heavy Chain
source                  1..119
                        mol_type = protein
                        organism = synthetic construct
SEQUENCE: 102
EVQLLESGGG LVQPGGSLRL SCAASGFTFS SYAMSWVRQA PGKGLEWVSS IDPEGRQTYY  60
ADSVKGRFTI SRDNSKNTLY LQMNSLRAED TAVYYCAKDI GGRSAFDYWG QGTLVTVSS   119

SEQ ID NO: 103          moltype = AA  length = 108
FEATURE                 Location/Qualifiers
REGION                  1..108
                        note = Variable 4E7 Light Chain
source                  1..108
                        mol_type = protein
                        organism = synthetic construct
SEQUENCE: 103
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SLVAPLTFGQ GTKVEIKR              108

SEQ ID NO: 104          moltype = AA  length = 116
FEATURE                 Location/Qualifiers
REGION                  1..116
                        note = Variable 4E7 Heavy Chain
source                  1..116
                        mol_type = protein
                        organism = synthetic construct
SEQUENCE: 104
EVQLLESGGG LVQPGGSLRL SCAASGFTFS SYAMSWVRQA PGKGLEWVSS IEEMGWQTKY  60
ADSVKGRFTI SRDNSKNTLY LQMNSLRAED TAVYYCAKSA AAFDYWGQGT LVTVSS      116

SEQ ID NO: 105          moltype = AA  length = 108
FEATURE                 Location/Qualifiers
REGION                  1..108
                        note = Variable 4E11 Light Chain
source                  1..108
                        mol_type = protein
                        organism = synthetic construct
SEQUENCE: 105
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ ALDAPLMFGQ GTKVEIKR              108

SEQ ID NO: 106          moltype = AA  length = 119
FEATURE                 Location/Qualifiers
REGION                  1..119
                        note = Variable 4E11 Heavy Chain
source                  1..119
                        mol_type = protein
                        organism = synthetic construct
SEQUENCE: 106
EVQLLESGGG LVQPGGSLRL SCAASGFTFS SYAMSWVRQA PGKGLEWVSS IEPMGQLTEY  60
ADSVKGRFTI SRDNSKNTLY LQMNSLRAED TAVYYCAKDI GGRSAFDYWG QGTLVTVSS   119

SEQ ID NO: 107          moltype = AA  length = 108
FEATURE                 Location/Qualifiers
REGION                  1..108
                        note = Variable 6B7 Light Chain
source                  1..108
                        mol_type = protein
```

```
                         organism = synthetic construct
SEQUENCE: 107
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ ALVAPLTFGQ GTKVEIKR               108

SEQ ID NO: 108           moltype = AA  length = 116
FEATURE                  Location/Qualifiers
REGION                   1..116
                         note = Variable 6B7 Heavy Chain
source                   1..116
                         mol_type = protein
                         organism = synthetic construct
SEQUENCE: 108
EVQLLESGGG LVQPGGSLRL SCAASGFTFS SYAMSWVRQA PGKGLEWVSS IDEMGWQTYY  60
ADSVKGRFTI SRDNSKNTLY LQMNSLRAED TAVYYCAKSA AAFDYWGQGT LVTVSS      116

SEQ ID NO: 109           moltype = AA  length = 108
FEATURE                  Location/Qualifiers
REGION                   1..108
                         note = Variable 6F8 Light Chain
source                   1..108
                         mol_type = protein
                         organism = synthetic construct
SEQUENCE: 109
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ ALVAPLTFGQ GTKVEIKR               108

SEQ ID NO: 110           moltype = AA  length = 116
FEATURE                  Location/Qualifiers
REGION                   1..116
                         note = Variable 6F8 Heavy Chain
source                   1..116
                         mol_type = protein
                         organism = synthetic construct
SEQUENCE: 110
EVQLLESGGG LVQPGGSLRL SCAASGFTFS SYAMSWVRQA PGKGLEWVSS IDEMGWQTYY  60
ADSVKGRFTI SRDNSKNTLY LQMNSLRAED TAVYYCAKSA AAFDYWGQGT LVTVSS      116

SEQ ID NO: 111           moltype = AA  length = 214
FEATURE                  Location/Qualifiers
REGION                   1..214
                         note = 4D11 Light Chain
source                   1..214
                         mol_type = protein
                         organism = synthetic construct
SEQUENCE: 111
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ TVVAPPLFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 112           moltype = AA  length = 449
FEATURE                  Location/Qualifiers
REGION                   1..449
                         note = 4D11 Heavy Chain
source                   1..449
                         mol_type = protein
                         organism = synthetic construct
SEQUENCE: 112
EVQLLESGGG LVQPGGSLRL SCAASGFTFS SYAMSWVRQA PGKGLEWVSS IDPEGRQTYY  60
ADSVKGRFTI SRDNSKNTLY LQMNSLRAED TAVYYCAKDI GGRSAFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 113           moltype = AA  length = 449
FEATURE                  Location/Qualifiers
REGION                   1..449
                         note = 4D11v2 Heavy Chain
source                   1..449
                         mol_type = protein
                         organism = synthetic construct
SEQUENCE: 113
EVHLLESGGG LVQPGGSLRL SCAASGFTFS SYAMSWVRQA PGKGLEWVSS IDPEGRQTYY  60
ADSVKGRFTI SRDNSKNTLY LQMNSLRAED TAVYYCAKDI GGRSAFDYWG QGTLVTVSSA  120
STKGPSVFPL APSSKSTSGG TAALGCLVKD YFPEPVTVSW NSGALTSGVH TFPAVLQSSG  180
```

-continued

```
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 114         moltype = AA  length = 214
FEATURE                Location/Qualifiers
REGION                 1..214
                       note = 4D11v2 Light Chain
VARIANT                182
                       note = misc_feature - Xaa may be any amino acid
source                 1..214
                       mol_type = protein
                       organism = synthetic construct
SEQUENCE: 114
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ TVVAPPLFGQ GTKVEIKRTV AAPSVFIFPP  120
SDEQLKSGTA SVVCLLNNFY PREAKVQWKV DNALQSGNSQ ESVTEQDSKD STYSLSSTLT  180
LXKADYEKHK VYACEVTHQG LSSPVTKSFN RGEC                             214

SEQ ID NO: 115         moltype = AA  length = 258
FEATURE                Location/Qualifiers
REGION                 1..258
                       note = 4792 10419 AV1
source                 1..258
                       mol_type = protein
                       organism = synthetic construct
SEQUENCE: 115
QGQSGQYGSC SWNYVHIFMD CGSSGGSGGS GGSGISSGLS SGGSDIQMTQ SPSSLSASVG  60
DRVTITCRAS QDISSYLNWY QQKPGKAPKL LIYYTSRLHS GVPSRFSGSG SGTDFTFTIS  120
SLQPEDIATY YCQQGNTLPY TFGQGTKVEI KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                               258

SEQ ID NO: 116         moltype = DNA  length = 774
FEATURE                Location/Qualifiers
misc_feature           1..774
                       note = 4792 10419 AV1
source                 1..774
                       mol_type = other DNA
                       organism = synthetic construct
SEQUENCE: 116
caaggccagt ctggccagta tgggtcctgc agttggaact atgtacacat attcatggat  60
tgcggctcga gcggtggcag cggtggctct ggtggctcag gtattagtag tggtcttagc  120
agtggcggtt ctgacatcca gatgactcag tctcctagct ccctgtccgc ctctgtgggg  180
gaccgagtca ccatcacatg cagagccagc caggatattt ctagttacct gaactggtat  240
cagcagaagc ccggaaaagc acctaagctg ctgatctact atacctccag gctgcactct  300
ggcgtgccca gtcggttcag tggctcaggg agcggaaccg acttcacttt taccatctca  360
agcctgcagc cagaggatat tgccacatac tattgtcagc agggcaatac actgccctac  420
acttttggcc aggggaccaa ggtggaaatc aaacgtacgg tggctgcacc atctgtcttc  480
atcttcccgc catctgatga gcagttgaaa tctggaactg cctctgttgt gtgcctgctg  540
aataacttct atcccagaga ggccaaagta cagtggaagg tggataacgc cctccaatcg  600
ggtaactccc aggagagtgt cacagagcag gacagcaagg acagcaccta cagcctcagc  660
agcaccctga cgctgagcaa agcagactac gagaaacaca aagtctacgc ctgcgaagtc  720
acccatcagg gcctgagctc gcccgtcaca aagagcttca acaggggaga gtgt        774

SEQ ID NO: 117         moltype = AA  length = 258
FEATURE                Location/Qualifiers
REGION                 1..258
                       note = 4792 559 AV1
source                 1..258
                       mol_type = protein
                       organism = synthetic construct
SEQUENCE: 117
QGQSGQYGSC SWNYVHIFMD CGSSGGSGGS GGSQNQALRM AGGSDIQMTQ SPSSLSASVG  60
DRVTITCRAS QDISSYLNWY QQKPGKAPKL LIYYTSRLHS GVPSRFSGSG SGTDFTFTIS  120
SLQPEDIATY YCQQGNTLPY TFGQGTKVEI KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                               258

SEQ ID NO: 118         moltype = DNA  length = 774
FEATURE                Location/Qualifiers
misc_feature           1..774
                       note = 4792 559 AV1
source                 1..774
                       mol_type = other DNA
                       organism = synthetic construct
SEQUENCE: 118
```

-continued

```
caaggccagt ctggccagta tgggtcctgc agttggaact atgtacacat attcatggat  60
tgcggctcga gcggtggcag cggtggctct ggtggctcac agaatcaggc attacgtatg  120
gcaggcggtt ctgacatcca gatgactcag tctcctagct ccctgtccgc ctctgtgggg  180
gaccgagtca ccatcacatg cagagccagc caggatattt ctagttacct gaactggtat  240
cagcagaagc ccggaaaagc acctaagctg ctgatctact atacctccag gctgcactct  300
ggcgtgccca gtcggttcag tggctcaggg agcggaaccg acttcacttt taccatctca  360
agcctgcagc cagaggatat tgccacatac tattgtcagc agggcaatac actgccctac  420
acttttggcc aggggaccaa ggtggaaatc aaacgtacgg tggctgcacc atctgtcttc  480
atcttcccgc catctgatga gcagttgaaa tctggaactg cctctgttgt gtgcctgctg  540
aataacttct atcccagaga ggccaaagta cagtggaagg tggataacgc cctccaatcg  600
ggtaactccc aggagagtgt cacagagcag gacagcaagg acagcaccta cagcctcagc  660
agcaccctga cgctgagcaa agcagactac gagaaacaca aagtctacgc ctgcgaagtc  720
acccatcagg gcctgagctc gcccgtcaca aagagcttca acaggggaga gtgt        774

SEQ ID NO: 119         moltype = AA  length = 258
FEATURE                Location/Qualifiers
REGION                 1..258
                       note = 4792 601 AV1
source                 1..258
                       mol_type = protein
                       organism = synthetic construct
SEQUENCE: 119
QGQSGQYGSC SWNYVHIFMD CGSSGGSGGS GGSAQNLLGM VGGSDIQMTQ SPSSLSASVG  60
DRVTITCRAS QDISSYLNWY QQKPGKAPKL LIYYTSRLHS GVPSRFSGSG SGTDFTFTIS  120
SLQPEDIATY YCQQGNTLPY TFGQGTKVEI KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 120         moltype = DNA  length = 774
FEATURE                Location/Qualifiers
misc_feature           1..774
                       note = 4792 601 AV1
source                 1..774
                       mol_type = other DNA
                       organism = synthetic construct
SEQUENCE: 120
caaggccagt ctggccagta tgggtcctgc agttggaact atgtacacat attcatggat  60
tgcggctcga gcggtggcag cggtggctct ggtggctcag cacagaatct gttaggtatg  120
gtaggcggtt ctgacatcca gatgactcag tctcctagct ccctgtccgc ctctgtgggg  180
gaccgagtca ccatcacatg cagagccagc caggatattt ctagttacct gaactggtat  240
cagcagaagc ccggaaaagc acctaagctg ctgatctact atacctccag gctgcactct  300
ggcgtgccca gtcggttcag tggctcaggg agcggaaccg acttcacttt taccatctca  360
agcctgcagc cagaggatat tgccacatac tattgtcagc agggcaatac actgccctac  420
acttttggcc aggggaccaa ggtggaaatc aaacgtacgg tggctgcacc atctgtcttc  480
atcttcccgc catctgatga gcagttgaaa tctggaactg cctctgttgt gtgcctgctg  540
aataacttct atcccagaga ggccaaagta cagtggaagg tggataacgc cctccaatcg  600
ggtaactccc aggagagtgt cacagagcag gacagcaagg acagcaccta cagcctcagc  660
agcaccctga cgctgagcaa agcagactac gagaaacaca aagtctacgc ctgcgaagtc  720
acccatcagg gcctgagctc gcccgtcaca aagagcttca acaggggaga gtgt        774

SEQ ID NO: 121         moltype = AA  length = 258
FEATURE                Location/Qualifiers
REGION                 1..258
                       note = 4792 3457 AV1
source                 1..258
                       mol_type = protein
                       organism = synthetic construct
SEQUENCE: 121
QGQSGQYGSC SWNYVHIFMD CGSSGGSGGS GGSSTFPFGM FGGSDIQMTQ SPSSLSASVG  60
DRVTITCRAS QDISSYLNWY QQKPGKAPKL LIYYTSRLHS GVPSRFSGSG SGTDFTFTIS  120
SLQPEDIATY YCQQGNTLPY TFGQGTKVEI KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 122         moltype = DNA  length = 774
FEATURE                Location/Qualifiers
misc_feature           1..774
                       note = 4792 3457 AV1
source                 1..774
                       mol_type = other DNA
                       organism = synthetic construct
SEQUENCE: 122
caaggccagt ctggccagta tgggtcctgc agttggaact atgtacacat attcatggat  60
tgcggctcga gcggtggcag cggtggctct ggtggctcaa gtacatttcc attcggtatg  120
ttcggcggtt ctgacatcca gatgactcag tctcctagct ccctgtccgc ctctgtgggg  180
gaccgagtca ccatcacatg cagagccagc caggatattt ctagttacct gaactggtat  240
cagcagaagc ccggaaaagc acctaagctg ctgatctact atacctccag gctgcactct  300
ggcgtgccca gtcggttcag tggctcaggg agcggaaccg acttcacttt taccatctca  360
agcctgcagc cagaggatat tgccacatac tattgtcagc agggcaatac actgccctac  420
```

-continued

```
acttttggcc aggggaccaa ggtggaaatc aaacgtacgg tggctgcacc atctgtcttc  480
atcttcccgc catctgatga gcagttgaaa tctggaactg cctctgttgt gtgcctgctg  540
aataacttct atcccagaga ggccaaagta cagtggaagg tggataacgc cctccaatcg  600
ggtaactccc aggagagtgt cacagagcag gacagcaagg acagcaccta cagcctcagc  660
agcaccctga cgctgagcaa agcagactac gagaaacaca aagtctacgc ctgcgaagtc  720
acccatcagg gcctgagctc gcccgtcaca aagagcttca acaggggaga gtgt        774

SEQ ID NO: 123         moltype = AA  length = 258
FEATURE                Location/Qualifiers
REGION                 1..258
                       note = 4792 3458 AV1
source                 1..258
                       mol_type = protein
                       organism = synthetic construct
SEQUENCE: 123
QGQSGQYGSC SWNYVHIFMD CGSSGGSGGS GGSPVGYTSS LGGSDIQMTQ SPSSLSASVG  60
DRVTITCRAS QDISSYLNWY QQKPGKAPKL LIYYTSRLHS GVPSRFSGSG SGTDFTFTIS  120
SLQPEDIATY YCQQGNTLPY TFGQGTKVEI KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 124         moltype = DNA  length = 774
FEATURE                Location/Qualifiers
misc_feature           1..774
                       note = 4792 3458 AV1
source                 1..774
                       mol_type = other DNA
                       organism = synthetic construct
SEQUENCE: 124
caaggccagt ctggccagta tgggtcctgc agttggaact atgtacacat attcatggat  60
tgcggctcga gcggtggcag cggtggctct ggtggctcac ctgttggata tacgagtagt  120
ctgggcggtt ctgacatcca gatgactcag tctcctagct ccctgtccgc ctctgtgggg  180
gaccgagtca ccatcacatg cagagccagc caggatattt ctagttacct gaactggtat  240
cagcagaagc ccggaaaagc acctaagctg ctgatctact atacctccag gctgcactct  300
ggcgtgccca gtcggttcag tggctcaggg agcggaaccg acttcacttt taccatctca  360
agcctgcagc cagaggatat tgccacatac tattgtcagc agggcaatac actgccctac  420
acttttggcc aggggaccaa ggtggaaatc aaacgtacgg tggctgcacc atctgtcttc  480
atcttcccgc catctgatga gcagttgaaa tctggaactg cctctgttgt gtgcctgctg  540
aataacttct atcccagaga ggccaaagta cagtggaagg tggataacgc cctccaatcg  600
ggtaactccc aggagagtgt cacagagcag gacagcaagg acagcaccta cagcctcagc  660
agcaccctga cgctgagcaa agcagactac gagaaacaca aagtctacgc ctgcgaagtc  720
acccatcagg gcctgagctc gcccgtcaca aagagcttca acaggggaga gtgt        774

SEQ ID NO: 125         moltype = AA  length = 258
FEATURE                Location/Qualifiers
REGION                 1..258
                       note = 4792 3463 AV1
source                 1..258
                       mol_type = protein
                       organism = synthetic construct
SEQUENCE: 125
QGQSGQYGSC SWNYVHIFMD CGSSGGSGGS GGSDWLYWPG IGGSDIQMTQ SPSSLSASVG  60
DRVTITCRAS QDISSYLNWY QQKPGKAPKL LIYYTSRLHS GVPSRFSGSG SGTDFTFTIS  120
SLQPEDIATY YCQQGNTLPY TFGQGTKVEI KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 126         moltype = AA  length = 8
FEATURE                Location/Qualifiers
REGION                 1..8
                       note = cleavable moiety
source                 1..8
                       mol_type = protein
                       organism = synthetic construct
SEQUENCE: 126
SAGFSLPA                                                           8

SEQ ID NO: 127         moltype = AA  length = 8
FEATURE                Location/Qualifiers
REGION                 1..8
                       note = cleavable linker sequence
source                 1..8
                       mol_type = protein
                       organism = synthetic construct
SEQUENCE: 127
PRFKIIGG                                                           8

SEQ ID NO: 128         moltype = AA  length = 8
FEATURE                Location/Qualifiers
```

```
REGION                  1..8
                        note = cleavable linker sequence
source                  1..8
                        mol_type = protein
                        organism = synthetic construct
SEQUENCE: 128
PRFRIIGG                                                                8

SEQ ID NO: 129          moltype = AA  length = 9
FEATURE                 Location/Qualifiers
REGION                  1..9
                        note = cleavable linker sequence
source                  1..9
                        mol_type = protein
                        organism = synthetic construct
SEQUENCE: 129
SSRHRRALD                                                               9

SEQ ID NO: 130          moltype = AA  length = 14
FEATURE                 Location/Qualifiers
REGION                  1..14
                        note = cleavable linker sequence
source                  1..14
                        mol_type = protein
                        organism = synthetic construct
SEQUENCE: 130
RKSSIIIRMR DVVL                                                         14

SEQ ID NO: 131          moltype = AA  length = 15
FEATURE                 Location/Qualifiers
REGION                  1..15
                        note = cleavable linker sequence
source                  1..15
                        mol_type = protein
                        organism = synthetic construct
SEQUENCE: 131
SSSFDKGKYK KGDDA                                                        15

SEQ ID NO: 132          moltype = AA  length = 15
FEATURE                 Location/Qualifiers
REGION                  1..15
                        note = cleavable linker sequence
source                  1..15
                        mol_type = protein
                        organism = synthetic construct
SEQUENCE: 132
SSSFDKGKYK RGDDA                                                        15

SEQ ID NO: 133          moltype = AA  length = 4
FEATURE                 Location/Qualifiers
REGION                  1..4
                        note = cleavable linker sequence
source                  1..4
                        mol_type = protein
                        organism = synthetic construct
SEQUENCE: 133
IEGR                                                                    4

SEQ ID NO: 134          moltype = AA  length = 4
FEATURE                 Location/Qualifiers
REGION                  1..4
                        note = cleavable linker sequence
source                  1..4
                        mol_type = protein
                        organism = synthetic construct
SEQUENCE: 134
IDGR                                                                    4

SEQ ID NO: 135          moltype = AA  length = 7
FEATURE                 Location/Qualifiers
REGION                  1..7
                        note = cleavable linker sequence
source                  1..7
                        mol_type = protein
                        organism = synthetic construct
SEQUENCE: 135
GGSIDGR                                                                 7

SEQ ID NO: 136          moltype = AA  length = 6
```

-continued

```
FEATURE                 Location/Qualifiers
REGION                  1..6
                        note = cleavable linker sequence
source                  1..6
                        mol_type = protein
                        organism = synthetic construct
SEQUENCE: 136
PLGLWA                                                                      6

SEQ ID NO: 137          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 137
GPQGIAGQ                                                                    8

SEQ ID NO: 138          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 138
GPQGLLGA                                                                    8

SEQ ID NO: 139          moltype = AA  length = 5
FEATURE                 Location/Qualifiers
REGION                  1..5
                        note = cleavable linker sequence
source                  1..5
                        mol_type = protein
                        organism = synthetic construct
SEQUENCE: 139
GIAGQ                                                                       5

SEQ ID NO: 140          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 140
GPLGIAGI                                                                    8

SEQ ID NO: 141          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 141
GPEGLRVG                                                                    8

SEQ ID NO: 142          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 142
YGAGLGVV                                                                    8

SEQ ID NO: 143          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 143
AGLGVVER                                                                    8
```

```
SEQ ID NO: 144          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 144
AGLGISST                                                                  8

SEQ ID NO: 145          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 145
EPQALAMS                                                                  8

SEQ ID NO: 146          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 146
QALAMSAI                                                                  8

SEQ ID NO: 147          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 147
AAYHLVSQ                                                                  8

SEQ ID NO: 148          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 148
MDAFLESS                                                                  8

SEQ ID NO: 149          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 149
ESLPVVAV                                                                  8

SEQ ID NO: 150          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 150
SAPAVESE                                                                  8

SEQ ID NO: 151          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 151
DVAQFVLT                                                                  8
```

```
SEQ ID NO: 152          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 152
VAQFVLTE                                                          8

SEQ ID NO: 153          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 153
AQFVLTEG                                                          8

SEQ ID NO: 154          moltype = AA  length = 8
FEATURE                 Location/Qualifiers
REGION                  1..8
                        note = cleavable linker sequence
source                  1..8
                        mol_type = protein
                        organism = synthetic construct
SEQUENCE: 154
PVQPIGPQ                                                          8

SEQ ID NO: 155          moltype = AA  length = 16
FEATURE                 Location/Qualifiers
REGION                  1..16
                        note = linking peptide
source                  1..16
                        mol_type = protein
                        organism = synthetic construct
SEQUENCE: 155
GSSGGSGGSG GSGGGS                                                 16

SEQ ID NO: 156          moltype = AA  length = 10
FEATURE                 Location/Qualifiers
REGION                  1..10
                        note = linking peptide
source                  1..10
                        mol_type = protein
                        organism = synthetic construct
SEQUENCE: 156
GSSGGSGGSG                                                        10

SEQ ID NO: 157          moltype = AA  length = 11
FEATURE                 Location/Qualifiers
REGION                  1..11
                        note = linking peptide
source                  1..11
                        mol_type = protein
                        organism = synthetic construct
SEQUENCE: 157
GSSGGSGGSG S                                                      11

SEQ ID NO: 158          moltype = AA  length = 4
FEATURE                 Location/Qualifiers
REGION                  1..4
                        note = linking peptide
source                  1..4
                        mol_type = protein
                        organism = synthetic construct
SEQUENCE: 158
GGGS                                                              4

SEQ ID NO: 159          moltype = AA  length = 7
FEATURE                 Location/Qualifiers
REGION                  1..7
                        note = cleavable moiety
source                  1..7
                        mol_type = protein
                        organism = synthetic construct
SEQUENCE: 159
```

```
ISSGLSS                                                                 7

SEQ ID NO: 160          moltype = AA  length = 15
FEATURE                 Location/Qualifiers
REGION                  1..15
                        note = masking moiety
source                  1..15
                        mol_type = protein
                        organism = synthetic construct
SEQUENCE: 160
CISPRGCPDG PYVMY                                                        15

SEQ ID NO: 161          moltype = AA  length = 15
FEATURE                 Location/Qualifiers
REGION                  1..15
                        note = N-terminal AV1 light chain sequence
source                  1..15
                        mol_type = protein
                        organism = synthetic construct
SEQUENCE: 161
YGSCSWNYVH IFMDC                                                        15

SEQ ID NO: 162          moltype = AA  length = 16
FEATURE                 Location/Qualifiers
REGION                  1..16
                        note = N-terminal AV1 light chain sequence
source                  1..16
                        mol_type = protein
                        organism = synthetic construct
SEQUENCE: 162
QGDFDIPFPA HWVPIT                                                       16

SEQ ID NO: 163          moltype = AA  length = 18
FEATURE                 Location/Qualifiers
REGION                  1..18
                        note = N-terminal AV1 light chain sequence
source                  1..18
                        mol_type = protein
                        organism = synthetic construct
SEQUENCE: 163
MGVPAGCVWN YAHIFMDC                                                     18

SEQ ID NO: 164          moltype = AA  length = 21
FEATURE                 Location/Qualifiers
REGION                  1..21
                        note = N-terminal AV1 light chain sequence
source                  1..21
                        mol_type = protein
                        organism = synthetic construct
SEQUENCE: 164
QGQSGQYGSC SWNYVHIFMD C                                                 21

SEQ ID NO: 165          moltype = AA  length = 21
FEATURE                 Location/Qualifiers
REGION                  1..21
                        note = N-terminal AV1 light chain sequence
source                  1..21
                        mol_type = protein
                        organism = synthetic construct
SEQUENCE: 165
QGQSGQGDFD IPFPAHWVPI T                                                 21

SEQ ID NO: 166          moltype = AA  length = 24
FEATURE                 Location/Qualifiers
REGION                  1..24
                        note = N-terminal AV1 light chain sequence
source                  1..24
                        mol_type = protein
                        organism = synthetic construct
SEQUENCE: 166
QGQSGQMGVP AGCVWNYAHI FMDC                                              24

SEQ ID NO: 167          moltype = AA  length = 6
FEATURE                 Location/Qualifiers
REGION                  1..6
                        note = masking moiety
source                  1..6
                        mol_type = protein
                        organism = synthetic construct
```

```
SEQUENCE: 167
CISPRG                                                  6

SEQ ID NO: 168         moltype = AA  length = 8
FEATURE                Location/Qualifiers
REGION                 1..8
                       note = masking moiety
source                 1..8
                       mol_type = protein
                       organism = synthetic construct
SEQUENCE: 168
CISPRGCG                                                8

SEQ ID NO: 169         moltype = AA  length = 14
FEATURE                Location/Qualifiers
REGION                 1..14
                       note = masking moiety
source                 1..14
                       mol_type = protein
                       organism = synthetic construct
SEQUENCE: 169
CISPRGCPDG PYVM                                         14

SEQ ID NO: 170         moltype = AA  length = 15
FEATURE                Location/Qualifiers
REGION                 1..15
                       note = masking moiety
source                 1..15
                       mol_type = protein
                       organism = synthetic construct
SEQUENCE: 170
CISPRGCEPG TYVPT                                        15

SEQ ID NO: 171         moltype = AA  length = 15
FEATURE                Location/Qualifiers
REGION                 1..15
                       note = masking moiety
source                 1..15
                       mol_type = protein
                       organism = synthetic construct
SEQUENCE: 171
CISPRGCPGQ IWHPP                                        15

SEQ ID NO: 172         moltype = AA  length = 15
FEATURE                Location/Qualifiers
REGION                 1..15
                       note = masking moiety
source                 1..15
                       mol_type = protein
                       organism = synthetic construct
SEQUENCE: 172
GSHCLIPINM GAPSC                                        15

SEQ ID NO: 173         moltype = AA  length = 32
FEATURE                Location/Qualifiers
REGION                 1..32
                       note = masking moiety
source                 1..32
                       mol_type = protein
                       organism = synthetic construct
SEQUENCE: 173
CISPRGCGGS SASQSGQGSH CLIPINMGAP SC                     32

SEQ ID NO: 174         moltype = AA  length = 19
FEATURE                Location/Qualifiers
REGION                 1..19
                       note = masking moiety
source                 1..19
                       mol_type = protein
                       organism = synthetic construct
SEQUENCE: 174
CNHHYFYTCG CISPRGCPG                                    19

SEQ ID NO: 175         moltype = AA  length = 19
FEATURE                Location/Qualifiers
REGION                 1..19
                       note = masking moiety
source                 1..19
                       mol_type = protein
```

```
                        organism = synthetic construct
SEQUENCE: 175
ADHVFWGSYG CISPRGCPG                                                19

SEQ ID NO: 176          moltype = AA  length = 19
FEATURE                 Location/Qualifiers
REGION                  1..19
                        note = masking moiety
source                  1..19
                        mol_type = protein
                        organism = synthetic construct
SEQUENCE: 176
CHHVYWGHCG CISPRGCPG                                                19

SEQ ID NO: 177          moltype = AA  length = 19
FEATURE                 Location/Qualifiers
REGION                  1..19
                        note = masking moiety
source                  1..19
                        mol_type = protein
                        organism = synthetic construct
SEQUENCE: 177
CPHFTTTSCG CISPRGCPG                                                19

SEQ ID NO: 178          moltype = AA  length = 19
FEATURE                 Location/Qualifiers
REGION                  1..19
                        note = masking moiety
source                  1..19
                        mol_type = protein
                        organism = synthetic construct
SEQUENCE: 178
CNHHYHYYCG CISPRGCPG                                                19

SEQ ID NO: 179          moltype = AA  length = 19
FEATURE                 Location/Qualifiers
REGION                  1..19
                        note = masking moiety
source                  1..19
                        mol_type = protein
                        organism = synthetic construct
SEQUENCE: 179
CPHVSFGSCG CISPRGCPG                                                19

SEQ ID NO: 180          moltype = AA  length = 19
FEATURE                 Location/Qualifiers
REGION                  1..19
                        note = masking moiety
source                  1..19
                        mol_type = protein
                        organism = synthetic construct
SEQUENCE: 180
CPYYTLSYCG CISPRGCPG                                                19

SEQ ID NO: 181          moltype = AA  length = 19
FEATURE                 Location/Qualifiers
REGION                  1..19
                        note = masking moiety
source                  1..19
                        mol_type = protein
                        organism = synthetic construct
SEQUENCE: 181
CNHVYFGTCG CISPRGCPG                                                19

SEQ ID NO: 182          moltype = AA  length = 19
FEATURE                 Location/Qualifiers
REGION                  1..19
                        note = masking moiety
source                  1..19
                        mol_type = protein
                        organism = synthetic construct
SEQUENCE: 182
CNHFTLTTCG CISPRGCPG                                                19

SEQ ID NO: 183          moltype = AA  length = 19
FEATURE                 Location/Qualifiers
REGION                  1..19
                        note = masking moiety
source                  1..19
```

```
                        mol_type = protein
                        organism = synthetic construct
SEQUENCE: 183
CHHFTLTTCG CISPRGCPG                                              19

SEQ ID NO: 184          moltype = AA  length = 18
FEATURE                 Location/Qualifiers
REGION                  1..18
                        note = masking moiety
source                  1..18
                        mol_type = protein
                        organism = synthetic construct
SEQUENCE: 184
YNPCATPMCC ISPRGCPG                                               18

SEQ ID NO: 185          moltype = AA  length = 18
FEATURE                 Location/Qualifiers
REGION                  1..18
                        note = masking moiety
source                  1..18
                        mol_type = protein
                        organism = synthetic construct
SEQUENCE: 185
CNHHYFYTCG CISPRGCG                                               18

SEQ ID NO: 186          moltype = AA  length = 18
FEATURE                 Location/Qualifiers
REGION                  1..18
                        note = masking moiety
source                  1..18
                        mol_type = protein
                        organism = synthetic construct
SEQUENCE: 186
CNHHYHYYCG CISPRGCG                                               18

SEQ ID NO: 187          moltype = AA  length = 18
FEATURE                 Location/Qualifiers
REGION                  1..18
                        note = masking moiety
source                  1..18
                        mol_type = protein
                        organism = synthetic construct
SEQUENCE: 187
CNHVYFGTCG CISPRGCG                                               18

SEQ ID NO: 188          moltype = AA  length = 18
FEATURE                 Location/Qualifiers
REGION                  1..18
                        note = masking moiety
source                  1..18
                        mol_type = protein
                        organism = synthetic construct
SEQUENCE: 188
CHHVYWGHCG CISPRGCG                                               18

SEQ ID NO: 189          moltype = AA  length = 18
FEATURE                 Location/Qualifiers
REGION                  1..18
                        note = masking moiety
source                  1..18
                        mol_type = protein
                        organism = synthetic construct
SEQUENCE: 189
CPHFTTTSCG CISPRGCG                                               18

SEQ ID NO: 190          moltype = AA  length = 18
FEATURE                 Location/Qualifiers
REGION                  1..18
                        note = masking moiety
source                  1..18
                        mol_type = protein
                        organism = synthetic construct
SEQUENCE: 190
CNHFTLTTCG CISPRGCG                                               18

SEQ ID NO: 191          moltype = AA  length = 18
FEATURE                 Location/Qualifiers
REGION                  1..18
                        note = masking moiety
```

```
source                  1..18
                        mol_type = protein
                        organism = synthetic construct
SEQUENCE: 191
CHHFTLTTCG CISPRGCG                                                18

SEQ ID NO: 192          moltype = AA  length = 18
FEATURE                 Location/Qualifiers
REGION                  1..18
                        note = masking moiety
source                  1..18
                        mol_type = protein
                        organism = synthetic construct
SEQUENCE: 192
CPYYTLSYCG CISPRGCG                                                18

SEQ ID NO: 193          moltype = AA  length = 18
FEATURE                 Location/Qualifiers
REGION                  1..18
                        note = masking moiety
source                  1..18
                        mol_type = protein
                        organism = synthetic construct
SEQUENCE: 193
CPHVSFGSCG CISPRGCG                                                18

SEQ ID NO: 194          moltype = AA  length = 18
FEATURE                 Location/Qualifiers
REGION                  1..18
                        note = masking moiety
source                  1..18
                        mol_type = protein
                        organism = synthetic construct
SEQUENCE: 194
ADHVFWGSYG CISPRGCG                                                18

SEQ ID NO: 195          moltype = AA  length = 17
FEATURE                 Location/Qualifiers
REGION                  1..17
                        note = masking moiety
source                  1..17
                        mol_type = protein
                        organism = synthetic construct
SEQUENCE: 195
YNPCATPMCC ISPRGCG                                                 17

SEQ ID NO: 196          moltype = AA  length = 18
FEATURE                 Location/Qualifiers
REGION                  1..18
                        note = masking moiety
source                  1..18
                        mol_type = protein
                        organism = synthetic construct
SEQUENCE: 196
CHHVYWGHCG CISPRGCG                                                18

SEQ ID NO: 197          moltype = AA  length = 18
FEATURE                 Location/Qualifiers
REGION                  1..18
                        note = masking moiety
VARIANT                 2
                        note = misc_feature - Xaa may be Asn or Phe
VARIANT                 4
                        note = misc_feature - Xaa may be His, Val or Phe
VARIANT                 5
                        note = misc_feature - Xaa may be Tyr or Thr
VARIANT                 6
                        note = misc_feature - Xaa may be Phe, Trp, Thr or Leu
VARIANT                 7
                        note = misc_feature - Xaa may be Tyr, Gly, Thr or Ser
VARIANT                 8
                        note = misc_feature - Xaa may be Thr, Ser, Tyr or His
source                  1..18
                        mol_type = protein
                        organism = synthetic construct
SEQUENCE: 197
CXHXXXXXCG CISPRGCG                                                18

SEQ ID NO: 198          moltype = AA  length = 15
```

```
FEATURE               Location/Qualifiers
REGION                1..15
                      note = masking moiety
source                1..15
                      mol_type = protein
                      organism = synthetic construct
SEQUENCE: 198
CISPRGCGQP IPSVK                                                            15

SEQ ID NO: 199        moltype = AA  length = 15
FEATURE               Location/Qualifiers
REGION                1..15
                      note = masking moiety
source                1..15
                      mol_type = protein
                      organism = synthetic construct
SEQUENCE: 199
CISPRGCTQP YHVSR                                                            15

SEQ ID NO: 200        moltype = AA  length = 15
FEATURE               Location/Qualifiers
REGION                1..15
                      note = masking moiety
source                1..15
                      mol_type = protein
                      organism = synthetic construct
SEQUENCE: 200
CISPRGCNAV SGLGS                                                            15

SEQ ID NO: 201        moltype = AA  length = 26
FEATURE               Location/Qualifiers
REGION                1..26
                      note = masking moiety
source                1..26
                      mol_type = protein
                      organism = synthetic construct
SEQUENCE: 201
QGQSGQGQQQ WCNIWINGGD CRGWNG                                                26

SEQ ID NO: 202        moltype = AA  length = 15
FEATURE               Location/Qualifiers
REGION                1..15
                      note = masking moiety
source                1..15
                      mol_type = protein
                      organism = synthetic construct
SEQUENCE: 202
PWCMQRQDFL RCPQP                                                            15

SEQ ID NO: 203        moltype = AA  length = 15
FEATURE               Location/Qualifiers
REGION                1..15
                      note = masking moiety
source                1..15
                      mol_type = protein
                      organism = synthetic construct
SEQUENCE: 203
QLGLPAYMCT FECLR                                                            15

SEQ ID NO: 204        moltype = AA  length = 15
FEATURE               Location/Qualifiers
REGION                1..15
                      note = masking moiety
source                1..15
                      mol_type = protein
                      organism = synthetic construct
SEQUENCE: 204
CNLWVSGGDC GGLQG                                                            15

SEQ ID NO: 205        moltype = AA  length = 15
FEATURE               Location/Qualifiers
REGION                1..15
                      note = masking moiety
source                1..15
                      mol_type = protein
                      organism = synthetic construct
SEQUENCE: 205
SCSLWTSGSC LPHSP                                                            15
```

-continued

```
SEQ ID NO: 206          moltype = AA  length = 15
FEATURE                 Location/Qualifiers
REGION                  1..15
                        note = masking moiety
source                  1..15
                        mol_type = protein
                        organism = synthetic construct
SEQUENCE: 206
YCLQLPHYMQ AMCGR                                                  15

SEQ ID NO: 207          moltype = AA  length = 15
FEATURE                 Location/Qualifiers
REGION                  1..15
                        note = masking moiety
source                  1..15
                        mol_type = protein
                        organism = synthetic construct
SEQUENCE: 207
CFLYSCTDVS YWNNT                                                  15

SEQ ID NO: 208          moltype = AA  length = 15
FEATURE                 Location/Qualifiers
REGION                  1..15
                        note = masking moiety
source                  1..15
                        mol_type = protein
                        organism = synthetic construct
SEQUENCE: 208
PWCMQRQDYL RCPQP                                                  15

SEQ ID NO: 209          moltype = AA  length = 15
FEATURE                 Location/Qualifiers
REGION                  1..15
                        note = masking moiety
source                  1..15
                        mol_type = protein
                        organism = synthetic construct
SEQUENCE: 209
CNLWISGGDC RGLAG                                                  15

SEQ ID NO: 210          moltype = AA  length = 15
FEATURE                 Location/Qualifiers
REGION                  1..15
                        note = masking moiety
source                  1..15
                        mol_type = protein
                        organism = synthetic construct
SEQUENCE: 210
CNLWVSGGDC RGVQG                                                  15

SEQ ID NO: 211          moltype = AA  length = 15
FEATURE                 Location/Qualifiers
REGION                  1..15
                        note = masking moiety
source                  1..15
                        mol_type = protein
                        organism = synthetic construct
SEQUENCE: 211
CNLWVSGGDC RGLRG                                                  15

SEQ ID NO: 212          moltype = AA  length = 15
FEATURE                 Location/Qualifiers
REGION                  1..15
                        note = masking moiety
source                  1..15
                        mol_type = protein
                        organism = synthetic construct
SEQUENCE: 212
CNLWISGGDC RGLPG                                                  15

SEQ ID NO: 213          moltype = AA  length = 15
FEATURE                 Location/Qualifiers
REGION                  1..15
                        note = masking moiety
source                  1..15
                        mol_type = protein
                        organism = synthetic construct
SEQUENCE: 213
CNLWVSGGDC RDAPW                                                  15
```

-continued

```
SEQ ID NO: 214         moltype = AA  length = 15
FEATURE                Location/Qualifiers
REGION                 1..15
                       note = masking moiety
source                 1..15
                       mol_type = protein
                       organism = synthetic construct
SEQUENCE: 214
CNLWVSGGDC RDLLG                                                  15

SEQ ID NO: 215         moltype = AA  length = 15
FEATURE                Location/Qualifiers
REGION                 1..15
                       note = masking moiety
source                 1..15
                       mol_type = protein
                       organism = synthetic construct
SEQUENCE: 215
CNLWVSGGDC RGLQG                                                  15

SEQ ID NO: 216         moltype = AA  length = 15
FEATURE                Location/Qualifiers
REGION                 1..15
                       note = masking moiety
source                 1..15
                       mol_type = protein
                       organism = synthetic construct
SEQUENCE: 216
CNLWLHGGDC RGWQG                                                  15

SEQ ID NO: 217         moltype = AA  length = 15
FEATURE                Location/Qualifiers
REGION                 1..15
                       note = masking moiety
source                 1..15
                       mol_type = protein
                       organism = synthetic construct
SEQUENCE: 217
CNIWLVGGDC RGWQG                                                  15

SEQ ID NO: 218         moltype = AA  length = 15
FEATURE                Location/Qualifiers
REGION                 1..15
                       note = masking moiety
source                 1..15
                       mol_type = protein
                       organism = synthetic construct
SEQUENCE: 218
CTTWFCGGDC GVMRG                                                  15

SEQ ID NO: 219         moltype = AA  length = 15
FEATURE                Location/Qualifiers
REGION                 1..15
                       note = masking moiety
source                 1..15
                       mol_type = protein
                       organism = synthetic construct
SEQUENCE: 219
CNIWGPSVDC GALLG                                                  15

SEQ ID NO: 220         moltype = AA  length = 15
FEATURE                Location/Qualifiers
REGION                 1..15
                       note = masking moiety
source                 1..15
                       mol_type = protein
                       organism = synthetic construct
SEQUENCE: 220
CNIWVNGGDC RSFEG                                                  15

SEQ ID NO: 221         moltype = AA  length = 15
FEATURE                Location/Qualifiers
REGION                 1..15
                       note = masking moiety
source                 1..15
                       mol_type = protein
                       organism = synthetic construct
SEQUENCE: 221
```

```
YCLNLPRYMQ DMCWA                                                    15

SEQ ID NO: 222          moltype = AA  length = 15
FEATURE                 Location/Qualifiers
REGION                  1..15
                        note = masking moiety
source                  1..15
                        mol_type = protein
                        organism = synthetic construct
SEQUENCE: 222
YCLALPHYMQ ADCAR                                                    15

SEQ ID NO: 223          moltype = AA  length = 15
FEATURE                 Location/Qualifiers
REGION                  1..15
                        note = masking moiety
source                  1..15
                        mol_type = protein
                        organism = synthetic construct
SEQUENCE: 223
CFLYSCGDVS YWGSA                                                    15

SEQ ID NO: 224          moltype = AA  length = 15
FEATURE                 Location/Qualifiers
REGION                  1..15
                        note = masking moiety
source                  1..15
                        mol_type = protein
                        organism = synthetic construct
SEQUENCE: 224
CYLYSCTDSA FWNNR                                                    15

SEQ ID NO: 225          moltype = AA  length = 15
FEATURE                 Location/Qualifiers
REGION                  1..15
                        note = masking moiety
source                  1..15
                        mol_type = protein
                        organism = synthetic construct
SEQUENCE: 225
CYLYSCNDVS YWSNT                                                    15

SEQ ID NO: 226          moltype = AA  length = 12
FEATURE                 Location/Qualifiers
REGION                  1..12
                        note = masking moiety
source                  1..12
                        mol_type = protein
                        organism = synthetic construct
SEQUENCE: 226
CFLYSCTDVS YW                                                       12

SEQ ID NO: 227          moltype = AA  length = 15
FEATURE                 Location/Qualifiers
REGION                  1..15
                        note = masking moiety
source                  1..15
                        mol_type = protein
                        organism = synthetic construct
SEQUENCE: 227
CFLYSCTDVA YWNSA                                                    15

SEQ ID NO: 228          moltype = AA  length = 15
FEATURE                 Location/Qualifiers
REGION                  1..15
                        note = masking moiety
source                  1..15
                        mol_type = protein
                        organism = synthetic construct
SEQUENCE: 228
CFLYSCTDVS YWGDT                                                    15

SEQ ID NO: 229          moltype = AA  length = 15
FEATURE                 Location/Qualifiers
REGION                  1..15
                        note = masking moiety
source                  1..15
                        mol_type = protein
                        organism = synthetic construct
```

SEQUENCE: 229
CFLYSCTDVS YWGNS 15

SEQ ID NO: 230 moltype = AA length = 15
FEATURE Location/Qualifiers
REGION 1..15
note = masking moiety
source 1..15
mol_type = protein
organism = synthetic construct
SEQUENCE: 230
CFLYSCTDVA YWNNT 15

SEQ ID NO: 231 moltype = AA length = 18
FEATURE Location/Qualifiers
REGION 1..18
note = masking moiety
source 1..18
mol_type = protein
organism = synthetic construct
SEQUENCE: 231
CFLYSCGDVS YWGNPGLS 18

SEQ ID NO: 232 moltype = AA length = 15
FEATURE Location/Qualifiers
REGION 1..15
note = masking moiety
source 1..15
mol_type = protein
organism = synthetic construct
SEQUENCE: 232
CFLYSCTDVA YWSGL 15

SEQ ID NO: 233 moltype = AA length = 15
FEATURE Location/Qualifiers
REGION 1..15
note = masking moiety
source 1..15
mol_type = protein
organism = synthetic construct
SEQUENCE: 233
CYLYSCTDGS YWNST 15

SEQ ID NO: 234 moltype = AA length = 15
FEATURE Location/Qualifiers
REGION 1..15
note = masking moiety
source 1..15
mol_type = protein
organism = synthetic construct
SEQUENCE: 234
CFLYSCSDVS YWGNI 15

SEQ ID NO: 235 moltype = AA length = 12
FEATURE Location/Qualifiers
REGION 1..12
note = masking moiety
source 1..12
mol_type = protein
organism = synthetic construct
SEQUENCE: 235
CFLYSCTDVA YW 12

SEQ ID NO: 236 moltype = AA length = 15
FEATURE Location/Qualifiers
REGION 1..15
note = masking moiety
source 1..15
mol_type = protein
organism = synthetic construct
SEQUENCE: 236
CFLYSCTDVS YWGST 15

SEQ ID NO: 237 moltype = AA length = 15
FEATURE Location/Qualifiers
REGION 1..15
note = masking moiety
source 1..15
mol_type = protein

```
                         organism = synthetic construct
SEQUENCE: 237
CFLYSCTDVA YWGDT                                                    15

SEQ ID NO: 238           moltype = AA  length = 20
FEATURE                  Location/Qualifiers
REGION                   1..20
                         note = masking moiety
source                   1..20
                         mol_type = protein
                         organism = synthetic construct
SEQUENCE: 238
GCNIWLNGGD CRGWVDPLQG                                               20

SEQ ID NO: 239           moltype = AA  length = 20
FEATURE                  Location/Qualifiers
REGION                   1..20
                         note = masking moiety
source                   1..20
                         mol_type = protein
                         organism = synthetic construct
SEQUENCE: 239
GCNIWLVGGD CRGWIGDTNG                                               20

SEQ ID NO: 240           moltype = AA  length = 20
FEATURE                  Location/Qualifiers
REGION                   1..20
                         note = masking moiety
source                   1..20
                         mol_type = protein
                         organism = synthetic construct
SEQUENCE: 240
GCNIWLVGGD CRGWIEDSNG                                               20

SEQ ID NO: 241           moltype = AA  length = 20
FEATURE                  Location/Qualifiers
REGION                   1..20
                         note = masking moiety
source                   1..20
                         mol_type = protein
                         organism = synthetic construct
SEQUENCE: 241
GCNIWANGGD CRGWIDNIDG                                               20

SEQ ID NO: 242           moltype = AA  length = 20
FEATURE                  Location/Qualifiers
REGION                   1..20
                         note = masking moiety
source                   1..20
                         mol_type = protein
                         organism = synthetic construct
SEQUENCE: 242
GCNIWLVGGD CRGWLGEAVG                                               20

SEQ ID NO: 243           moltype = AA  length = 20
FEATURE                  Location/Qualifiers
REGION                   1..20
                         note = masking moiety
source                   1..20
                         mol_type = protein
                         organism = synthetic construct
SEQUENCE: 243
GCNIWLVGGD CRGWLEEAVG                                               20

SEQ ID NO: 244           moltype = AA  length = 20
FEATURE                  Location/Qualifiers
REGION                   1..20
                         note = masking moiety
source                   1..20
                         mol_type = protein
                         organism = synthetic construct
SEQUENCE: 244
GGPALCNIWL NGGDCRGWSG                                               20

SEQ ID NO: 245           moltype = AA  length = 20
FEATURE                  Location/Qualifiers
REGION                   1..20
                         note = masking moiety
source                   1..20
```

```
                        mol_type = protein
                        organism = synthetic construct
SEQUENCE: 245
GAPVFCNIWL NGGDCRGWMG                                              20

SEQ ID NO: 246          moltype = AA  length = 20
FEATURE                 Location/Qualifiers
REGION                  1..20
                        note = masking moiety
source                  1..20
                        mol_type = protein
                        organism = synthetic construct
SEQUENCE: 246
GQQQWCNIWI NGGDCRGWNG                                              20

SEQ ID NO: 247          moltype = AA  length = 20
FEATURE                 Location/Qualifiers
REGION                  1..20
                        note = masking moiety
source                  1..20
                        mol_type = protein
                        organism = synthetic construct
SEQUENCE: 247
GKSEFCNIWL NGGDCRGWIG                                              20

SEQ ID NO: 248          moltype = AA  length = 20
FEATURE                 Location/Qualifiers
REGION                  1..20
                        note = masking moiety
source                  1..20
                        mol_type = protein
                        organism = synthetic construct
SEQUENCE: 248
GTPGGCNIWA NGGDCRGWEG                                              20

SEQ ID NO: 249          moltype = AA  length = 20
FEATURE                 Location/Qualifiers
REGION                  1..20
                        note = masking moiety
source                  1..20
                        mol_type = protein
                        organism = synthetic construct
SEQUENCE: 249
GASQYCNLWI NGGDCRGWRG                                              20

SEQ ID NO: 250          moltype = AA  length = 18
FEATURE                 Location/Qualifiers
REGION                  1..18
                        note = masking moiety
source                  1..18
                        mol_type = protein
                        organism = synthetic construct
SEQUENCE: 250
GCNIWLVGGD CRPWVEGG                                                18

SEQ ID NO: 251          moltype = AA  length = 18
FEATURE                 Location/Qualifiers
REGION                  1..18
                        note = masking moiety
source                  1..18
                        mol_type = protein
                        organism = synthetic construct
SEQUENCE: 251
GCNIWAVGGD CRPFVDGG                                                18

SEQ ID NO: 252          moltype = AA  length = 18
FEATURE                 Location/Qualifiers
REGION                  1..18
                        note = masking moiety
source                  1..18
                        mol_type = protein
                        organism = synthetic construct
SEQUENCE: 252
GCNIWLNGGD CRAWVDTG                                                18

SEQ ID NO: 253          moltype = AA  length = 18
FEATURE                 Location/Qualifiers
REGION                  1..18
                        note = masking moiety
```

```
source                1..18
                      mol_type = protein
                      organism = synthetic construct
SEQUENCE: 253
GCNIWIVGGD CRPFINDG                                                18

SEQ ID NO: 254        moltype = AA  length = 18
FEATURE               Location/Qualifiers
REGION                1..18
                      note = masking moiety
source                1..18
                      mol_type = protein
                      organism = synthetic construct
SEQUENCE: 254
GCNIWLNGGD CRPVVFGG                                                18

SEQ ID NO: 255        moltype = AA  length = 18
FEATURE               Location/Qualifiers
REGION                1..18
                      note = masking moiety
source                1..18
                      mol_type = protein
                      organism = synthetic construct
SEQUENCE: 255
GCNIWLSGGD CRMFMNEG                                                18

SEQ ID NO: 256        moltype = AA  length = 18
FEATURE               Location/Qualifiers
REGION                1..18
                      note = masking moiety
source                1..18
                      mol_type = protein
                      organism = synthetic construct
SEQUENCE: 256
GCNIWVNGGD CRSFVYSG                                                18

SEQ ID NO: 257        moltype = AA  length = 18
FEATURE               Location/Qualifiers
REGION                1..18
                      note = masking moiety
source                1..18
                      mol_type = protein
                      organism = synthetic construct
SEQUENCE: 257
GCNIWLNGGD CRGWEASG                                                18

SEQ ID NO: 258        moltype = AA  length = 18
FEATURE               Location/Qualifiers
REGION                1..18
                      note = masking moiety
source                1..18
                      mol_type = protein
                      organism = synthetic construct
SEQUENCE: 258
GCNIWAHGGD CRGFIEPG                                                18

SEQ ID NO: 259        moltype = AA  length = 18
FEATURE               Location/Qualifiers
REGION                1..18
                      note = masking moiety
source                1..18
                      mol_type = protein
                      organism = synthetic construct
SEQUENCE: 259
GCNIWLNGGD CRTFVASG                                                18

SEQ ID NO: 260        moltype = AA  length = 18
FEATURE               Location/Qualifiers
REGION                1..18
                      note = masking moiety
source                1..18
                      mol_type = protein
                      organism = synthetic construct
SEQUENCE: 260
GCNIWAHGGD CRGFIEPG                                                18

SEQ ID NO: 261        moltype = AA  length = 18
FEATURE               Location/Qualifiers
REGION                1..18
```

```
                        note = masking moiety
source                  1..18
                        mol_type = protein
                        organism = synthetic construct
SEQUENCE: 261
GFLENCNIWL NGGDCRTG                                                 18

SEQ ID NO: 262          moltype = AA  length = 18
FEATURE                 Location/Qualifiers
REGION                  1..18
                        note = masking moiety
source                  1..18
                        mol_type = protein
                        organism = synthetic construct
SEQUENCE: 262
GIYENCNIWL NGGDCRMG                                                 18

SEQ ID NO: 263          moltype = AA  length = 18
FEATURE                 Location/Qualifiers
REGION                  1..18
                        note = masking moiety
source                  1..18
                        mol_type = protein
                        organism = synthetic construct
SEQUENCE: 263
GIPDNCNIWI NGGDCRYG                                                 18

SEQ ID NO: 264          moltype = AA  length = 21
FEATURE                 Location/Qualifiers
REGION                  1..21
                        note = masking moiety
source                  1..21
                        mol_type = protein
                        organism = synthetic construct
SEQUENCE: 264
QGQSGQYGSC SWNYVHIFMD C                                             21

SEQ ID NO: 265          moltype = AA  length = 21
FEATURE                 Location/Qualifiers
REGION                  1..21
                        note = masking moiety
source                  1..21
                        mol_type = protein
                        organism = synthetic construct
SEQUENCE: 265
QGQSGQGDFD IPFPAHWVPI T                                             21

SEQ ID NO: 266          moltype = AA  length = 24
FEATURE                 Location/Qualifiers
REGION                  1..24
                        note = masking moiety
source                  1..24
                        mol_type = protein
                        organism = synthetic construct
SEQUENCE: 266
QGQSGQMGVP AGCVWNYAHI FMDC                                          24

SEQ ID NO: 267          moltype = AA  length = 15
FEATURE                 Location/Qualifiers
REGION                  1..15
                        note = masking moiety
source                  1..15
                        mol_type = protein
                        organism = synthetic construct
SEQUENCE: 267
YRSCNWNYVS IFLDC                                                    15

SEQ ID NO: 268          moltype = AA  length = 16
FEATURE                 Location/Qualifiers
REGION                  1..16
                        note = masking moiety
source                  1..16
                        mol_type = protein
                        organism = synthetic construct
SEQUENCE: 268
PGAFDIPFPA HWVPNT                                                   16

SEQ ID NO: 269          moltype = AA  length = 15
FEATURE                 Location/Qualifiers
```

```
REGION                1..15
                      note = masking moiety
source                1..15
                      mol_type = protein
                      organism = synthetic construct
SEQUENCE: 269
ESSCVWNYVH IYMDC                                                          15

SEQ ID NO: 270        moltype = AA  length = 15
FEATURE               Location/Qualifiers
REGION                1..15
                      note = masking moiety
source                1..15
                      mol_type = protein
                      organism = synthetic construct
SEQUENCE: 270
YPGCKWNYDR IFLDC                                                          15

SEQ ID NO: 271        moltype = AA  length = 15
FEATURE               Location/Qualifiers
REGION                1..15
                      note = masking moiety
source                1..15
                      mol_type = protein
                      organism = synthetic construct
SEQUENCE: 271
YRTCSWNYVG IFLDC                                                          15

SEQ ID NO: 272        moltype = AA  length = 15
FEATURE               Location/Qualifiers
REGION                1..15
                      note = masking moiety
source                1..15
                      mol_type = protein
                      organism = synthetic construct
SEQUENCE: 272
YGSCSWNYVH IFLDC                                                          15

SEQ ID NO: 273        moltype = AA  length = 15
FEATURE               Location/Qualifiers
REGION                1..15
                      note = masking moiety
source                1..15
                      mol_type = protein
                      organism = synthetic construct
SEQUENCE: 273
YGSCNWNYVH IFLDC                                                          15

SEQ ID NO: 274        moltype = AA  length = 15
FEATURE               Location/Qualifiers
REGION                1..15
                      note = masking moiety
source                1..15
                      mol_type = protein
                      organism = synthetic construct
SEQUENCE: 274
YTSCNWNYVH IFMDC                                                          15

SEQ ID NO: 275        moltype = AA  length = 15
FEATURE               Location/Qualifiers
REGION                1..15
                      note = masking moiety
source                1..15
                      mol_type = protein
                      organism = synthetic construct
SEQUENCE: 275
YPGCKWNYDR IFLDC                                                          15

SEQ ID NO: 276        moltype = AA  length = 15
FEATURE               Location/Qualifiers
REGION                1..15
                      note = masking moiety
source                1..15
                      mol_type = protein
                      organism = synthetic construct
SEQUENCE: 276
WRSCNWNYAH IFLDC                                                          15

SEQ ID NO: 277        moltype = AA  length = 15
```

```
FEATURE                Location/Qualifiers
REGION                 1..15
                       note = masking moiety
source                 1..15
                       mol_type = protein
                       organism = synthetic construct
SEQUENCE: 277
WSNCHWNYVH IFLDC                                                             15

SEQ ID NO: 278         moltype = AA  length = 15
FEATURE                Location/Qualifiers
REGION                 1..15
                       note = masking moiety
source                 1..15
                       mol_type = protein
                       organism = synthetic construct
SEQUENCE: 278
DRSCTWNYVR ISYDC                                                             15

SEQ ID NO: 279         moltype = AA  length = 15
FEATURE                Location/Qualifiers
REGION                 1..15
                       note = masking moiety
source                 1..15
                       mol_type = protein
                       organism = synthetic construct
SEQUENCE: 279
SGSCKWDYVH IFLDC                                                             15

SEQ ID NO: 280         moltype = AA  length = 15
FEATURE                Location/Qualifiers
REGION                 1..15
                       note = masking moiety
source                 1..15
                       mol_type = protein
                       organism = synthetic construct
SEQUENCE: 280
SRSCIWNYAH IHLDC                                                             15

SEQ ID NO: 281         moltype = AA  length = 15
FEATURE                Location/Qualifiers
REGION                 1..15
                       note = masking moiety
source                 1..15
                       mol_type = protein
                       organism = synthetic construct
SEQUENCE: 281
SMSCYWQYER IFLDC                                                             15

SEQ ID NO: 282         moltype = AA  length = 15
FEATURE                Location/Qualifiers
REGION                 1..15
                       note = masking moiety
source                 1..15
                       mol_type = protein
                       organism = synthetic construct
SEQUENCE: 282
YRSCNWNYVS IFLDC                                                             15

SEQ ID NO: 283         moltype = AA  length = 15
FEATURE                Location/Qualifiers
REGION                 1..15
                       note = masking moiety
source                 1..15
                       mol_type = protein
                       organism = synthetic construct
SEQUENCE: 283
SGSCKWDYVH IFLDC                                                             15

SEQ ID NO: 284         moltype = AA  length = 15
FEATURE                Location/Qualifiers
REGION                 1..15
                       note = masking moiety
source                 1..15
                       mol_type = protein
                       organism = synthetic construct
SEQUENCE: 284
YKSCHWDYVH IFLDC                                                             15
```

```
SEQ ID NO: 285          moltype = AA  length = 15
FEATURE                 Location/Qualifiers
REGION                  1..15
                        note = masking moiety
source                  1..15
                        mol_type = protein
                        organism = synthetic construct
SEQUENCE: 285
YGSCTWNYVH IFMEC                                                   15

SEQ ID NO: 286          moltype = AA  length = 15
FEATURE                 Location/Qualifiers
REGION                  1..15
                        note = masking moiety
source                  1..15
                        mol_type = protein
                        organism = synthetic construct
SEQUENCE: 286
FSSCNWNYVH IFLDC                                                   15

SEQ ID NO: 287          moltype = AA  length = 15
FEATURE                 Location/Qualifiers
REGION                  1..15
                        note = masking moiety
source                  1..15
                        mol_type = protein
                        organism = synthetic construct
SEQUENCE: 287
WRSCNWNYAH IFLDC                                                   15

SEQ ID NO: 288          moltype = AA  length = 15
FEATURE                 Location/Qualifiers
REGION                  1..15
                        note = masking moiety
source                  1..15
                        mol_type = protein
                        organism = synthetic construct
SEQUENCE: 288
YGSCQWNYVH IFLDC                                                   15

SEQ ID NO: 289          moltype = AA  length = 15
FEATURE                 Location/Qualifiers
REGION                  1..15
                        note = masking moiety
source                  1..15
                        mol_type = protein
                        organism = synthetic construct
SEQUENCE: 289
YRSCNWNYVH IFLDC                                                   15

SEQ ID NO: 290          moltype = AA  length = 15
FEATURE                 Location/Qualifiers
REGION                  1..15
                        note = masking moiety
source                  1..15
                        mol_type = protein
                        organism = synthetic construct
SEQUENCE: 290
NMSCHWDYVH IFLDC                                                   15

SEQ ID NO: 291          moltype = AA  length = 15
FEATURE                 Location/Qualifiers
REGION                  1..15
                        note = masking moiety
source                  1..15
                        mol_type = protein
                        organism = synthetic construct
SEQUENCE: 291
FGPCTWNYAR ISWDC                                                   15

SEQ ID NO: 292          moltype = AA  length = 15
FEATURE                 Location/Qualifiers
REGION                  1..15
                        note = masking moiety
VARIANT                 1..2
                        note = misc_feature - Xaa may be any amino acid
VARIANT                 5
                        note = misc_feature - Xaa may be any amino acid
VARIANT                 7
```

```
                        note = misc_feature - Xaa may be any amino acid
VARIANT                 13
                        note = misc_feature - Xaa may be any amino acid
source                  1..15
                        mol_type = protein
                        organism = synthetic construct
SEQUENCE: 292
XXSCXWXYVH IFXDC                                                   15

SEQ ID NO: 293          moltype = AA  length = 18
FEATURE                 Location/Qualifiers
REGION                  1..18
                        note = masking moiety
source                  1..18
                        mol_type = protein
                        organism = synthetic construct
SEQUENCE: 293
RDTGGQCRWD YVHIFMDC                                                18

SEQ ID NO: 294          moltype = AA  length = 18
FEATURE                 Location/Qualifiers
REGION                  1..18
                        note = masking moiety
source                  1..18
                        mol_type = protein
                        organism = synthetic construct
SEQUENCE: 294
AGVPAGCTWN YVHIFMEC                                                18

SEQ ID NO: 295          moltype = AA  length = 18
FEATURE                 Location/Qualifiers
REGION                  1..18
                        note = masking moiety
source                  1..18
                        mol_type = protein
                        organism = synthetic construct
SEQUENCE: 295
VGVPNGCVWN YAHIFMEC                                                18

SEQ ID NO: 296          moltype = AA  length = 18
FEATURE                 Location/Qualifiers
REGION                  1..18
                        note = masking moiety
source                  1..18
                        mol_type = protein
                        organism = synthetic construct
SEQUENCE: 296
DGGPAGCSWN YVHIFMEC                                                18

SEQ ID NO: 297          moltype = AA  length = 18
FEATURE                 Location/Qualifiers
REGION                  1..18
                        note = masking moiety
source                  1..18
                        mol_type = protein
                        organism = synthetic construct
SEQUENCE: 297
AVGPAGCWWN YVHIFMEC                                                18

SEQ ID NO: 298          moltype = AA  length = 18
FEATURE                 Location/Qualifiers
REGION                  1..18
                        note = masking moiety
source                  1..18
                        mol_type = protein
                        organism = synthetic construct
SEQUENCE: 298
CTWNYVHIFM DCGEGEGP                                                18

SEQ ID NO: 299          moltype = AA  length = 18
FEATURE                 Location/Qualifiers
REGION                  1..18
                        note = masking moiety
source                  1..18
                        mol_type = protein
                        organism = synthetic construct
SEQUENCE: 299
GGVPEGCTWN YAHIFMEC                                                18
```

```
SEQ ID NO: 300          moltype = AA  length = 18
FEATURE                 Location/Qualifiers
REGION                  1..18
                        note = masking moiety
source                  1..18
                        mol_type = protein
                        organism = synthetic construct
SEQUENCE: 300
AEVPAGCWWN YVHIFMEC                                                18

SEQ ID NO: 301          moltype = AA  length = 18
FEATURE                 Location/Qualifiers
REGION                  1..18
                        note = masking moiety
source                  1..18
                        mol_type = protein
                        organism = synthetic construct
SEQUENCE: 301
AGVPAGCTWN YVHIFMEC                                                18

SEQ ID NO: 302          moltype = AA  length = 18
FEATURE                 Location/Qualifiers
REGION                  1..18
                        note = masking moiety
source                  1..18
                        mol_type = protein
                        organism = synthetic construct
SEQUENCE: 302
SGASGGCKWN YVHIFMDC                                                18

SEQ ID NO: 303          moltype = AA  length = 18
FEATURE                 Location/Qualifiers
REGION                  1..18
                        note = masking moiety
source                  1..18
                        mol_type = protein
                        organism = synthetic construct
SEQUENCE: 303
TPGCRWNYVH IFMECEAL                                                18

SEQ ID NO: 304          moltype = AA  length = 18
FEATURE                 Location/Qualifiers
REGION                  1..18
                        note = masking moiety
source                  1..18
                        mol_type = protein
                        organism = synthetic construct
SEQUENCE: 304
VGVPNGCVWN YAHIFMEC                                                18

SEQ ID NO: 305          moltype = AA  length = 16
FEATURE                 Location/Qualifiers
REGION                  1..16
                        note = masking moiety
source                  1..16
                        mol_type = protein
                        organism = synthetic construct
SEQUENCE: 305
PGAFDIPFPA HWVPNT                                                  16

SEQ ID NO: 306          moltype = AA  length = 16
FEATURE                 Location/Qualifiers
REGION                  1..16
                        note = masking moiety
source                  1..16
                        mol_type = protein
                        organism = synthetic construct
SEQUENCE: 306
RGACDIPFPA HWIPNT                                                  16

SEQ ID NO: 307          moltype = AA  length = 16
FEATURE                 Location/Qualifiers
REGION                  1..16
                        note = masking moiety
VARIANT                 1
                        note = misc_feature - Xaa may be any amino acid
source                  1..16
                        mol_type = protein
                        organism = synthetic construct
```

```
SEQUENCE: 307
XGAFDIPFPA HWVPNT                                                   16

SEQ ID NO: 308          moltype = AA  length = 19
FEATURE                 Location/Qualifiers
REGION                  1..19
                        note = masking moiety
source                  1..19
                        mol_type = protein
                        organism = synthetic construct
SEQUENCE: 308
RGDGNDSDIP FPAHWVPRT                                                19

SEQ ID NO: 309          moltype = AA  length = 19
FEATURE                 Location/Qualifiers
REGION                  1..19
                        note = masking moiety
source                  1..19
                        mol_type = protein
                        organism = synthetic construct
SEQUENCE: 309
SGVGRDRDIP FPAHWVPRT                                                19

SEQ ID NO: 310          moltype = AA  length = 19
FEATURE                 Location/Qualifiers
REGION                  1..19
                        note = masking moiety
source                  1..19
                        mol_type = protein
                        organism = synthetic construct
SEQUENCE: 310
WAGGNDCDIP FPAHWIPNT                                                19

SEQ ID NO: 311          moltype = AA  length = 19
FEATURE                 Location/Qualifiers
REGION                  1..19
                        note = masking moiety
source                  1..19
                        mol_type = protein
                        organism = synthetic construct
SEQUENCE: 311
WGDGMDVDIP FPAHWVPVT                                                19

SEQ ID NO: 312          moltype = AA  length = 19
FEATURE                 Location/Qualifiers
REGION                  1..19
                        note = masking moiety
source                  1..19
                        mol_type = protein
                        organism = synthetic construct
SEQUENCE: 312
AGSGNDSDIP FPAHWVPRT                                                19

SEQ ID NO: 313          moltype = AA  length = 19
FEATURE                 Location/Qualifiers
REGION                  1..19
                        note = masking moiety
source                  1..19
                        mol_type = protein
                        organism = synthetic construct
SEQUENCE: 313
ESRSGYADIP FPAHWVPRT                                                19

SEQ ID NO: 314          moltype = AA  length = 19
FEATURE                 Location/Qualifiers
REGION                  1..19
                        note = masking moiety
source                  1..19
                        mol_type = protein
                        organism = synthetic construct
SEQUENCE: 314
RECGRCGDIP FPAHWVPRT                                                19

SEQ ID NO: 315          moltype = AA  length = 7
FEATURE                 Location/Qualifiers
REGION                  1..7
                        note = cleavable moiety
source                  1..7
                        mol_type = protein
```

-continued

```
                        organism = synthetic construct
SEQUENCE: 315
GPRSFGL                                                                   7

SEQ ID NO: 316          moltype = AA  length = 6
FEATURE                 Location/Qualifiers
REGION                  1..6
                        note = cleavable moiety
source                  1..6
                        mol_type = protein
                        organism = synthetic construct
SEQUENCE: 316
GPRSFG                                                                    6

SEQ ID NO: 317          moltype =   length =
SEQUENCE: 317
000

SEQ ID NO: 318          moltype =   length =
SEQUENCE: 318
000

SEQ ID NO: 319          moltype =   length =
SEQUENCE: 319
000

SEQ ID NO: 320          moltype =   length =
SEQUENCE: 320
000

SEQ ID NO: 321          moltype =   length =
SEQUENCE: 321
000

SEQ ID NO: 322          moltype = AA  length = 8
FEATURE                 Location/Qualifiers
REGION                  1..8
                        note = MMP9 Cleavable Core CM Consensus Sequence 1 subgenus
                         1.5
VARIANT                 1
                        note = misc_feature - Xaa may be Pro or Arg
VARIANT                 4
                        note = misc_feature - Xaa may be Gly or Pro
VARIANT                 5
                        note = misc_feature - Xaa may be Met or Arg
VARIANT                 7
                        note = misc_feature - Xaa may be Ala or Ser
source                  1..8
                        mol_type = protein
                        organism = synthetic construct
SEQUENCE: 322
XPSXXWXY                                                                  8

SEQ ID NO: 323          moltype =   length =
SEQUENCE: 323
000

SEQ ID NO: 324          moltype =   length =
SEQUENCE: 324
000

SEQ ID NO: 325          moltype =   length =
SEQUENCE: 325
000

SEQ ID NO: 326          moltype =   length =
SEQUENCE: 326
000

SEQ ID NO: 327          moltype = AA  length = 8
FEATURE                 Location/Qualifiers
REGION                  1..8
                        note = MMP9 Cleavable Core CM Consensus Sequence 2 subgenus
                         2.3
VARIANT                 3
                        note = misc_feature - Xaa may be His, Gln or Trp
VARIANT                 5
                        note = misc_feature - Xaa may be Ile or Arg
VARIANT                 7
```

```
                         note = misc_feature - Xaa may be Leu, Met or Val
source                   1..8
                         mol_type = protein
                         organism = synthetic construct
SEQUENCE: 327
WDXPXSXL                                                               8

SEQ ID NO: 328           moltype = AA  length = 8
FEATURE                  Location/Qualifiers
REGION                   1..8
                         note = cleavable moiety
source                   1..8
                         mol_type = protein
                         organism = synthetic construct
SEQUENCE: 328
WDHPISLL                                                               8

SEQ ID NO: 329           moltype =   length =
SEQUENCE: 329
000

SEQ ID NO: 330           moltype =   length =
SEQUENCE: 330
000

SEQ ID NO: 331           moltype =   length =
SEQUENCE: 331
000

SEQ ID NO: 332           moltype =   length =
SEQUENCE: 332
000

SEQ ID NO: 333           moltype =   length =
SEQUENCE: 333
000

SEQ ID NO: 334           moltype =   length =
SEQUENCE: 334
000

SEQ ID NO: 335           moltype = AA  length = 8
FEATURE                  Location/Qualifiers
REGION                   1..8
                         note = MMP9 Cleavable Core CM Consensus Sequence 3 subgenus
                          3.6
VARIANT                  3
                         note = misc_feature - Xaa may be Phe or Val
VARIANT                  4
                         note = misc_feature - Xaa may be Leu or Pro
VARIANT                  5
                         note = misc_feature - Xaa may be Phe or Leu
VARIANT                  7
                         note = misc_feature - Xaa may be Ile or Met
source                   1..8
                         mol_type = protein
                         organism = synthetic construct
SEQUENCE: 335
STXXXGXF                                                               8

SEQ ID NO: 336           moltype = AA  length = 8
FEATURE                  Location/Qualifiers
REGION                   1..8
                         note = cleavable moiety
source                   1..8
                         mol_type = protein
                         organism = synthetic construct
SEQUENCE: 336
LTFPTYIF                                                               8

SEQ ID NO: 337           moltype = AA  length = 8
FEATURE                  Location/Qualifiers
REGION                   1..8
                         note = cleavable moiety
source                   1..8
                         mol_type = protein
                         organism = synthetic construct
SEQUENCE: 337
MTFPTYIF                                                               8
```

```
SEQ ID NO: 338          moltype = AA  length = 8
FEATURE                 Location/Qualifiers
REGION                  1..8
                        note = cleavable moiety
source                  1..8
                        mol_type = protein
                        organism = synthetic construct
SEQUENCE: 338
LTFPTYWF                                                    8

SEQ ID NO: 339          moltype = AA  length = 8
FEATURE                 Location/Qualifiers
REGION                  1..8
                        note = cleavable moiety
source                  1..8
                        mol_type = protein
                        organism = synthetic construct
SEQUENCE: 339
MTFPTYWF                                                    8

SEQ ID NO: 340          moltype =   length =
SEQUENCE: 340
000

SEQ ID NO: 341          moltype =   length =
SEQUENCE: 341
000

SEQ ID NO: 342          moltype =   length =
SEQUENCE: 342
000

SEQ ID NO: 343          moltype =   length =
SEQUENCE: 343
000

SEQ ID NO: 344          moltype = AA  length = 8
FEATURE                 Location/Qualifiers
REGION                  1..8
                        note = MMP9 Cleavable Core CM Consensus Sequence 4 subgenus
                         4.4
VARIANT                 3
                        note = misc_feature - Xaa may be His or Leu
VARIANT                 4
                        note = misc_feature - Xaa may be Leu or Tyr
VARIANT                 7
                        note = misc_feature - Xaa may be Leu or Pro
VARIANT                 8
                        note = misc_feature - Xaa may be Gly, Ile, Ser or Thr
source                  1..8
                        mol_type = protein
                        organism = synthetic construct
SEQUENCE: 344
HWXXGPXX                                                    8

SEQ ID NO: 345          moltype = AA  length = 8
FEATURE                 Location/Qualifiers
REGION                  1..8
                        note = MMP9 Cleavable Core CM Consensus Sequence 4 subgenus
                         4.5
VARIANT                 3
                        note = misc_feature - Xaa may be His or Leu
VARIANT                 4
                        note = misc_feature - Xaa may be Leu or Tyr
source                  1..8
                        mol_type = protein
                        organism = synthetic construct
SEQUENCE: 345
HWXXGPPT                                                    8

SEQ ID NO: 346          moltype =   length =
SEQUENCE: 346
000

SEQ ID NO: 347          moltype =   length =
SEQUENCE: 347
000
```

```
SEQ ID NO: 348          moltype = AA  length = 8
FEATURE                 Location/Qualifiers
REGION                  1..8
                        note = cleavable moiety
source                  1..8
                        mol_type = protein
                        organism = synthetic construct
SEQUENCE: 348
DWLYWMGI                                                                8

SEQ ID NO: 349          moltype = AA  length = 8
FEATURE                 Location/Qualifiers
REGION                  1..8
                        note = cleavable moiety
source                  1..8
                        mol_type = protein
                        organism = synthetic construct
SEQUENCE: 349
DWLYWMSI                                                                8

SEQ ID NO: 350          moltype = AA  length = 8
FEATURE                 Location/Qualifiers
REGION                  1..8
                        note = cleavable moiety
source                  1..8
                        mol_type = protein
                        organism = synthetic construct
SEQUENCE: 350
DWLYWPSI                                                                8

SEQ ID NO: 351          moltype = AA  length = 8
FEATURE                 Location/Qualifiers
REGION                  1..8
                        note = cleavable moiety
source                  1..8
                        mol_type = protein
                        organism = synthetic construct
SEQUENCE: 351
HWHLGPPT                                                                8

SEQ ID NO: 352          moltype =   length =
SEQUENCE: 352
000

SEQ ID NO: 353          moltype =   length =
SEQUENCE: 353
000

SEQ ID NO: 354          moltype =   length =
SEQUENCE: 354
000

SEQ ID NO: 355          moltype =   length =
SEQUENCE: 355
000

SEQ ID NO: 356          moltype =   length =
SEQUENCE: 356
000

SEQ ID NO: 357          moltype =   length =
SEQUENCE: 357
000

SEQ ID NO: 358          moltype = AA  length = 8
FEATURE                 Location/Qualifiers
REGION                  1..8
                        note = MMP14 Cleavable Core CM Consensus Sequence 5
                         subgenus 5.6
VARIANT                 2
                        note = misc_feature - Xaa may be Leu, Ser or Val
source                  1..8
                        mol_type = protein
                        organism = synthetic construct
SEQUENCE: 358
TXSGLRSP                                                                8

SEQ ID NO: 359          moltype =   length =
SEQUENCE: 359
```

```
000

SEQ ID NO: 360          moltype =   length =
SEQUENCE: 360
000

SEQ ID NO: 361          moltype =   length =
SEQUENCE: 361
000

SEQ ID NO: 362          moltype =   length =
SEQUENCE: 362
000

SEQ ID NO: 363          moltype = AA  length = 8
FEATURE                 Location/Qualifiers
REGION                  1..8
                        note = MMP14 Cleavable Core CM Consensus Sequence 5
                         subgenus 5.11
VARIANT                 1
                        note = misc_feature - Xaa may be Ala or Ser
VARIANT                 2
                        note = misc_feature - Xaa may be Leu or Val
VARIANT                 6
                        note = misc_feature - Xaa may be Leu or Arg
VARIANT                 8
                        note = misc_feature - Xaa may be His or Ser
source                  1..8
                        mol_type = protein
                        organism = synthetic construct
SEQUENCE: 363
XXSGLXSX                                                                8

SEQ ID NO: 364          moltype = AA  length = 8
FEATURE                 Location/Qualifiers
REGION                  1..8
                        note = cleavable moiety
source                  1..8
                        mol_type = protein
                        organism = synthetic construct
SEQUENCE: 364
SVSGLLSH                                                                8

SEQ ID NO: 365          moltype = AA  length = 8
FEATURE                 Location/Qualifiers
REGION                  1..8
                        note = cleavable moiety
source                  1..8
                        mol_type = protein
                        organism = synthetic construct
SEQUENCE: 365
SVSGLLSS                                                                8

SEQ ID NO: 366          moltype = AA  length = 8
FEATURE                 Location/Qualifiers
REGION                  1..8
                        note = cleavable moiety
source                  1..8
                        mol_type = protein
                        organism = synthetic construct
SEQUENCE: 366
SVSGLRSH                                                                8

SEQ ID NO: 367          moltype = AA  length = 8
FEATURE                 Location/Qualifiers
REGION                  1..8
                        note = cleavable moiety
source                  1..8
                        mol_type = protein
                        organism = synthetic construct
SEQUENCE: 367
SVSGLRSS                                                                8

SEQ ID NO: 368          moltype = AA  length = 8
FEATURE                 Location/Qualifiers
REGION                  1..8
                        note = cleavable moiety
source                  1..8
                        mol_type = protein
```

```
                        organism = synthetic construct
SEQUENCE: 368
TLSGLRSP                                                    8

SEQ ID NO: 369          moltype = AA  length = 8
FEATURE                 Location/Qualifiers
REGION                  1..8
                        note = cleavable moiety
source                  1..8
                        mol_type = protein
                        organism = synthetic construct
SEQUENCE: 369
TSSGLRSP                                                    8

SEQ ID NO: 370          moltype = AA  length = 8
FEATURE                 Location/Qualifiers
REGION                  1..8
                        note = cleavable moiety
source                  1..8
                        mol_type = protein
                        organism = synthetic construct
SEQUENCE: 370
TVSGLRSP                                                    8

SEQ ID NO: 371          moltype =   length =
SEQUENCE: 371
000

SEQ ID NO: 372          moltype =   length =
SEQUENCE: 372
000

SEQ ID NO: 373          moltype =   length =
SEQUENCE: 373
000

SEQ ID NO: 374          moltype =   length =
SEQUENCE: 374
000

SEQ ID NO: 375          moltype =   length =
SEQUENCE: 375
000

SEQ ID NO: 376          moltype =   length =
SEQUENCE: 376
000

SEQ ID NO: 377          moltype =   length =
SEQUENCE: 377
000

SEQ ID NO: 378          moltype = AA  length = 7
FEATURE                 Location/Qualifiers
REGION                  1..7
                        note = MMP14 Cleavable Core CM Consensus Sequence 6A
                         Subgenus 6A.3
VARIANT                 2
                        note = misc_feature - Xaa may be Phe, His or Asn
source                  1..7
                        mol_type = protein
                        organism = synthetic construct
SEQUENCE: 378
AXQALRM                                                     7

SEQ ID NO: 379          moltype = AA  length = 7
FEATURE                 Location/Qualifiers
REGION                  1..7
                        note = cleavable moiety
source                  1..7
                        mol_type = protein
                        organism = synthetic construct
SEQUENCE: 379
AFQALRM                                                     7

SEQ ID NO: 380          moltype = AA  length = 7
FEATURE                 Location/Qualifiers
REGION                  1..7
                        note = cleavable moiety
```

```
source                1..7
                      mol_type = protein
                      organism = synthetic construct
SEQUENCE: 380
AHQALRM                                                                   7

SEQ ID NO: 381        moltype = AA  length = 7
FEATURE               Location/Qualifiers
REGION                1..7
                      note = cleavable moiety
source                1..7
                      mol_type = protein
                      organism = synthetic construct
SEQUENCE: 381
ANQALRM                                                                   7

SEQ ID NO: 382        moltype = AA  length = 8
FEATURE               Location/Qualifiers
REGION                1..8
                      note = cleavable moiety
source                1..8
                      mol_type = protein
                      organism = synthetic construct
SEQUENCE: 382
ANQALRMA                                                                  8

SEQ ID NO: 383        moltype = AA  length = 8
FEATURE               Location/Qualifiers
REGION                1..8
                      note = cleavable moiety
source                1..8
                      mol_type = protein
                      organism = synthetic construct
SEQUENCE: 383
LLEALRAL                                                                  8

SEQ ID NO: 384        moltype = AA  length = 8
FEATURE               Location/Qualifiers
REGION                1..8
                      note = cleavable moiety
source                1..8
                      mol_type = protein
                      organism = synthetic construct
SEQUENCE: 384
LLNALRAL                                                                  8

SEQ ID NO: 385        moltype = AA  length = 8
FEATURE               Location/Qualifiers
REGION                1..8
                      note = cleavable moiety
source                1..8
                      mol_type = protein
                      organism = synthetic construct
SEQUENCE: 385
LLQALRAL                                                                  8

SEQ ID NO: 386        moltype = AA  length = 8
FEATURE               Location/Qualifiers
REGION                1..8
                      note = cleavable moiety
source                1..8
                      mol_type = protein
                      organism = synthetic construct
SEQUENCE: 386
LLSALRAL                                                                  8

SEQ ID NO: 387        moltype = AA  length = 8
FEATURE               Location/Qualifiers
REGION                1..8
                      note = cleavable moiety
source                1..8
                      mol_type = protein
                      organism = synthetic construct
SEQUENCE: 387
LLESLRAL                                                                  8

SEQ ID NO: 388        moltype = AA  length = 8
FEATURE               Location/Qualifiers
REGION                1..8
```

```
                        note = cleavable moiety
source                  1..8
                        mol_type = protein
                        organism = synthetic construct
SEQUENCE: 388
LLNSLRAL                                                                     8

SEQ ID NO: 389          moltype = AA  length = 8
FEATURE                 Location/Qualifiers
REGION                  1..8
                        note = cleavable moiety
source                  1..8
                        mol_type = protein
                        organism = synthetic construct
SEQUENCE: 389
LLQSLRAL                                                                     8

SEQ ID NO: 390          moltype = AA  length = 8
FEATURE                 Location/Qualifiers
REGION                  1..8
                        note = cleavable moiety
source                  1..8
                        mol_type = protein
                        organism = synthetic construct
SEQUENCE: 390
LLSSLRAL                                                                     8

SEQ ID NO: 391          moltype = AA  length = 7
FEATURE                 Location/Qualifiers
REGION                  1..7
                        note = cleavable moiety
source                  1..7
                        mol_type = protein
                        organism = synthetic construct
SEQUENCE: 391
QFQALRM                                                                      7

SEQ ID NO: 392          moltype = AA  length = 7
FEATURE                 Location/Qualifiers
REGION                  1..7
                        note = cleavable moiety
source                  1..7
                        mol_type = protein
                        organism = synthetic construct
SEQUENCE: 392
QHQALRM                                                                      7

SEQ ID NO: 393          moltype = AA  length = 7
FEATURE                 Location/Qualifiers
REGION                  1..7
                        note = cleavable moiety
source                  1..7
                        mol_type = protein
                        organism = synthetic construct
SEQUENCE: 393
QNQALRM                                                                      7

SEQ ID NO: 394          moltype =   length =
SEQUENCE: 394
000

SEQ ID NO: 395          moltype =   length =
SEQUENCE: 395
000

SEQ ID NO: 396          moltype =   length =
SEQUENCE: 396
000

SEQ ID NO: 397          moltype = AA  length = 8
FEATURE                 Location/Qualifiers
REGION                  1..8
                        note = MMP14 Cleavable Core CM Consensus Sequence 7
                         Subgenus 7.3
VARIANT                 2
                        note = misc_feature - Xaa may be Lys, Arg or Tyr
VARIANT                 4
                        note = misc_feature - Xaa may be Ala or Leu
VARIANT                 6
```

```
                        note = misc_feature - Xaa may be Gly, Arg or Val
VARIANT                 8
                        note = misc_feature - Xaa may be Ala or Leu
source                  1..8
                        mol_type = protein
                        organism = synthetic construct
SEQUENCE: 397
LXAXPXWX                                                                   8

SEQ ID NO: 398          moltype =   length =
SEQUENCE: 398
000

SEQ ID NO: 399          moltype =   length =
SEQUENCE: 399
000

SEQ ID NO: 400          moltype =   length =
SEQUENCE: 400
000

SEQ ID NO: 401          moltype = AA  length = 8
FEATURE                 Location/Qualifiers
REGION                  1..8
                        note = MMP14 Cleavable Core CM Consensus Sequence 7
                         Subgenus 7.7
VARIANT                 2
                        note = misc_feature - Xaa may be Lsy or Tyr
VARIANT                 4
                        note = misc_feature - Xaa may be Ala or Ile
VARIANT                 6
                        note = misc_feature - Xaa may be Arg or Val
VARIANT                 8
                        note = misc_feature - Xaa may be Ala or Phe
source                  1..8
                        mol_type = protein
                        organism = synthetic construct
SEQUENCE: 401
LXAXPXWX                                                                   8

SEQ ID NO: 402          moltype = AA  length = 7
FEATURE                 Location/Qualifiers
REGION                  1..7
                        note = cleavable moiety
source                  1..7
                        mol_type = protein
                        organism = synthetic construct
SEQUENCE: 402
LPAGLLL                                                                    7

SEQ ID NO: 403          moltype = AA  length = 8
FEATURE                 Location/Qualifiers
REGION                  1..8
                        note = cleavable moiety
source                  1..8
                        mol_type = protein
                        organism = synthetic construct
SEQUENCE: 403
LKAAPVWA                                                                   8

SEQ ID NO: 404          moltype = AA  length = 8
FEATURE                 Location/Qualifiers
REGION                  1..8
                        note = cleavable moiety
source                  1..8
                        mol_type = protein
                        organism = synthetic construct
SEQUENCE: 404
LKAAPRWF                                                                   8

SEQ ID NO: 405          moltype = AA  length = 8
FEATURE                 Location/Qualifiers
REGION                  1..8
                        note = cleavable moiety
source                  1..8
                        mol_type = protein
                        organism = synthetic construct
SEQUENCE: 405
LKAAPVWF                                                                   8
```

```
SEQ ID NO: 406          moltype = AA  length = 8
FEATURE                 Location/Qualifiers
REGION                  1..8
                        note = cleavable moiety
source                  1..8
                        mol_type = protein
                        organism = synthetic construct
SEQUENCE: 406
LYAAPRWA                                                                  8

SEQ ID NO: 407          moltype = AA  length = 8
FEATURE                 Location/Qualifiers
REGION                  1..8
                        note = cleavable moiety
source                  1..8
                        mol_type = protein
                        organism = synthetic construct
SEQUENCE: 407
LYAAPVWA                                                                  8

SEQ ID NO: 408          moltype = AA  length = 8
FEATURE                 Location/Qualifiers
REGION                  1..8
                        note = cleavable moiety
source                  1..8
                        mol_type = protein
                        organism = synthetic construct
SEQUENCE: 408
LYAAPRWF                                                                  8

SEQ ID NO: 409          moltype = AA  length = 8
FEATURE                 Location/Qualifiers
REGION                  1..8
                        note = cleavable moiety
source                  1..8
                        mol_type = protein
                        organism = synthetic construct
SEQUENCE: 409
LYAAPVWF                                                                  8

SEQ ID NO: 410          moltype =   length =
SEQUENCE: 410
000

SEQ ID NO: 411          moltype =   length =
SEQUENCE: 411
000

SEQ ID NO: 412          moltype =   length =
SEQUENCE: 412
000

SEQ ID NO: 413          moltype =   length =
SEQUENCE: 413
000

SEQ ID NO: 414          moltype =   length =
SEQUENCE: 414
000

SEQ ID NO: 415          moltype =   length =
SEQUENCE: 415
000

SEQ ID NO: 416          moltype =   length =
SEQUENCE: 416
000

SEQ ID NO: 417          moltype =   length =
SEQUENCE: 417
000

SEQ ID NO: 418          moltype =   length =
SEQUENCE: 418
000

SEQ ID NO: 419          moltype = AA  length = 7
FEATURE                 Location/Qualifiers
```

```
REGION                  1..7
                        note = MMP14 Cleavable Core CM Consensus Sequence 8
                         Subgenus 8.9
VARIANT                 3
                        note = misc_feature - Xaa may be Ala, Asn, Gln or Ser
VARIANT                 5
                        note = misc_feature - Xaa may be Ile or Leu
source                  1..7
                        mol_type = protein
                        organism = synthetic construct
SEQUENCE: 419
LPXHXVL                                                                   7

SEQ ID NO: 420          moltype = AA  length = 8
FEATURE                 Location/Qualifiers
REGION                  1..8
                        note = cleavable moiety
source                  1..8
                        mol_type = protein
                        organism = synthetic construct
SEQUENCE: 420
LPAGLLLR                                                                  8

SEQ ID NO: 421          moltype = AA  length = 8
FEATURE                 Location/Qualifiers
REGION                  1..8
                        note = cleavable moiety
source                  1..8
                        mol_type = protein
                        organism = synthetic construct
SEQUENCE: 421
LPAHLVLL                                                                  8

SEQ ID NO: 422          moltype = AA  length = 8
FEATURE                 Location/Qualifiers
REGION                  1..8
                        note = cleavable moiety
source                  1..8
                        mol_type = protein
                        organism = synthetic construct
SEQUENCE: 422
LPSHLVLL                                                                  8

SEQ ID NO: 423          moltype = AA  length = 8
FEATURE                 Location/Qualifiers
REGION                  1..8
                        note = cleavable moiety
source                  1..8
                        mol_type = protein
                        organism = synthetic construct
SEQUENCE: 423
LPAHLVLV                                                                  8

SEQ ID NO: 424          moltype = AA  length = 8
FEATURE                 Location/Qualifiers
REGION                  1..8
                        note = cleavable moiety
source                  1..8
                        mol_type = protein
                        organism = synthetic construct
SEQUENCE: 424
LPSHLVLV                                                                  8

SEQ ID NO: 425          moltype =   length =
SEQUENCE: 425
000

SEQ ID NO: 426          moltype =   length =
SEQUENCE: 426
000

SEQ ID NO: 427          moltype =   length =
SEQUENCE: 427
000

SEQ ID NO: 428          moltype =   length =
SEQUENCE: 428
000
```

-continued

```
SEQ ID NO: 429          moltype = AA  length = 8
FEATURE                 Location/Qualifiers
REGION                  1..8
                        note = MMP14 Cleavable Core CM Consensus Sequence 9
                         Subgenus 9.4
VARIANT                 3
                        note = misc_feature - Xaa may be Ala or His
VARIANT                 4
                        note = misc_feature - Xaa may be Ala or Asp
VARIANT                 6
                        note = misc_feature - Xaa may be Leu or Val
VARIANT                 8
                        note = misc_feature - Xaa may be Ala, Ser or Val
source                  1..8
                        mol_type = protein
                        organism = synthetic construct
SEQUENCE: 429
RRXXGXRX                                                                8

SEQ ID NO: 430          moltype =   length =
SEQUENCE: 430
000

SEQ ID NO: 431          moltype =   length =
SEQUENCE: 431
000

SEQ ID NO: 432          moltype =   length =
SEQUENCE: 432
000

SEQ ID NO: 433          moltype =   length =
SEQUENCE: 433
000

SEQ ID NO: 434          moltype = AA  length = 8
FEATURE                 Location/Qualifiers
REGION                  1..8
                        note = cleavable moiety
source                  1..8
                        mol_type = protein
                        organism = synthetic construct
SEQUENCE: 434
RRHDGLRA                                                                8

SEQ ID NO: 435          moltype = AA  length = 8
FEATURE                 Location/Qualifiers
REGION                  1..8
                        note = cleavable moiety
source                  1..8
                        mol_type = protein
                        organism = synthetic construct
SEQUENCE: 435
RRHDGLRS                                                                8

SEQ ID NO: 436          moltype =   length =
SEQUENCE: 436
000

SEQ ID NO: 437          moltype =   length =
SEQUENCE: 437
000

SEQ ID NO: 438          moltype =   length =
SEQUENCE: 438
000

SEQ ID NO: 439          moltype =   length =
SEQUENCE: 439
000

SEQ ID NO: 440          moltype =   length =
SEQUENCE: 440
000

SEQ ID NO: 441          moltype =   length =
SEQUENCE: 441
000
```

-continued

```
SEQ ID NO: 442          moltype =   length =
SEQUENCE: 442
000

SEQ ID NO: 443          moltype = AA  length = 8
FEATURE                 Location/Qualifiers
REGION                  1..8
                        note = MMP14 Cleavable Core CM Consensus Sequence 10
                         Subgenus 10.7
VARIANT                 3
                        note = misc_feature - Xaa may be Asn or Ser
VARIANT                 4
                        note = misc_feature - Xaa may be Gly or Leu
VARIANT                 8
                        note = misc_feature - Xaa may be Leu or Val
source                  1..8
                        mol_type = protein
                        organism = synthetic construct
SEQUENCE: 443
AYXXLSRX                                                                  8

SEQ ID NO: 444          moltype =   length =
SEQUENCE: 444
000

SEQ ID NO: 445          moltype =   length =
SEQUENCE: 445
000

SEQ ID NO: 446          moltype =   length =
SEQUENCE: 446
000

SEQ ID NO: 447          moltype =   length =
SEQUENCE: 447
000

SEQ ID NO: 448          moltype =   length =
SEQUENCE: 448
000

SEQ ID NO: 449          moltype = AA  length = 8
FEATURE                 Location/Qualifiers
REGION                  1..8
                        note = MMP14 Cleavable Core CM Consensus Sequence 10
                         Subgenus 10.13
VARIANT                 2
                        note = misc_feature - Xaa may be Ala, Leu or Gln
VARIANT                 4
                        note = misc_feature - Xaa may be Leu or Val
VARIANT                 8
                        note = misc_feature - Xaa may be Leu or Val
source                  1..8
                        mol_type = protein
                        organism = synthetic construct
SEQUENCE: 449
IXNXLSMX                                                                  8

SEQ ID NO: 450          moltype = AA  length = 8
FEATURE                 Location/Qualifiers
REGION                  1..8
                        note = cleavable moiety
source                  1..8
                        mol_type = protein
                        organism = synthetic construct
SEQUENCE: 450
IANLLSMV                                                                  8

SEQ ID NO: 451          moltype = AA  length = 8
FEATURE                 Location/Qualifiers
REGION                  1..8
                        note = cleavable moiety
source                  1..8
                        mol_type = protein
                        organism = synthetic construct
SEQUENCE: 451
ILNLLSMV                                                                  8

SEQ ID NO: 452          moltype = AA  length = 8
```

```
FEATURE                Location/Qualifiers
REGION                 1..8
                       note = cleavable moiety
source                 1..8
                       mol_type = protein
                       organism = synthetic construct
SEQUENCE: 452
IQNLLSMV                                                    8

SEQ ID NO: 453         moltype =   length =
SEQUENCE: 453
000

SEQ ID NO: 454         moltype =   length =
SEQUENCE: 454
000

SEQ ID NO: 455         moltype =   length =
SEQUENCE: 455
000

SEQ ID NO: 456         moltype = AA  length = 8
FEATURE                Location/Qualifiers
REGION                 1..8
                       note = MMP14 Cleavable Core CM Consensus Sequence 11
                        Subgenus 11.3
VARIANT                3
                       note = misc_feature - Xaa may be Pro or Ser
VARIANT                4
                       note = misc_feature - Xaa may be Leu or Val
source                 1..8
                       mol_type = protein
                       organism = synthetic construct
SEQUENCE: 456
PAXXWYTQ                                                    8

SEQ ID NO: 457         moltype = AA  length = 8
FEATURE                Location/Qualifiers
REGION                 1..8
                       note = cleavable moiety
source                 1..8
                       mol_type = protein
                       organism = synthetic construct
SEQUENCE: 457
PASLWYTQ                                                    8

SEQ ID NO: 458         moltype =   length =
SEQUENCE: 458
000

SEQ ID NO: 459         moltype =   length =
SEQUENCE: 459
000

SEQ ID NO: 460         moltype =   length =
SEQUENCE: 460
000

SEQ ID NO: 461         moltype =   length =
SEQUENCE: 461
000

SEQ ID NO: 462         moltype =   length =
SEQUENCE: 462
000

SEQ ID NO: 463         moltype = AA  length = 8
FEATURE                Location/Qualifiers
REGION                 1..8
                       note = MMP14 Cleavable Core CM Consensus Sequence 12
                        Subgenus 12.5
VARIANT                1
                       note = misc_feature - Xaa may be Ala or Ser
VARIANT                3
                       note = misc_feature - Xaa may be Gly, Asn or Ser
VARIANT                4
                       note = misc_feature - Xaa may be Leu or Ser
VARIANT                6
                       note = misc_feature - Xaa may be Arg or Ser
```

```
source                  1..8
                        mol_type = protein
                        organism = synthetic construct
SEQUENCE: 463
XLXXLXLP                                                                    8

SEQ ID NO: 464          moltype =   length =
SEQUENCE: 464
000

SEQ ID NO: 465          moltype =   length =
SEQUENCE: 465
000

SEQ ID NO: 466          moltype =   length =
SEQUENCE: 466
000

SEQ ID NO: 467          moltype =   length =
SEQUENCE: 467
000

SEQ ID NO: 468          moltype =   length =
SEQUENCE: 468
000

SEQ ID NO: 469          moltype = AA  length = 8
FEATURE                 Location/Qualifiers
REGION                  1..8
                        note = MMP14 Cleavable Core CM Consensus Sequence 12
                         Subgenus 12.11
VARIANT                 1
                        note = misc_feature - Xaa may be Ala or Pro
VARIANT                 3
                        note = misc_feature - Xaa may be Gly or Asn
source                  1..8
                        mol_type = protein
                        organism = synthetic construct
SEQUENCE: 469
XSXLLRFP                                                                    8

SEQ ID NO: 470          moltype = AA  length = 8
FEATURE                 Location/Qualifiers
REGION                  1..8
                        note = cleavable moiety
source                  1..8
                        mol_type = protein
                        organism = synthetic construct
SEQUENCE: 470
ALGLLRLP                                                                    8

SEQ ID NO: 471          moltype = AA  length = 8
FEATURE                 Location/Qualifiers
REGION                  1..8
                        note = cleavable moiety
source                  1..8
                        mol_type = protein
                        organism = synthetic construct
SEQUENCE: 471
ALGLLSLP                                                                    8

SEQ ID NO: 472          moltype = AA  length = 8
FEATURE                 Location/Qualifiers
REGION                  1..8
                        note = cleavable moiety
source                  1..8
                        mol_type = protein
                        organism = synthetic construct
SEQUENCE: 472
ASGLLRFP                                                                    8

SEQ ID NO: 473          moltype =   length =
SEQUENCE: 473
000

SEQ ID NO: 474          moltype = AA  length = 8
FEATURE                 Location/Qualifiers
REGION                  1..8
                        note = cleavable moiety
```

```
source                  1..8
                        mol_type = protein
                        organism = synthetic construct
SEQUENCE: 474
LLLPAHGG                                                                  8

SEQ ID NO: 475          moltype =   length =
SEQUENCE: 475
000

SEQ ID NO: 476          moltype =   length =
SEQUENCE: 476
000

SEQ ID NO: 477          moltype =   length =
SEQUENCE: 477
000

SEQ ID NO: 478          moltype =   length =
SEQUENCE: 478
000

SEQ ID NO: 479          moltype = AA  length = 8
FEATURE                 Location/Qualifiers
REGION                  1..8
                        note = MMP14 Cleavable Core CM Consensus Sequence 13
                         Subgenus 13.5
VARIANT                 1
                        note = misc_feature - Xaa may be Leu or Val
VARIANT                 2
                        note = misc_feature - Xaa may be Ala or Leu
VARIANT                 3
                        note = misc_feature - Xaa may be Leu or Ser
VARIANT                 6
                        note = misc_feature - Xaa may be His or Leu
source                  1..8
                        mol_type = protein
                        organism = synthetic construct
SEQUENCE: 479
XXXPLXGS                                                                  8

SEQ ID NO: 480          moltype =   length =
SEQUENCE: 480
000

SEQ ID NO: 481          moltype =   length =
SEQUENCE: 481
000

SEQ ID NO: 482          moltype =   length =
SEQUENCE: 482
000

SEQ ID NO: 483          moltype = AA  length = 8
FEATURE                 Location/Qualifiers
REGION                  1..8
                        note = cleavable moiety
source                  1..8
                        mol_type = protein
                        organism = synthetic construct
SEQUENCE: 483
LLLPLLGS                                                                  8

SEQ ID NO: 484          moltype = AA  length = 8
FEATURE                 Location/Qualifiers
REGION                  1..8
                        note = cleavable moiety
source                  1..8
                        mol_type = protein
                        organism = synthetic construct
SEQUENCE: 484
VAGRSMRP                                                                  8

SEQ ID NO: 485          moltype =   length =
SEQUENCE: 485
000

SEQ ID NO: 486          moltype =   length =
SEQUENCE: 486
```

```
000

SEQ ID NO: 487          moltype =   length =
SEQUENCE: 487
000

SEQ ID NO: 488          moltype =   length =
SEQUENCE: 488
000

SEQ ID NO: 489          moltype =   length =
SEQUENCE: 489
000

SEQ ID NO: 490          moltype =   length =
SEQUENCE: 490
000

SEQ ID NO: 491          moltype = AA  length = 8
FEATURE                 Location/Qualifiers
REGION                  1..8
                        note = MMP14 Cleavable Extended Core CM Consensus Sequence
                         8A Subgenus 8A.5
VARIANT                 1
                        note = misc_feature - Xaa may be Phe, Leu or Ser
VARIANT                 3
                        note = misc_feature - Xaa may be Ala, Gln or Ser
VARIANT                 5
                        note = misc_feature - Xaa may be Ile, Leu or Met
VARIANT                 6
                        note = misc_feature - Xaa may be Leu or Val
source                  1..8
                        mol_type = protein
                        organism = synthetic construct
SEQUENCE: 491
XPXGXXLR                                                                   8

SEQ ID NO: 492          moltype = AA  length = 8
FEATURE                 Location/Qualifiers
REGION                  1..8
                        note = MMP14 Cleavable Extended Core CM Consensus Sequence
                         8A Subgenus 8A.6
VARIANT                 1
                        note = misc_feature - Xaa may be Phe, Leu or Ser
VARIANT                 3
                        note = misc_feature - Xaa may be Ala or Ser
VARIANT                 5
                        note = misc_feature - Xaa may be Ile, Leu or Met
VARIANT                 6
                        note = misc_feature - Xaa may be Leu or Val
source                  1..8
                        mol_type = protein
                        organism = synthetic construct
SEQUENCE: 492
XPXGXXLR                                                                   8

SEQ ID NO: 493          moltype =   length =
SEQUENCE: 493
000

SEQ ID NO: 494          moltype =   length =
SEQUENCE: 494
000

SEQ ID NO: 495          moltype = AA  length = 8
FEATURE                 Location/Qualifiers
REGION                  1..8
                        note = MMP14 Cleavable Extended Core CM Consensus Sequence
                         8A Subgenus 8A.9
VARIANT                 3
                        note = misc_feature - Xaa may be Ala, Asn, Gln or Ser
VARIANT                 5
                        note = misc_feature - Xaa may be Ile or Leu
VARIANT                 8
                        note = misc_feature - Xaa may be Leu or Val
source                  1..8
                        mol_type = protein
                        organism = synthetic construct
SEQUENCE: 495
```

```
LPXHXVLX                                                    8

SEQ ID NO: 496         moltype = AA  length = 21
FEATURE                Location/Qualifiers
REGION                 1..21
                       note = masking moiety
source                 1..21
                       mol_type = protein
                       organism = synthetic construct
SEQUENCE: 496
QGQSGQCNIW LVGGDCRGWQ G                                     21

SEQ ID NO: 497         moltype = AA  length = 7
FEATURE                Location/Qualifiers
REGION                 1..7
                       note = masking moiety
source                 1..7
                       mol_type = protein
                       organism = synthetic construct
SEQUENCE: 497
CISPRGC                                                     7

SEQ ID NO: 498         moltype = AA  length = 5
FEATURE                Location/Qualifiers
REGION                 1..5
                       note = anti-Jagged antigen binding fragment VH CDR1 sequence
source                 1..5
                       mol_type = protein
                       organism = synthetic construct
SEQUENCE: 498
SYAMS                                                       5

SEQ ID NO: 499         moltype = AA  length = 17
FEATURE                Location/Qualifiers
REGION                 1..17
                       note = anti-Jagged antigen binding fragment VH CDR2 sequence
source                 1..17
                       mol_type = protein
                       organism = synthetic construct
SEQUENCE: 499
SIDPEGRQTY YADSVKG                                          17

SEQ ID NO: 500         moltype = AA  length = 10
FEATURE                Location/Qualifiers
REGION                 1..10
                       note = anti-Jagged antigen binding fragment VH CDR3 sequence
source                 1..10
                       mol_type = protein
                       organism = synthetic construct
SEQUENCE: 500
DIGGRSAFDY                                                  10

SEQ ID NO: 501         moltype = AA  length = 9
FEATURE                Location/Qualifiers
REGION                 1..9
                       note = anti-Jagged antigen binding fragment VL CDR1 sequence
source                 1..9
                       mol_type = protein
                       organism = synthetic construct
SEQUENCE: 501
RASQSISSY                                                   9

SEQ ID NO: 502         moltype = AA  length = 7
FEATURE                Location/Qualifiers
REGION                 1..7
                       note = anti-Jagged antigen binding fragment VL CDR2 sequence
source                 1..7
                       mol_type = protein
                       organism = synthetic construct
SEQUENCE: 502
AASSLQS                                                     7

SEQ ID NO: 503         moltype = AA  length = 9
FEATURE                Location/Qualifiers
REGION                 1..9
                       note = anti-Jagged antigen binding fragment VL CDR3 sequence
source                 1..9
                       mol_type = protein
                       organism = synthetic construct
```

```
SEQUENCE: 503
QQTVVAPPL                                                    9

SEQ ID NO: 504          moltype = AA  length = 5
FEATURE                 Location/Qualifiers
REGION                  1..5
                        note = anti-EGFR antigen binding fragment VH CDR1 sequence
source                  1..5
                        mol_type = protein
                        organism = synthetic construct
SEQUENCE: 504
NYGVH                                                        5

SEQ ID NO: 505          moltype = AA  length = 16
FEATURE                 Location/Qualifiers
REGION                  1..16
                        note = anti-EGFR antigen binding fragment VH CDR2 sequence
source                  1..16
                        mol_type = protein
                        organism = synthetic construct
SEQUENCE: 505
VIWSGGNTDY NTPFTS                                            16

SEQ ID NO: 506          moltype = AA  length = 11
FEATURE                 Location/Qualifiers
REGION                  1..11
                        note = anti-EGFR antigen binding fragment VH CDR3 sequence
source                  1..11
                        mol_type = protein
                        organism = synthetic construct
SEQUENCE: 506
ALTYYDYEFA Y                                                 11

SEQ ID NO: 507          moltype = AA  length = 11
FEATURE                 Location/Qualifiers
REGION                  1..11
                        note = anti-EGFR antigen binding fragment VL CDR1 sequence
source                  1..11
                        mol_type = protein
                        organism = synthetic construct
SEQUENCE: 507
RASQSIGTNI H                                                 11

SEQ ID NO: 508          moltype = AA  length = 8
FEATURE                 Location/Qualifiers
REGION                  1..8
                        note = anti-EGFR antigen binding fragment VL CDR2 sequence
source                  1..8
                        mol_type = protein
                        organism = synthetic construct
SEQUENCE: 508
KYASESIS                                                     8

SEQ ID NO: 509          moltype = AA  length = 9
FEATURE                 Location/Qualifiers
REGION                  1..9
                        note = anti-EGFR antigen binding fragment VL CDR3 sequence
source                  1..9
                        mol_type = protein
                        organism = synthetic construct
SEQUENCE: 509
QQNNNWPTT                                                    9

SEQ ID NO: 510          moltype = AA  length = 273
FEATURE                 Location/Qualifiers
REGION                  1..273
                        note = anti-CTLA-4 scFv
source                  1..273
                        mol_type = protein
                        organism = synthetic construct
SEQUENCE: 510
GGGSGGGGSG SGGGSGGGGS GGGEIVLTQS PGTLSLSPGE RATLSCRASQ SVSSSYLAWY  60
QQKPGQAPRL LIYGASSRAT GIPDRFSGSG SGTDFTLTIS RLEPEDFAVY YCQQYGSSPL  120
TFGGGTKVEI KRSGGSTITS YNVYYTKLSS SGTQVQLVQT GGGVVQPGRS LRLSCAASGS  180
TFSSYAMSWV RQAPGKGLEW VSAISGSGGS TYYADSVKGR FTISRDNSKN TLYLQMNSLR  240
AEDTAVYYCA TNSLYWYFDL WGRGTLVTVS SAS                              273

SEQ ID NO: 511          moltype = AA  length = 264
FEATURE                 Location/Qualifiers
```

-continued

```
REGION                  1..264
                        note = anti-CD3 epsilon scFv
source                  1..264
                        mol_type = protein
                        organism = synthetic construct
SEQUENCE: 511
GGGSGGGGSG SGGGSGGGGS GGGQVQLQQS GAELARPGAS VKMSCKASGY TFTRYTMHWV  60
KQRPGQGLEW IGYINPSRGY TNYNQKFKDK ATLTTDKSSS TAYMQLSSLT SEDSAVYYCA  120
RYYDDHYCLD YWGQGTTLTV SSGGGGSGGG GSGGGGSQIV LTQSPAIMSA SPGEKVTMTC  180
SASSSVSYMN WYQQKSGTSP KRWIYDTSKL ASGVPAHFRG SGSGTSYSLT ISGMEAEDAA  240
TYYCQQWSSN PFTFGSGTKL EINR                                         264

SEQ ID NO: 512          moltype = AA  length = 194
FEATURE                 Location/Qualifiers
REGION                  1..194
                        note = Display Platform CYTX-DP-XXXXXXXX peptide
VARIANT                 17..24
                        note = misc_feature - Xaa may be any amino acid
source                  1..194
                        mol_type = protein
                        organism = synthetic construct
SEQUENCE: 512
GQSGQEYMPM EGGSGQXXXX XXXXSGGQGG SGGSGGSGGS GGSAYYGITA GPAYRINDWA  60
SIYGVVGVGY GSGPGGSYGF SYGAGLQFNP MENVALDFSY EQSRIRSVDV GTWILSVGYR  120
FGSKSRRATS TVTGGYAQSD AQGQMNKMGG FNLKYRYEED NSPLGVIGSF TYTGGSGGSS  180
GQAAAGHHHH HHHH                                                    194

SEQ ID NO: 513          moltype = AA  length = 217
FEATURE                 Location/Qualifiers
REGION                  1..217
                        note = SP-CYTX-DP-XXXXXXXX peptide
VARIANT                 40..47
                        note = misc_feature - Xaa may be any amino acid
source                  1..217
                        mol_type = protein
                        organism = synthetic construct
SEQUENCE: 513
MKKIACLSAL AAVLAFTAGT SVAGQSGQEY MPMEGGSGQX XXXXXXXSGG QGGSGGSGGS  60
GGSGGSAYYG ITAGPAYRIN DWASIYGVVG VGYGSGPGGS YGFSYGAGLQ FNPMENVALD  120
FSYEQSRIRS VDVGTWILSV GYRFGSKSRR ATSTVTGGYA QSDAQGQMNK MGGFNLKYRY  180
EEDNSPLGVI GSFTYTGGSG GSSGQAAAGH HHHHHH                             217

SEQ ID NO: 514          moltype =   length =
SEQUENCE: 514
000

SEQ ID NO: 515          moltype = AA  length = 8
FEATURE                 Location/Qualifiers
REGION                  1..8
                        note = linker sequence
source                  1..8
                        mol_type = protein
                        organism = synthetic construct
SEQUENCE: 515
GGGSGGGS                                                           8
```

What is claimed:

1. A polypeptide comprising: a cleavable moiety (CM) comprising the amino acid sequence selected from the group consisting of SEQ ID NOs: 15 and 379-393, wherein the cleavable moiety is a substrate for a protease; and an antibody or antigen binding fragment thereof (AB) that binds a target.

2. The polypeptide of claim 1, wherein the CM comprises an amino acid sequence selected from the group consisting of SEQ ID NOs: 15, 379, 380, 382, and 391-393.

3. The polypeptide of claim 1, wherein the CM comprises the amino acid sequence of SEQ ID NO: 15.

4. The polypeptide of claim 1, wherein the CM comprises the amino acid sequence of SEQ ID NO: 379.

5. The polypeptide of claim 1, wherein the CM comprises the amino acid sequence of SEQ ID NO: 380.

6. The polypeptide of claim 1, wherein the CM comprises the amino acid sequence of SEQ ID NO: 382.

7. The polypeptide of claim 1, wherein the CM comprises the amino acid sequence of SEQ ID NO: 391.

8. The polypeptide of claim 1, wherein the CM comprises the amino acid sequence of SEQ ID NO: 392.

9. The polypeptide of claim 1, wherein the CM comprises the amino acid sequence of SEQ ID NO: 393.

10. The polypeptide of claim 1, wherein the CM is cleaved by at least one matrix metalloprotease (MMP).

11. The polypeptide of claim 1, wherein the CM is cleaved by at least one of MMP9 or MMP14.

12. The polypeptide of claim 1, wherein the CM is cleaved by at least MMP14.

13. The polypeptide of claim 1, wherein the CM is cleaved by at least MMP9.

14. The polypeptide of claim 1, wherein the CM consists of the amino acid sequence of SEQ ID NO: 382.

15. The polypeptide of claim 1, wherein the CM consists of the amino acid sequence of SEQ ID NO: 391.

16. The polypeptide of claim 1, wherein the CM consists of the amino acid sequence of SEQ ID NO: 392.

17. The polypeptide of claim 1, wherein the CM consists of the amino acid sequence of SEQ ID NO: 393.

18. The polypeptide of claim 1, further comprises a linking peptide.

19. The polypeptide of claim 18, wherein the linking peptide is 2 to 20 amino acids in length.

20. The polypeptide of claim 18, wherein the linking peptide comprises an amino acid sequence selected from the group consisting of $(GS)_n$, $(GGS)_n$, (GSGGS) n (SEQ ID NO: 1), $(GGGS)_n$ (SEQ ID NO: 2), GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8).

21. The polypeptide of claim 18, wherein the linking peptide comprises an amino acid sequence selected from the group consisting of GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 155), GSSGGSGGSG (SEQ ID NO: 156), or GSSGGSGGSGS (SEQ ID NO: 157).

* * * * *